(12) United States Patent
Wang et al.

(10) Patent No.: US 11,555,032 B2
(45) Date of Patent: Jan. 17, 2023

(54) ISOXAZOLE DERIVATIVES AS FXR AGONISTS AND METHODS OF USE THEREOF

(71) Applicant: Enanta Pharmaceuticals, Inc., Watertown, MA (US)

(72) Inventors: Guoqiang Wang, Belmont, MA (US); Jun Ma, Belmont, MA (US); Bin Wang, Newton, MA (US); Ruichao Shen, Belmont, MA (US); Xuechao Xing, Wilmington, MA (US); Yong He, Lexington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 5 days.

(21) Appl. No.: 16/871,551

(22) Filed: May 11, 2020

(65) Prior Publication Data

US 2020/0361920 A1    Nov. 19, 2020

Related U.S. Application Data

(60) Provisional application No. 62/847,006, filed on May 13, 2019.

(51) Int. Cl.
| | |
|---|---|
| *C07D 417/12* | (2006.01) |
| *C07D 413/12* | (2006.01) |
| *C07D 417/14* | (2006.01) |
| *C07D 261/08* | (2006.01) |
| *C07D 413/14* | (2006.01) |

(52) U.S. Cl.
CPC ......... *C07D 413/12* (2013.01); *C07D 261/08* (2013.01); *C07D 413/14* (2013.01); *C07D 417/12* (2013.01); *C07D 417/14* (2013.01)

(58) Field of Classification Search
CPC .................................................. C07D 417/12
See application file for complete search history.

(56) References Cited

U.S. PATENT DOCUMENTS

| | | |
|---|---|---|
| 5,571,809 A | 11/1996 | Hargrave et al. |
| 6,974,830 B2 | 12/2005 | Giegrich et al. |
| 7,319,109 B2 | 1/2008 | Boggs et al. |
| 7,846,960 B2 | 12/2010 | Bell et al. |
| 7,863,302 B2 | 1/2011 | Bell et al. |
| 7,897,773 B2 | 3/2011 | Aletru et al. |
| 7,902,373 B2 | 3/2011 | Blake et al. |
| 8,952,042 B2 | 2/2015 | Kremoser et al. |
| 9,751,874 B2 | 9/2017 | Gege et al. |
| 10,080,741 B2 | 9/2018 | Or et al. |
| 10,080,742 B2 | 9/2018 | Or et al. |
| 10,080,743 B2 | 9/2018 | Or et al. |
| 10,138,228 B2 | 11/2018 | Or et al. |
| 10,144,729 B2 | 12/2018 | Or et al. |
| 10,149,835 B2 | 12/2018 | Or et al. |
| 10,450,306 B2 | 10/2019 | Ma et al. |
| 10,597,391 B2 | 3/2020 | He et al. |
| 10,689,391 B2 | 6/2020 | Or et al. |
| 10,808,742 B2 | 10/2020 | Ryan et al. |
| 10,829,486 B2 | 11/2020 | Shen et al. |
| 11,034,684 B2 | 6/2021 | Ma et al. |
| 2004/0048316 A1 | 3/2004 | Haffner et al. |
| 2007/0054902 A1 | 3/2007 | Fukui et al. |
| 2007/0142340 A1 | 6/2007 | Pellicciari et al. |
| 2008/0167356 A1 | 7/2008 | Caldwell et al. |
| 2009/0163474 A1 | 6/2009 | Zhang et al. |
| 2010/0063697 A1 | 3/2010 | Lindgren et al. |
| 2010/0099703 A1 | 4/2010 | Garcia-López et al. |
| 2010/0120775 A1 | 5/2010 | Bass, III et al. |
| 2010/0152166 A1 | 6/2010 | Genin et al. |
| 2010/0184809 A1 | 7/2010 | Kremoser et al. |
| 2010/0210660 A1 | 8/2010 | Kremoser et al. |

(Continued)

FOREIGN PATENT DOCUMENTS

| | | |
|---|---|---|
| CN | 106588804 A | 4/2017 |
| CN | 106632294 A | 5/2017 |

(Continued)

OTHER PUBLICATIONS

Banker et al., Prodrugs, Modern Pharmaceutics, 3rd edition, Revised and Expanded, pp. 451 and 596.*
Jordan "Tamoxifen . . . " Nature Rev. v.2. p. 205-913 (2003).*
Ettmayer et al. "Lessons Learned from Marketed and Investigational Prodrugs." J. Med. Chern., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*

(Continued)

*Primary Examiner* — John S Kenyon
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts and esters thereof:

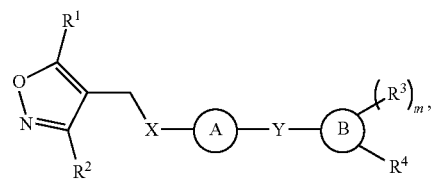

pharmaceutical compositions comprising these compounds and methods of using these compounds to treat or prevent a disease or disorder mediated as FXR modulators. Specifically, the present invention relates to isoxazole derivatives useful as agonists for FXR, and methods for their preparation and use.

17 Claims, No Drawings

(56) References Cited

U.S. PATENT DOCUMENTS

| | | |
|---|---|---|
| 2010/0249179 A1 | 9/2010 | Deaton et al. |
| 2010/0292212 A1 | 11/2010 | Ackermann et al. |
| 2011/0034507 A1 | 2/2011 | Akwabi-Ameyaw et al. |
| 2011/0275595 A1 | 11/2011 | Eckhardt et al. |
| 2012/0004164 A1 | 1/2012 | Dales et al. |
| 2013/0261108 A1 | 10/2013 | Tully et al. |
| 2014/0038947 A1 | 2/2014 | Glick et al. |
| 2014/0221659 A1 | 8/2014 | Kinzel et al. |
| 2015/0299210 A1 | 10/2015 | Bailey et al. |
| 2015/0366856 A1 | 12/2015 | Mutnick et al. |
| 2016/0130297 A1 | 5/2016 | Xing et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0030003 A1 | 2/2018 | Wang et al. |
| 2018/0099957 A1 | 4/2018 | Shen et al. |
| 2018/0141941 A1 | 5/2018 | He et al. |
| 2019/0194216 A1 | 6/2019 | Or et al. |
| 2019/0248777 A1 | 8/2019 | Shen et al. |

FOREIGN PATENT DOCUMENTS

| | | | |
|---|---|---|---|
| CN | 106946867 A | 7/2017 | |
| CN | 106995416 A | 8/2017 | |
| CN | 107021957 A | 8/2017 | |
| CN | 108017636 A | 5/2018 | |
| CN | 108341822 A | 7/2018 | |
| CN | 109053751 A | 12/2018 | |
| WO | 2004046162 A2 | 6/2004 | |
| WO | 2007089768 A2 | 8/2007 | |
| WO | 2008115385 A2 | 9/2008 | |
| WO | 2009012125 A1 | 1/2009 | |
| WO | 2009127321 A1 | 10/2009 | |
| WO | 2009149795 A2 | 12/2009 | |
| WO | 2011020615 A1 | 2/2011 | |
| WO | 2011021645 A1 | 2/2011 | |
| WO | 2012087519 A1 | 6/2012 | |
| WO | 2012087520 A1 | 6/2012 | |
| WO | 2012087521 A1 | 6/2012 | |
| WO | WO-2012087519 A1 * | 6/2012 | ............ A61K 31/46 |
| WO | 2013007387 A1 | 1/2013 | |
| WO | 2013037482 A1 | 3/2013 | |
| WO | 2013166176 A1 | 11/2013 | |
| WO | 2015036442 A1 | 3/2015 | |
| WO | 2017118294 A1 | 7/2017 | |
| WO | 2017128896 A1 | 8/2017 | |
| WO | 2017145041 A1 | 8/2017 | |
| WO | 2017133521 A1 | 10/2017 | |
| WO | 2017201150 A1 | 11/2017 | |
| WO | 2018024224 A1 | 2/2018 | |
| WO | 2018039386 A1 | 3/2018 | |
| WO | 2018067704 A1 | 4/2018 | |
| WO | 2018075207 A1 | 4/2018 | |
| WO | 2018085148 A1 | 5/2018 | |
| WO | 2018133730 A1 | 7/2018 | |
| WO | 2018170173 A1 | 9/2018 | |
| WO | 2018190643 A1 | 10/2018 | |
| WO | 2018214959 A1 | 11/2018 | |
| WO | 2019007418 A1 | 1/2019 | |

OTHER PUBLICATIONS

Balant ed in Wolff et al. Burger's Medicinal Chemistry and Drug Discovery. 5th ed. vol. 1: Principles and Practice, pp. 949-982, 1996.*

Bundgaard, Design of Prodrugs, Chapter 1, p. 1, 1985.*

Silverman, Prodrugs and Drug Delivery Systems, The Organic Chemistry of Drug Design and Drug action, Chapter 8, pp. 352-400, 1992.*

Medline Plus. Hardening of the Arteries. (2018). Web: http://www.nim.nih.gov/medlineplus/ency/article/000171.htm.

Merck Manual, Diabetes Mellitus. (2017. Web: http://www.merck.com/mmpe/print/sec12/ch_158/ch_158b.html.

Pubchem CID 123486225 Create Date: Jan. 25, 2017 (Jan. 25, 2017) Date Accessed: Apr. 1, 2019 (Apr. 1, 2019).

Ali, et al., "Recent advances in the development of farnesoid X receptor agonists", Ann Transl Med, 3(1), Cited in 1284—Cited in Some of the Other Related Cases So Did Not Remove (Take out On Case By Case Basis), 2015, 1-16.

Buijsman, et al., "Non-Steroidal Steroid Receptor Modulators", Current Medicinal Chemistry, 12, 2005, 1017-1075.

Crawley, "Farnesoid X Receptor Modulators: a patent review", Expert Opinion on Therapeutic Patents, 20(8), 2010, 1047-1057.

Gura, Trisha, "Systems for Identifying New Drugs Are Often Faulty", Science, 278, 1997, 1041-1042.

Johnson, J. I. et al., "Relationships between drug activity in NCI preclinical in vitro and in vivo models and early clinical trials", British Journal of Cancer, 84, 2001, 1424-1431.

Pearce, Homer L. et al., "Failure modes in anticancer drug discovery and development", Cancer Drug Design and Discovery Edited by Stephen Neidle, Chapter 18, 2008, 424-435.

Ruano, J.L. G. et al., "4-(diethoxymethyl)-3-pyridin-3-ylisoxazole-5-carboxylates: useful scaffold for highly functionalised 3-(pyridin-3-yl)isoxazole", Tetrahedron, 61(18), 2005, 4363-4371.

Sepe, et al., "Farnesoid X receptor modulators (2011-2014): a patent review", Expert Opinion on Therapeutic Patents, 25:8, 2015, 885-896.

Simone, J. V., Oncology: Introduction, Cecil Textbook of Medicine, 20th Edition, vol. 1, 1996, 1004-1010.

Bass, et al., "Substituted isoxazole analogs of farnesoid X receptor (FXR) agonist GW4064", Bioorganic & Medicinal Chemistry Letters, vol. 19, 2009, 2969-2973.

Heizmann, P., et al., "Pharmacokinetics and Bioavailability of Midazolam in Man," Br. J. Clin. Pharmac., vol. 16, 43S-49S, 1983.

* cited by examiner

ISOXAZOLE DERIVATIVES AS FXR AGONISTS AND METHODS OF USE THEREOF

RELATED APPLICATION

This application claims the benefit of U.S. Provisional Application No. 62/847,006, filed on May 13, 2019. The entire teachings of the above application are incorporated herein by reference.

TECHNICAL FIELD

The present invention relates generally to compounds and pharmaceutical compositions useful as FXR agonists. Specifically, the present invention relates to isoxazole compounds containing a bicycloalkylamine linkage and methods for their preparation and use.

BACKGROUND OF THE INVENTION

Farnesoid X Receptor (FXR, NR1H4) is a member of the nuclear receptor family of ligand-activated transcription factors that includes receptors for the steroid, retinoid, and thyroid hormones (D. J. Mangelsdorf, et al., *Cell*, 1995, 83(6), 841-850). FXR was originally identified from a rat liver cDNA library. Farnesol and derivatives, collectively termed farnesoids, activate the rat ortholog at high concentration, but they do not modulate the human or mouse receptors. FXR is primarily expressed in the liver, kidney, and intestine (W. Seol, et al., *Mol. Endocrinol.*, 1995, 9(1), 72-85; B. M. Forman, et al., *Cell*, 1995, 81(5), 687-693). The relevant physiological ligands of FXR include the primary bile acids cholic acid (CA) and chenodeoxycholic acid (CDCA) and the secondary bile acids deoxycholic acid (DCA) and lithocholic acid (LCA) (D. Parks, et al., *Science*, 1999, 284(5418), 1362-1365). The most potent physiological ligand for FXR is CDCA, which plays a key role in regulating the expression of several genes that participate in bile acid homeostasis. FXR functions as a heterodimer with the retinoid X receptor (RXR) and binds to response elements in the promoter region of target genes to regulate gene transcription. FXR seems to be also involved in paracrine and endocrine signaling by upregulating the expression of the cytokine Fibroblast Growth Factor (J. Holt, et al., *Genes Dev.*, 2003, 17(13), 1581-1591; T. Inagaki, et al., *Cell Metab.*, 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/073767, WO 2016/116054, WO 2016/103037, WO 2016/096116, WO 2016/096115, WO 2016/097933, WO 2016/081918, WO 2016/127924, WO 2016/130809, WO 2016/145295, WO 2016/173524, CN 106632294, CN 106588804, WO 2017/027396, WO 2017/049172, WO 2017/049173, WO 2017/049176, WO 2017/049177, WO 2017/053826, WO 2017/062763, WO 2017/118294, WO 2017/128896, WO 2017/129125, WO 2017/133521, WO 2017/143134, WO 2017/147074, WO 2017/147174, WO 2017/145041, WO 2017/156024, WO 2017/201150, WO 2017/201152, WO2017/201155, WO 2017/205684, WO 2017/205633, CN 106518708, CN 106518946, CN 106478759, CN 106478447, CN 106478452, CN 106478453, CN 106478759, CN 106518708, CN 106518946, CN 106588804, CN 106632294, CN 106946867, CN 106986910, CN 106995416, CN 107021957, CN 108017636, CN 108341822, US 2017/0196893, US 2017/0233431, US 2017/0240585, US 2017/0240586, US 2017/0240587, US 2017/0304270, US 2017/0304271, US 2017/0304272, US 2017/0355685, US 2017/0355693, US 2017/0355694, US 20180148469, CN 108017636, WO 2018081285, CN 107973790, WO 2018075207, WO 2018039386, WO 2018024224, WO 2018067704, WO 2018133730, WO 2018152171, WO 2018170165, WO 2018170166, WO 2018170167, WO 2018170173, WO 2018170182, WO 2018190643, WO 2018214959, CN 109053751, WO 2019007418, WO 2019020067.

Further small molecule FXR modulators have been recently reviewed (R. C. Buijsman, et al., *Curr. Med. Chem.* 2005, 12(9), 1017-1075; Crawley, M. L. *Expert Opin. Ther. Patents* 2010, 20(8), 1047-1057; V. Sepe, et al., *Expert Opin. Ther. Patents* 2015, 25(8), 885-896; Xu, Y., *J. Med. Chem.* 2016, 59 (14), 6553-6579).

There is a need for development of FXR modulators for the treatment and prevention of diseases.

SUMMARY OF THE INVENTION

In one aspect, the invention provides compounds represented by Formula I, and pharmaceutically acceptable salts thereof:

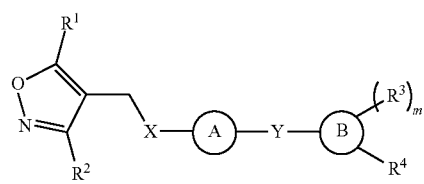

I wherein:
$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted —$C_3$-$C_6$ cycloalkyl, or optionally substituted 3- to 6-membered heterocycloalkyl. Preferably, $R^1$ is optionally substituted isopropyl, optionally substituted tert-butyl, or optionally substituted cyclopropyl;
$R^2$ is optionally substituted aryl, optionally substituted heteroaryl, optionally substituted arylalkyl, optionally substituted heteroarylalkyl, optionally substituted cycloalkenyl, or optionally substituted 3- to 8-membered heterocycloalkyl;
X is O or $NR^x$, where $R^x$ is selected from the group consisting of hydrogen, —$C_1$-$C_6$-alkyl, —$C_1$-$C_6$ haloalkyl, —$C_3$-$C_6$ cycloalkyl, and formyl; preferably, $R^x$ is hydrogen;

A is

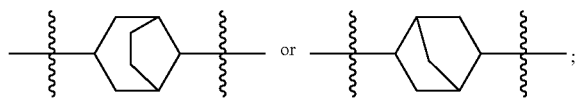 [SMILES: *C1CC2CCC(C1)C2* ; *C1CC2CC1CC2*]

Y is absent, O, $NR^{x1}$, S, SO, $SO_2$, or $NR^{x1}SO_2$, where $R^{x1}$ is selected from the group consisting of hydrogen, —$C_1$-$C_6$-alkyl, —$C_1$-$C_6$ haloalkyl, —$C_3$-$C_6$ cycloalkyl, and formyl;

B is aryl, heteroaryl, heterocycloalkyl, arylalkyl, or heteroarylalkyl;

Each $R^3$ is independently selected from the group consisting of halo, hydroxy, —OMe, —$OCH_2F$, —$OCHF_2$, —$OCF_3$, —$C_2$-$C_6$-alkoxy, —$C_1$-$C_6$-alkyl, —$C_1$-$C_6$ haloalkyl, —$C_2$-$C_6$ alkenyl, —$C_2$-$C_6$ alkynyl, —$C_3$-$C_6$ cycloalkyl, —O—$C_1$-$C_2$alkylphenyl, —$C_1$-$C_6$-hydroxylalkyl, —$C_1$-$C_6$ hydroxylhaloalkyl, —$C_3$-$C_6$ hydroxylcycloalkyl, aryl, heteroaryl, cyano, —$SCF_3$, —$NH_2$, —NHMe, —$NMe_2$, —$C_1$-$C_6$-alkylamine, tetrazole, arylalkyl, and heteroarylalkyl; alternatively, two adjacent or geminal $R^3$ groups are taken together with the atom or atoms to which they are attached to form an optionally substituted carbocyclic or heterocyclic;

m is 0, 1, 2, 3;

$R^4$ is hydrogen, hydroxy, protected hydroxy, —O-(hydroxy prodrug group), tetrazolyl, cyano,

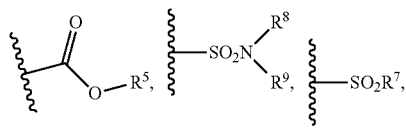

—$(C(R^{10})_2)_nC(O)OR^5$, —$CONH(CH_2)_nCO_2R^6$, or —$CONH(CH_2)_nSO_2R^7$;

n is 1, 2, 3 or 4;

$R^5$ and $R^6$ are independently selected from the group consisting of hydrogen, —$C_1$-$C_8$ alkyl, and —$C_3$-$C_8$ cycloalkyl.

$R^7$ is selected from the group consisting of OH, —$C_1$-$C_8$ alkyl, —$C_3$-$C_8$ cycloalkyl, aryl, and heteroaryl.

$R^8$ and $R^9$ are each independently selected from hydrogen, optionally substituted —$C_1$-$C_8$ alkyl, optionally substituted —$C_2$-$C_8$ alkenyl, optionally substituted $C_2$-$C_8$ alkynyl, optionally substituted —$C_3$-$C_8$ cycloalkyl, optionally substituted aryl, optionally substituted alkylaryl, optionally substituted heterocycloalkyl, optionally substituted heteroaryl, and optionally substituted alkylheteroaryl; alternatively, $R^8$ and $R^9$ are taken together with the nitrogen atom to which they are attached to form an optionally substituted heterocyclic ring; and each $R^{10}$ is independently hydrogen or halogen, preferably fluoro, or two geminal $R^{10}$ groups, together with the carbon atom to which they are attached, form a $C_3$-$C_6$-cyclcoalkyl, preferably cyclopropyl.

In another embodiment, the present invention provides a pharmaceutical composition comprising a compound or combination of compounds of the present invention, or a pharmaceutically acceptable salt thereof, and a pharmaceutically acceptable carrier or excipient.

In another embodiment, the present invention provides a method for preventing or treating an FXR mediated disease or condition in a subject in need thereof. The method comprises administering to the subject a therapeutically effective amount of a compound of Formula (I) or a pharmaceutically acceptable salt thereof. The present invention also provides the use of a compound of Formula (I) or a pharmaceutically acceptable salt thereof in the manufacture of a medicament for the prevention or treatment of an FXR mediated disease or condition.

DETAILED DESCRIPTION OF THE INVENTION

In one embodiment, the present invention provides a compound of Formula (I) as described above, or a pharmaceutically acceptable salt thereof.

In certain embodiments, the present invention relates to compounds of Formula (I), and pharmaceutically acceptable salts thereof, wherein $R^1$ is optionally substituted isopropyl, optionally substituted cyclopropyl, or optionally substituted tert-butyl.

In certain embodiments, the present invention relates to compounds of Formula (I), and pharmaceutically acceptable salts thereof, wherein $R^2$ is cyclohexyl or cyclopentyl, each of which is optionally substituted with up to 3 groups which are independently selected from halogen, optionally substituted —$C_1$-$C_6$ alkyl, optionally substituted —$C_1$-$C_6$ alkoxy, optionally substituted —$C_3$-$C_6$ cycloalkyl, optionally substituted, —$C_3$-$C_6$ cycloalkenyl, optionally substituted aryl, and optionally substituted heteroaryl.

In certain embodiments, the present invention relates to compounds of Formula (I), and pharmaceutically acceptable salts thereof, wherein $R^2$ is optionally substituted phenyl.

In certain embodiments, the present invention relates to compounds of Formula (I), and pharmaceutically acceptable salts thereof, wherein $R^2$ is optionally substituted heteroaryl.

In certain embodiments, the present invention relates to compounds of Formula (I), and pharmaceutically acceptable salts thereof, wherein $R^2$ is selected from the groups set forth below:

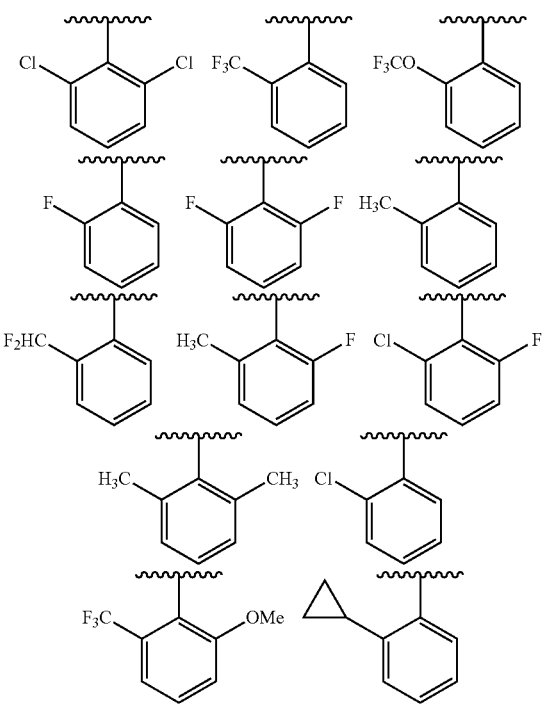

-continued

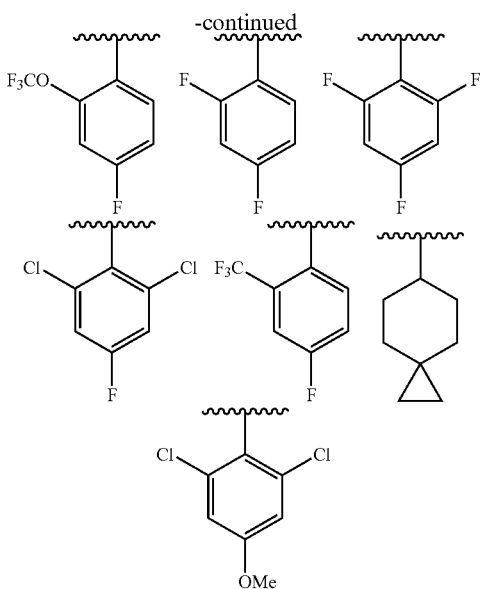

In certain embodiments, the present invention relates to compounds of Formula (I), and pharmaceutically acceptable salts thereof, wherein X is O.

In certain embodiments, the present invention relates to compounds of Formula (I), and pharmaceutically acceptable salts thereof, wherein X is $NR^x$ and $R^x$ is selected from hydrogen and —$C_1$-$C_6$-alkyl.

In certain embodiments, the present invention relates to compounds of Formula (I), and pharmaceutically acceptable salts thereof, wherein A is

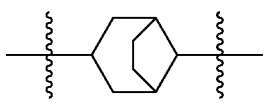

In certain embodiments, the present invention relates to compounds of Formula (I), and pharmaceutically acceptable salts thereof, wherein Y is O, $NR^{x1}$, S, $SO_2$, $NR^{x1}SO_2$.

In certain embodiments, the present invention relates to compounds of Formula (I), and pharmaceutically acceptable salts thereof, wherein Y is O.

In certain embodiments, the present invention relates to compounds of Formula (I), and pharmaceutically acceptable salts thereof, wherein Y is NH.

In certain embodiments, the present invention relates to compounds of Formula (I), and pharmaceutically acceptable salts thereof, wherein Y is S.

In certain embodiments, the present invention relates to compounds of Formula (I), and pharmaceutically acceptable salts thereof, wherein Y is $SO_2$.

In certain embodiments, the present invention relates to compounds of Formula (I), and pharmaceutically acceptable salts thereof, wherein Y is $NR^{x1}SO_2$.

In certain embodiments, the present invention relates to compounds of Formula (I), and pharmaceutically acceptable salts thereof, wherein Y is $NHSO_2$.

In certain embodiments, the present invention relates to compounds of Formula (I), and pharmaceutically acceptable salts thereof, wherein B is aryl.

In certain embodiments, the present invention relates to compounds of Formula (I), and pharmaceutically acceptable salts thereof, wherein B is heteroaryl.

In certain embodiments, the present invention relates to compounds of Formula (I), and pharmaceutically acceptable salts thereof, wherein B is arylalkyl.

In certain embodiments, the present invention relates to compounds of Formula (I), and pharmaceutically acceptable salts thereof, wherein B is fused aryl.

In certain embodiments, the present invention relates to compounds of Formula (I), and pharmaceutically acceptable salts thereof, wherein B is fused heteroaryl.

In certain embodiments, the present invention relates to compounds of Formula (I), and pharmaceutically acceptable salts thereof, wherein B is heteroarylalkyl.

In certain embodiments, the present invention relates to compounds of Formula (I), and pharmaceutically acceptable salts thereof, wherein B is selected from the groups set forth below by removing two hydrogen atoms:

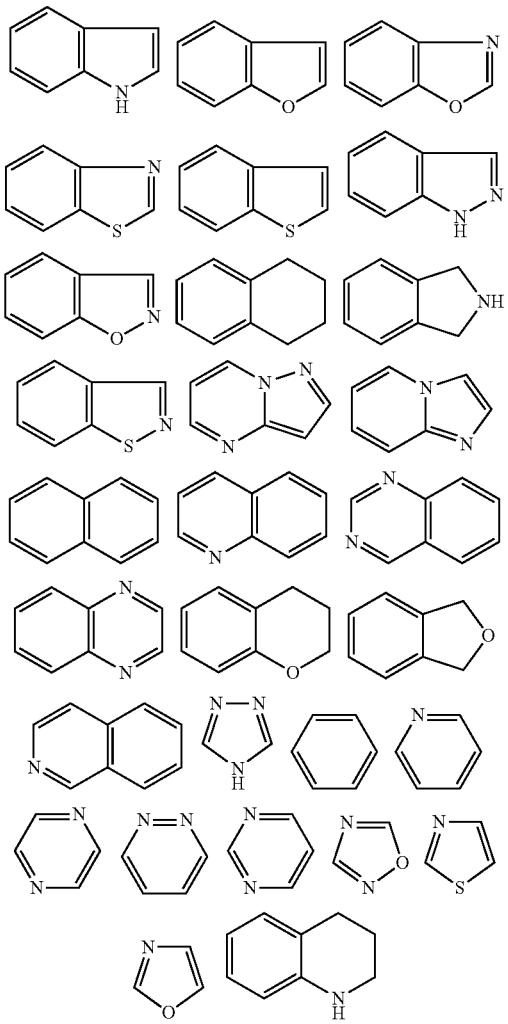

In certain embodiments, the present invention relates to compounds of Formula (I), and pharmaceutically acceptable salts thereof, wherein $R^4$ is tetrazolyl.

In certain embodiments, the present invention relates to compounds of Formula (I), and pharmaceutically acceptable salts thereof, wherein $R^4$ is

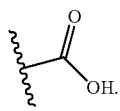

In certain embodiments, the present invention relates to compounds of Formula (I), and pharmaceutically acceptable salts thereof, wherein $R^4$ is

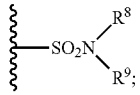

alternatively, $R^8$ and $R^9$ are taken together with the nitrogen atom to which they are attached to form an optionally substituted heterocyclic ring.

In certain embodiments, the present invention relates to compounds of Formula (I), and pharmaceutically acceptable salts thereof, wherein $R^4$ is hydrogen.

In certain embodiments, the invention provides compounds represented by Formula (IIa), Formula (IIb) and Formula (IIc), and pharmaceutically acceptable salts thereof:

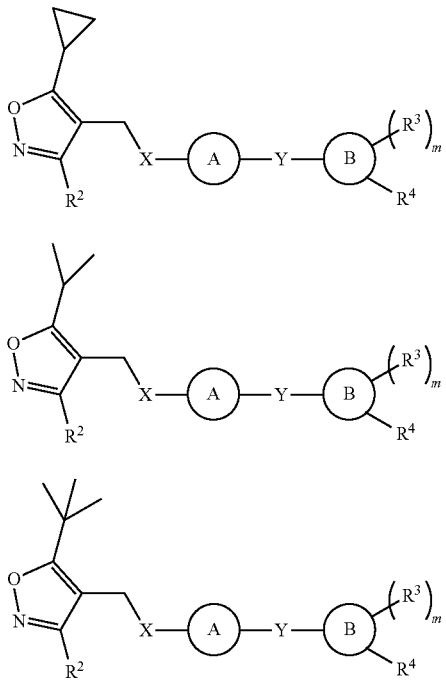

wherein $R^2$, X, A, Y, $R^3$, m, B and $R^4$ are as previously defined.

In certain embodiments, the invention provides compounds represented by Formula (IIIa) and Formula (IIb), and pharmaceutically acceptable salts thereof:

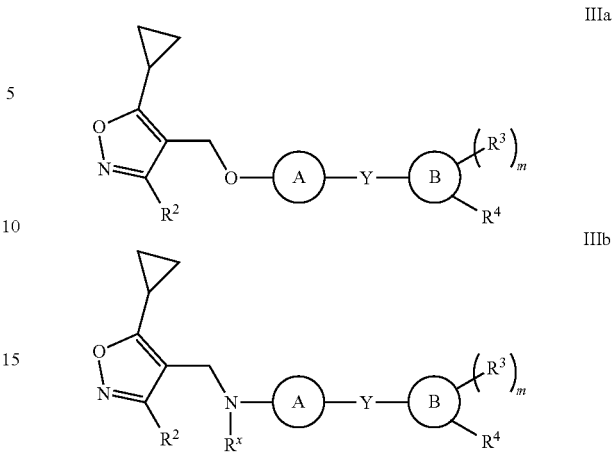

wherein $R^2$, R, A, Y, $R^3$, m, B and $R^4$ are as previously defined.

In certain embodiments, the invention provides compounds represented by Formula (IVa), Formula (IVb), Formula (IVc) and Formula (IVd), and pharmaceutically acceptable salts thereof:

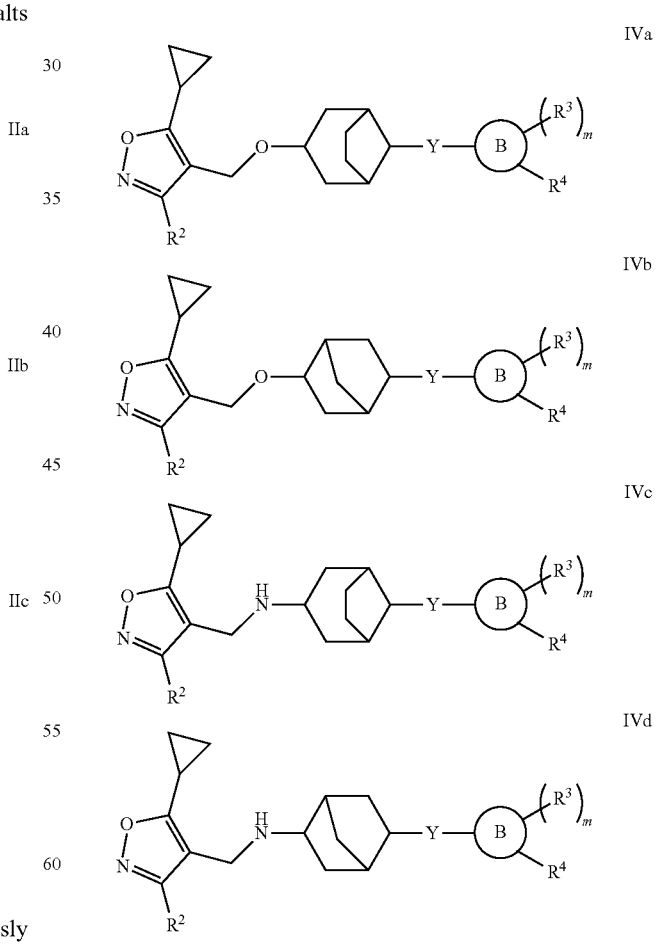

wherein $R^2$, Y, $R^3$, m, B and $R^4$ are as previously defined.

In certain embodiments, the invention provides compounds represented by Formula (Va), Formula (Vb), Formula (Vc), Formula (Vd) and Formula (Ve), and pharmaceutically acceptable salts thereof:

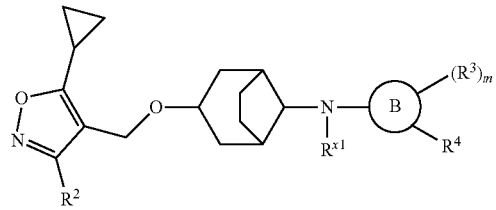
Va

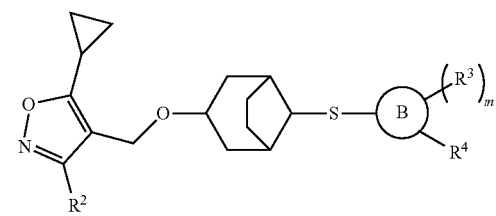
Vb

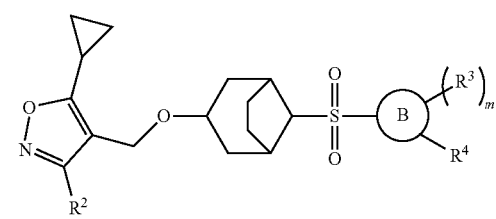
Vc

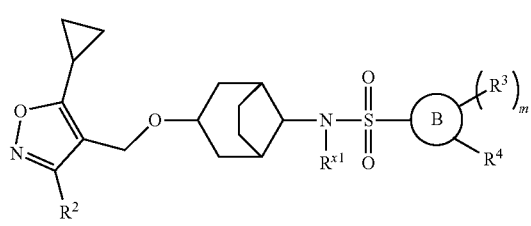
Vd

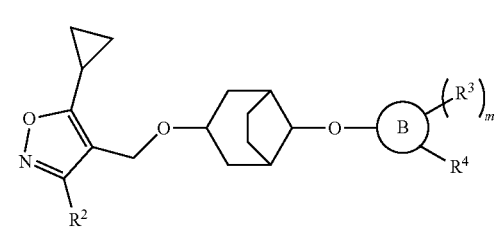
Ve wherein $R^2$, R, $R^3$, m, B and $R^4$ are as previously defined.

In certain embodiments, the invention provides compounds represented by Formula (VIa), Formula (VIb), Formula (VIc), Formula (VId) and Formula (VIe), and pharmaceutically acceptable salts thereof:

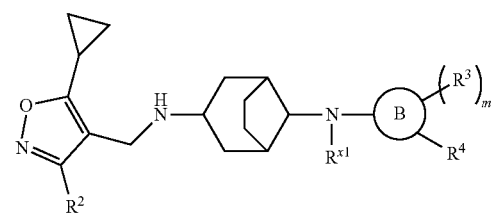
VIa

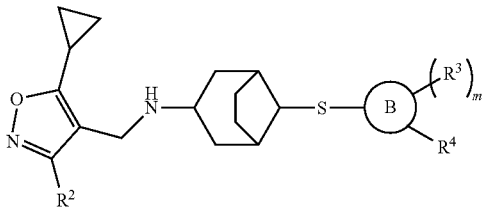
VIb

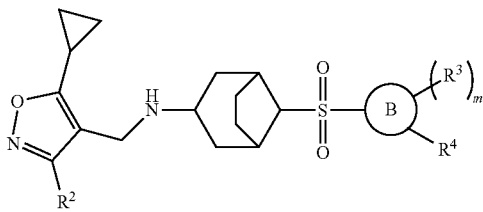
VIc

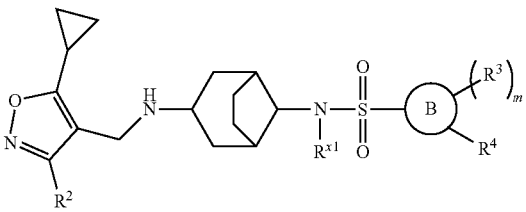
VId

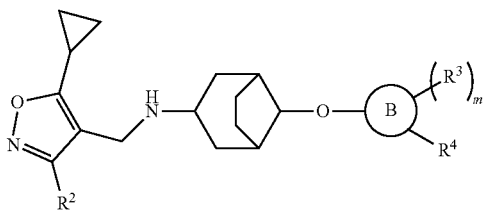
VIe wherein $R^2$, $R^{x1}$, $R^3$, m, B and $R^4$ are as previously defined.

In certain embodiments, the invention provides compounds represented by Formula (VIIa), Formula (VIIb), Formula (VIIc), Formula (VIId) and Formula (VIIe), and pharmaceutically acceptable salts thereof:

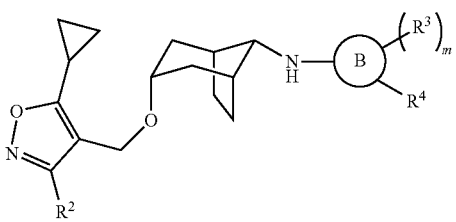
VIIa

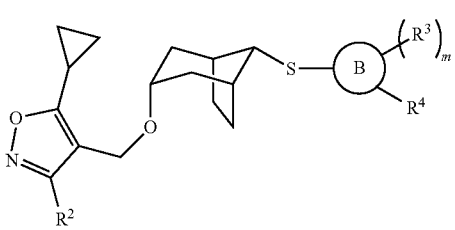
VIIb

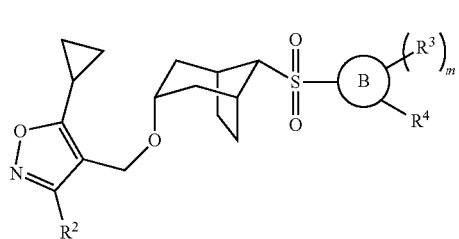

VIIc

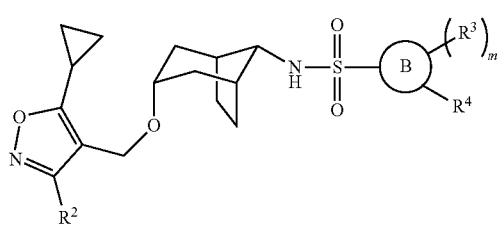

VIId

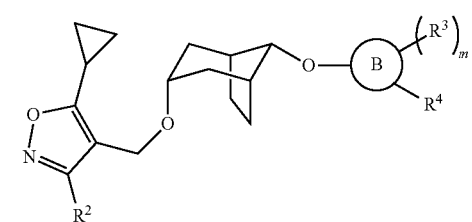

VIIe wherein $R^2$, B, $R^3$, m and $R^4$ are as previously defined.

In certain embodiments, the invention provides compounds represented by Formula (VIIIa), Formula (VIIIb), Formula (VIIIc), Formula (VIIId) and Formula (VIIIe), and pharmaceutically acceptable salts thereof:

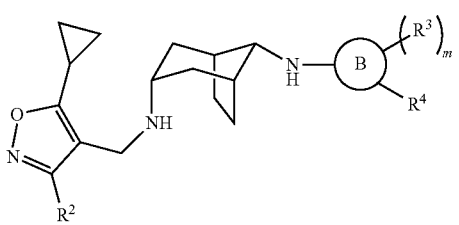

VIIIa

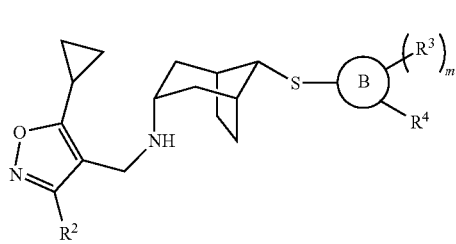

VIIIb

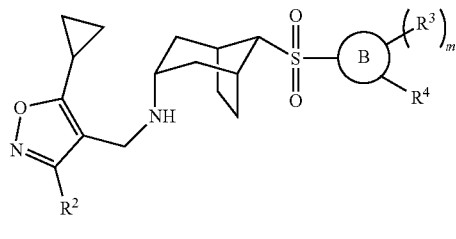

VIIIc

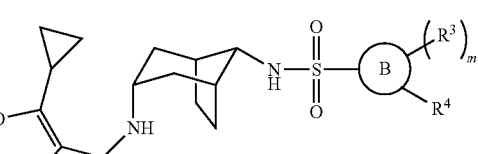

VIIId

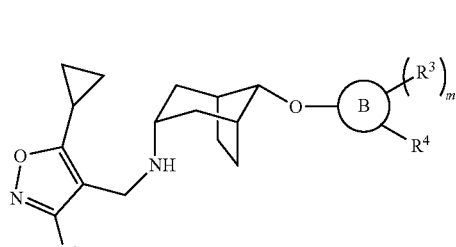

VIIIe wherein $R^2$, B, $R^3$, m and $R^4$ are as previously defined.

In certain embodiments, the invention provides compounds represented by Formula (I), Formulae (IIa)~(IIc), Formulae (IIIa)~(IIIb), Formulae (IIa)~(IIc), Formulae (IVa)~(IVd), Formulae (Va)~(Ve), Formulae (VIa)~(VIe), Formulae (VIIa)~(VIIe), Formulae (VIIIa)~(VIIIe), and pharmaceutically acceptable salts thereof, wherein $R^2$ and

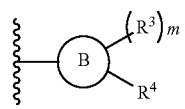

are delineated in Table 1.

TABLE 1
| Entry | R² | 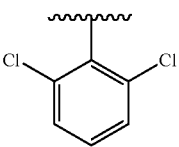 [SMILES: *c1c(Cl)cccc1Cl] |
|---|---|---|
| 1 | 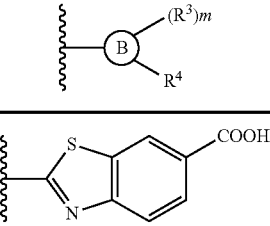 | 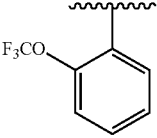 [SMILES: *c1ccccc1OC(F)(F)F] |
| 2 | 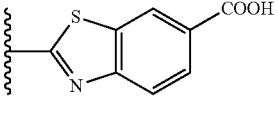 | 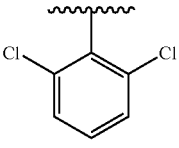 [SMILES: *c1c(Cl)cccc1Cl] |
| 3 | 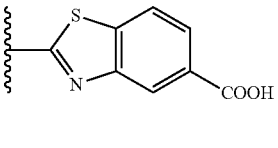 [SMILES: *c1nc2cc(C(=O)O)ccc2s1] | 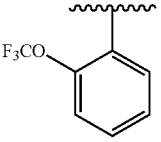 [SMILES: *c1ccccc1OC(F)(F)F] |
| 4 | 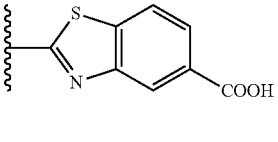 [SMILES: *c1nc2cc(C(=O)O)ccc2s1] | 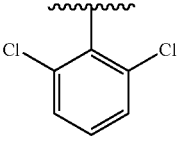 [SMILES: *c1c(Cl)cccc1Cl] |
| 5 | 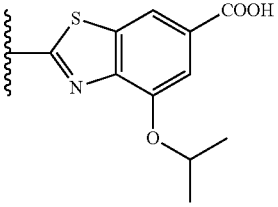 [SMILES: *c1nc2c(OC(C)C)cc(C(=O)O)cc2s1] | 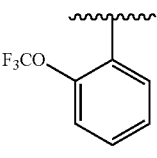 [SMILES: *c1ccccc1OC(F)(F)F] |
| 6 | 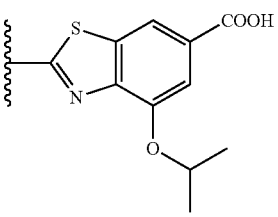 [SMILES: *c1nc2c(OC(C)C)cc(C(=O)O)cc2s1] | 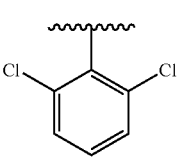 |
| 7 | 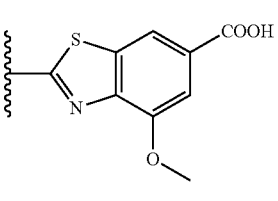 [SMILES: *c1nc2c(OC)cc(C(=O)O)cc2s1] | 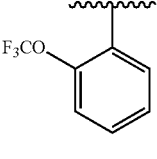 [SMILES: *c1ccccc1OC(F)(F)F] |
| 8 | 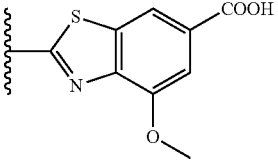 [SMILES: *c1nc2c(OC)cc(C(=O)O)cc2s1] | |

TABLE 1-continued

| Entry | R² | (structure with B, (R³)ₘ, R⁴) |
|---|---|---|
| 9 | 2,6-dichlorophenyl 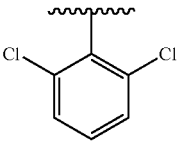 [SMILES: *c1c(Cl)cccc1Cl] | benzothiazole-6-COOH, 7-OCF₃ 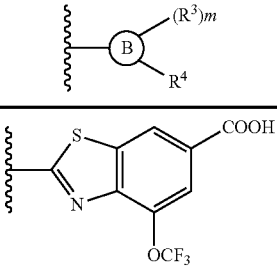 |
| 10 | 2-(trifluoromethoxy)phenyl 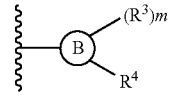 | benzothiazole-6-COOH, 7-OCF₃ 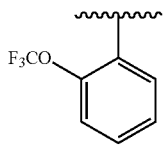 [SMILES: *c1ccccc1OC(F)(F)F] |
| 11 | 2,6-dichlorophenyl 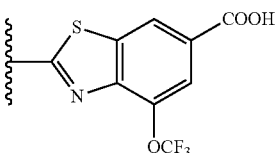 | benzothiazole-6-COOH, 7-cyclopropyl 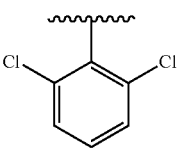 [SMILES: *c1c(Cl)cccc1Cl] |
| 12 | 2-(trifluoromethoxy)phenyl 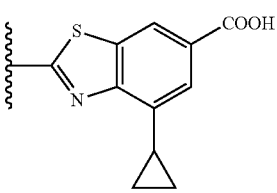 | benzothiazole-6-COOH, 7-cyclopropyl 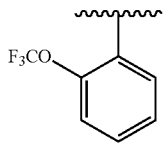 [SMILES: *c1ccccc1OC(F)(F)F] |
| 13 | 2,6-dichlorophenyl 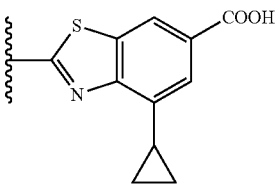 [SMILES: *c1nc2c(C3CC3)cc(C(=O)O)cc2s1] | benzothiazole-6-COOH, 7-F 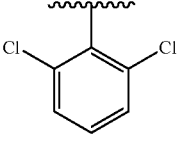 [SMILES: *c1c(Cl)cccc1Cl] |
| 14 | 2-(trifluoromethoxy)phenyl 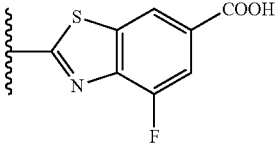 [SMILES: *c1nc2c(F)cc(C(=O)O)cc2s1] | benzothiazole-6-COOH, 7-F 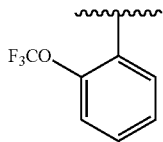 [SMILES: *c1ccccc1OC(F)(F)F] |
| 15 | 2,6-dichlorophenyl 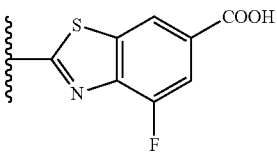 [SMILES: *c1nc2c(F)cc(C(=O)O)cc2s1] | benzothiazole-6-COOH, 7-OCHF₂ 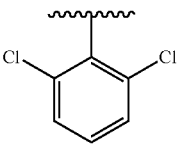 [SMILES: *c1c(Cl)cccc1Cl] |
| 16 | 2-(trifluoromethoxy)phenyl 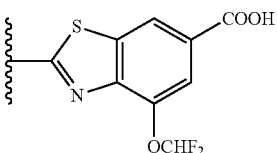 [SMILES: *c1nc2c(C)cc(C(=O)O)cc2s1] | benzothiazole-6-COOH, 7-OCHF₂ 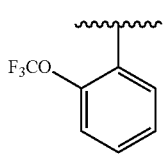 [SMILES: *c1ccccc1OC(F)(F)F] |
| 17 | 2,6-dichlorophenyl 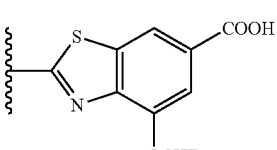 | benzothiazole-6-COOH, 7-OCH₂F 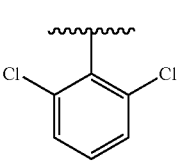 [SMILES: *c1c(Cl)cccc1Cl] |

TABLE 1-continued

| Entry | R² | ![B ring with (R³)m and R⁴] |
|---|---|---|
| 18 | 2-(trifluoromethoxy)phenyl | 7-(fluoromethoxy)-benzothiazole-6-carboxylic acid (OCH₂F at 7-position) |
| 19 | 2,6-dichlorophenyl | 7-isopropyl-benzothiazole-6-carboxylic acid |
| 20 | 2-(trifluoromethoxy)phenyl | 7-isopropyl-benzothiazole-6-carboxylic acid |
| 21 | 2,6-dichlorophenyl | 7-tert-butyl-benzothiazole-6-carboxylic acid |
| 22 | 2-(trifluoromethoxy)phenyl | 7-tert-butyl-benzothiazole-6-carboxylic acid |
| 23 | 2,6-dichlorophenyl | 7-cyclobutyl-benzothiazole-6-carboxylic acid |
| 24 | 2-(trifluoromethoxy)phenyl | 7-cyclobutyl-benzothiazole-6-carboxylic acid |

TABLE 1-continued

| Entry | R² | B(R³)ₘ / R⁴ structure |
|---|---|---|
| 25 | 2,6-dichlorophenyl | 2-substituted-7-(cyclopentyl)benzothiazole-6-carboxylic acid |
| 26 | 2-(trifluoromethoxy)phenyl | 2-substituted-7-(cyclopentyl)benzothiazole-6-carboxylic acid |
| 27 | 2,6-dichlorophenyl | 2-substituted-7-(tetrahydrofuran-3-yl)benzothiazole-6-carboxylic acid |
| 28 | 2-(trifluoromethoxy)phenyl | 2-substituted-7-(tetrahydrofuran-3-yl)benzothiazole-6-carboxylic acid |
| 29 | 2,6-dichlorophenyl | 2-substituted-7-(pyrrolidin-1-yl)benzothiazole-6-carboxylic acid |
| 30 | 2-(trifluoromethoxy)phenyl | 2-substituted-7-(pyrrolidin-1-yl)benzothiazole-6-carboxylic acid |
| 31 | 2,6-dichlorophenyl | 2-substituted-7-(trifluoromethyl)benzothiazole-6-carboxylic acid |

TABLE 1-continued

| Entry | R² | B ring with (R³)ₘ and R⁴ |
|---|---|---|
| 32 | 2-(trifluoromethoxy)phenyl | 2-benzothiazolyl-6-COOH, 7-CF₃ |
| 33 | 2,6-dichlorophenyl | 2-benzothiazolyl-6-COOH, 7-Me |
| 34 | 2-(trifluoromethoxy)phenyl | 2-benzothiazolyl-6-COOH, 7-Me |
| 35 | 2,6-dichlorophenyl | 2-benzothiazolyl-6-COOH, 7-F, 4-OCF₃ |
| 36 | 2-(trifluoromethoxy)phenyl | 2-benzothiazolyl-6-COOH, 7-F, 4-OCF₃ |
| 37 | 2,6-dichlorophenyl | 2-benzothiazolyl-6-COOH, 7-F, 4-cyclopropyl |
| 38 | 2-(trifluoromethoxy)phenyl | 2-benzothiazolyl-6-COOH, 7-F, 4-cyclopropyl |
| 39 | 2,6-dichlorophenyl | 2-benzothiazolyl-6-COOH, 5-Ph |

TABLE 1-continued

| Entry | R² | B ring with (R³)m and R⁴ |
|---|---|---|
| 40 | 2-(F₃CO)phenyl | 2-yl-6-phenyl-benzothiazole-5-COOH |
| 41 | 2,6-dichlorophenyl | 2-yl-6-OCF₃-benzothiazole-5-COOH |
| 42 | 2-(F₃CO)phenyl | 2-yl-6-OCF₃-benzothiazole-5-COOH |
| 43 | 2,6-dichlorophenyl | 2-yl-6-cyclopropyl-benzothiazole-5-COOH |
| 44 | 2-(F₃CO)phenyl | 2-yl-6-cyclopropyl-benzothiazole-5-COOH |
| 45 | 2,6-dichlorophenyl | 2-yl-naphtho[1,2-d]thiazole-COOH |
| 46 | 2-(F₃CO)phenyl | 2-yl-naphtho[1,2-d]thiazole-COOH |
| 47 | 2,6-dichlorophenyl | 2-yl-benzoxazole-6-COOH |
| 48 | 2-(F₃CO)phenyl | 2-yl-benzoxazole-6-COOH |

TABLE 1-continued

| Entry | R² | B ring with (R³)m and R⁴ |
|---|---|---|
| 49 | 2,6-dichlorophenyl | benzoxazole-6-COOH, 7-OCF₃ |
| 50 | 2-(trifluoromethoxy)phenyl | benzoxazole-6-COOH, 7-OCF₃ |
| 51 | 2,6-dichlorophenyl | benzoxazole-6-COOH, 7-F |
| 52 | 2-(trifluoromethoxy)phenyl | benzoxazole-6-COOH, 7-F |
| 53 | 2,6-dichlorophenyl | benzoxazole-6-COOH, 7-CF₃ |
| 54 | 2-(trifluoromethoxy)phenyl | benzoxazole-6-COOH, 7-CF₃ |
| 55 | 2,6-dichlorophenyl | benzoxazole-6-COOH, 7-cyclopropyl |
| 56 | 2-(trifluoromethoxy)phenyl | benzoxazole-6-COOH, 7-cyclopropyl |
| 57 | 2,6-dichlorophenyl | quinoline-7-COOH |

TABLE 1-continued
| Entry | R² | B with (R³)m and R⁴ |
|---|---|---|
| 58 | 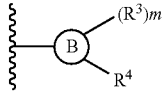 | 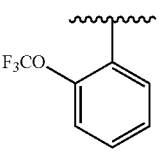 [SMILES: *c1ccccc1OC(F)(F)F] |
| 59 | 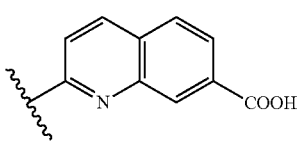 [SMILES: *c1ccc2ccc(C(=O)O)cc2n1] | 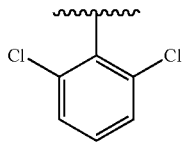 [SMILES: *c1c(Cl)cccc1Cl] |
| 60 | 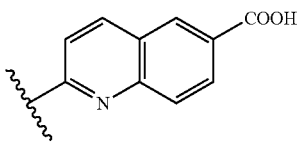 [SMILES: *c1ccc2cc(C(=O)O)ccc2n1] | 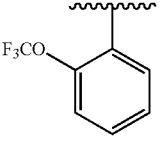 [SMILES: *c1ccccc1OC(F)(F)F] |
| 61 | 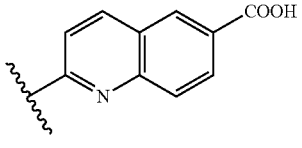 [SMILES: *c1ccc2cc(C(=O)O)ccc2n1] | 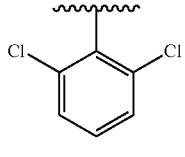 [SMILES: *c1c(Cl)cccc1Cl] |
| 62 | 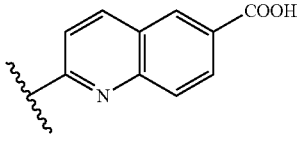 [SMILES: *c1ccc2cc(C(=O)O)ccc2n1] | 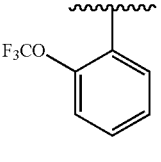 [SMILES: *c1ccccc1OC(F)(F)F] |
| 63 | 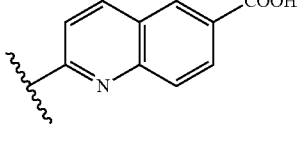 | 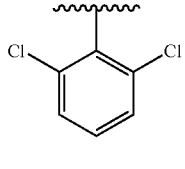 [SMILES: *c1c(Cl)cccc1Cl] |
| 64 | 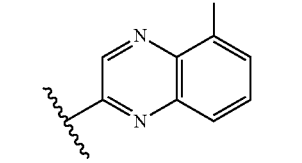 | 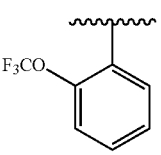 [SMILES: *c1ccccc1OC(F)(F)F] |
| 65 | 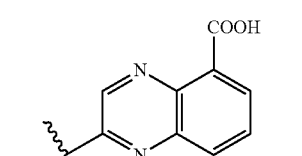 | 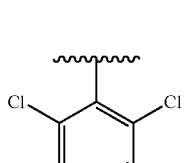 |
| 66 | 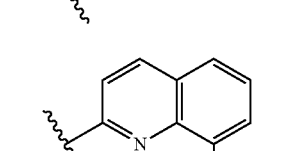 | 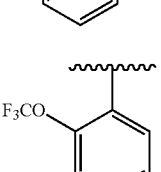 |

TABLE 1-continued

| Entry | R² | [B ring with (R³)m and R⁴] |
|---|---|---|
| 67 | 2,6-dichlorophenyl | 5-fluoro-quinoline-6-carboxylic acid (linked at 2-position) |
| 68 | 2-(trifluoromethoxy)phenyl | 5-fluoro-quinoline-6-carboxylic acid (linked at 2-position) |
| 69 | 2,6-dichlorophenyl | quinoxaline-5-carboxylic acid (linked at 3-position) |
| 70 | 2-(trifluoromethoxy)phenyl | quinoxaline-5-carboxylic acid (linked at 3-position) |
| 71 | 2,6-dichlorophenyl | quinoxaline-6-carboxylic acid (linked at 2-position) |
| 72 | 2-(trifluoromethoxy)phenyl | quinoxaline-6-carboxylic acid (linked at 2-position) |
| 73 | 2,6-dichlorophenyl | quinoxaline-6-carboxylic acid (linked at 3-position) |
| 74 | 2-(trifluoromethoxy)phenyl | quinoxaline-6-carboxylic acid (linked at 3-position) |
| 75 | 2,6-dichlorophenyl | 8-(trifluoromethoxy)quinoxaline-6-carboxylic acid (linked at 2-position) |

TABLE 1-continued

| Entry | R² | B ring with (R³)m and R⁴ |
|---|---|---|
| 76 | 2-(OCF₃)phenyl | 8-(OCF₃)quinoxaline-6-carboxylic acid |
| 77 | 2,6-dichlorophenyl | 3-MeO-quinoline-6-carboxylic acid |
| 78 | 2-(OCF₃)phenyl | 3-MeO-quinoline-6-carboxylic acid |
| 79 | 2,6-dichlorophenyl | 3-(OCF₃)quinoline-6-carboxylic acid |
| 80 | 2-(OCF₃)phenyl | 3-(OCF₃)quinoline-6-carboxylic acid |
| 81 | 2,6-dichlorophenyl | 3-MeO-quinoxaline-6-carboxylic acid |
| 82 | 2-(OCF₃)phenyl | 3-MeO-quinoxaline-6-carboxylic acid |
| 83 | 2,6-dichlorophenyl | 3-F-quinoline-6-carboxylic acid |
| 84 | 2-(OCF₃)phenyl | 3-F-quinoline-6-carboxylic acid |

TABLE 1-continued
| Entry | R² | 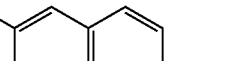 |
|---|---|---|
| 85 | 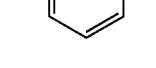 | 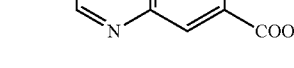 |
| 86 | 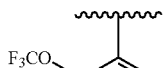 | 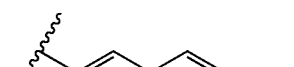 |
| 87 | 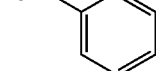 | 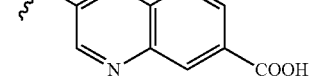 |
| 88 |  |  |
| 89 | 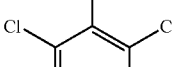 | 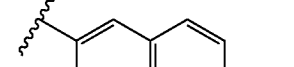 |
| 90 | 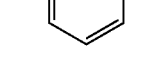 | 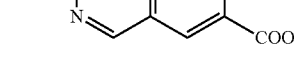 |
| 91 | 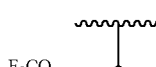 | 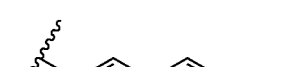 |
| 92 | 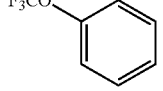 | 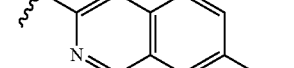 |
| 93 |  | 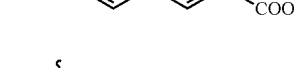 |

TABLE 1-continued
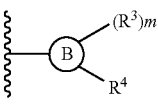

TABLE 1-continued
| Entry | R² | B ring with (R³)m and R⁴ |
|---|---|---|
| 104 | 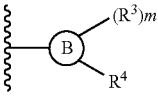 | 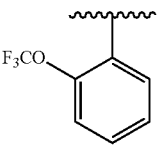 [SMILES: *c1ccccc1OC(F)(F)F] |
| 105 | 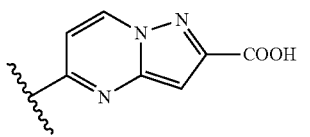 [SMILES: *c1ccn2nc(C(=O)O)cc2n1] | 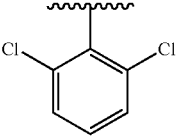 [SMILES: *c1c(Cl)cccc1Cl] |
| 106 | 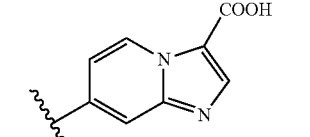 | 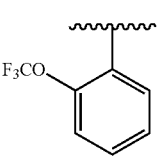 [SMILES: *c1ccccc1OC(F)(F)F] |
| 107 | 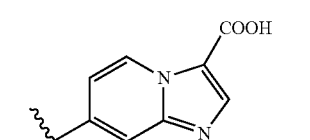 | 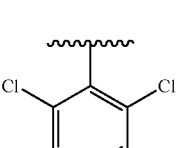 |
| 108 | 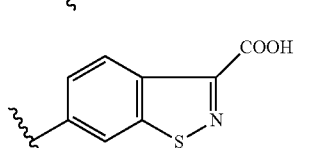 | 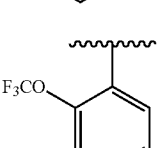 |
| 109 | 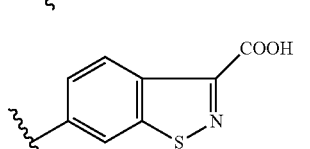 | 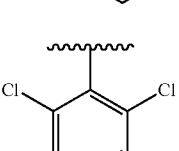 |
| 110 | 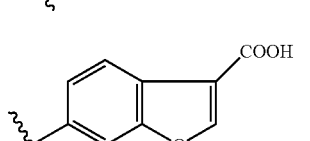 | 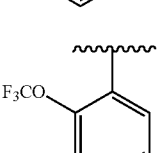 |
| 111 | 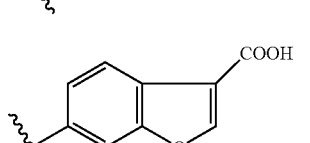 | 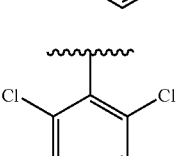 |
| 112 | 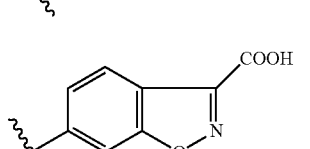 | 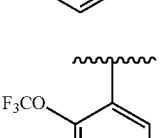 |

TABLE 1-continued

| Entry | R² | ![B ring with (R³)m and R⁴] |
|---|---|---|
| 113 | 2,6-dichlorophenyl | 4-COOH-phenyl |
| 114 | 2-(trifluoromethoxy)phenyl | 4-COOH-phenyl |
| 115 | 2,6-dichlorophenyl | 3-fluoro-4-COOH-phenyl |
| 116 | 2-(trifluoromethoxy)phenyl | 3-fluoro-4-COOH-phenyl |
| 117 | 2,6-dichlorophenyl | 6-COOH-pyridin-3-yl |
| 118 | 2-(trifluoromethoxy)phenyl | 6-COOH-pyridin-3-yl |
| 119 | 2,6-dichlorophenyl | 5-fluoro-6-COOH-pyridin-3-yl |
| 120 | 2-(trifluoromethoxy)phenyl | 5-fluoro-6-COOH-pyridin-3-yl |
| 121 | 2,6-dichlorophenyl | 3-cyano-4-COOH-phenyl |
| 122 | 2-(trifluoromethoxy)phenyl | 3-cyano-4-COOH-phenyl |

TABLE 1-continued

| Entry | R² | B group with (R³)m and R⁴ |
|---|---|---|
| 123 | 2,6-dichlorophenyl | pyrimidin-2-yl-5-COOH |
| 124 | 2-(trifluoromethoxy)phenyl | pyrimidin-2-yl-5-COOH |
| 125 | 2,6-dichlorophenyl | pyrimidin-2-yl-4-COOH |
| 126 | 2-(trifluoromethoxy)phenyl | pyrimidin-2-yl-4-COOH |
| 127 | 2,6-dichlorophenyl | pyrazin-2-yl-5-COOH |
| 128 | 2-(trifluoromethoxy)phenyl | pyrazin-2-yl-5-COOH |
| 129 | 2,6-dichlorophenyl | 1,2,4-oxadiazol-3-yl-5-COOH |
| 130 | 2-(trifluoromethoxy)phenyl | 1,2,4-oxadiazol-3-yl-5-COOH |
| 131 | 2,6-dichlorophenyl | thiazol-2-yl-5-COOH |

TABLE 1-continued

| Entry | R² | B with (R³)m and R⁴ |
|---|---|---|
| 132 | 2-(trifluoromethoxy)phenyl | 2-thiazolyl-5-COOH |
| 133 | 2,6-dichlorophenyl | pyridazine-3-COOH (6-linked) |
| 134 | 2-(trifluoromethoxy)phenyl | pyridazine-3-COOH (6-linked) |
| 135 | 2,6-dichlorophenyl | 1,2,3,4-tetrahydroquinoline-6-COOH (2-linked) |
| 136 | 2-(trifluoromethoxy)phenyl | 1,2,3,4-tetrahydroquinoline-6-COOH (2-linked) |
| 137 | 2,6-dichlorophenyl | chroman-6-COOH (2-linked) |
| 138 | 2-(trifluoromethoxy)phenyl | chroman-6-COOH (2-linked) |
| 139 | 2,6-dichlorophenyl | 1,2,3,4-tetrahydronaphthalene-2,6-dicarboxy (6-linked, 2-COOH) |
| 140 | 2-(trifluoromethoxy)phenyl | 1,2,3,4-tetrahydronaphthalene-2,6-dicarboxy (6-linked, 2-COOH) |
| 141 | 2,6-dichlorophenyl | 3-fluoro-pyridine with -CH2CH2COOH |

TABLE 1-continued
| Entry | R² | 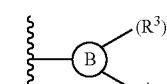 |
|---|---|---|
| 142 | 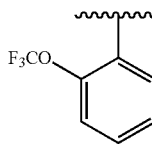 | 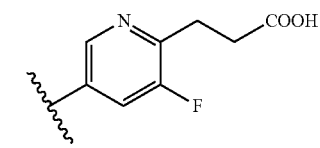 [SMILES: *c1cnc(CCC(=O)O)c(F)c1] |
| 143 | 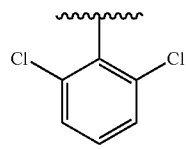 [SMILES: *c1c(Cl)cccc1Cl] | 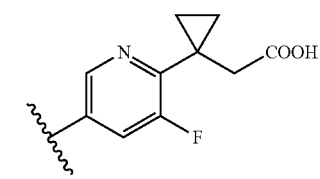 [SMILES: *c1cnc(C2(CC(=O)O)CC2)c(F)c1] |
| 144 | 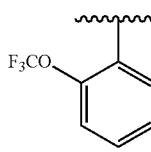 | 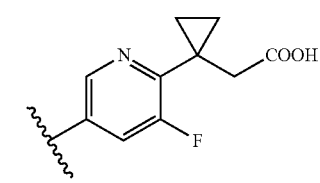 [SMILES: *c1cnc(C2(CC(=O)O)CC2)c(F)c1] |
| 145 | 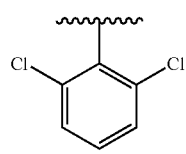 [SMILES: *c1c(Cl)cccc1Cl] | 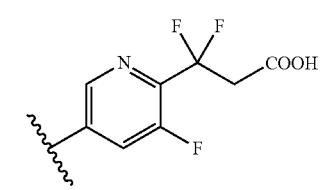 [SMILES: *c1cnc(C(F)(F)CC(=O)O)c(F)c1] |
| 146 | 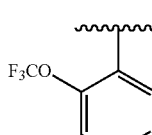 | 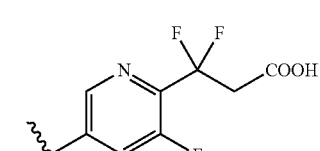 |
| 147 | 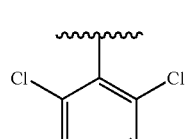 | 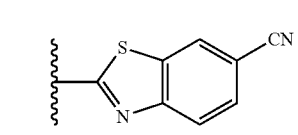 [SMILES: *c1nc2ccc(C#N)cc2s1] |
| 148 | 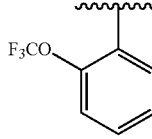 | 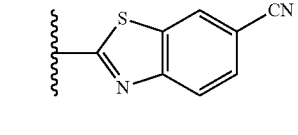 |
| 149 | 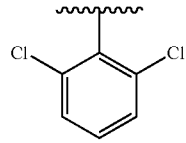 [SMILES: *c1c(Cl)cccc1Cl] | 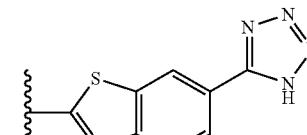 |

TABLE 1-continued

| Entry | R² | B with (R³)m and R⁴ |
|---|---|---|
| 150 | 2-(OCF₃)phenyl | 6-(1H-tetrazol-5-yl)benzothiazol-2-yl |
| 151 | 2,6-dichlorophenyl | 6-cyano-4-(OiPr)benzothiazol-2-yl |
| 152 | 2-(OCF₃)phenyl | 6-cyano-4-(OiPr)benzothiazol-2-yl |
| 153 | 2,6-dichlorophenyl | 6-(hydroxymethyl)-4-(OiPr)benzothiazol-2-yl |
| 154 | 2-(OCF₃)phenyl | 6-(hydroxymethyl)-4-(OiPr)benzothiazol-2-yl |
| 155 | 2,6-dichlorophenyl | 6-(SO₂NH₂)-4-(OiPr)benzothiazol-2-yl |
| 156 | 2-(OCF₃)phenyl | 6-(SO₂NH₂)-4-(OiPr)benzothiazol-2-yl |
| 157 | 2,6-dichlorophenyl | 6-(SO₂NH₂)quinoxalin-2-yl |
| 158 | 2-(OCF₃)phenyl | 6-(SO₂NH₂)quinoxalin-2-yl |

TABLE 1-continued

| Entry | R² | ![B ring with (R³)m and R⁴] |
|---|---|---|
| 159 | 2,6-dichlorophenyl | 6-(pyrrolidin-1-ylsulfonyl)-4-(isopropoxy)benzothiazol-2-yl |
| 160 | 2-(trifluoromethoxy)phenyl | 6-(pyrrolidin-1-ylsulfonyl)-4-(isopropoxy)benzothiazol-2-yl |
| 161 | 2,6-dichlorophenyl | 6-(cyclopentylsulfonyl)-4-(isopropoxy)benzothiazol-2-yl |
| 162 | 2-(trifluoromethoxy)phenyl | 6-(cyclopentylsulfonyl)-4-(isopropoxy)benzothiazol-2-yl |
| 163 | 2,6-dichlorophenyl | 6-(((1H-tetrazol-5-yl)thio)methyl)-4-(isopropoxy)benzothiazol-2-yl |
| 164 | 2-(trifluoromethoxy)phenyl | 6-(((1H-tetrazol-5-yl)thio)methyl)-4-(isopropoxy)benzothiazol-2-yl |
| 165 | 2,6-dichlorophenyl | 6-(carboxymethyl)-4-(isopropoxy)benzothiazol-2-yl |

TABLE 1-continued

| Entry | R² | ![B ring with (R³)m and R⁴] |
|---|---|---|
| 166 | 2-(trifluoromethoxy)phenyl | 2-[4-isopropoxy-benzothiazol-6-yl]acetic acid |
| 167 | 2,6-dichlorophenyl | 1-[4-isopropoxy-benzothiazol-6-yl]cyclopropane-1-carboxylic acid |
| 168 | 2-(trifluoromethoxy)phenyl | 1-[4-isopropoxy-benzothiazol-6-yl]cyclopropane-1-carboxylic acid |
| 169 | 2,6-dichlorophenyl | 2,2-difluoro-2-[4-isopropoxy-benzothiazol-6-yl]acetic acid |
| 170 | 2-(trifluoromethoxy)phenyl | 2,2-difluoro-2-[4-isopropoxy-benzothiazol-6-yl]acetic acid |
| 171 | 2,6-dichlorophenyl | N-(5-fluoropyridine-2-carbonyl)glycine |

TABLE 1-continued

| Entry | R² | (structure with B ring, (R³)m, R⁴) |
|---|---|---|
| 172 | 2-(F₃CO)phenyl | 5-fluoro-6-pyridyl-C(O)NH-CH₂-COOH |
| 173 | 2,6-dichlorophenyl | 5-fluoro-6-pyridyl-C(O)NH-CH₂CH₂-SO₃H |
| 174 | 2-(F₃CO)phenyl | 5-fluoro-6-pyridyl-C(O)NH-CH₂CH₂-SO₃H |
| 175 | 2,6-dichlorophenyl | 4-OiPr-benzothiazol-2,6-diyl-C(O)NH-CH₂-COOH |
| 176 | 2-(F₃CO)phenyl | 4-OiPr-benzothiazol-2,6-diyl-C(O)NH-CH₂-COOH |
| 177 | 2,6-dichlorophenyl | 4-OiPr-benzothiazol-2,6-diyl-C(O)NH-CH₂CH₂-SO₃H |
| 178 | 2-(F₃CO)phenyl | 4-OiPr-benzothiazol-2,6-diyl-C(O)NH-CH₂CH₂-SO₃H |
| 179 | 2,6-dichlorophenyl | 4-OiPr-benzothiazol-2,6-diyl-C(CH₃)₂OH |

TABLE 1-continued

| Entry | R² | ![B ring with (R³)m and R⁴] |
|---|---|---|
| 180 | 2-(trifluoromethoxy)phenyl | 4-(OiPr)-6-(2-hydroxypropan-2-yl)benzo[d]thiazol-2-yl |
| 181 | 2,6-dichlorophenyl | 4-(OiPr)-6-(hydroxymethyl)benzo[d]thiazol-2-yl |
| 182 | 2-(trifluoromethoxy)phenyl | 4-(OiPr)-6-(hydroxymethyl)benzo[d]thiazol-2-yl |
| 183 | 2,6-dichlorophenyl | 5-phenylpyrimidin-2-yl |
| 184 | 2-(trifluoromethoxy)phenyl | 5-phenylpyrimidin-2-yl |
| 185 | 2,6-dichlorophenyl | 4-phenylpyrimidin-2-yl |
| 186 | 2-(trifluoromethoxy)phenyl | 4-phenylpyrimidin-2-yl |
| 187 | 2,6-dichlorophenyl | phenethyl |
| 188 | 2-(trifluoromethoxy)phenyl | phenethyl |

TABLE 1-continued
| Entry | R² | (structure with B, (R³)m, R⁴) |
|---|---|---|
| 189 | 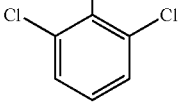 | 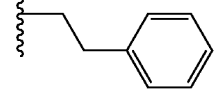 |
| 190 | 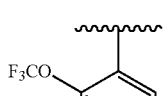 | 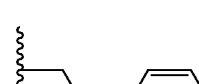 |
| 191 | 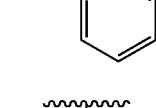 | 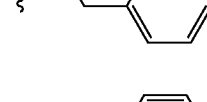 |
| 192 | 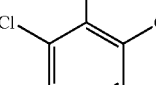 | 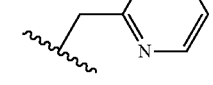 |
| 193 | 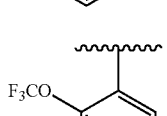 | 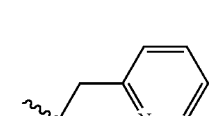 |
| 194 | 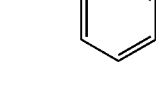 | 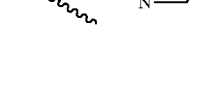 |
| 195 | 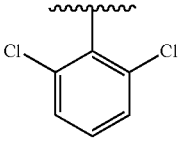 [SMILES: *c1c(Cl)cccc1Cl] | 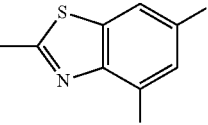 |
| 196 |  | 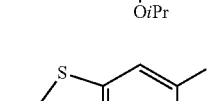 |
| 197 | 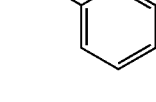 | 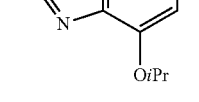 |

TABLE 1-continued

| Entry | R² | (structure with B, (R³)m, R⁴) |
|---|---|---|
| 198 | 2-(trifluoromethoxy)phenyl | quinazoline-6-carboxylic acid (CO₂H) |
| 199 | 2,6-dichlorophenyl | quinazoline-8-carboxylic acid (COOH) |
| 200 | 2-(trifluoromethoxy)phenyl | quinazoline-8-carboxylic acid (COOH) |
| 201 | 2,6-dichlorophenyl | 4-cyclopropyl-benzothiazole-6-carbonitrile (CN) |
| 202 | 2-(trifluoromethoxy)phenyl | 4-cyclopropyl-benzothiazole-6-carbonitrile (CN) |
| 203 | 2,6-dichlorophenyl | 4-cyclopropyl-6-(1H-tetrazol-5-yl)benzothiazole |
| 204 | 2-(trifluoromethoxy)phenyl | 4-cyclopropyl-6-(1H-tetrazol-5-yl)benzothiazole |

TABLE 1-continued

| Entry | R² | B ring with (R³)m and R⁴ |
|---|---|---|
| 205 | 2,6-dichlorophenyl | quinoxaline-5-CN (attached at 2-position) |
| 206 | 2-(trifluoromethoxy)phenyl | quinoxaline-5-CN (attached at 2-position) |
| 207 | 2,6-dichlorophenyl | 5-(1H-tetrazol-5-yl)quinoxalin-2-yl |
| 208 | 2-(trifluoromethoxy)phenyl | 5-(1H-tetrazol-5-yl)quinoxalin-2-yl |
| 209 | 2,6-dichlorophenyl | 4-(isopropoxy)-6-(1H-tetrazol-5-yl)benzo[d]thiazol-2-yl |
| 210 | 2-(trifluoromethoxy)phenyl | 4-(isopropoxy)-6-(1H-tetrazol-5-yl)benzo[d]thiazol-2-yl |

In certain embodiments, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesterolemia, or hyperlipidemia chronic liver disease, gastrointestinal disease, fibrotic diseases such as primary biliary cirrhosis, primary sclerosing cholangitis, pulmonary fibrosis, renal fibrosis, liver fibrosis, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the compound is a selective FXR agonist over TGR5 activator.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl, benzoisothiazolyl, benzothiazolyl, benzofuranyl, benzooxazole, benzothiophenyl, indazolyl, benzoisoxazolyl, pyrazolopyrimidinyl, imidazopyridinyl. A polycyclic heteroaryl is a polycyclic ring system that comprises at least one aromatic ring, and the said aromatic ring can have one or more ring atom selected from S, O and N, or can have none ring atom selected from S, O and N. A polycyclic heteroaryl can comprise fused rings, covalently attached rings or a combination thereof.

The term "alkylaryl" refers to a $C_1$-$C_4$ alkyl group as defined wherein one of the hydrogens is replaced by an aryl substituent as defined herein which replacement can be at any site on the alkyl chain. Examples of alkylaryl include, but not limited to, benzyl, ethylphenyl, propylphenyl, butylphenyl, 1-methylbenzyl, 1,1-dimethyl benzyl, 1-methylcyclopropyl benzyl, 1,1-difluoroethyl benzyl.

The term "alkylheteroaryl" refers to a $C_1$-$C_4$ alkyl group as defined wherein one of the hydrogens is replaced by an heteroaryl substituent as defined herein which replacement can be at any site on the alkyl chain. Examples of $C_1$-$C_4$ alkylaryl include, but not limited to, pyridinylmethyl, 1,1-dimethyl pyridinyl, 1-methylcyclopropyl pyridinyl, 1,1-difluoroethyl pyridinyl.

In accordance with the invention, aromatic groups can be substituted or unsubstituted.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "carbocyclic" refers to a cyclic group in which all of the ring atoms are carbon. A carbocyclic can be saturated, partially unsaturated or aromatic, and can have 3 to 12 ring atoms, preferably 3 to 6 ring atoms.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

It is understood that any alkyl, alkenyl, alkynyl, cycloalkyl, heterocyclic and cycloalkenyl moiety described herein can also be an aliphatic group or an alicyclic group.

The term "substituted" as used herein, refers to independent replacement of one, two, three or more of the hydrogen atoms thereon with substituents including, but not limited to, deuterium, tritium, —F, —Cl, —Br, —I, —OH, $C_1$-$C_{12}$-alkyl; $C_2$-$C_{12}$-alkenyl, $C_2$-$C_{12}$-alkynyl, protected hydroxy, —NO$_2$, —CN, —NH$_2$, —N$_3$, protected amino, alkoxy, thioalkoxy, oxo, thioxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_2$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_2$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_2$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_2$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, NHC(S)NH$_2$, —NHC(S)NH— C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_2$-cycloalkyl, —S-aryl, —S-heteroaryl, —S-heterocycloalkyl, methylthiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy, —CN; —OH; NH$_2$; C$_1$-C$_4$-alkylamino; di(C$_1$-C$_4$-alkyl)amino; and NO$_2$. It is understood that the aryls, heteroaryls, alkyls, and the like can be further substituted. In some cases, each substituent in a substituted moiety is additionally optionally substituted when possible with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$. Preferably, a substituted alkyl group, such as a substituted methyl group, is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein may contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of Pharmaceutical Sciences, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
Alloc for allyloxycarbonyl;
Bn for benzyl;
Boc for tert-butoxycarbonyl;
Cbz for benzyloxycarbonyl;
Cbz for benzyloxycarbonyl;
Boc for tert-butyloxycarbonyl;
BOM for Benzyloxymethyl;
BOP-Cl for bis(2-oxo-3-oxazolidinyl)phosphinic chloride;
CDI for carbonyldiimidazole;
DBU for 1,8-diazabicycloundec-7-ene;
DCC for N,N'-dicyclohexylcarbodiimide;
DCM for dichloromethane;
DMAP for N,N-dimethylaminopyridine;
DMF for N,N-dimethyl formamide;
DMP for Dess-Martin periodinane;
DPPA for diphenylphosphoryl azide;
EDC for 1-(3-diethylaminopropyl)-3-ethylcarbodiimide hydrochloride;
Et₃N for triethylamine;
EtOAc for ethyl acetate;
HATU for 1-[bis(dimethylamino)methylene]-1H-1,2,3-triazolo[4,5-b]pyridinium 3-oxid hexafluorophosphate;
HCl for hydrochloric acid;
Hunig's base for N,N-Diisopropylethylamine;
LAH for lithium aluminum hydride;
LHMDS for Lithium bis(trimethylsilyl)amide;
Ms for methanesulfonyl;
MTBE for methyl tert-butyl ether;
MeOH for methanol;
NaHMDS for sodium bis(trimethylsilyl)amide;
OTf for trifluoromethanesulfonate or triflate;
PG for protecting group;
PMB for 4-methoxybenzyl;
PTSA for p-toluene sulfonic acid;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
TBAB for Tetrabutylammonium bromide;
TBAI for Tetrabutylammonium iodide;
TBS for tert-butyl dimethyl silyl;
TBDPS for tert-butyl diphenyl silyl;
TEA for triethyl amine;
TIPS for triisopropyl silyl;
TFFH for tetramethylfluoroformamidinium hexafluorophosphate;
THF for tetrahydrofuran;
Ts for 4-Toluenesulfonyl.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

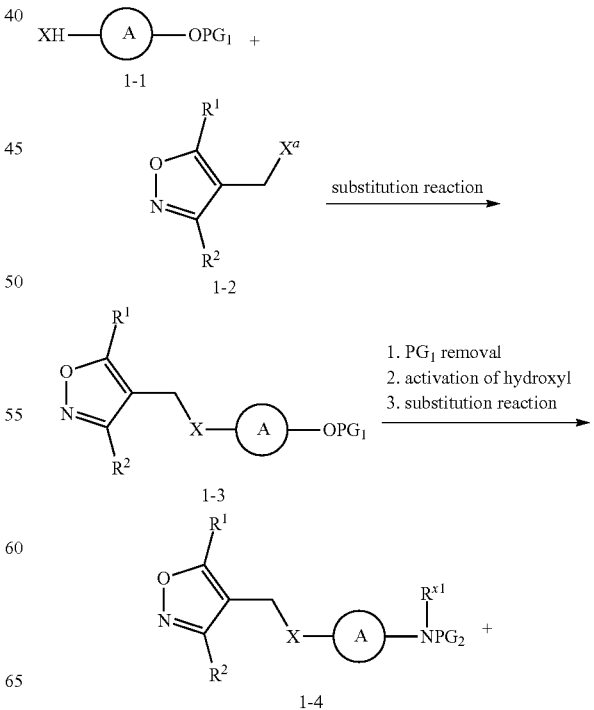

Scheme 1

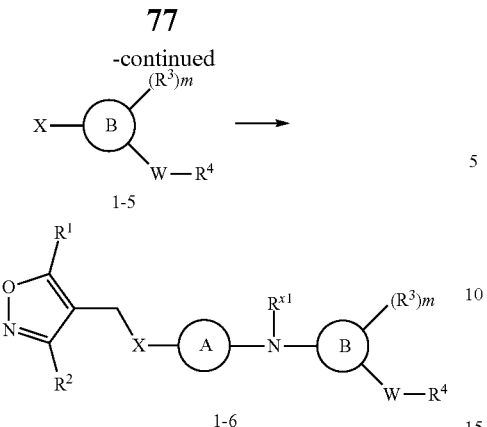

Wherein $R^1$, $R^2$, X, A, $R^{x1}$, $R^3$, m, B, and $R^4$ are as previously defined. As shown in Scheme 1, isoxazole compounds of Formula (1-6) can be prepared from the substitution reaction between compounds of Formula (1-1) and isoxazole compounds of Formula (1-2), wherein $PG_1$ is the protecting group of the hydroxyl group such as, but not limited to, TBS, TBDPS, TIPS, Boc, Cbz, Bn, allyl, BOM, PMB, Alloc, etc and $X^a$ is Br, I, Cl, OMs, OTs, —OS(O)$_2$CF$_2$CF$_2$CF$_3$ or OTf. This substitution reaction may take place in the presence of a base such as, but not limited to, sodium tert-butoxide, potassium tert-butoxide, sodium hydride, NaHMDS or LiHMDS, while a phase transfer reagents such as TBAI, TBAB, 18-crown-6, or 16-crown-5 may be added to the reaction. The compounds of Formula (1-3) can be deprotected to give the hydroxyl intermediate, and this hydroxyl group can be activated into a suitable leaving group such as, but not limited to, Br, I, Cl, OMs, OTs, OS(O)$_2$CF$_2$CF$_2$CF$_3$ or OTf. To produce a compound of formula (1-4), this activated hydroxyl group is displaced by a suitable amine source such as a protected amine or azide followed by suitable standard transformation such as azide reduction or amine protection if applicable. $PG_2$ is either hydrogen or an amino protecting group such as, but not limited to, Boc, Cbz, Bn, Alloc, etc. The coupling of a compound of Formula (1-4) with a compound of Formula (1-5) provides a compound of Formation (1-6). This coupling reaction can be achieved by copper-catalyzed Ullmann-type reactions or Buchwald-Hartwig amination. For selected reviews on copper-catalyzed Ullman-type reactions, see: Ma, D. et al., *Acc. Chem. Res.* 2008, 41, 1450; Evano, G. et al., *Chem. Rev.* 2008, 108, 3054; Monnier, F. et al., *Angew. Chem., Int. Ed.* 2009, 48, 6954; Ma, D. et al., *Angew. Chem. Int. Ed.* 2017, 56, 16136. More detail about Buchwald-Hartwig amination can be found in the literature. (Buchwald, S. L. et al., *Topics in Curr. Chem.,* 2002, 219, 131; Lundgren, R. J. et al., *Aldrichimica Acta,* 2012, 45, 59; Senra, J. D. et al., *Current Organic Synthesis,* 2011, 81, 53; Buchwald S. L. et al., *Chem. Sci.,* 2011, 2, 27).

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 1

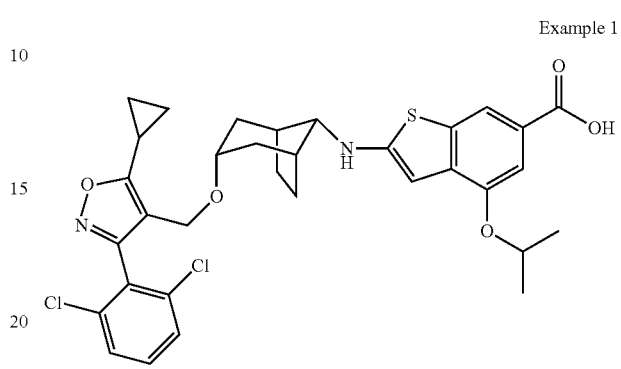

Example 1

Step 1a:

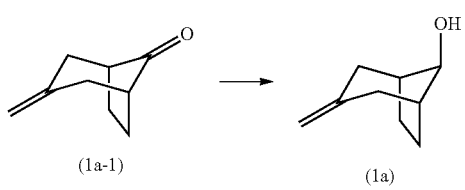

To (1R,5S)-3-methylenebicyclo[3.2.1]octan-8-one (1a-1) (3.3 g, 24.23 mmol) in THF (100 ml) was added LAH (1.0 M in THF) (24.23 ml, 24.23 mmol) at −78° C. over 10 min. The mixture was stirred at this temperature for 30 min, then quenched at 0° C. by the addition of 1 mL water followed by 1 mL 2N NaOH and 1 ml of water. The mixture was filtered through celite to give (1R,5S,8r)-3-methylenebicyclo[3.2.1] octan-8-ol, compound (1a) (3.1 g) as a colorless solid. $^1$H NMR (400 MHz, Chloroform-d) δ 4.75 (t, J=2.2 Hz, 2H), 4.08 (t, J=5.0 Hz, 1H), 2.70 (dd, J=14.3, 2.6 Hz, 2H), 2.14-2.07 (m, 2H), 2.02-1.86 (m, 2H), 1.76-1.61 (m, 2H), 1.52-1.37 (m, 2H).

Step 1b:

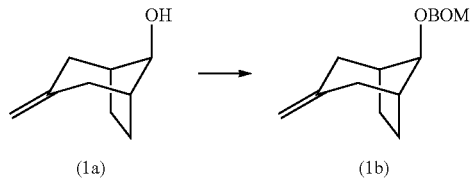

To (1R,5S,8r)-3-methylenebicyclo[3.2.1]octan-8-ol (1a) (3 g, 21.71 mmol) in THF (100 ml) was added DIPEA (4.93 ml, 28.2 mmol), ((chloromethoxy)methyl)benzene (4.91 g, 28.2 mmol) and TBAI (0.802 g, 2.171 mmol) and the resulting mixture was stirred at 60° C. for 16 h. The mixture was cooled down to rt, concentrated under vacuo, diluted with EtOAc, and then washed with 1N HCl, sat. NaHCO$_3$ solution, and brine. The organic layer was dried (Na$_2$SO$_4$) and concentrated. The residue was dissolved in EtOAc/hexane (50/50) and filtered through a silica gel plug, and the filtrate was concentrated to give (1R,5S,8r)-8-((benzyloxy)methoxy)-3-methylenebicyclo[3.2.1]octane (1b) (6.0 g).

Step 1c:

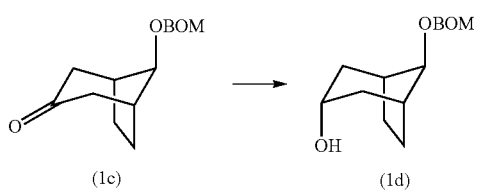

(1b) → (1c)

To (1R,5S,8r)-8-((benzyloxy)methoxy)-3-methylenebicyclo[3.2.1]octane (1b) (330 mg, 1.277 mmol) in Dioxane (3 ml) and Water (1.000 ml) was added osmium tetroxide (2.5% in tBuOH) (0.321 ml, 0.026 mmol), 2,6-lutidine (137 mg, 1.277 mmol), sodium periodate (1093 mg, 5.11 mmol) and the resulting mixture was stirred at RT for 16 h. The mixture was diluted with EtOAc, washed with water, brine, dried, filtered and concentrated to give (1R,5S,8r)-8-((benzyloxy)methoxy)bicyclo[3.2.1]octan-3-one (1c) (217 mg, 0.834 mmol, 65.3% yield) as an oil. $^1$H NMR (400 MHz, Chloroform-d) δ 7.45-7.30 (m, 5H), 4.95 (s, 2H), 4.70 (s, 2H), 4.10 (t, J=4.9 Hz, 1H), 2.99-2.76 (m, 2H), 2.48 (dh, J=5.6, 3.0 Hz, 2H), 2.19 (dtd, J=15.4, 2.2, 1.1 Hz, 2H), 1.93-1.75 (m, 2H), 1.65-1.44 (m, 2H).

Step 1d:

(1c) → (1d)

To (1R,5S,8r)-8-((benzyloxy)methoxy)bicyclo[3.2.1]octan-3-one (1c) (655 mg, 2.52 mmol) in THF (20 ml) at −78° C. was added L-selectride (1 M in THF) (3.8 ml, 3.77 mmol) and the mixture was stirred at −78° C. for 2 h, then warmed up to 0° C. The mixture was quenched with water, concentrated to remove THF, and extracted with EtOAc. The organic layer was separated, washed with water, brine, dried, filtered and concentrated. The residue was purified by CombiFalsh eluting with 0-40% EtOAc/hexane to give a (1R,3r,5S,8r)-8-((benzyloxy)methoxy)bicyclo[3.2.1]octan-3-ol (1d) (360 mg) as colorless oil. $^1$H NMR (400 MHz, Chloroform-d) δ 7.46-7.30 (m, 5H), 4.85 (s, 2H), 4.66 (s, 2H), 4.10 (t, J=5.2 Hz, 1H), 3.89 (t, J=5.0 Hz, 1H), 2.25 (dt, J=14.9, 4.3 Hz, 2H), 2.14 (b, 2H), 2.04-1.94 (m, 2H), 1.75-1.67 (m, 2H), 1.59 (b, 1H), 1.55 (b, 1H).

Step 1e:

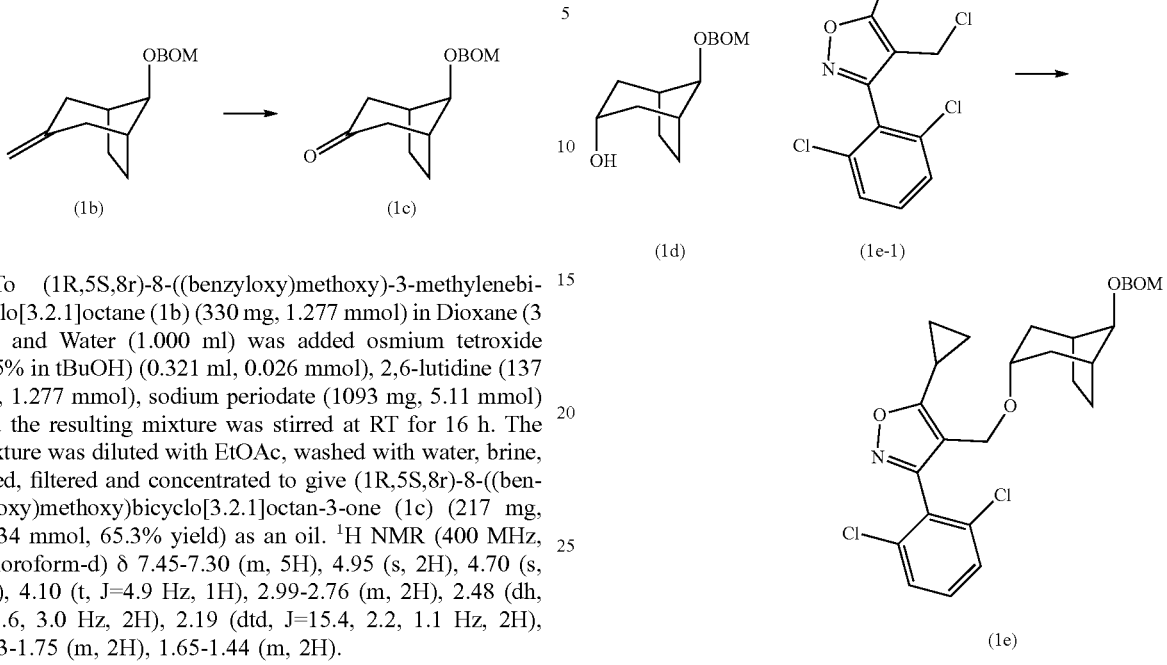

To (1R,3r,5S,8r)-8-((benzyloxy)methoxy)bicyclo[3.2.1]octan-3-ol (122 mg, 0.465 mmol) in THF (2 ml) was added 4-(chloromethyl)-5-cyclopropyl-3-(2,6-dichlorophenyl)isoxazole (211 mg, 0.698 mmol), 18-crown-6 (123 mg, 0.465 mmol) and potassium tert-butoxide (78 mg, 0.698 mmol) the mixture was stirred at RT for 16 h. TLC showed not much product. The mixture was heated up to 60° C. and stirred for 3 h. MS not showing too much product. TBAI (17.18 mg, 0.047 mmol) was added and stirred at 60° C. for 4 h. The mixture was diluted with EtOAc, washed with water, brine, dried, filtered and concentrated. The residue was purified by CombiFlash on silica gel eluting with 0-30% EtOAc/hexane to give 4-((((1R,3r,5S,8r)-8-((benzyloxy)methoxy)-bicyclo[3.2.1]octan-3-yl)oxy)methyl)-5-cyclopropyl-3-(2,6-dichlorophenyl)isoxazole (1e) (110 mg, 45%). LC/MS observed [M+H], 528.17; $^1$H NMR (400 MHz, Chloroform-d) δ 7.51-7.23 (m, 8H), 4.82 (s, 2H), 4.64 (s, 2H), 4.24 (s, 2H), 3.81 (t, J=4.7 Hz, 1H), 3.48 (t, J=5.1 Hz, 1H), 2.19 (tt, J=8.4, 5.1 Hz, 1H), 2.08-1.91 (m, 4H), 1.71-1.61 (m, 2H), 1.61-1.42 (m, 4H), 1.31-1.22 (m, 2H), 1.22-0.98 (m, 2H).

Step 1f:

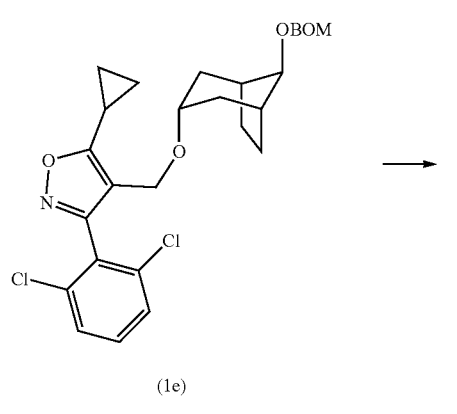

(1e)

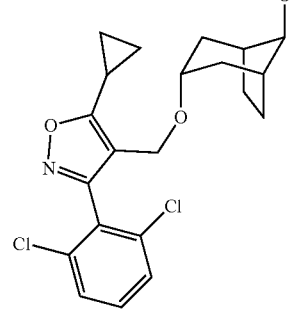

(1f)

To 4-((((1R,3r,5S,8r)-8-((benzyloxy)methoxy)bicyclo[3.2.1]octan-3-yl)oxy)methyl)-5-cyclopropyl-3-(2,6-dichlorophenyl)isoxazole (1e) (110 mg, 0.208 mmol) in DCM (4 ml) was added borontrichloride (1 M in DCM) (0.312 ml, 0.312 mmol) at −78° C. and the mixture was stirred for 1 h, then slowly warmed up to 0° C. The mixture was quenched with HCl (1N) and extracted with EtOAc. The organic layer was separated, washed with water, brine, dried, filtered and concentrated. The residue was purified by CombiFlash eluting with 0-40% acetone/hexane to give (1R,3r,5S,8r)-3-((5-cyclopropyl-3-(2,6-dichlorophenyl)isoxazol-4-yl)methoxy)bicyclo[3.2.1]octan-8-ol (1f) (56 mg, 66%). LC/MS observed [M+H], 408.12; $^1$H NMR (400 MHz, Chloroform-d) δ 7.49-7.31 (m, 3H), 4.23 (s, 2H), 3.94 (t, J=5.0 Hz, 1H), 3.46 (t, J=5.3 Hz, 1H), 2.24-2.15 (m, 1H), 1.99 (ddd, J=14.9, 5.2, 2.9 Hz, 2H), 1.86 (q, J=4.1 Hz, 2H), 1.72-1.59 (m, 2H), 1.59-1.44 (m, 4H), 1.36-1.22 (m, 2H), 1.22-1.05 (m, 2H).

Step 1g:

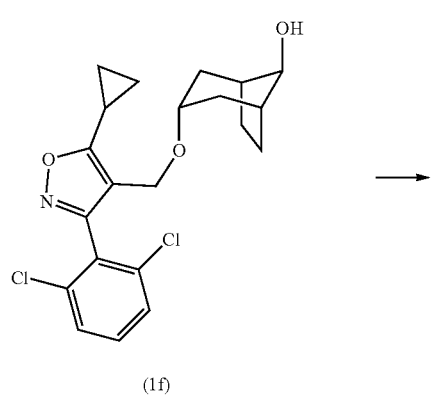

(1f)

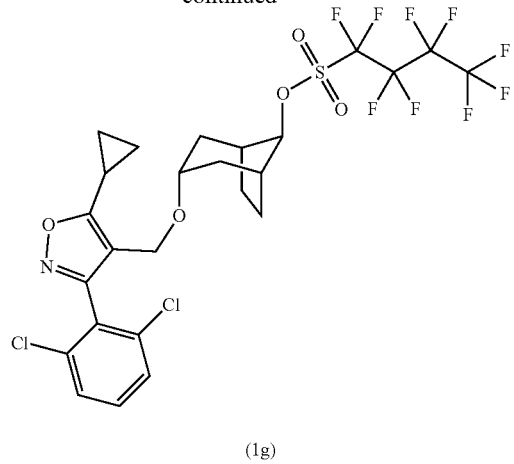

(1g)

To (1R,3r,5S,8r)-3-((5-cyclopropyl-3-(2,6-dichlorophenyl)isoxazol-4-yl)methoxy)bicyclo[3.2.1]octan-8-ol (f) (56 mg, 0.137 mmol) in DCM (1.5 ml) was added DBU (0.052 ml, 0.343 mmol) and nonafluorobutane-1-sulfonyl fluoride (0.049 ml, 0.274 mmol) and the mixture was stirred at RT for 2 h and the mixture was diluted with EtOAc, washed with NaHCO$_3$ solution, water, 1N HCl, water, brine, dried, filtered and concentrated to give (1R,3r,5S,8r)-3-((5-cyclopropyl-3-(2,6-dichlorophenyl)isoxazol-4-yl)methoxy)bicyclo[3.2.1]octan-8-yl nonafluorobutane-1-sulfonate (1g) (98 mg).

Step 1h:

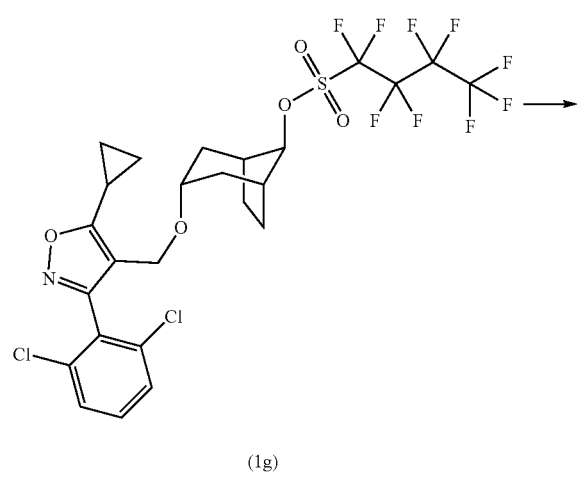

(1g)

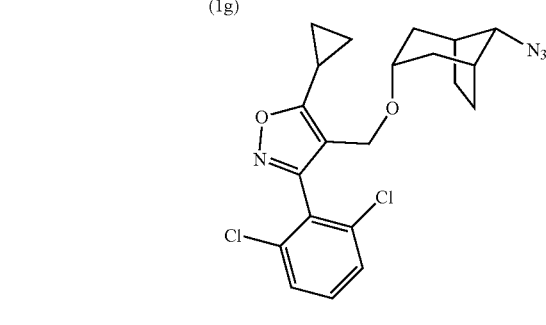

(1h)

To (1R,3r,5S,8r)-3-((5-cyclopropyl-3-(2,6-dichlorophenyl)isoxazol-4-yl)methoxy)bicyclo[3.2.1]octan-8-yl nonafluorobutane-1-sulfonate (1g) (50 mg, 0.072 mmol) in DMF (1 ml) was added sodium azide (37.7 mg, 0.579 mmol) and the mixture was heated at 80° C. for 16 h. The mixture was diluted with EtOAc, washed with water, brine, dried, filtered and concentrate to give 4-((((1R,3r,5S,8s)-8-azido-bicyclo[3.2.1]octan-3-yl)oxy)methyl)-5-cyclopropyl-3-(2,6-dichlorophenyl)isoxazole (13 mg, 41.4%). LC/MS observed [M+H], 433.13; $^1$H NMR (400 MHz, Chloroform-d) δ 7.40-7.23 (m, 3H), 4.11 (s, 2H), 3.34-3.19 (m, 1H), 2.12-1.98 (m, 3H), 1.88-1.72 (m, 2H), 1.66-1.44 (m, 6H), 1.26-1.12 (m, 2H), 1.11-0.95 (m, 2H).

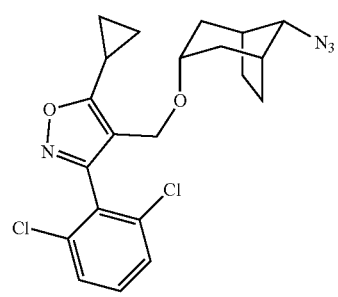

(1h)

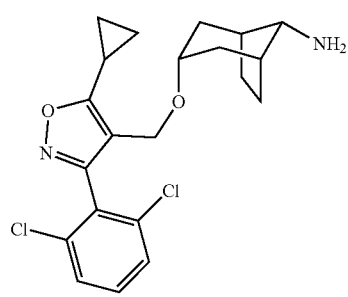

(1i)

To 4-((((1R,3r,5S,8s)-8-azidobicyclo[3.2.1]octan-3-yl)oxy)methyl)-5-cyclopropyl-3-(2,6-dichlorophenyl)isoxazole (h) (13 mg, 0.030 mmol) in THF (1 ml) was added triphenylphosphine (9.44 mg, 0.036 mmol) and the mixture was stirred at RT for 3 h. Water (0.33 ml) was added and the mixture was stirred at 70° C. for 16 h. The mixture was concentrated, chased with ACN, and the crude product was used directly to next step.

Step 1j:

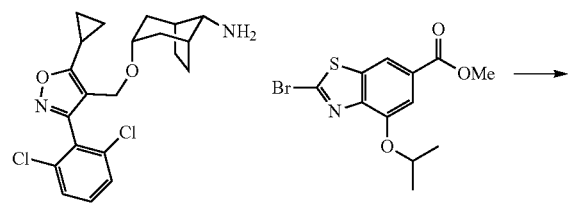

(1i)                    (1j-1)

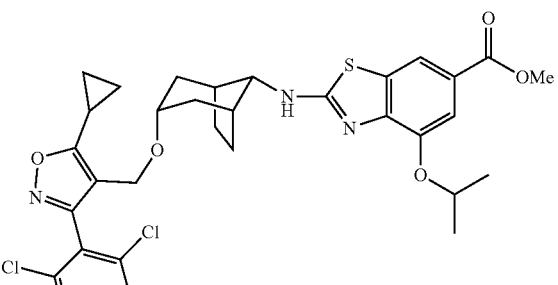

(1j)

To (1R,3r,5S,8s)-3-((5-cyclopropyl-3-(2,6-dichlorophenyl)isoxazol-4-yl)methoxy)bicyclo[3.2.1]octan-8-amine (1i) (13 mg, 0.032 mmol), methyl 2-bromo-4-isopropoxybenzo[d]thiazole-6-carboxylate (1j-1) (21.1 mg, 0.064 mmol), copper(I) iodide (3.0 mg, 0.016 mmol) in DMSO (1.5 ml) was added 2-((2,6-dimethylphenyl)amino)-2-oxoacetic acid (9.25 mg, 0.048 mmol) and potassium phosphate (13.55 mg, 0.064 mmol). The resulting mixture was stirred at 75° C. for 16 h, then diluted with EtOAc, washed with water, brine, dried, filtered and concentrated. The residue was purified by CombiFlash eluting with 0-50% EtOAc/hexane to give methyl 2-(((1R,3r,5S,8s)-3-((5-cyclopropyl-3-(2,6-dichlorophenyl)isoxazol-4-yl)methoxy)bicyclo[3.2.1]octan-8-yl)amino)-4-isopropoxybenzo[d]thiazole-6-carboxylate (1j) (6 mg, 9.14 μmol, 28.6% yield). LC/MS observed [M+H], 656.17; $^1$H NMR (400 MHz, Chloroform-d) δ 7.95 (d, J=1.5 Hz, 1H), 7.51 (d, J=1.5 Hz, 1H), 7.49-7.33 (m, 3H), 4.83 (p, J=6.0 Hz, 1H), 4.23 (s, 2H), 3.93 (s, 3H), 3.46 (t, J=5.0 Hz, 1H), 3.31 (d, J=5.2 Hz, 1H), 2.25 (b, 2H), 2.19-2.08 (m, 1H), 1.92 (m, 2H), 1.84-1.69 (m, 4H), 1.61 (b, 4H), 1.46 (d, J=6.0 Hz, 6H), 1.28 (d, J=4.5 Hz, 2H), 1.20-1.08 (m, 2H).

Step 1k:

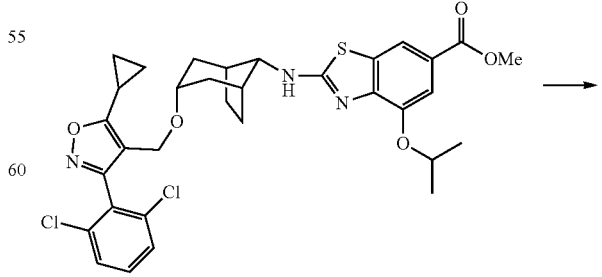

(1j)

Step 2a:

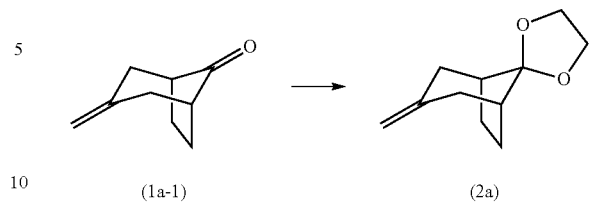

(1a-1)    (2a)

To (1R,5S)-3-methylenebicyclo[3.2.1]octan-8-one (1a-1) (3 g, 22.03 mmol) and ethylene glycol (4.10 g, 66.1 mmol) in DCM (45 ml) was added PTSA (0.284 g, 1.652 mmol) and Na2SO4 (600 mg) and the resulting mixture was stirred at 40° C. for 40 hours. Et₃N (3.07 ml, 22.03 mmol) was introduced and the mixture was passed through a cake of SiO₂ and MgSO₄. The cake was washed with DCM and the combined filtrates were concentrated to give (1R,5S)-3-methylenespiro[bicyclo[3.2.1]octane-8,2'-[1,3]dioxolane] (2a) (3.92 g, 21.75 mmol, 99% yield). ¹H NMR (400 MHz, Chloroform-d) δ 4.80 (t, J=2.2 Hz, 2H), 4.06-3.93 (m, 4H), 2.77-2.56 (m, 2H), 2.15-1.97 (m, 2H), 1.92 (dq, J=4.9, 2.8, 2.4 Hz, 2H), 1.88-1.74 (m, 2H), 1.49-1.37 (m, 2H).

Step 2b:

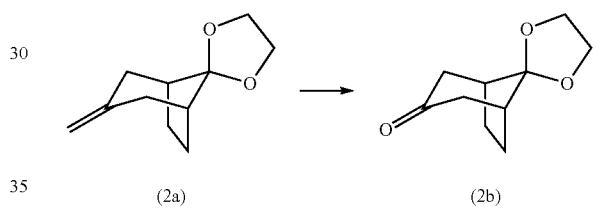

(2a)    (2b)

To (1R,5S)-3-methylenespiro[bicyclo[3.2.1]octane-8,2'-[1,3]dioxolane] (2a) (730 mg, 4.05 mmol) in dioxane (14 ml) and water (7 ml) was added ruthenium(III) chloride (42.0 mg, 0.202 mmol) and a suspension of sodium periodate (3.465 g, 16.20 mmol) in water (7 ml). The resulting mixture was stirred at RT for 17 h, and the mixture was diluted with EtOAc, filtered through celite/Na₂SO₄, and the filtrate was collected and concentrated to give (1R,5S)-spiro[bicyclo[3.2.1]octane-8,2'-[1,3]dioxolan]-3-one (2b) (896 mg). ¹H NMR (500 MHz, Chloroform-d) δ 4.12-4.02 (m, 4H), 3.02-2.82 (m, 2H), 2.28 (ddd, J=15.2, 3.1, 2.0 Hz, 2H), 2.15 (tt, J=3.6, 2.1 Hz, 2H), 2.11-2.01 (m, 2H), 1.67-1.47 (m, 2H).

Step 2c:

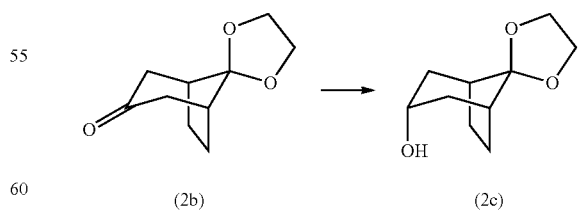

(2b)    (2c)

(1R,5S)-spiro[bicyclo[3.2.1]octane-8,2'-[1,3]dioxolan]-3-one (2b) (1.3 g, 7.13 mmol) was dissolved in THF (35.7 ml) and cooled to −78° C. A L-selectride solution (8.92 ml, 8.92 mmol, 1.0 M in THF) was added dropwise. The mixture was stirred at −78° C. for 1 h. At 0° C. the reaction was

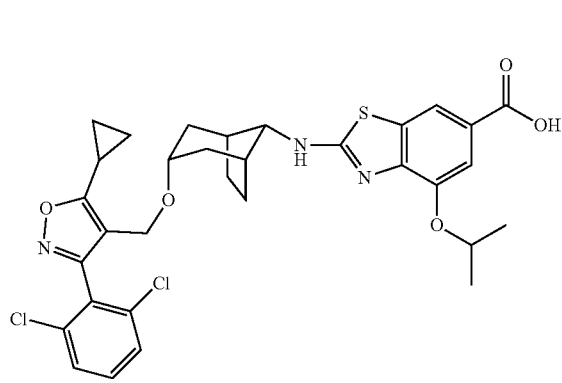

Example 1

To methyl 2-(((1R,3r,5S,8s)-3-((5-cyclopropyl-3-(2,6-dichlorophenyl)isoxazol-4-yl)methoxy)bicyclo[3.2.1]octan-8-yl)amino)-4-isopropoxybenzo[d]thiazole-6-carboxylate (1j) (6 mg, 9.14 μmol) in THF (0.6 ml) and MeOH (0.3 ml) at RT was added NaOH (1 N) (0.037 ml, 0.037 mmol) and the mixture was stirred at RT for 16 h. The mixture was heated up at 45° C. for 8 h and then diluted with EtOAc, acidified with 1N HCl, washed with water, brine, dried, filtered and concentrated to give 2-(((1R,3r,5S,8s)-3-((5-cyclopropyl-(2,6-dichlorophenyl)isoxazol-4-yl)methoxy)bicyclo[3.2.1] octan-8-yl)amino)-4-isopropoxybenzo[d]thiazole-6-carboxylic acid (Example 1) (6.1 mg, 9.49 μmol). LC/MS observed [M+H], 642.15; ¹H NMR (400 MHz, Chloroform-d) δ 7.87 (s, 1H), 7.54 (s, 1H), 7.46-7.24 (m, 3H), 4.70 (s, 1H), 4.15 (s, 2H), 3.39 (s, 1H), 3.15 (s, 1H), 2.39-2.24 (m, 2H), 2.05 (s, 2H), 1.96-1.54 (m, 6H), 1.40 (d, J=5.8 Hz, 6H), 1.29-1.12 (m, 4H), 1.10-0.98 (m, 2H).

Example 2

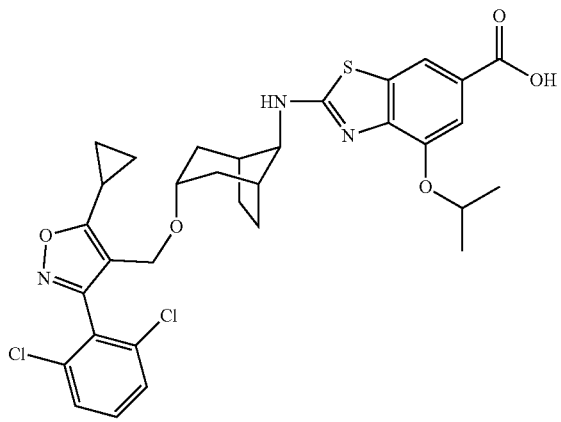

Example 2 carefully quenched with 2 M sodium hydroxide solution (21.4 ml, 42.8 mmol) and 50% hydrogen peroxide solution (2.027 ml, 35.7 mmol). The mixture was stirred at 0° C. for 1 h, and at RT for 1 h. Water was added and the mixture was extracted with MTBE. The organic layer was washed with water and brine, dried over Na$_2$SO$_4$, and concentrated in vacuo. The residue was purified by CombiFlash on silica gel eluting with 0-50% EtOAc/hexane provided (1R,3r,5S)-spiro[bicyclo[3.2.1]octane-8,2'-[1,3]dioxolan]-3-ol (2c) (1.3 g, 7.06 mmol, 99% yield) as a white solid. $^1$H NMR (500 MHz, Chloroform-d) δ 4.04 (tt, J=5.3, 1.3 Hz, 1H), 4.00-3.90 (m, 4H), 2.29-2.20 (m, 2H), 2.01-1.90 (m, 2H), 1.86 (tdd, J=7.8, 4.5, 3.0 Hz, 4H), 1.78 (dq, J=14.8, 1.6 Hz, 2H).

Step 2d:

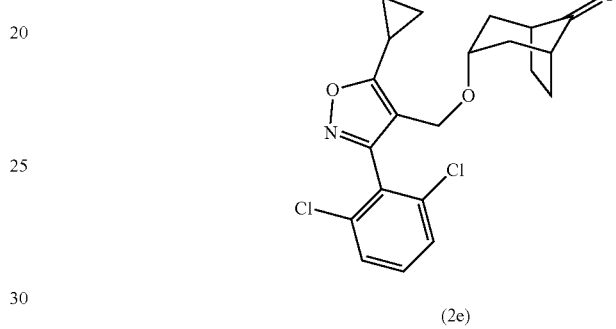

(2c)   (2d-1)

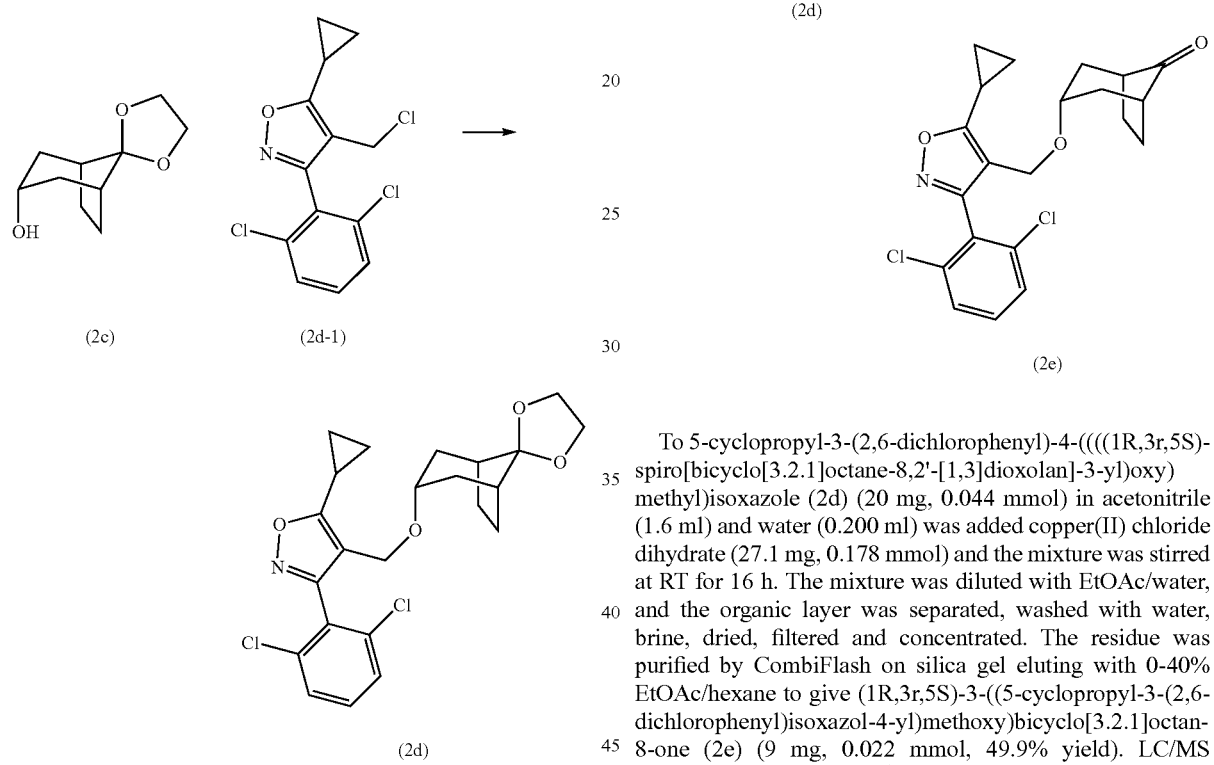

(2d)

To (1R,3r,5S)-spiro[bicyclo[3.2.1]octane-8,2'-[1,3]dioxolan]-3-ol (2c) (30 mg, 0.163 mmol), 4-(chloromethyl)-5-cyclopropyl-3-(2,6-dichlorophenyl)isoxazole (2d-1) (73.9 mg, 0.244 mmol), TBAI (6.01 mg, 0.016 mmol) and 18-crown-6 (43.0 mg, 0.163 mmol) in Tetrahydrofuran (2 ml) was added potassium tert-butoxide (27.4 mg, 0.244 mmol) and the mixture was heated at 60° C. for 16 h. The mixture was quenched with NaHCO$_3$ solution, extracted with EtOAc, and the organic layer was separated, washed with water, brine, dried, filtered and concentrated. The residue was purified by CombiFlash eluting with 0 to 40% EtOAc/hexane to give 5-cyclopropyl-3-(2,6-dichlorophenyl)-4-((((1R,3r,5S)-spiro[bicyclo[3.2.1]octane-8,2'-[1,3]dioxolan]-3-yl)oxy)methyl)isoxazole (2d) (19.5 mg, 0.043 mmol, 26.6% yield). LC/MS observed [M+H], 450.13; $^1$H NMR (500 MHz, Chloroform-d) δ 7.33-7.14 (m, 3H), 4.05 (s, 2H), 3.79-3.67 (m, 4H), 3.24 (t, J=5.3 Hz, 1H), 2.03-1.95 (m, 1H), 1.83-1.75 (m, 2H), 1.65-1.54 (m, 4H), 1.50-1.34 (m, 4H), 1.13-1.05 (m, 2H), 1.03-0.89 (m, 2H).

Step 2e:

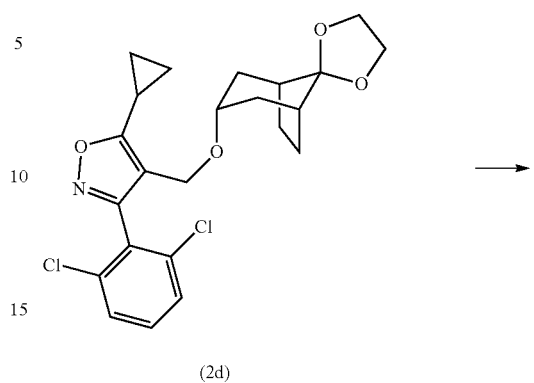

(2d)

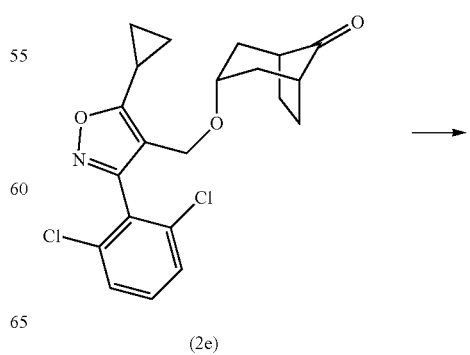

(2e)

To 5-cyclopropyl-3-(2,6-dichlorophenyl)-4-((((1R,3r,5S)-spiro[bicyclo[3.2.1]octane-8,2'-[1,3]dioxolan]-3-yl)oxy)methyl)isoxazole (2d) (20 mg, 0.044 mmol) in acetonitrile (1.6 ml) and water (0.200 ml) was added copper(II) chloride dihydrate (27.1 mg, 0.178 mmol) and the mixture was stirred at RT for 16 h. The mixture was diluted with EtOAc/water, and the organic layer was separated, washed with water, brine, dried, filtered and concentrated. The residue was purified by CombiFlash on silica gel eluting with 0-40% EtOAc/hexane to give (1R,3r,5S)-3-((5-cyclopropyl-3-(2,6-dichlorophenyl)isoxazol-4-yl)methoxy)bicyclo[3.2.1]octan-8-one (2e) (9 mg, 0.022 mmol, 49.9% yield). LC/MS observed [M+H], 406.11; $^1$H NMR (500 MHz, Chloroform-d) δ 7.46-7.23 (m, 3H), 4.20 (s, 2H), 3.42 (tt, J=4.0, 1.5 Hz, 1H), 2.19-1.97 (m, 5H), 1.96-1.83 (m, 2H), 1.76-1.62 (m, 2H), 1.51 (s, 2H), 1.23-1.16 (m, 2H), 1.13-0.97 (m, 2H).

Step 2f:

(2e)

-continued

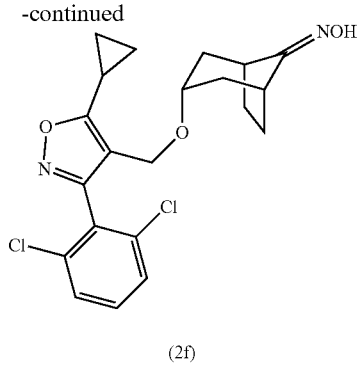

(2f)

To (1R,3r,5S)-3-((5-cyclopropyl-3-(2,6-dichlorophenyl)isoxazol-4-yl)methoxy)bicycle [3.2.1]octan-8-one (66 mg, 0.162 mmol) in ethanol (812 μl) was added hydroxylamine hydrochloride (22.58 mg, 0.325 mmol). The resulting mixture was stirred at RT for 1 h, quenched with sat. NaHCO₃, and extracted with EtOAc. The organic layer was dried over Na₂SO₄ and concentrated in vacuo. The residue was purified by CombiFlash on silica gel eluting with 0-100% EtOAc/hexane to provide (1R,3r,5S)-3-((5-cyclopropyl-3-(2,6-dichlorophenyl)isoxazol-4-yl)methoxy)bicyclo[3.2.1]octan-8-one oxime (2f) (41 mg, 0.097 mmol, 60% yield).

Step 2g:

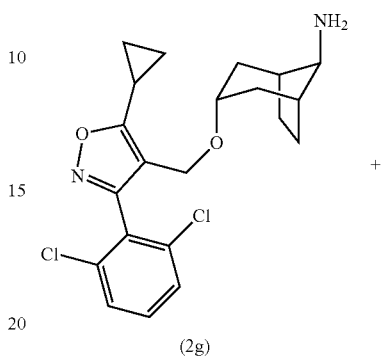

To a solution of (1R,3r,5S)-3-((5-cyclopropyl-3-(2,6-dichlorophenyl)isoxazol-4-yl)methoxy)bicyclo[3.2.1]octan-8-one oxime (2f) (41 mg, 0.097 mmol) in MeOH (1622 μl) was added ammonium acetate (150 mg, 1.946 mmol), sodium cyanoborohydride (36.7 mg, 0.584 mmol) and titanium(III) chloride (20% in 3% HCl) (252 μl, 0.389 mmol). The resulting mixture was stirred at RT for 3 h, quenched with sat. NaHCO₃, and extracted with EtOAc. The organic layer was dried over Na₂SO₄ and concentrated in vacuo to give (1R,3r,5S,8r)-3-((5-cyclopropyl-3-(2,6-dichlorophenyl)isoxazol-4-yl)methoxy)bicyclo[3.2.1]octan-8-amine (2g) (41 mg), LC/MS observed [M+H], 407.3. This material was directly used for the next step without further purification.

Step 2h:

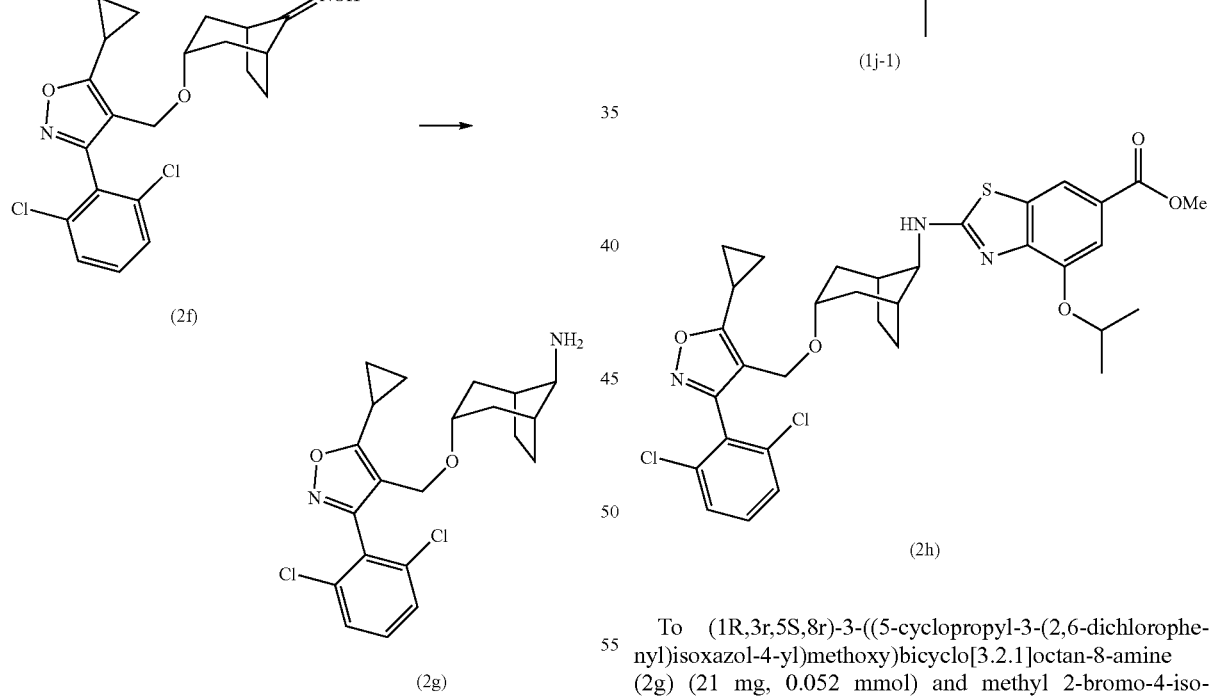

To (1R,3r,5S,8r)-3-((5-cyclopropyl-3-(2,6-dichlorophenyl)isoxazol-4-yl)methoxy)bicyclo[3.2.1]octan-8-amine (2g) (21 mg, 0.052 mmol) and methyl 2-bromo-4-isopropoxybenzo[d]thiazole-6-carboxylate (1j-1) (17.02 mg, 0.052 mmol) in DMA (0.25 ml) was added Hunig's base (9.00 μl, 0.052 mmol) and the resulting mixture was heated in microwave at 170° C. for 20 min. The reaction mixture was purified on silica gel eluting with 0-40% EtOAc/hexane to provide Methyl 2-(((1R,3r,5S,8r)-3-((5-cyclopropyl-3-(2,6-dichlorophenyl)isoxazol-4-yl)methoxy)bicyclo[3.2.1]octan-8-yl)amino)-4-isopropoxybenzo[d]thiazole-6-carboxylate (2h) (9.1 mg, 0.014 mmol, 26.9% yield). LC/MS observed [M+H]⁺, 656.4.

Step 2i:

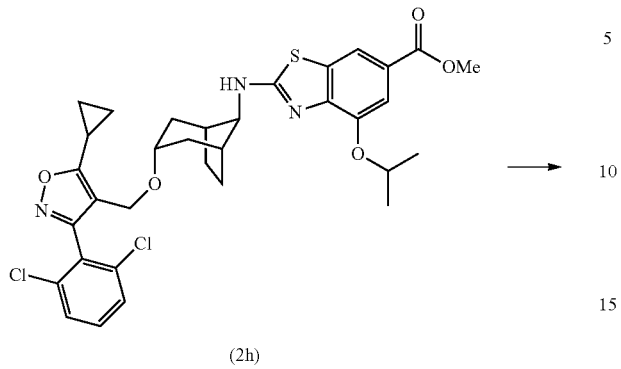

(2h)

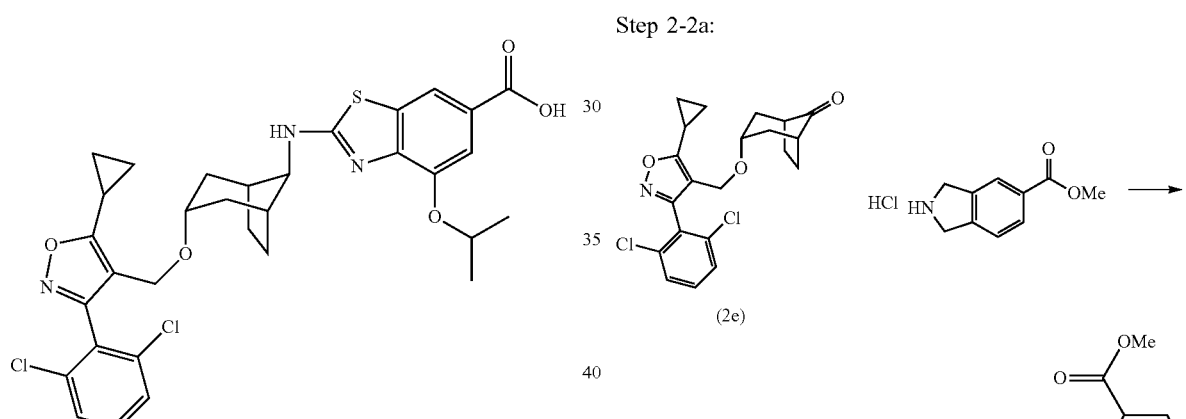

Example 2

Methyl 2-(((1R,3r,5S,8r)-3-((5-cyclopropyl-3-(2,6-dichlorophenyl)isoxazol-4-yl)methoxy)bicyclo[3.2.1]octan-8-yl)amino)-4-isopropoxybenzo[d]thiazole-6-carboxylate (9 mg, 0.014 mmol) was dissolved in THF (0.5 ml), MeOH (0.5 ml) and water (0.5 ml). A 1 N aq. sodium hydroxide (0.82 ml, 0.822 mmol) solution was added. The mixture was stirred at 50° C. for 2 h, cooled to RT, quenched with 1 M HCl (0.82 mL), and extracted with EtOAc. The organic layer was loaded on silica gel and eluted with 50% acetone/hexane to afford 2-(((1R,3r,5S,8r)-3-((5-cyclopropyl-3-(2,6-dichlorophenyl)isoxazol-4-yl)methoxy)bicyclo[3.2.1]octan-8-yl)amino)-4-isopropoxybenzo[d]thiazole-6-carboxylic acid (Example 2) (7.6 mg, 0.012 mmol, 86% yield). LC/MS observed [M+H]$^+$, 642.4.

Example 2-2

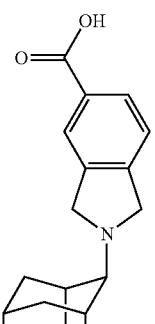

Step 2-2a:

A solution of ((1R,3r,5S)-3-((5-cyclopropyl-3-(2,6-dichlorophenyl)isoxazol-4-yl)methoxy)bicyclo[3.2.1]octan-8-one (2e) (16 mg, 0.039 mmol) and methyl isoindoline-5-carboxylate hydrochloride (12.62 mg, 0.059 mmol) in trifluoroethanol (2 ml) was heated up to 45° C. for 1 h, then added sodium borohydride (4.47 mg, 0.118 mmol) and the mixture was stirred at 45° C. for 16 h, the mixture was quenched with water, concentrated and the residue was purified by CombiFlash eluting with 0-40% acetone/hexane to give methyl 2-((1R,3r,5S,8r)-3-((5-cyclopropyl-3-(2,6-dichlorophenyl)isoxazol-4-yl)methoxy)bicyclo[3.2.1]octan-8-yl)isoindoline-5-carboxylate (2-2a) (17 mg, 0.030 mmol, 76% yield). LC/MS observed [M+H], 567.18; $^1$H NMR (500 MHz, Chloroform-d) δ 7.82 (dd, J=7.9, 1.6 Hz, 1H), 7.79 (s, 1H), 7.35-7.30 (m, 2H), 7.26-7.15 (m, 2H), 4.13 (s, 2H), 3.86-3.81 (m, 4H), 3.83 (s, 3H), 3.39 (t, J=5.2 Hz, 1H), 2.35 (t, J=4.3 Hz, 1H), 2.13-2.04 (m, 1H), 1.97-1.83 (m, 4H), 1.63 (t, J=6.5 Hz, 2H), 1.54-1.47 (m, 2H), 1.47-1.39 (m, 2H), 1.21-1.12 (m, 2H), 1.08-0.97 (m, 2H).

2.17-2.01 (m, 1H), 1.93 (d, J=18.3 Hz, 4H), 1.64 (t, J=6.5 Hz, 2H), 1.55-1.39 (m, 4H), 1.29-1.08 (m, 2H), 1.08-0.89 (m, 2H).

Example 3

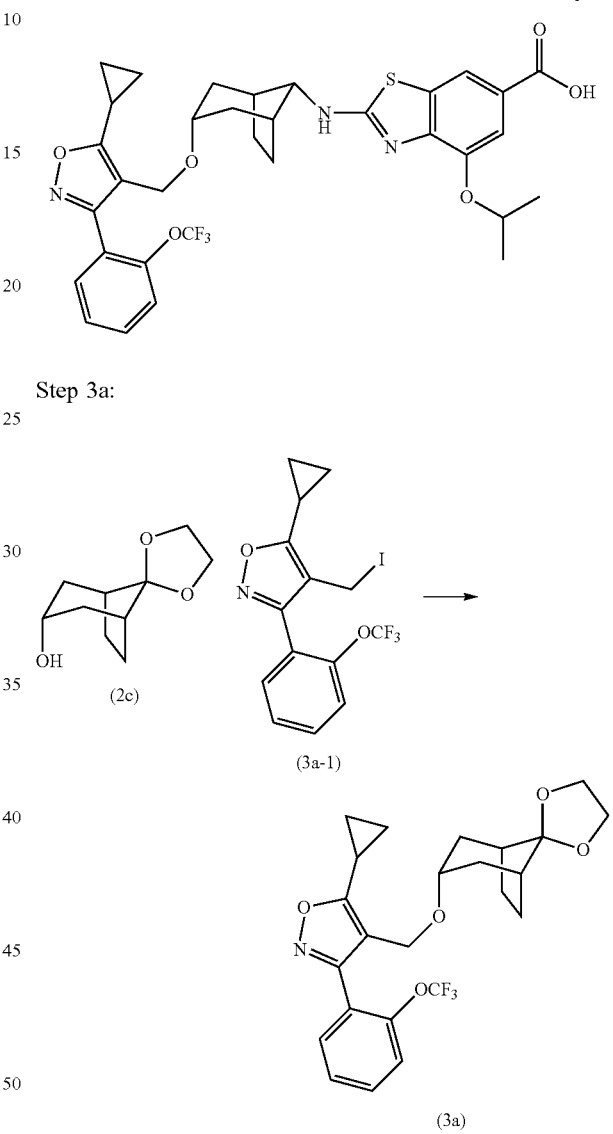

Example 3

Step 3a:

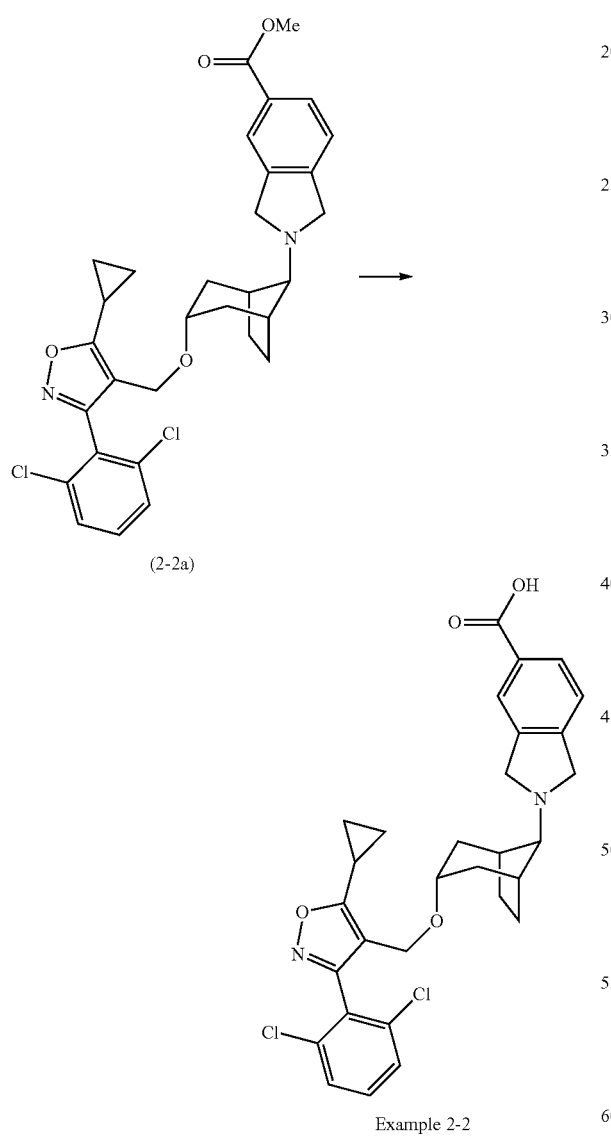

Example 2-2

Example 2-2 was prepared from compound (2-2a) following a similar procedure as in Step 2i. LC/MS observed [M+H]$^+$, 553.17; $^1$H NMR (400 MHz, Chloroform-d) δ 7.90-7.79 (m, 1H), 7.46-7.15 (m, 5H), 4.12 (s, 2H), 3.95 (d, J=4.3 Hz, 4H), 3.38 (d, J=5.0 Hz, 1H), 2.44 (s, 1H), To a solution of (1R,3r,5S)-spiro[bicyclo[3.2.1]octane-8,2'-[1,3]dioxolan]-3-ol (2c) (1 g, 5.43 mmol) in DMSO (15 mL) was added potassium tert-butoxide (0.731 g, 6.51 mmol) and the resulting mixture was stirred at RT for 30 min. To the reaction mixture was added a solution of 5-cyclopropyl-4-(iodomethyl)-3-(2-(trifluoromethoxy)phenyl)isoxazole (3a-1) (2.78 g, 6.78 mmol) in DMSO (3 mL) was added dropwise. The reaction mixture was stirred at RT for 1 h, quenched with sat.NH$_4$Cl, and extracted with MTBE. The organic layer was washed with water and brine, dried over Na$_2$SO$_4$, and concentrated in vacuo. The residue was purified by CombiFlash on silica gel eluting with 0-30% EtOAc/hexane to provide 5-cyclopropyl-4-((((1R,3r,5S)-spiro[bicyclo[3.2.1]octane-8,2'-[1,3]dioxolan]-3-yl)oxy)

methyl)-3-(2-(trifluoromethoxy)phenyl)isoxazole (3a) (1.64 g, 3.52 mmol, 64.9% yield). $^1$H NMR (400 MHz, Chloroform-d) δ 7.58 (dd, J=7.8, 1.8 Hz, 1H), 7.55-7.44 (m, 1H), 7.43-7.29 (m, 2H), 4.27 (s, 2H), 3.97-3.86 (m, 4H), 3.44 (t, J=5.2 Hz, 1H), 2.16 (tt, J=8.4, 5.1 Hz, 1H), 1.98 (dtt, J=11.4, 7.9, 4.4 Hz, 2H), 1.81-1.71 (m, 4H), 1.69-1.54 (m, 4H), 1.27-1.19 (m, 2H), 1.16-1.06 (m, 2H).

Step 3b:

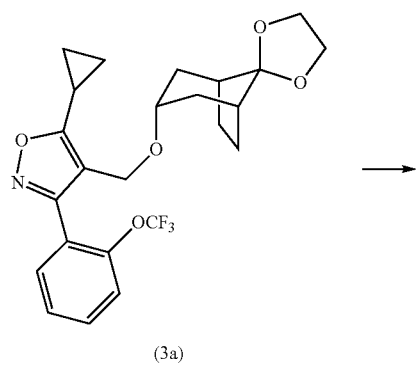

(3a)

To 5-cyclopropyl-4-(((((1R,3r,5S)-spiro[bicyclo[3.2.1]octane-8,2'-[1,3]dioxolan]-3-yl)oxy)methyl)-3-(2-(trifluoromethoxy)phenyl)isoxazole (3a) (0.87 g, 1.9 mmol) was added AcOH (7.5 ml) and water (1.9 ml) and the resulting mixture was stirred at 45° C. for 5 d. The solvent was removed under vacuum and the residue was diluted with EtOAc, washed with water, Sat.NaHCO$_3$ and brine, dried over Na$_2$SO$_4$, filtered and concentrated to give (1R,3r,5S)-3-((5-cyclopropyl-3-(2-(trifluoromethoxy)phenyl)isoxazol-4-yl)methoxy)bicyclo[3.2.1]octan-8-one (3b) (0.75 g) as a colorless oil. The material was directly used in next step without further purification. LC/MS observed [M+H]$^+$, 422.33. $^1$H NMR (400 MHz, Chloroform-d) δ 7.55-7.51 (m, 1H), 7.50-7.47 (m, 1H), 7.39-7.34 (m, 2H), 4.31 (s, 2H), 3.51-3.43 (m, 1H), 2.20-2.05 (m, 7H), 1.95-1.88 (m, 2H), 1.76-1.67 (m, 2H), 1.23-1.19 (m, 2H), 1.13-1.06 (m, 2H).

Step 3c:

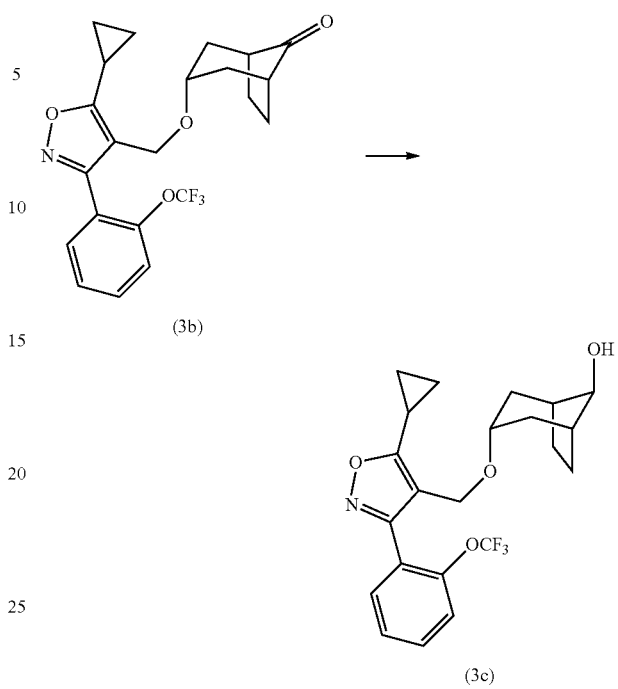

To (1R,3r,5S)-3-((5-cyclopropyl-3-(2-(trifluoromethoxy)phenyl)isoxazol-4-yl)methoxy)bicyclo[3.2.1]octan-8-one (3b) (0.790 g, 1.875 mmol) in THF (9.37 ml), was added LAH (1 M in THF) (1.875 ml, 1.875 mmol) at −78° C. over 10 min. The mixture was stirred at this temperature for 30 min, then the reaction mixture was quenched at 0° C. by the addition of 0.5 mL water followed by 0.5 mL 1N NaOH and 0.5 ml of water. The mixture was stirred at 0° C. for 20 min. The mixture was filtered through celite and the filtrate was concentrated. The residue was purified by Combiflash on silica gel eluting with 0-50% EtOAc/hexane to give (1R,3r,5S,8r)-3-((5-cyclopropyl-3-(2-(trifluoromethoxy)phenyl) isoxazol-4-yl)methoxy)bicyclo[3.2.1]octan-8-ol (3c) (658 mg) as a colorless oil. LC/MS observed [M+H]$^+$, 424.18. $^1$H NMR (400 MHz, Chloroform-d) δ 7.55 (dd, J=7.8, 1.8 Hz, 1H), 7.50-7.44 (m, 1H), 7.38-7.32 (m, 2H), 4.24 (s, 2H), 3.92 (t, J=5.0 Hz, 1H), 3.45 (t, J=5.3 Hz, 1H), 2.18-2.08 (m, 1H), 2.02-1.98 (m, 1H), 1.98-1.94 (m, 1H), 1.87-1.81 (m, 2H), 1.68-1.61 (m, 2H), 1.56-1.45 (m, 4H), 1.23-1.16 (m, 2H), 1.10-1.03 (m, 2H).

Step 3d:

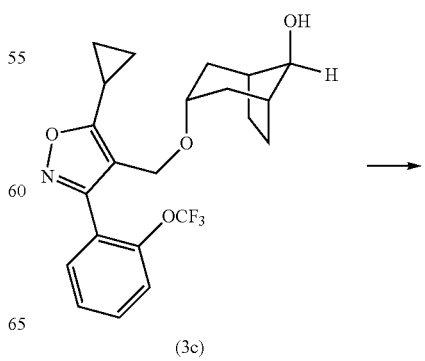

(3c)

-continued

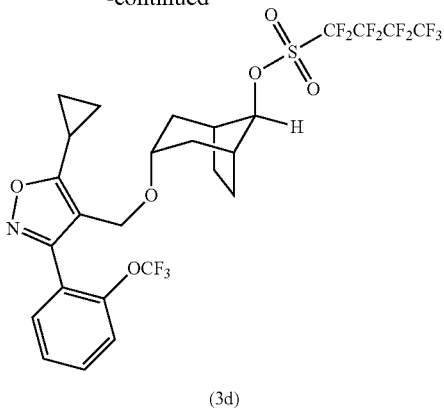

(3d)

To a solution of (1R,3r,5S,8r)-3-((5-cyclopropyl-3-(2-(trifluoromethoxy)phenyl)isoxazol-4-yl)methoxy)bicyclo[3.2.1]octan-8-ol (3c) (650 mg, 1.535 mmol) and DBU (301 μl, 1.996 mmol) in DCM (20 ml) was added nonafluoro-1-sulfonyl fluoride (304 μl, 1.689 mmol) at 0° C. and the mixture was stirred at 0° C. for 1 h. It was diluted with DCM, washed with HCl (1N), Sat. NaHCO₃ and brine, dried over Na₂SO₄, filtered, concentrated under vacuum to give (1R,3r,5S,8r)-3-((5-cyclopropyl-3-(2-(trifluoromethoxy)phenyl)isoxazol-4-yl)methoxy)bicyclo[3.2.1]octan-8-yl nonafluorobutane-1-sulfonate (3d) (1100 mg) as colorless oil. LC/MS observed [M+H]⁺, 706.10; ¹H NMR (400 MHz, Chloroform-d) δ 7.54-7.50 (m, 1H), 7.50-7.45 (m, 1H), 7.38-7.32 (m, 2H), 4.96 (t, J=5.2 Hz, 1H), 4.27 (s, 2H), 3.48 (t, J=5.2 Hz, 1H), 2.24-2.16 (m, 2H), 2.13-2.02 (m, 1H), 1.99-1.89 (m, 2H), 1.80-1.70 (m, 2H), 1.68-1.58 (m, 2H), 1.58-1.45 (m, 2H), 1.24-1.17 (m, 2H), 1.11-1.03 (m, 2H).

Step 3e:

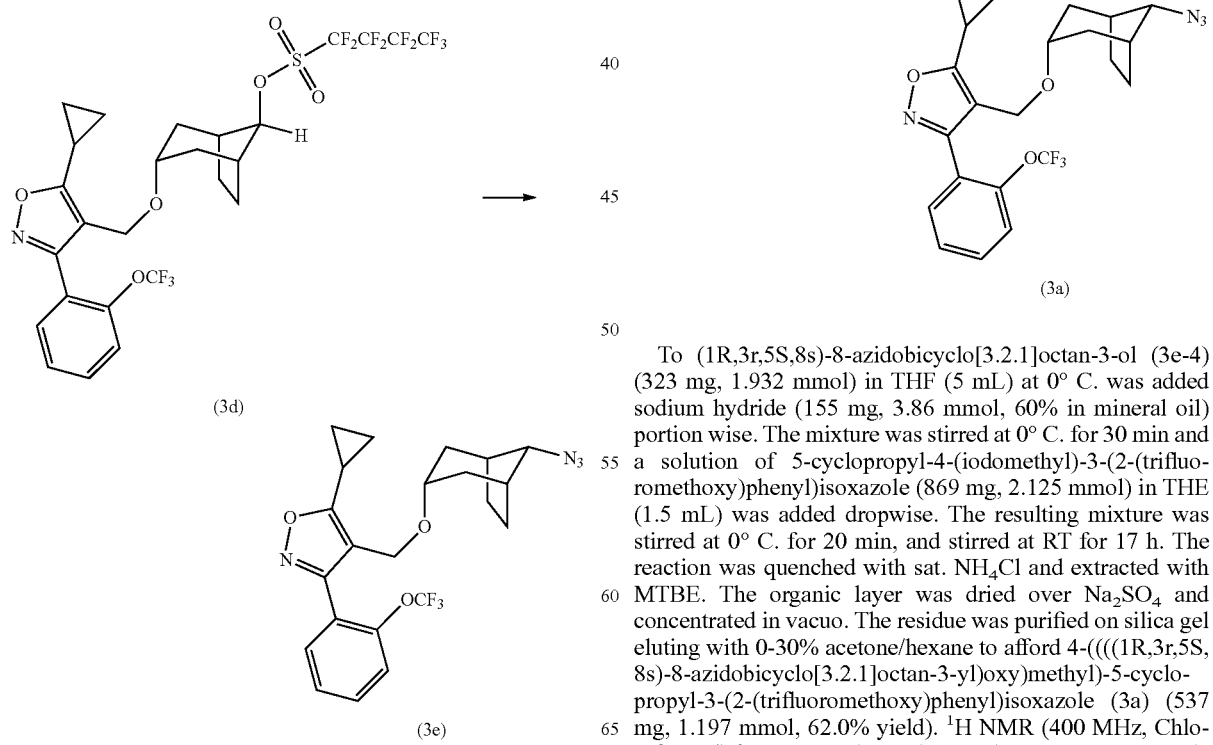

To a solution of (1R,3r,5S,8r)-3-((5-cyclopropyl-3-(2-(trifluoromethoxy)phenyl)isoxazol-4-yl)methoxy)bicyclo[3.2.1]octan-8-yl, nonafluorobutane-1-sulfonate (3d) (550 mg, 0.780 mmol) in DMSO (2.6 ml) was added sodium azide (253 mg, 3.90 mmol) and the resulting mixture was stirred at 60° C. for 1 h, quenched with water, and extracted with MTBE. The organic layer was washed with water and brine, dried over Na₂SO₄ and concentrated in vacuo. The residue was purified by CombiFlash on silica gel eluting with 0-50% EtOAc/hexane to give 4-((((1R,3r,5S,8s)-8-azidobicyclo[3.2.1]octan-3-yl)oxy)methyl)-5-cyclopropyl-3-(2-(trifluoromethoxy)phenyl)isoxazole (3e) (238 mg) as colorless oil. LC/MS observed [M+H]⁺, 706.10; ¹H NMR (400 MHz, Chloroform-d) δ 7.64-7.47 (m, 2H), 7.40 (tt, J=7.6, 1.1 Hz, 2H), 4.26 (d, J=1.9 Hz, 2H), 3.53 (d, J=12.4 Hz, 1H), 3.44-3.37 (m, 1H), 2.22-2.11 (m, 2H), 2.15-2.08 (m, 1H), 1.96-1.82 (m, 2H), 1.74-1.53 (m, 4H), 1.38-1.24 (m, 2H), 1.27-1.20 (m, 2H), 1.24-1.01 (m, 2H).

Compound (3e) could also be synthesized from the coupling reaction between alcohol (3e-4) and iodide (3a-1) (see step 3e1).

Step 3e1:

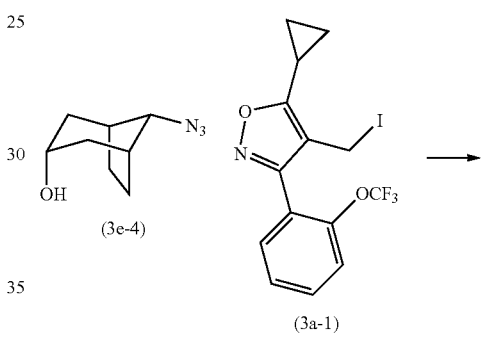

(3e-4)              (3a-1)

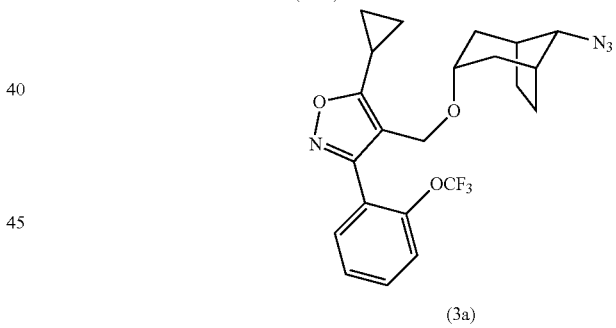

(3a)

To (1R,3r,5S,8s)-8-azidobicyclo[3.2.1]octan-3-ol (3e-4) (323 mg, 1.932 mmol) in THF (5 mL) at 0° C. was added sodium hydride (155 mg, 3.86 mmol, 60% in mineral oil) portion wise. The mixture was stirred at 0° C. for 30 min and a solution of 5-cyclopropyl-4-(iodomethyl)-3-(2-(trifluoromethoxy)phenyl)isoxazole (869 mg, 2.125 mmol) in THF (1.5 mL) was added dropwise. The resulting mixture was stirred at 0° C. for 20 min, and stirred at RT for 17 h. The reaction was quenched with sat. NH₄Cl and extracted with MTBE. The organic layer was dried over Na₂SO₄ and concentrated in vacuo. The residue was purified on silica gel eluting with 0-30% acetone/hexane to afford 4-((((1R,3r,5S,8s)-8-azidobicyclo[3.2.1]octan-3-yl)oxy)methyl)-5-cyclopropyl-3-(2-(trifluoromethoxy)phenyl)isoxazole (3a) (537 mg, 1.197 mmol, 62.0% yield). ¹H NMR (400 MHz, Chloroform-d) δ 7.64-7.47 (m, 2H), 7.40 (tt, J=7.6, 1.1 Hz, 2H), 4.26 (d, J=1.9 Hz, 2H), 3.53 (d, J=12.4 Hz, 1H), 3.44-3.37

(m, 1H), 2.22-2.11 (m, 2H), 2.15-2.08 (m, 1H), 1.96-1.82 (m, 2H), 1.74-1.53 (m, 4H), 1.38-1.24 (m, 2H), 1.27-1.20 (m, 2H), 1.24-1.01 (m, 2H).

Compound (3e-4) could be synthesized from compound (3e-1) (see step 3e2).

Step 3e2:

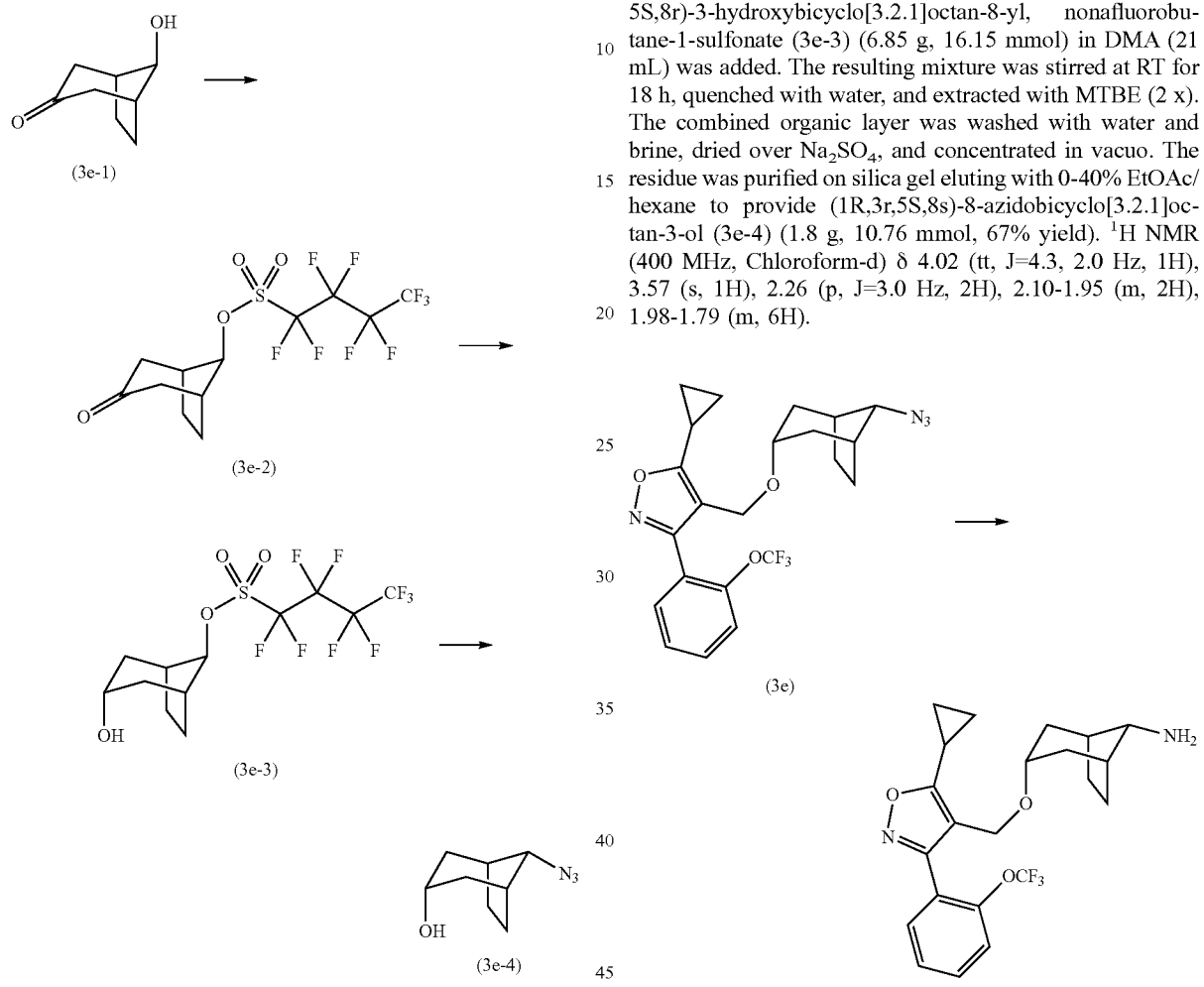

washed with water and brine, dried over Na$_2$SO$_4$, and concentrated in vacuo. The residue was purified on silica gel eluting with 0-50% EtOAc/hexane to provide (1R,3r,5S,8r)-3-hydroxybicyclo[3.2.1]octan-8-yl nonafluorobutane-1-sulfonate (3e-3) (10.2 g, 24.04 mmol, 73.0% yield).

A mixture of sodium azide (3.15 g, 48.4 mmol) in DMA (60 mL) was stirred at rt for 10 min. A solution of (1R,3r,5S,8r)-3-hydroxybicyclo[3.2.1]octan-8-yl, nonafluorobutane-1-sulfonate (3e-3) (6.85 g, 16.15 mmol) in DMA (21 mL) was added. The resulting mixture was stirred at RT for 18 h, quenched with water, and extracted with MTBE (2 x). The combined organic layer was washed with water and brine, dried over Na$_2$SO$_4$, and concentrated in vacuo. The residue was purified on silica gel eluting with 0-40% EtOAc/hexane to provide (1R,3r,5S,8s)-8-azidobicyclo[3.2.1]octan-3-ol (3e-4) (1.8 g, 10.76 mmol, 67% yield). $^1$H NMR (400 MHz, Chloroform-d) δ 4.02 (tt, J=4.3, 2.0 Hz, 1H), 3.57 (s, 1H), 2.26 (p, J=3.0 Hz, 2H), 2.10-1.95 (m, 2H), 1.98-1.79 (m, 6H).

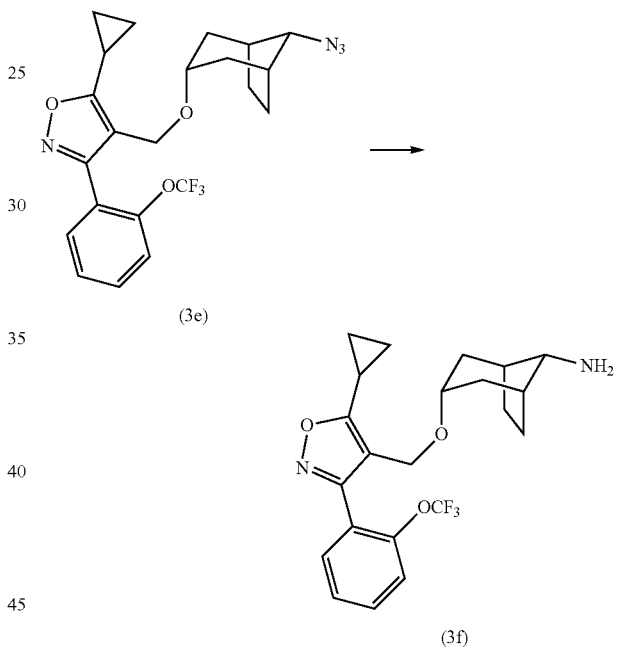

To (1R,5S,8r)-8-hydroxybicyclo[3.2.1]octan-3-one (3e-1) (6.6 g, 47.1 mmol) in CH$_2$Cl$_2$ (94 ml) at 0° C. was added DBU (7.10 ml, 47.1 mmol) and nonafluoro-1-butanesulfonyl fluoride (8.46 ml, 47.1 mmol). The mixture was stirred at 0° C. for 30 min, quenched with water, and extracted with DCM (2 x). The organic layer was washed with sat. NaHCO$_3$, brine, dried over Na$_2$SO$_4$, and concentrated in vacuo. The residue was purified on silica gel eluting with 0-20% EtOAc/hexane to provide (1R,5S,8r)-3-oxobicyclo[3.2.1]octan-8-yl nonafluorobutane-1-sulfonate (3e-2) (13.9 g, 32.9 mmol, 70% yield).

To (1R,5S,8r)-3-oxobicyclo[3.2.1]octan-8-yl, nonafluorobutane-1-sulfonate (3e-2) (13.9 g, 32.9 mmol) in THF (130 mL) at −78° C. was added 1 M L-selectride solution (36.2 ml, 36.2 mmol) dropwise. The mixture was stirred at −78° C. for 1 h, warmed to 0° C., carefully quenched with 2 M sodium hydroxide solution (66 ml, 132 mmol) and 50% hydrogen peroxide solution (6.66 ml, 109 mmol). The mixture was stirred at 0° C. for 1 h, at rt for 1 h, and partitioned in MTBE and water. The organic layer was To 4-((((1R,3r,5S,8s)-8-azidobicyclo[3.2.1]octan-3-yl)oxy)methyl)-5-cyclopropyl-3-(2-(trifluoromethoxy)phenyl)isoxazole (3e) (535 mg, 1.193 mmol) in THF (6 mL) and water (3 mL) was added triphenylphosphine (469 mg, 1.790 mmol) and the resulting mixture was stirred at 70° C. for 16 h. The mixture was partitioned in EtOAc and water and the organic layer was separated, dried over Na$_2$SO$_4$ and concentrated in vacuo. The residue was purified by CombiFlash on silica gel eluting with 0-15% MeOH/DCM to provide (1R,3r,5S,8s)-3-((5-cyclopropyl-3-(2-(trifluoromethoxy)phenyl)isoxazol-4-yl)methoxy)bicyclo[3.2.1]octan-8-amine (3f) (285 mg, 0.675 mmol, 56.5% yield). $^1$H NMR (400 MHz, Chloroform-d) δ 7.58 (dd, J=7.8, 1.8 Hz, 1H), 7.55-7.47 (m, 1H), 7.43-7.35 (m, 2H), 4.25 (s, 2H), 3.39 (dd, J=5.8, 4.6 Hz, 1H), 2.86 (s, 1H), 2.15 (tt, J=8.4, 5.1 Hz, 1H), 1.93 (s, 2H), 1.83 (ddq, J=13.5, 2.8, 1.3 Hz, 2H), 1.76-1.63 (m, 4H), 1.67-1.57 (m, 2H), 1.32-1.20 (m, 2H), 1.20-1.05 (m, 2H).

Step 3g:

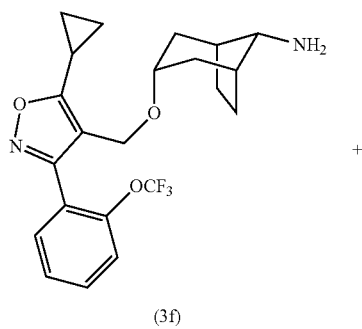

(3f)

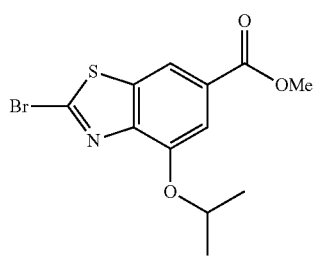

(1j-1)

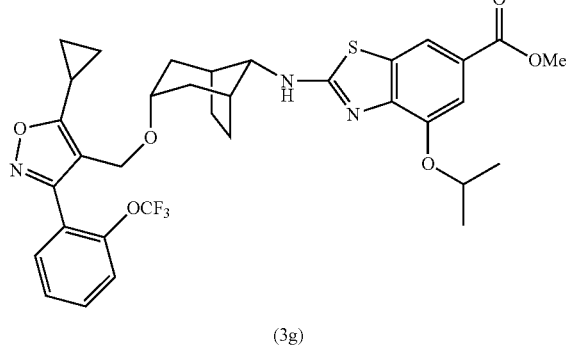

(3g)

To (1R,3r,5S,8s)-3-((5-cyclopropyl-3-(2-(trifluoromethoxy)phenyl)isoxazol-4-yl)methoxy)bicyclo[3.2.1]octan-8-amine (3f), methyl 2-bromo-4-isopropoxybenzo[d]thiazole-6-carboxylate (1j-1) (34.4 mg, 0.104 mmol) and copper(I) iodide (4.96 mg, 0.026 mmol) in DMSO (1042 μl) was added 2-((2,6-dimethylphenyl)amino)-2-oxoacetic acid (15.09 mg, 0.078 mmol) and potassium phosphate (22.11 mg, 0.104 mmol). The resulting mixture was stirred at 75° C. for 16 h, then diluted with EtOAc, washed with water, brine, dried, filtered and concentrated. The residue was purified by CombiFlash eluting with 0-50% EtOAc/hexane to give methyl 2-(((1R,3r,5S,8s)-3-((5-cyclopropyl-3-(2-(trifluoromethoxy)phenyl)isoxazol-4-yl)methoxy)bicyclo[3.2.1]octan-8-yl)amino)-4-isopropoxybenzo[d]thiazole-6-carboxylate (3g) (28 mg, 0.042 mmol, 80% yield) as white solid. LC/MS observed [M+H]+, 672.45; ¹H NMR (400 MHz, Chloroform-d) δ 7.91 (d, J=1.5 Hz, 1H), 7.53 (dd, J=7.8, 1.8 Hz, 1H), 7.51-7.46 (m, 2H), 7.38-7.33 (m, 2H), 5.65 (d, J=6.7 Hz, 1H), 4.79 (hept, 1H), 4.24 (s, 2H), 3.88 (s, 3H), 3.43 (t, J=5.1 Hz, 1H), 3.28 (d, J=6.6 Hz, 1H), 2.25-2.15 (m, 2H), 2.15-2.05 (m, 1H), 1.91-1.82 (m, 2H), 1.78-1.67 (m, 4H), 1.61-1.54 (m, 2H), 1.42 (d, J=6.1 Hz, 7H), 1.23-1.18 (m, 2H), 1.11-1.05 (m, 2H).

Step 3h:

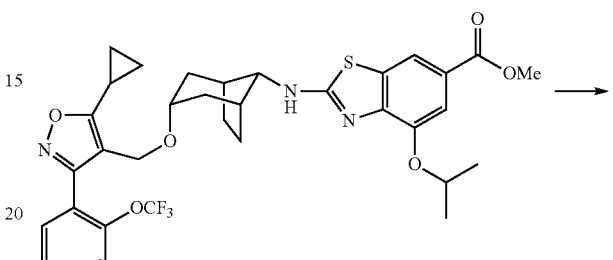

(3g)

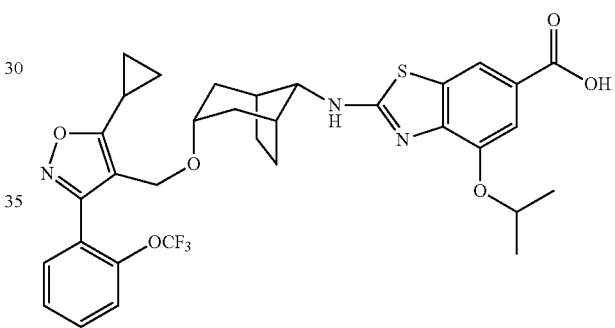

Example 3

To a solution of methyl 2-(((1R,3r,5S,8s)-3-((5-cyclopropyl-3-(2-(trifluoromethoxy)phenyl)isoxazol-4-yl)methoxy)bicyclo[3.2.1]octan-8-yl)amino)-4-isopropoxybenzo[d]thiazole-6-carboxylate (3g) (14 mg, 0.021 mmol) in MeOH (289 μl) and THF (289 μl) was added LiOH (1M) (208 μl, 0.208 mmol) and the resulting slightly cloudy solution was stirred at RT for 16 h. The mixture was diluted with EtOAc and water, acidified with 1M HCl to pH 5-6. The acidic mixture was extracted with EtOAc and the combined organic layers were washed with brine, dried over Na₂SO₄ and concentrated to provide 2-(((1R,3r,5S,8s)-3-((5-cyclopropyl-3-(2-(trifluoromethoxy)phenyl)isoxazol-4-yl)methoxy)bicyclo[3.2.1]octan-8-yl)amino)-4-isopropoxybenzo[d]thiazole-6-carboxylic acid (Example 3) (10 mg) as white solid. LC/MS observed [M+H]+, 658.46; ¹H NMR (400 MHz, DMSO-d6) δ 8.03 (s, 1H), 7.84 (s, 1H), 7.70-7.60 (m, 2H), 7.58-7.50 (m, 2H), 7.32 (d, J=1.5 Hz, 1H), 4.78 (hept, J=6.1 Hz, 1H), 4.26 (s, 2H), 3.55-3.44 (m, 1H), 2.37-2.25 (m, 1H), 2.17 (t, J=3.6 Hz, 2H), 1.80-1.68 (m, 4H), 1.66-1.50 (m, 4H), 1.27 (d, J=6.0 Hz, 6H), 1.17-1.10 (m, 2H), 1.10-1.04 (m, 2H).

Example 3-2

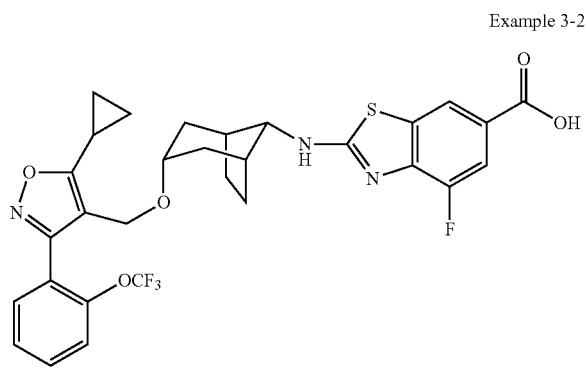 [SMILES: O=C(O)c1cc(F)c2nc(NC3C4CCC3CC(OCc3c(-c5ccccc5OC(F)(F)F)noc3C3CC3)C4)sc2c1]

Example 3-2

Example 3-2 was prepared from compound (3f) following the same protocol as Example 3. LC/MS observed [M+H]$^+$, 618.17; H NMR (400 MHz, Methanol-d4) δ 8.06 (d, J=1.5 Hz, 1H), 7.65-7.57 (m, 3H), 7.50 (td, J=7.6, 1.1 Hz, 2H), 4.33 (s, 2H), 3.78 (s, 1H), 3.51-3.45 (m, 1H), 2.31-2.25 (m, 1H), 2.25-2.21 (m, 2H), 1.87 (m, 4H), 1.76-1.65 (m, 4H), 1.19-1.12 (m, 4H).

Example 3-3

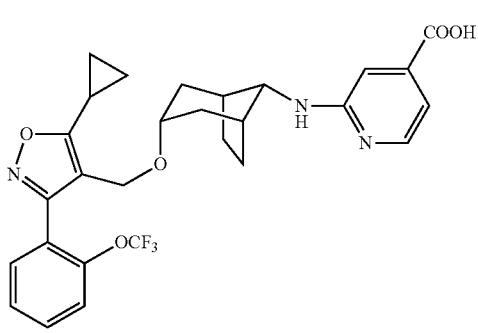

Example 3-3

Example 3-3 was prepared from compound (3f) following the same protocol as Example 3. LC/MS observed [M+H]$^+$, 544.21; $^1$H NMR (400 MHz, DMSO-d6) δ 8.04 (d, J=5.2 Hz, 1H), 7.72-7.59 (m, 2H), 7.58-7.48 (m, 2H), 7.00 (s, 1H), 6.80 (dd, J=5.2, 1.4 Hz, 1H), 6.47 (d, J=5.8 Hz, 1H), 4.26 (s, 2H), 3.59 (d, J=5.7 Hz, 1H), 3.44-3.39 (m, 1H), 2.37-2.26 (m, 1H), 2.05-1.95 (m, 2H), 1.79-1.45 (m, 8H), 1.17-1.10 (m, 2H), 1.10-1.02 (m, 2H).

Example 3-4

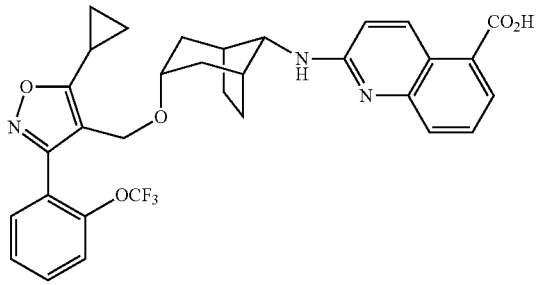

Example 3-4

Example 3-3 was prepared from compound (3f) following the same protocol as Example 3. LC/MS observed [M+H]$^+$, 594.23; H NMR (400 MHz, Methanol-d4) δ 9.10 (d, J=9.8 Hz, 1H), 8.00-7.87 (m, 2H), 7.78-7.69 (m, 1H), 7.67-7.55 (m, 2H), 7.54-7.45 (m, 2H), 7.12 (d, J=9.8 Hz, 1H), 4.37 (s, 2H), 3.86 (s, 1H), 3.56-3.52 (m, 1H), 2.31-2.22 (m, 3H), 2.01-1.55 (m, 8H), 1.19-1.13 (m, 4H).

Example 3-5

Example 3-5

Example 3-5 was prepared from compound (3f) following the same protocol as Example 3. LC/MS observed [M+H]$^+$, 612.12; H NMR (400 MHz, Methanol-d4) δ 8.83 (d, J=2.2 Hz, 1H), 8.21 (d, J=2.2 Hz, 1H), 7.66-7.55 (m, 2H), 7.53-7.45 (m, 2H), 4.34 (s, 2H), 4.00 (s, 1H), 3.52-3.46 (m, 1H), 2.32-2.21 (m, 1H), 2.17 (q, J=3.4 Hz, 2H), 1.95-1.70 (m, 6H), 1.57 (m, 2H), 1.19-1.11 (m, 4H).

Example 3-6

Example 3-6

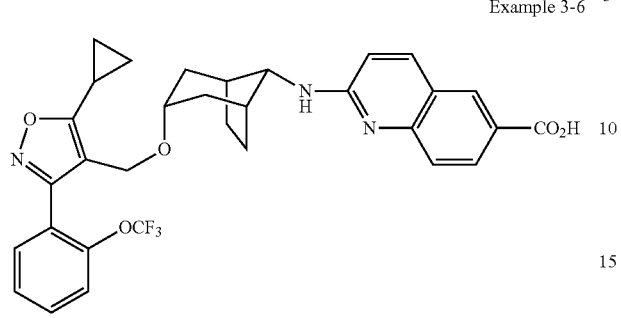

Example 3-6 was prepared from compound (3f) following the same protocol as Example 3. LC/MS observed [M+H]+, 594.12; 1H NMR (400 MHz, Methanol-d4) δ 8.34 (d, J=1.8 Hz, 1H), 8.18-8.09 (m, 1H), 8.00 (d, J=9.2 Hz, 1H), 7.70-7.55 (m, 3H), 7.48 (t, J=7.3 Hz, 2H), 6.94 (d, J=9.2 Hz, 1H), 4.34 (s, 2H), 3.87 (s, 1H), 3.54-3.49 (m, 1H), 2.31-2.23 (m, 1H), 2.23-2.18 (m, 2H), 1.97-1.82 (m, 4H), 1.82-1.67 (m, 4H), 1.19-1.10 (m, 4H).

Example 3-7

Example 3-7

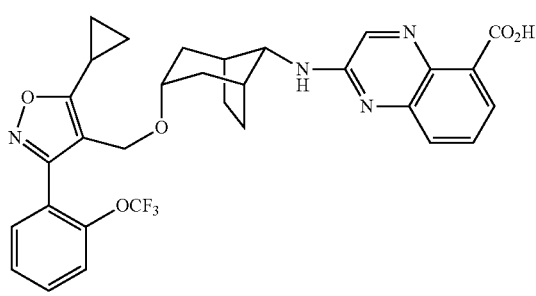

Example 3-7 was prepared from compound (3f) following the same protocol as Example 3. LC/MS observed [M+H]+, 595.22; H NMR (400 MHz, Chloroform-d) δ 8.34 (dd, J=7.4, 1.4 Hz, 1H), 8.13 (s, 1H), 7.87 (dd, J=8.4, 1.4 Hz, 1H), 7.73-7.66 (m, 1H), 7.55 (dd, J=7.8, 1.8 Hz, 1H), 7.53-7.45 (m, 1H), 7.40-7.32 (m, 2H), 5.08 (s, 1H), 3.89 (d, J=6.3 Hz, 1H), 3.49 (t, J=4.9 Hz, 1H), 2.27-2.20 (m, 2H), 2.18-2.09 (m, 1H), 1.95-1.76 (m, 6H), 1.69-1.60 (m, 2H), 1.27-1.19 (m, 2H), 1.12-1.06 (m, 2H)).

Example 3-8

Example 3-8

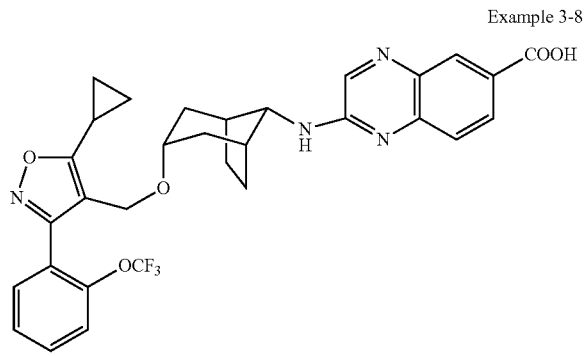 [SMILES: O=C(O)c1ccc2nc(NC3C4CCC3CC(OCc3c(-c5ccccc5OC(F)(F)F)noc3C3CC3)C4)cnc2c1]

Example 3-8 was prepared from compound (3f) following the same protocol as Example 3. LC/MS observed [M+H]+, 595.19; H NMR (400 MHz, Methanol-d4) δ 8.41 (d, J=2.0 Hz, 1H), 8.28 (s, 1H), 8.10 (dd, J=8.7, 2.0 Hz, 1H), 7.66-7.57 (m, 3H), 7.52-7.46 (m, 2H), 4.34 (s, 2H), 3.89 (s, 1H), 3.55-3.46 (m, 1H), 2.32-2.23 (m, 1H), 2.23-2.16 (m, 2H), 1.95-1.80 (m, 4H), 1.80-1.68 (m, 4H), 1.19-1.11 (m, 4H).

Example 3-9

Example 3-9

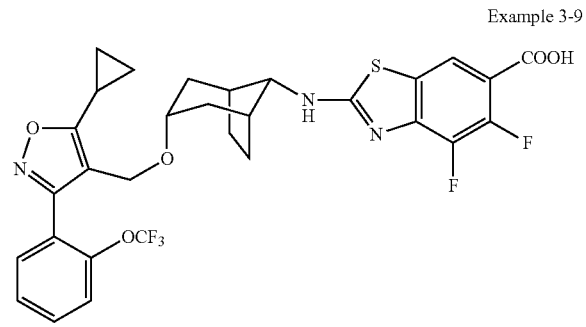 [SMILES: O=C(O)c1cc2sc(NC3C4CCC3CC(OCc3c(-c5ccccc5OC(F)(F)F)noc3C3CC3)C4)nc2c(F)c1F]

Example 3-9 was prepared from compound (3f) following the same protocol as Example 3. LC/MS observed [M+H]+, 636.16; 1HNMR (400 MHz, Methanol-d4) δ 7.92 (d, J=5.9 Hz, 1H), 7.67-7.55 (m, 2H), 7.50 (t, J=7.6 Hz, 2H), 4.34 (s, 2H), 3.82-3.74 (m, 1H), 3.52-3.44 (m, 1H), 2.32-2.12 (m, 3H), 1.97-1.79 (m, 4H), 1.77-1.62 (m, 4H), 1.22-1.10 (m, 4H).

Example 3-10

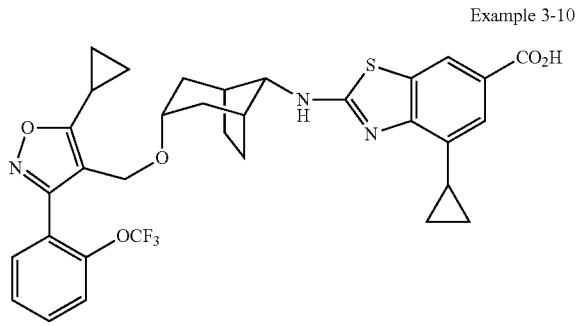 [SMILES: O=C(O)c1cc(C2CC2)c2nc(NC3C4CCC3CC(OCc3c(-c5ccccc5OC(F)(F)F)noc3C3CC3)C4)sc2c1]

Example 3-10

Example 3-10 was prepared from compound (3f) following the same protocol as Example 3. LC/MS observed [M+H]$^+$, 640.33; H NMR (400 MHz, Methanol-d4) δ 8.02 (d, J=1.7 Hz, 1H), 7.65-7.56 (m, 2H), 7.54-7.30 (m, 3H), 4.32 (s, 2H), 3.70 (s, 1H), 3.47 (t, J=4.9 Hz, 1H), 2.53-2.40 (m, 1H), 2.31-2.21 (m, 3H), 1.93-1.76 (m, 5H), 1.74-1.63 (m, 4H), 1.20-1.10 (m, 4H), 1.07-0.95 (m, 2H), 0.95-0.78 (m, 3H).

Example 3-11

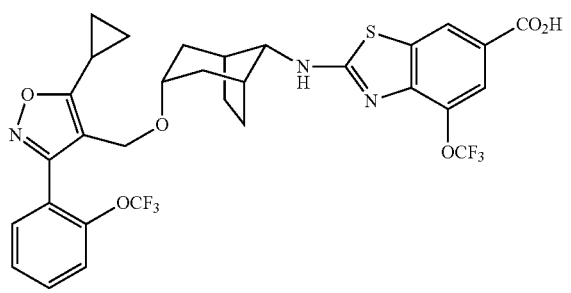

Example 3-11

Example 3-11 was prepared from compound (3f) following the same protocol as Example 3. LC/MS observed [M+H]$^+$, 684.40; H NMR (400 MHz, Methanol-d4) δ 8.22 (d, J=1.5 Hz, 1H), 7.78 (q, J=1.4 Hz, 1H), 7.65-7.56 (m, 2H), 7.55-7.28 (m, 2H), 4.32 (s, 2H), 3.82-3.69 (m, 1H), 3.52-3.44 (m, 1H), 2.29-2.20 (m, 3H), 1.93-1.78 (m, 5H), 1.75-1.64 (m, 4H), 1.18-1.11 (m, 5H).

Example 3-12

Example 3-12

Example 3-12 was prepared from compound (3f) following the same protocol as Example 3. LC/MS observed [M+H]$^+$, 595.20.

Example 3-13

Example 3-13

Example 3-13 was prepared from compound (3f) following the same protocol as Example 3. LC/MS observed [M+H]$^+$, 595.21; $^1$H NMR (500 MHz, DMSO-d6) δ 9.94 (s, 1H), 7.85-7.80 (m, 1H), 7.77 (t, J=7.8 Hz, 1H), 7.75-7.66 (m, 3H), 7.65-7.57 (m, 2H), 4.33 (s, 2H), 3.76 (d, J=5.5 Hz, 1H), 3.55-3.50 (m, 1H), 2.43-2.34 (m, 1H), 2.22 (s, 2H), 1.90-1.79 (m, 4H), 1.78-1.71 (m, 2H), 1.62-1.56 (m, 2H), 1.24-1.17 (m, 2H), 1.18-1.02 (m, 2H).

Example 4

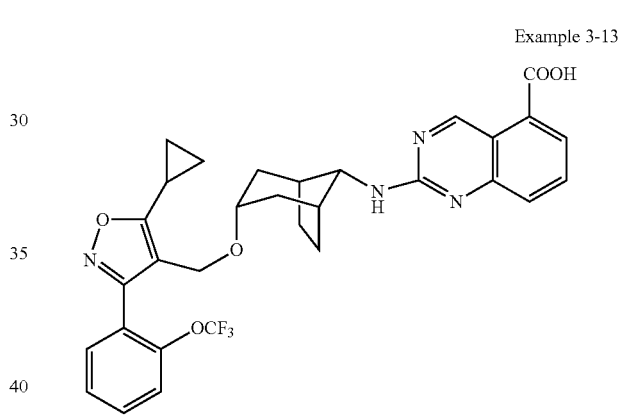

Example 4

Step 4a:

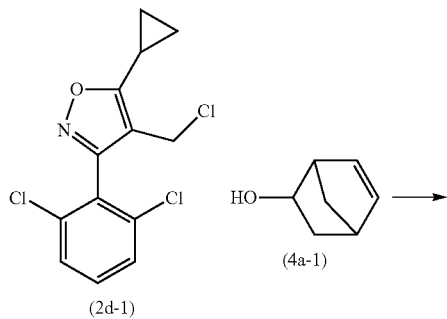

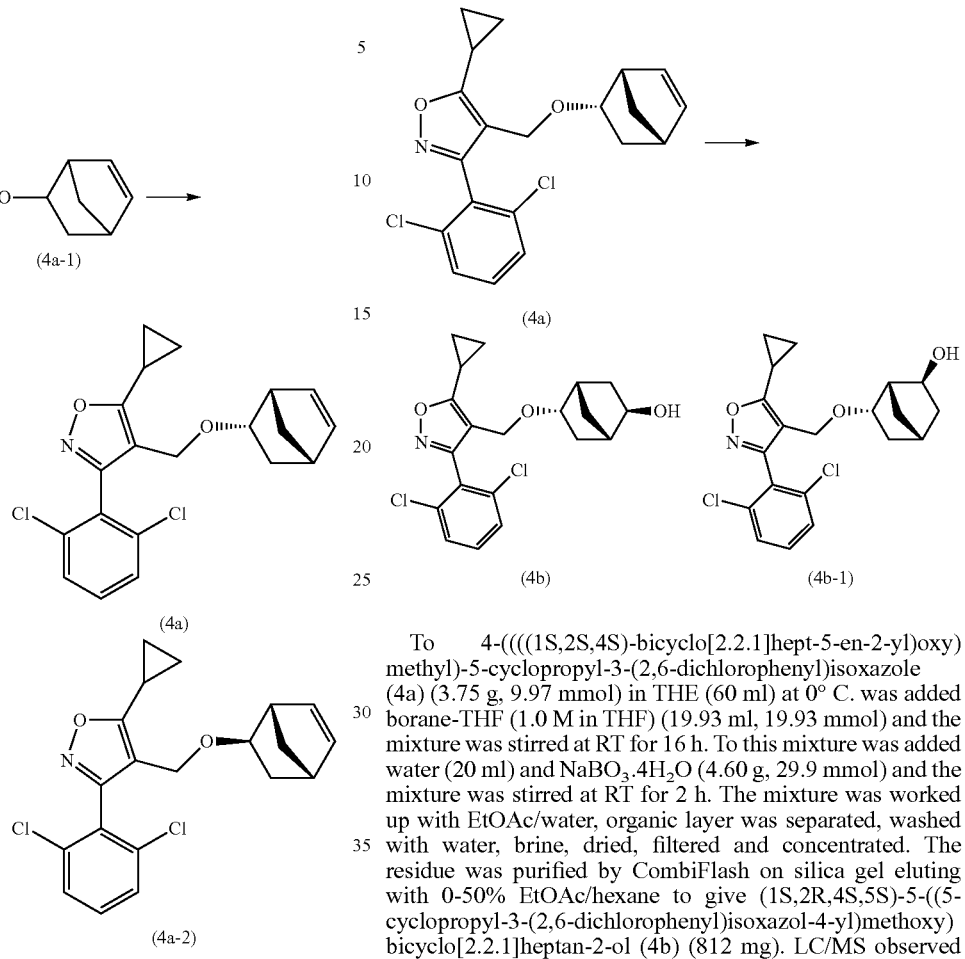

To bicyclo[2.2.1]hept-5-en-2-ol (2g, 18.16 mmol) (1:3.3 exo:endo isomers), 4-(chloromethyl)-5-cyclopropyl-3-(2,6-dichlorophenyl)isoxazole (6.59 g, 21.79 mmol) and 18-crown-6 (6.72 g, 25.4 mmol) in THF (100 ml) at 0° C. was added potassium tert-butoxide (2.85 g, 25.4 mmol) and the mixture was stirred at RT for 4 h, then quenched with NaHCO$_3$ solution, the mixture was diluted with EtOAc/water and organic layer was separated, washed with water, brine, dried, filtered and concentrated. The residue was purified by CombiFlash on Silica gel eluting with 0-30% EtOAc/hexane to give 4-((((1S,2S,4S)-bicyclo[2.2.1]hept-5-en-2-yl)oxy)methyl)-5-cyclopropyl-3-(2,6-dichlorophenyl)isoxazole (4a) (6.13 g). $^1$H NMR (400 MHz, Chloroform-d) δ 7.52-7.32 (m, 3H), 6.15 (dd, J=5.7, 3.0 Hz, 1H), 5.71 (dd, J=5.8, 2.9 Hz, 1H), 4.25 (q, J=12.1 Hz, 2H), 4.08 (dt, J=8.0, 3.2 Hz, 1H), 2.90 (s, 1H), 2.73 (s, 1H), 2.19-2.12 (m, 1H), 1.83 (ddd, J=11.9, 7.9, 3.8 Hz, 1H), 1.37 (ddt, J=8.1, 3.9, 2.0 Hz, 1H), 1.33-1.21 (m, 2H), 1.22-1.10 (m, 3H), 0.70 (dt, J=12.1, 3.2 Hz, 1H). The exo isomer 4-((((1S,2R,4S)-bicyclo[2.2.1]hept-5-en-2-yl)oxy)methyl)-5-cyclopropyl-3-(2,6-dichlorophenyl)isoxazole (4a-2) (2.01 g) was also collected. $^1$H NMR (400 MHz, Chloroform-d) δ 7.51-7.32 (m, 3H), 6.14 (dd, J=5.7, 2.9 Hz, 1H), 5.84 (dd, J=5.8, 3.2 Hz, 1H), 4.40-4.23 (m, 2H), 3.55-3.33 (m, 1H), 2.70 (b, 1H), 2.66 (b, 1H), 2.27-2.12 (m, 1H), 1.42 (dddd, J=10.6, 8.7, 6.2, 4.7 Hz, 3H), 1.32-1.24 (m, 2H), 1.21-1.08 (m, 3H).

Step 4b:

To 4-((((1S,2S,4S)-bicyclo[2.2.1]hept-5-en-2-yl)oxy)methyl)-5-cyclopropyl-3-(2,6-dichlorophenyl)isoxazole (4a) (3.75 g, 9.97 mmol) in THF (60 ml) at 0° C. was added borane-THF (1.0 M in THF) (19.93 ml, 19.93 mmol) and the mixture was stirred at RT for 16 h. To this mixture was added water (20 ml) and NaBO$_3$.4H$_2$O (4.60 g, 29.9 mmol) and the mixture was stirred at RT for 2 h. The mixture was worked up with EtOAc/water, organic layer was separated, washed with water, brine, dried, filtered and concentrated. The residue was purified by CombiFlash on silica gel eluting with 0-50% EtOAc/hexane to give (1S,2R,4S,5S)-5-((5-cyclopropyl-3-(2,6-dichlorophenyl)isoxazol-4-yl)methoxy)bicyclo[2.2.1]heptan-2-ol (4b) (812 mg). LC/MS observed [M+H], 394.12; $^1$H NMR (400 MHz, Chloroform-d) δ 7.47-7.33 (m, 3H), 4.35-4.14 (m, 2H), 4.05-3.95 (m, 1H), 3.76 (ddd, J=10.0, 4.4, 3.3 Hz, 1H), 2.33-2.25 (m, 1H), 2.23-2.08 (m, 3H), 1.74-1.51 (m, 3H), 1.34-1.23 (m, 3H), 1.19-1.08 (m, 3H), 0.62 (dt, J=12.8, 3.4 Hz, 1H). Compound (4b-1) (400 mg) is also obtained. $^1$H NMR (400 MHz, Chloroform-d) δ 7.56-7.32 (m, 3H), 4.29-4.05 (m, 2H), 3.74-3.52 (m, 2H), 2.33-2.22 (m, 1H), 2.13 (tt, J=8.4, 5.1 Hz, 1H), 2.01 (d, J=5.5 Hz, 1H), 1.93 (ddd, J=13.4, 6.9, 2.3 Hz, 1H), 1.74 (ddd, J=13.3, 9.9, 5.4 Hz, 1H), 1.59 (ddt, J=10.4, 3.7, 1.9 Hz, 2H), 1.34-1.24 (m, 2H), 1.22-1.09 (m, 3H), 0.99 (ddq, J=13.5, 4.6, 1.4 Hz, 1H), 0.54 (dt, J=13.4, 3.5 Hz, 1H).

Step 4c:

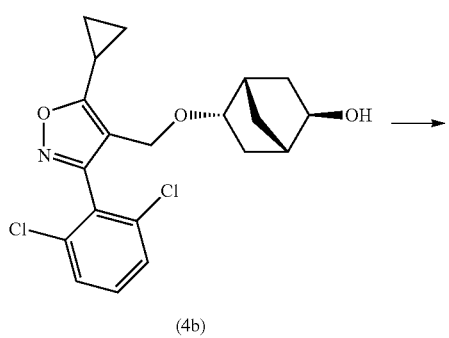

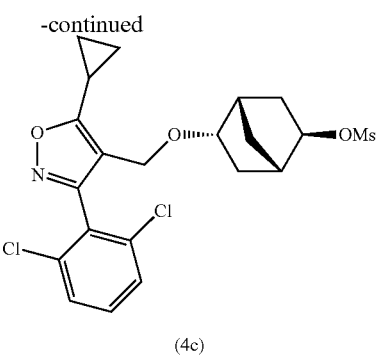

(4c)

To (1S,2R,4S,5S)-5-((5-cyclopropyl-3-(2,6-dichlorophenyl)isoxazol-4-yl)methoxy)-bicycle[2.2.1]heptan-2-ol (4b) (208 mg, 0.528 mmol) in DCM (6 ml) was added Et₃N (0.294 ml, 2.110 mmol) and MsCl (0.062 ml, 0.791 mmol). The mixture was stirred at RT for 10 min, and then concentrated. The residue was purified by CombiFlash on silica gel eluting with 0-40% EtOAc/hexane to give (1S,2R,4S,5S)-5-((5-cyclopropyl-3-(2,6-dichlorophenyl)isoxazol-4-yl)methoxy)bicyclo[2.2.1]heptan-2-yl methanesulfonate (4c) (185 mg, 0.392 mmol, 74.2% yield). $^1$H NMR (400 MHz, Chloroform-d) δ 7.52-7.29 (m, 3H), 4.39-4.34 (m, 1H), 4.26-4.06 (m, 2H), 3.67 (dtd, J=9.2, 3.8, 1.2 Hz, 1H), 2.97 (s, 3H), 2.37 (d, J=5.5 Hz, 1H), 2.34-2.28 (m, 1H), 2.11-1.96 (m, 2H), 1.78 (ddt, J=11.8, 9.1, 5.9 Hz, 1H), 1.62-1.53 (m, 1H), 1.45-1.30 (m, 1H), 1.30-1.20 (m, 3H), 1.16-1.06 (m, 2H), 0.54 (dt, J=13.8, 3.5 Hz, 1H).

Step 4d:

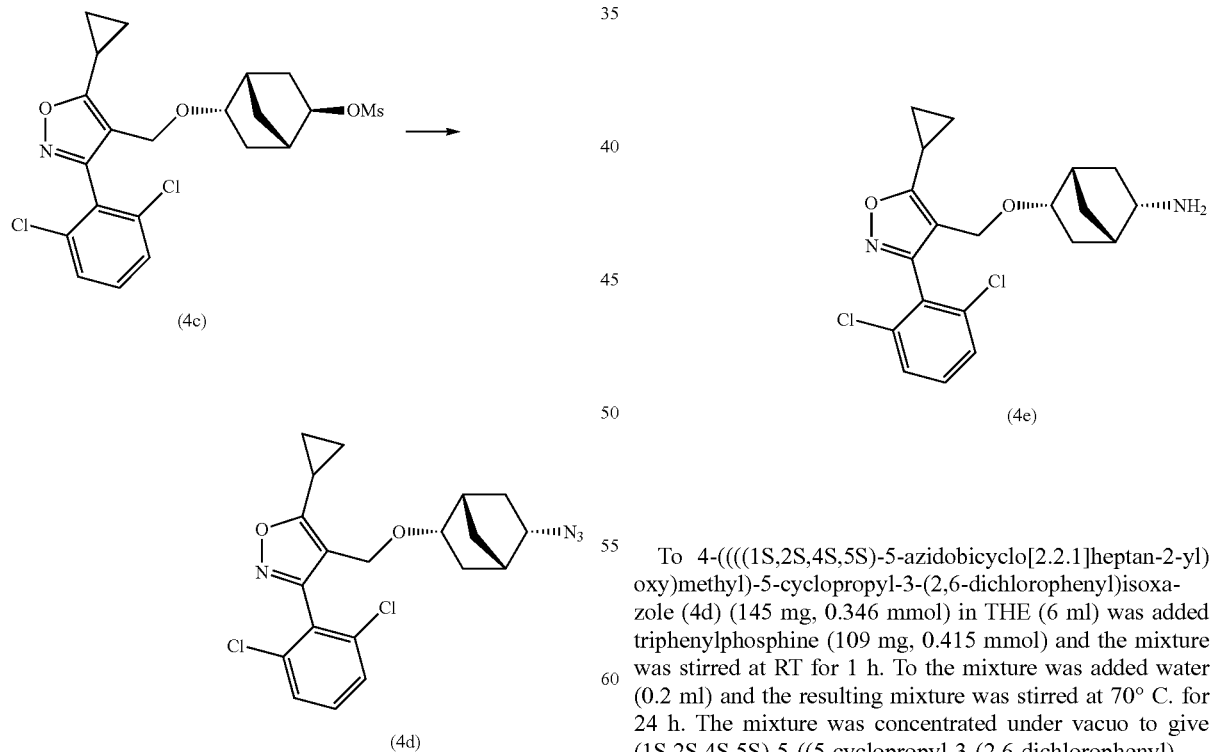

To (1S,2R,4S,5S)-5-((5-cyclopropyl-3-(2,6-dichlorophenyl)isoxazol-4-yl)methoxy)bicyclo[2.2.1]heptan-2-yl methanesulfonate (4c) (321 mg, 0.680 mmol) in DMF (6 ml) was added sodium azide (221 mg, 3.40 mmol) and the mixture was stirred at 90° C. for 16 h. The mixture was diluted with EtOAc, washed with water, brine, dried, filtered and concentrated. NaN3 (442 mg) was added and continue stirring at 110° C. for another 2 days. The residue was purified by CombiFlash on silica gel eluting with 0-60% EtOAc/Hexane to give 4-((((1S,2S,4S,5S)-5-azidobicyclo[2.2.1]heptan-2-yl)oxy)methyl)-5-cyclopropyl-3-(2,6-dichlorophenyl)isoxazole (4d) (145 mg, 50.9%). $^1$H NMR (400 MHz, Chloroform-d) δ 7.47-7.29 (m, 3H), 4.33-4.15 (m, 2H), 3.77 (dtd, J=10.3, 4.2, 1.5 Hz, 1H), 3.28 (d, J=6.8 Hz, 1H), 2.24 (t, J=4.7 Hz, 1H), 2.16-2.07 (m, 2H), 2.01-1.81 (m, 2H), 1.46-1.33 (m, 1H), 1.29-1.21 (m, 3H), 1.16-0.98 (m, 3H), 0.71 (dt, J=13.5, 3.6 Hz, 1H).

Step 4e:

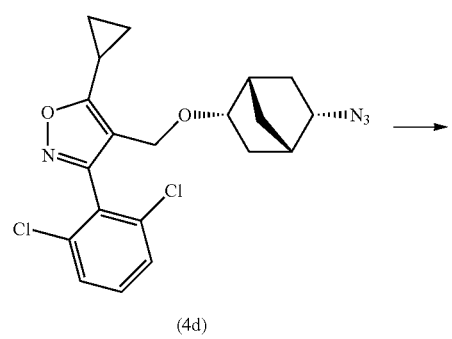

To 4-((((1S,2S,4S,5S)-5-azidobicyclo[2.2.1]heptan-2-yl)oxy)methyl)-5-cyclopropyl-3-(2,6-dichlorophenyl)isoxazole (4d) (145 mg, 0.346 mmol) in THF (6 ml) was added triphenylphosphine (109 mg, 0.415 mmol) and the mixture was stirred at RT for 1 h. To the mixture was added water (0.2 ml) and the resulting mixture was stirred at 70° C. for 24 h. The mixture was concentrated under vacuo to give (1S,2S,4S,5S)-5-((5-cyclopropyl-3-(2,6-dichlorophenyl)isoxazol-4-yl)methoxy)bicyclo[2.2.1]heptan-2-amine as crude product (260 mg). LC/MS observed [M+H]⁺, 393.13. This material was used directly to next step without further purification.

Step 4f:

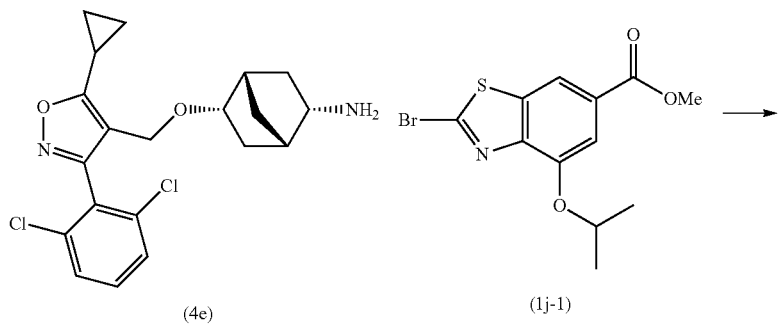

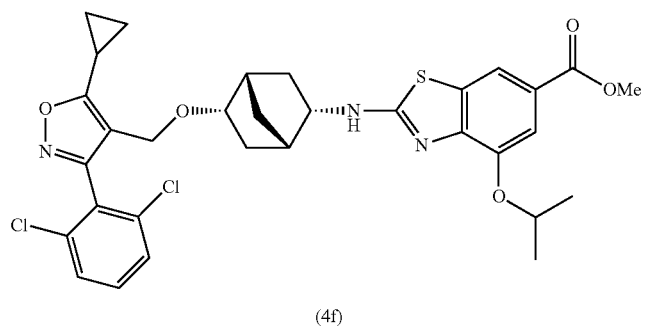

To crude (1S,2S,4S,5S)-5-((5-cyclopropyl-3-(2,6-dichlorophenyl)isoxazol-4-yl)methoxy)bicyclo[2.2.1]heptan-2-amine (4e) (0.178 mmol) and methyl 2-bromo-4-isopropoxybenzo[d]thiazole-6-carboxylate (1j-1) (88 mg, 0.267 mmol) in DMA (2 ml) was added cesium carbonate (174 mg, 0.534 mmol) and the mixture was stirred at 90° C. for 20 h. The mixture was diluted with EtOAc, washed with 1N HCl, water, and brine, dried, filtered and concentrated. The residue was purified by CombiFlash eluting with 0-70% EtOAc/hexane to give methyl 2-(((1S,2S,4S,5S)-5-((5-cyclopropyl-3-(2,6-dichlorophenyl)isoxazol-4-yl)methoxy)bicyclo[2.2.1]heptan-2-yl)amino)-4-isopropoxybenzo[d]thiazole-6-carboxylate (4f) (17.2 mg, 0.027 mmol, 15.0% yield). LC/MS observed [M+H]⁺, 642.15.

Step 4g:

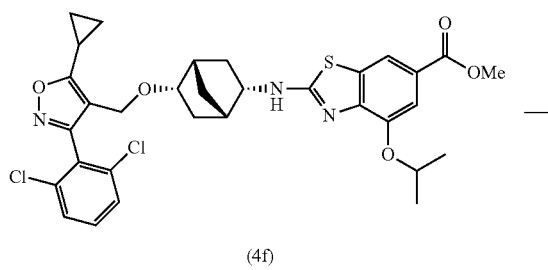

-continued

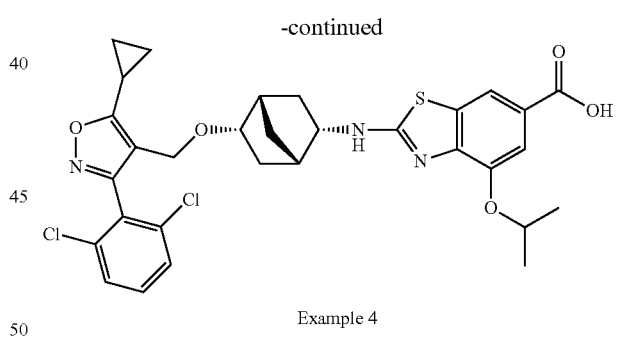

Example 4

To methyl 2-(((1S,2S,4S,5S)-5-((5-cyclopropyl-3-(2,6-dichlorophenyl)isoxazol-4-yl)methoxy)bicyclo[2.2.1]heptan-2-yl)amino)-4-isopropoxybenzo[d]thiazole-6-carboxylate (4f) (17.2 mg, 0.027 mmol) in THF (0.8 ml) was added NaOH (1 M) (0.054 ml, 0.054 mmol) and the mixture was stirred at RT for 16 h. To the mixture was added NaOH (1 M) (0.054 ml, 0.054 mmol) and the mixture was stirred at 45° C. for 6 h. The mixture was acidified by 1N HCl, and concentrated under vacuo. The residue was purified by HPLC eluting by 0.1% TFA in ACN/water to give 2-(((1S, 2S,4S,5S)-5-((5-cyclopropyl-3-(2,6-dichlorophenyl)isoxazol-4-yl)methoxy)bicyclo[2.2.1]heptan-2-yl)amino)-4-isopropoxybenzo[d]thiazole-6-carboxylic acid (Example 4) (14 mg, 83%). LC/MS observed [M+H], 628.14; ¹H NMR (400 MHz, Chloroform-d) δ 11.94 (s, 1H), 7.78 (s, 1H), 7.49 (s, 1H), 7.35-7.16 (m, 3H), 4.62 (p, J=6.1 Hz, 1H), 4.25-3.99

(m, 2H), 3.44-3.29 (m, 2H), 2.37 (d, J=4.3 Hz, 1H), 2.02-1.89 (m, 2H), 1.82 (ddd, J=14.2, 6.8, 2.2 Hz, 1H), 1.45-1.25 (m, 8H), 1.17-0.90 (m, 7H).

Example 5 and Example 6

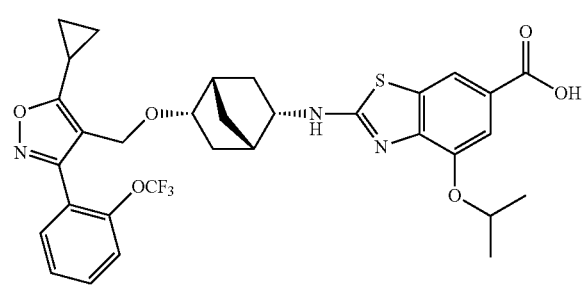

Example 5

Example 6

Step 5a:

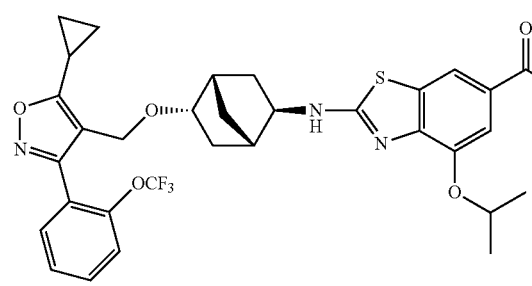

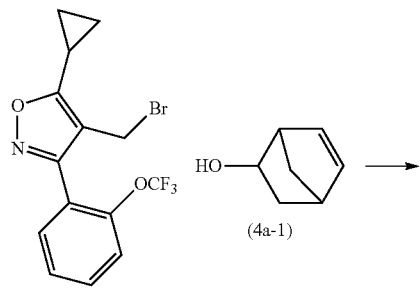

(5a)        (5a-2)

4-((((1S,2S,4S)-bicyclo[2.2.1]hept-5-en-2-yl)oxy)methyl)-5-cyclopropyl-3-(2-(trifluoromethoxy)phenyl)isoxazole (5a) was prepared with a similar procedure as in step 4a. ¹H NMR (400 MHz, Chloroform-d) δ 7.66-7.47 (m, 2H), 7.45-7.35 (m, 2H), 6.23 (dd, J=5.7, 3.0 Hz, 1H), 5.76 (dd, J=5.8, 2.9 Hz, 1H), 4.42-4.22 (m, 2H), 4.10 (dt, J=7.9, 3.2 Hz, 1H), 2.96 (b, 1H), 2.76 (b, 1H), 2.15 (tt, J=8.4, 5.2 Hz, 1H), 1.87 (ddd, J=11.9, 8.0, 3.8 Hz, 1H), 1.40 (ddt, J=8.7, 3.8, 2.0 Hz, 1H), 1.27-1.21 (m, 2H), 1.21-1.16 (m, 1H), 1.15-1.07 (m, 2H), 0.80 (dt, J=12.0, 3.3 Hz, 1H).

4-((((1S,2R,4S)-bicyclo[2.2.1]hept-5-en-2-yl)oxy)methyl)-5-cyclopropyl-3-(2-(trifluoromethoxy)phenyl)isoxazole (5a-2) was also isolated. ¹H NMR (400 MHz, Chloroform-d) δ 7.59-7.38 (m, 2H), 7.30 (ddt, J=7.6, 4.4, 1.3 Hz, 2H), 6.07 (dd, J=5.7, 2.8 Hz, 1H), 5.76 (dd, J=5.8, 3.2 Hz, 1H), 4.32-4.16 (m, 2H), 3.48-3.30 (m, 1H), 2.66 (t, J=4.4 Hz, 2H), 2.07 (tt, J=8.5, 5.1 Hz, 1H), 1.45-1.31 (m, 3H), 1.25-1.09 (m, 4H), 1.09-0.91 (m, 2H).

Step 5b:

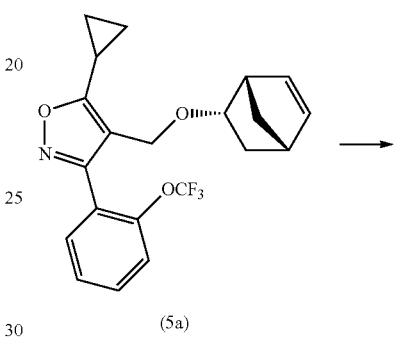

(5a)

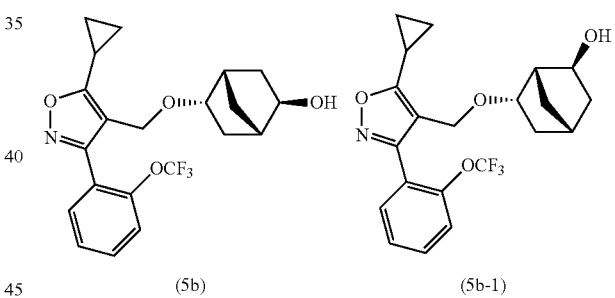

(5b)        (5b-1)

(1S,2R,4S,5S)-5-((5-cyclopropyl-3-(2-(trifluoromethoxy)phenyl)isoxazol-4-yl)methoxy)bicyclo[2.2.1]heptan-2-ol (5b) was prepared with a similar procedure as in step 4b. ¹H NMR (500 MHz, Chloroform-d) δ 7.56-7.40 (m, 2H), 7.39-7.27 (m, 2H), 4.21-4.03 (m, 2H), 3.67-3.54 (m, 2H), 2.23-2.16 (m, 1H), 2.04 (tt, J=8.5, 5.1 Hz, 1H), 1.99-1.94 (m, 1H), 1.91 (ddd, J=13.4, 6.9, 2.4 Hz, 1H), 1.68 (ddd, J=13.4, 9.9, 5.4 Hz, 1H), 1.52 (ddt, J=10.5, 3.5, 1.8 Hz, 1H), 1.17-1.13 (m, 2H), 1.11-1.06 (m, 1H), 1.05-1.00 (m, 2H), 0.97-0.91 (m, 1H), 0.56 (dt, J=13.4, 3.6 Hz, 1H).

(1S,2S,4R,6S)-6-((5-cyclopropyl-3-(2-(trifluoromethoxy)phenyl)isoxazol-4-yl)methoxy)bicyclo[2.2.1]heptan-2-ol (5b-1) is also obtained. ¹H NMR (500 MHz, Chloroform-d) δ 7.57-7.41 (m, 2H), 7.32 (td, J=7.7, 1.1 Hz, 2H), 4.33-4.11 (m, 2H), 3.99-3.91 (m, 1H), 3.68 (ddd, J=10.0, 4.4, 3.4 Hz, 1H), 2.22 (d, J=4.4 Hz, 1H), 2.11 (q, J=3.2 Hz, 1H), 2.04 (tt, J=8.5, 5.1 Hz, 1H), 1.67-1.59 (m, 2H), 1.57 (b, 1H), 1.49 (ddt, J=10.4, 3.6, 1.8 Hz, 1H), 1.29-0.95 (m, 6H), 0.66 (dt, J=12.9, 3.4 Hz, 1H).

Step 5c:

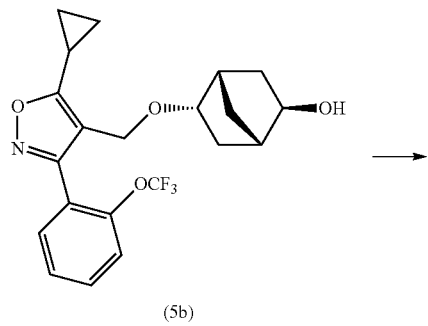

(5b)

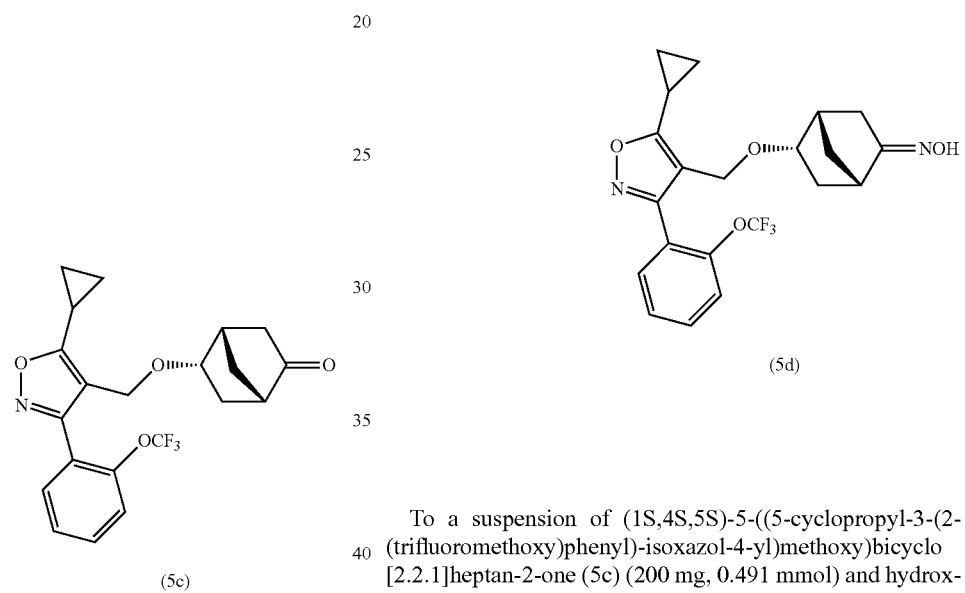

(5c)

To (1S,2R,4S,5S)-5-((5-cyclopropyl-3-(2-(trifluoromethoxy)phenyl)isoxazol-4-yl)methoxy)bicyclo[2.2.1]heptan-2-ol (5b) (201 mg, 0.491 mmol) n in DCM (3 ml) was added DMP (312 mg, 0.736 mmol) and the mixture was stirred at RT for 5 h. To the reaction mixture was added sodium bicarbonate (124 mg, 1.473 mmol) and another portion of DMP (312 mg, 0.736 mmol) and the mixture was stirred at RT for 16 h. The mixture was diluted with EtOAc, washed with NaHCO$_3$, water, and brine, dried, filtered and concentrated. The residue was dissolved in DCM and filtered through celite and the filtrate was collected and concentrated to give (1S,4S,5S)-5-((5-cyclopropyl-3-(2-(trifluoromethoxy)phenyl)isoxazol-4-yl)methoxy)bicyclo[2.2.1]heptan-2-one (5c) (227 mg, 0.557 mmol, 113% yield) as crude product. LC/MS observed [M+H], 408.16; $^1$H NMR (400 MHz, Chloroform-d) δ 7.49-7.41 (m, 2H), 7.37-7.26 (m, 2H), 4.31-4.14 (m, 2H), 3.97-3.88 (m, 1H), 2.59 (td, J=4.4, 1.9 Hz, 1H), 2.40 (d, J=5.2 Hz, 1H), 2.08 (dd, J=18.0, 4.2 Hz, 1H), 2.05-1.94 (m, 2H), 1.77-1.67 (m, 1H), 1.63 (ddt, J=10.9, 3.4, 1.8 Hz, 1H), 1.51 (ddt, J=10.9, 3.5, 1.4 Hz, 1H), 1.17-1.10 (m, 3H), 1.03 (dt, J=8.4, 3.4 Hz, 2H).

Step 5d:

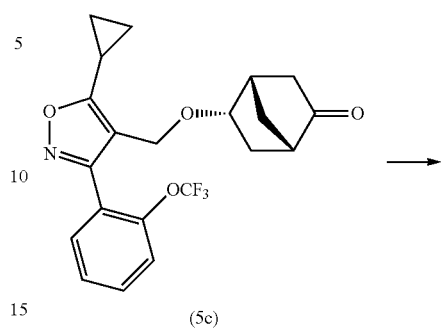

(5c)

(5d)

To a suspension of (1S,4S,5S)-5-((5-cyclopropyl-3-(2-(trifluoromethoxy)phenyl)-isoxazol-4-yl)methoxy)bicyclo[2.2.1]heptan-2-one (5c) (200 mg, 0.491 mmol) and hydroxylamine hydrochloride (68.2 mg, 0.982 mmol) in ethanol (3 ml) was added NaOH (1N) (1.178 ml, 1.178 mmol) and the mixture was stirred at 80° C. for 16 h. The mixture was concentrated, diluted with EtOAc, washed with water, brine, dried, filtered and concentrated to give (1S,4S,5S,E)-5-((5-cyclopropyl-3-(2-(trifluoromethoxy)phenyl)isoxazol-4-yl)methoxy)bicyclo[2.2.1]heptan-2-one oxime (5d) (235 mg). LC/MS observed [M+H], 423.16.

Step 5e:

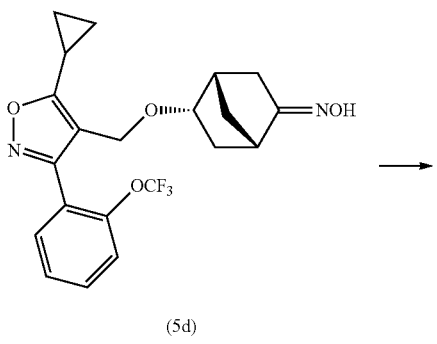

(5d)

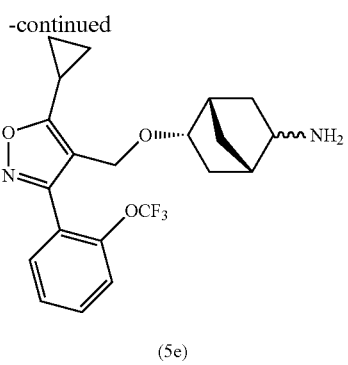

(5e)

To a solution of (1S,4S,5S,E)-5-((5-cyclopropyl-3-(2-(trifluoromethoxy)phenyl)isoxazol-4-yl)methoxy)bicyclo[2.2.1]heptan-2-one oxime (0.207 g, 0.491 mmol) in MeOH (8 ml) was added ammonium acetate (0.757 g, 9.82 mmol), sodium cyanoborohydride (0.185 g, 2.95 mmol) and then titanium(III) chloride (20% in 3% HCl) (1.270 ml, 1.964 mmol) dropwise over 3 min. The resulted black mixture was stirred at RT for 4 h, TLC showed SM mostly consumed. The mixture was concentrated to remove most of the volatile and then diluted with EtOAc, neutralized with NaOH (1N), a lot of precipitate. The mixture was filtered through celite and the organic layer was collected, washed with water, brine, dried, filtered and concentrated to give A mixture of (1S,4S,5S)-5-((5-cyclopropyl-3-(2-(trifluoromethoxy)phenyl)isoxazol-4-yl)methoxy)bicyclo[2.2.1]heptan-2-amine (5e) (201 mg) as white foam. LC/MS observed [M+H], 409.18.
Step 5f:

A mixture of (1S,4S,5S)-5-((5-cyclopropyl-3-(2-(trifluoromethoxy)phenyl)isoxazol-4-yl)methoxy)bicyclo[2.2.1]heptan-2-amine (5e) (30.0 mg, 0.073 mmol), copper(I) iodide (5.60 mg, 0.029 mmol), 2-((2,6-dimethylphenyl)amino)-2-oxoacetic acid (11.35 mg, 0.059 mmol) and potassium phosphate (31.2 mg, 0.147 mmol) was degassed than added DMSO (0.5 ml). The mixture was stirred at 75° C. for 18 h. The mixture was diluted with EtOAc, washed with water, brine, dried, filtered and concentrated. The residue was purified by CombiFlash on silica gel eluting with 0 to 80% EtOAc/hexane to give methyl 2-(((1S,2S,4S,5S)-5-((5-cyclopropyl-3-(2-(trifluoromethoxy)phenyl)isoxazol-4-yl)methoxy)bicyclo[2.2.1]heptan-2-yl)amino)-4-isopropoxybenzo[d]thiazole-6-carboxylate (5f) (22 mg). LC/MS observed [M+H], 658.21; $^1$H NMR (400 MHz, Chloroform-d) δ 7.95 (d, J=1.4 Hz, 1H), 7.64-7.47 (m, 4H), 7.44-7.36 (m, 2H), 5.90-5.76 (m, 1H), 4.84 (p, J=6.1 Hz, 1H), 4.31-4.23 (m, 2H), 3.93 (s, 3H), 3.87-3.77 (m, 3H), 2.58-2.51 (m, 1H), 2.31-2.26 (m, 1H), 2.14 (tt, J=8.3, 5.2 Hz, 1H), 1.94-1.79 (m, 1H), 1.77-1.60 (m, 3H), 1.47 (dd, J=6.1, 1.6 Hz, 6H), 1.32-1.23 (m, 6H), 1.20-1.09 (m, 2H).

Methyl 2-(((1S,2R,4S,5S)-5-((5-cyclopropyl-3-(2-(trifluoromethoxy)phenyl)isoxazol-4-yl)methoxy)bicyclo[2.2.1]heptan-2-yl)amino)-4-isopropoxybenzo[d]thiazole-6-carboxylate (5f-1) (10.8 mg) was also isolated. LC/MS observed [M+H], 658.21.

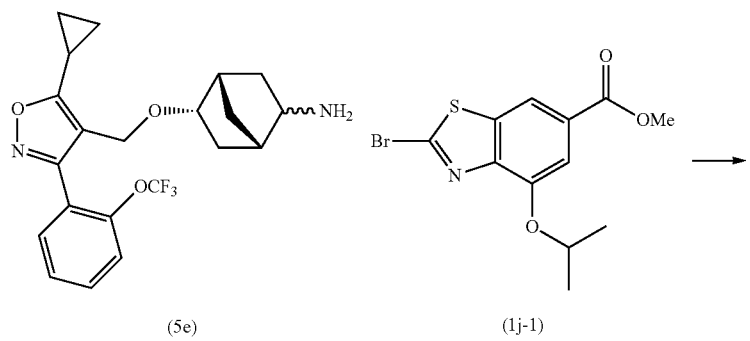

(5e) (1j-1)

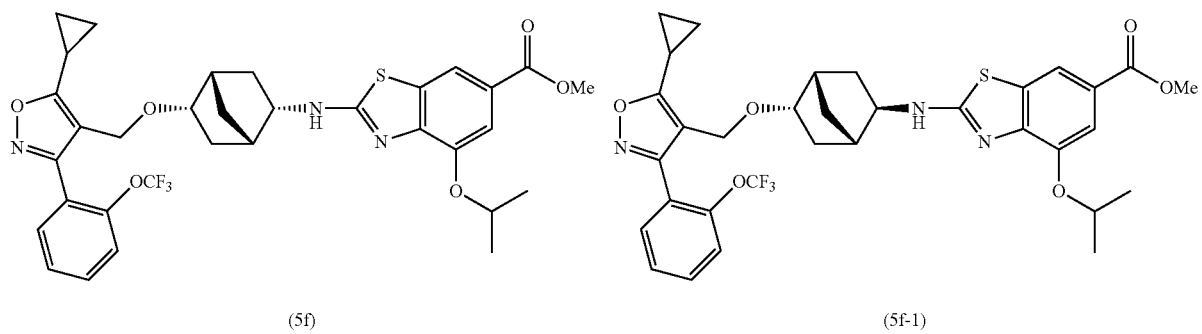

(5f) (5f-1)

Step 5g:

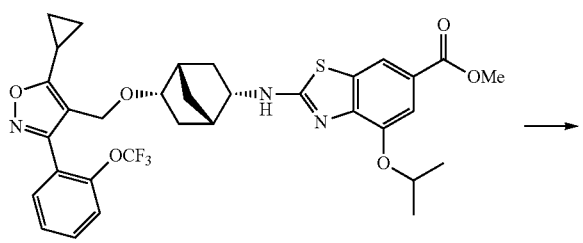

(5f)

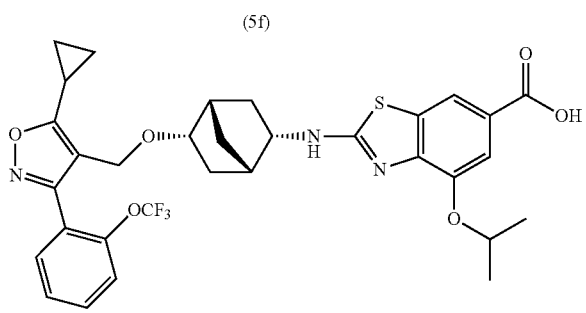

Example 5

Example 5 was prepared following a similar procedure as in Step 4g. LC/MS observed [M+H], 644.20; ¹H NMR (500 MHz, Chloroform-d) δ 7.85 (s, 1H), 7.51 (dd, J=7.9, 1.7 Hz, 2H), 7.37 (td, J=8.0, 7.5, 1.8 Hz, 1H), 7.27 (d, J=7.7 Hz, 2H), 4.72 (h, J=6.1 Hz, 1H), 4.20 (q, J=12.0 Hz, 2H), 3.72 (ddt, J=31.4, 10.2, 4.1 Hz, 2H), 2.46 (d, J=4.4 Hz, 1H), 2.21 (d, J=4.4 Hz, 1H), 2.08 (tt, J=8.5, 5.1 Hz, 1H), 1.78 (dq, J=12.3, 4.6 Hz, 1H), 1.59 (td, J=12.2, 10.1, 4.5 Hz, 1H), 1.53-1.33 (m, 10H), 1.10 (q, J=3.9 Hz, 2H), 1.01-0.88 (m, 2H).

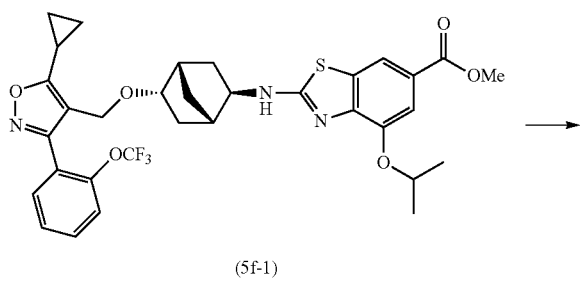

(5f-1)

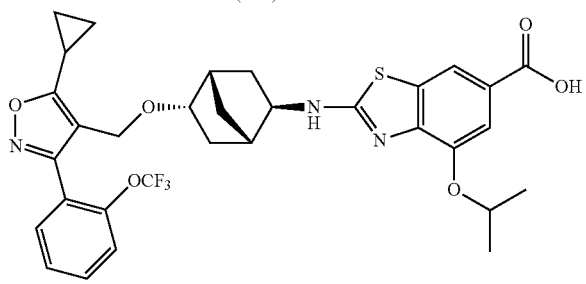

Example 6

Example 6 was prepared following a similar procedure as in Step 4g. LC/MS observed [M+H], 644.0; ¹H NMR (500 MHz, Chloroform-d) δ 7.85 (s, 1H), 7.51 (dd, J=7.9, 1.7 Hz, 2H), 7.37 (td, J=8.0, 7.5, 1.8 Hz, 1H), 7.27 (d, J=7.7 Hz, 2H), 4.72 (h, J=6.1 Hz, 1H), 4.20 (q, J=12.0 Hz, 2H), 3.72 (ddt, J=31.4, 10.2, 4.1 Hz, 2H), 2.46 (d, J=4.4 Hz, 1H), 2.21 (d, J=4.4 Hz, 1H), 2.08 (tt, J=8.5, 5.1 Hz, 1H), 1.78 (dq, J=12.3, 4.6 Hz, 1H), 1.59 (td, J=12.2, 10.1, 4.5 Hz, 1H), 1.53-1.33 (m, 10H), 1.10 (q, J=3.9 Hz, 2H), 1.01-0.88 (m, 2H).

Example 7

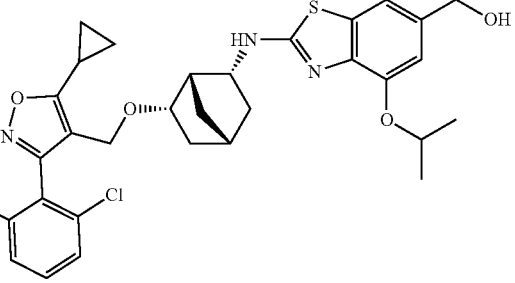

Example 7

Example 7 was prepared from (4b-1) following a similar protocols as Example 5. LC/MS observed [M+H], 628.14; ¹H NMR (400 MHz, Chloroform-d) δ 10.51 (b, 1H), 7.79 (s, 1H), 7.51 (s, 1H), 7.23-7.11 (m, 2H), 7.02 (t, J=8.1 Hz, 1H), 4.92-4.55 (m, 1H), 4.36 (d, J=13.7 Hz, 1H), 3.95 (d, J=8.9 Hz, 1H), 3.71 (s, 1H), 2.50 (s, 1H), 2.24 (d, J=18.1 Hz, 2H), 2.11 (s, 1H), 1.72 (q, J=12.5, 11.9 Hz, 1H), 1.46-1.27 (m, 7H), 1.27-1.09 (m, 4H), 1.01 (dd, J=8.2, 3.5 Hz, 2H).

Example 8

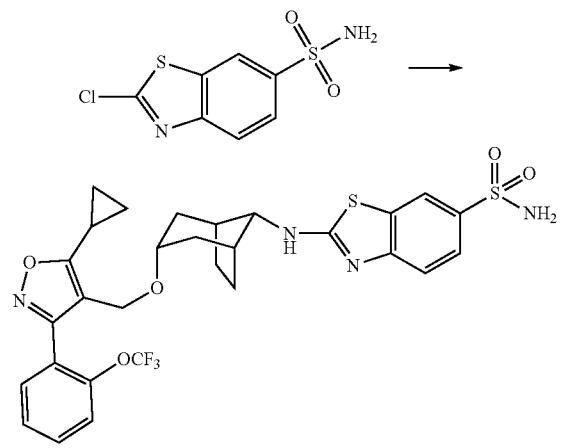

Example 8

To a mixture of (1R,3r,5S,8s)-3-((5-cyclopropyl-3-(2-(trifluoromethoxy)phenyl)isoxazol-4-yl)methoxy)bicyclo[3.2.1]octan-8-amine (3f) (12 mg, 0.028 mmol), 2-((2,6-dimethylphenyl)amino)-2-oxoacetic acid (8.23 mg, 0.043 mmol), 2-chlorobenzo[d]thiazole-6-sulfonamide (14.13 mg, 0.057 mmol) in DMSO (0.568 ml), was added copper(I) iodide (2.70 mg, 0.014 mmol) and potassium phosphate (12.06 mg, 0.057 mmol) under $N_2$. The resulting mixture was stirred at 75° C. for 16 h, and the mixture was diluted with EtOAc, washed with water, brine, dried, filtered and concentrated. The residue was purified by CombiFlash eluting with 0-50% EtOAc/hexane to give 2-(((1R,3r,5S,8s)-3-((5-cyclopropyl-3-(2-(trifluoromethoxy)phenyl)isoxazol-4-yl)methoxy)bicyclo[3.2.1]octan-8-yl)amino)benzo[d]thiazole-6-sulfonamide (Example 8) (13 mg, 0.020 mmol, 72.1% yield) as a white solid. LC/MS observed [M+H], 635.40; $^1$H NMR (400 MHz, Methanol-d4) δ 8.09 (d, J=1.9 Hz, 1H), 7.76 (dd, J=8.5, 2.0 Hz, 1H), 7.64-7.56 (m, 2H), 7.51-7.44 (m, 3H), 4.32 (s, 2H), 3.71 (s, 1H), 3.55-3.44 (m, 1H), 2.33-2.17 (m, 3H), 1.91-1.79 (m, 4H), 1.76-1.64 (m, 4H), 1.18-1.12 (m, 4H).

Example 8-2

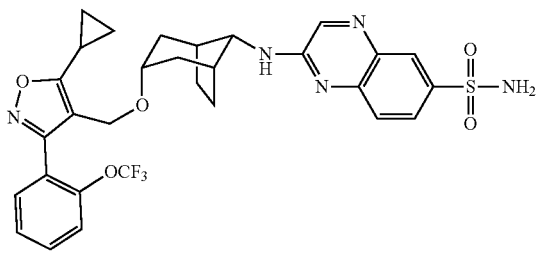

Example 8-2

Example 8-2 was prepared from compound (3f) following the same protocol as Example 8. LC/MS observed [M+H]+, 630.44; H NMR (400 MHz, Chloroform-d) δ 8.39 (d, J=2.2 Hz, 1H), 8.20 (s, 1H), 7.96 (dd, J=8.8, 2.2 Hz, 1H), 7.68 (d, J=8.8 Hz, 1H), 7.55 (dd, J=7.8, 1.8 Hz, 1H), 7.52-7.45 (m, 1H), 7.38-7.34 (m, 2H), 4.98 (s, 1H), 4.92 (s, 2H), 4.27 (s, 2H), 3.91 (d, J=6.4 Hz, 1H), 3.48 (t, J=5.0 Hz, 1H), 2.26-2.18 (m, 2H), 2.17-2.06 (m, 1H), 1.94-1.74 (m, 6H), 1.68-1.60 (m, 2H), 1.23-1.19 (m, 2H), 1.13-1.04 (m, 2H).

Example 8-3

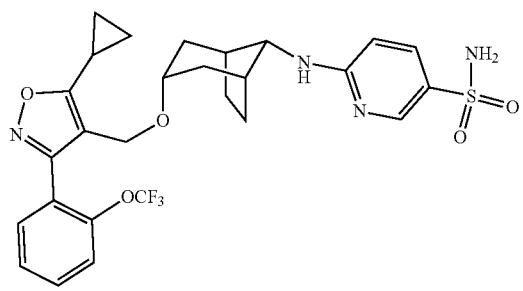

Example 8-3

Example 8-3 was prepared from compound (3f) following the same protocol as Example 8. LC/MS observed [M+H]+, 579.19; H NMR (400 MHz, Chloroform-d) δ 8.56 (d, J=2.4 Hz, 1H), 7.85 (dd, J=9.0, 2.5 Hz, 1H), 7.60-7.48 (m, 2H), 7.42-7.36 (m, 2H), 6.38 (d, J=9.0 Hz, 1H), 4.80 (s, 2H), 4.29 (s, 2H), 3.55-3.45 (m, 2H), 2.21-2.12 (m, 3H), 1.94-1.86 (m, 2H), 1.84-1.72 (m, 2H), 1.64 (s, 4H), 1.30-1.22 (m, 2H), 1.19-1.07 (m, 2H).

Example 8-4

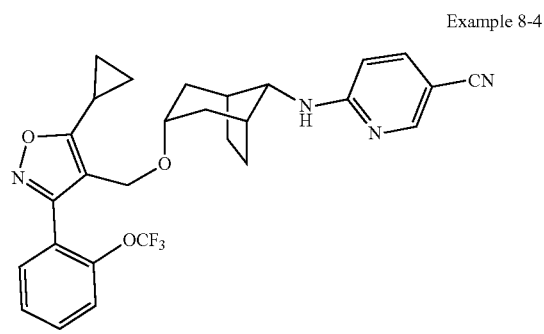 [SMILES: N#Cc1ccc(NC2C3CCC2CC(OCc2c(-c4ccccc4OC(F)(F)F)noc2C2CC2)C3)nc1]

Example 8-4

Example 8-4 was prepared from compound (3f) following the same protocol as Example 8. LC/MS observed [M+H]+, 525.21; H NMR (400 MHz, Acetonitrile-d3) δ 8.29 (dd, J=2.3, 0.8 Hz, 1H), 7.63-7.52 (m, 3H), 7.50-7.45 (m, 2H), 6.47 (dd, J=8.8, 0.8 Hz, 1H), 5.69 (d, J=6.1 Hz, 1H), 4.27 (s, 2H), 3.71-3.60 (m, 1H), 3.45 (tt, J=5.1, 1.4 Hz, 1H), 2.27-2.17 (m, 1H), 2.10-2.05 (m, 2H), 1.87-1.71 (m, 4H), 1.69-1.58 (m, 4H), 1.15-1.09 (m, 4H).

Example 8-5

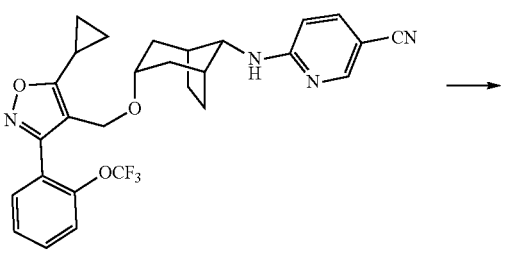

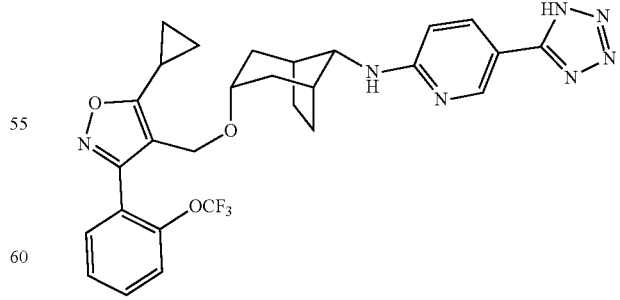

Example 8-5

To a suspension of 6-((((1R,3r,5S,8s)-3-((5-cyclopropyl-3-(2-(trifluoromethoxy)phenyl)isoxazol-4-yl)methoxy)bicyclo[3.2.1]octan-8-yl)amino)nicotinonitrile (Example 8-4)

(10 mg, 0.019 mmol) in Toluene (0.38 ml), was added TMSN$_3$ (5.06 μl, 0.038 mmol) and Bu$_2$SnO$_2$ (5.22 mg, 0.021 mmol). The reaction was allowed to stir at 100° C. for 24 h and then reaction was quenched with aq. NH$_4$Cl. The mixture was extracted with EtOAc and the organic layer was separated, and concentrated. The residue was purified by CombiFlash on silica gel eluting with 0-7% MeOH in DCM to afford N-((1R,3r,5S,8s)-3-((5-cyclopropyl-3-(2-(trifluoromethoxy)phenyl)isoxazol-4-yl)methoxy)bicyclo[3.2.1]octan-8-yl)-5-(1H-tetrazol-5-yl)pyridin-2-amine (Example 8-5) (6 mg) as a white solid. LC/MS observed [M+H]$^+$, 568.0; $^1$H NMR (400 MHz, Chloroform-d) δ 8.94 (s, 1H), 8.43 (d, J=9.1 Hz, 1H), 7.59-7.41 (m, 2H), 7.41-7.28 (m, 2H), 6.68 (d, J=9.2 Hz, 1H), 4.26 (s, 2H), 3.46 (s, 2H), 2.23 (s, 2H), 2.17-2.04 (m, 1H), 1.95-1.56 (m, 8H), 1.28-1.14 (m, 2H), 1.09 (dt, J=8.6, 3.4 Hz, 2H).

Example 8-6

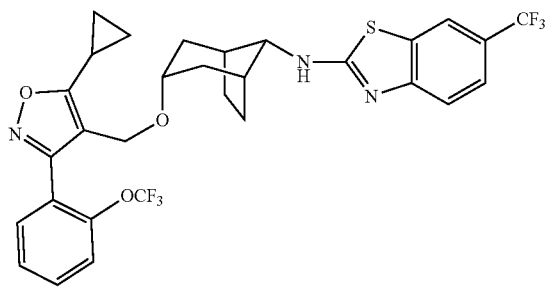

Example 8-6

Example 8-6 was prepared from compound (3f) following the same protocol as Example 8. LC/MS observed [M+H]$^+$, 624.18; $^1$H NMR (400 MHz, Chloroform-d) δ 7.73-7.68 (m, 1H), 7.63 (d, J=8.2 Hz, 1H), 7.53 (dd, J=7.8, 1.8 Hz, 1H), 7.51-7.45 (m, 1H), 7.38-7.32 (m, 2H), 7.31-7.26 (m, 1H), 5.37-5.22 (m, 1H), 4.25 (s, 2H), 3.51 (d, J=5.2 Hz, 1H), 3.44 (t, J=4.9 Hz, 1H), 2.30-2.18 (m, 2H), 2.16-2.05 (m, 1H), 1.94-1.80 (m, 2H), 1.80-1.55 (m, 6H), 1.23-1.18 (m, 2H), 1.11-1.05 (m, 2H).

Example 8-7

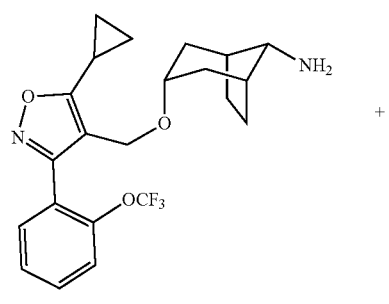

3f

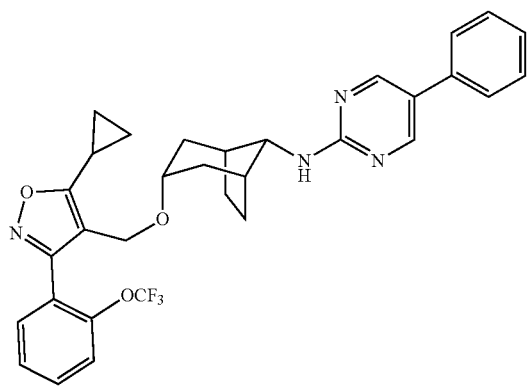

Example 8-7

To (1R,3r,5S,8s)-3-((5-cyclopropyl-3-(2-(trifluoromethoxy)phenyl)isoxazol-4-yl)methoxy)bicyclo[3.2.1]octan-8-amine (3f) (0.197 ml, 0.047 mmol, 0.24 M in THF) in a microwave vial was added Hunig's base (0.025 ml, 0.142 mmol), 2-chloro-5-phenylpyrimidine (9.93 mg, 0.052 mmol) and NMP (0.2 ml). The resulting mixture was heated in microwave reactor at 170° C. for 20 min. The mixture was cooled to RT, quenched with water, and extracted with MTBE. The organic layer was loaded on silica gel and eluted with 0-50% EtOAc/hexane to provide N-((1R,3r,5S,8s)-3-((5-cyclopropyl-3-(2-(trifluoromethoxy)phenyl)isoxazol-4-yl)methoxy)bicyclo[3.2.1]octan-8-yl)-5-phenylpyrimidin-2-amine (Example 8-7) (6.5 mg, 0.011 mmol, 23.81% yield). LC/MS observed [M+H]$^+$, 577.2.

Example 8-8

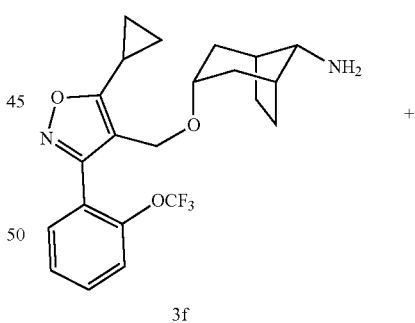

3f

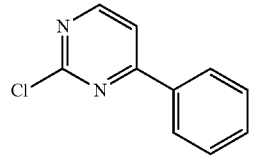

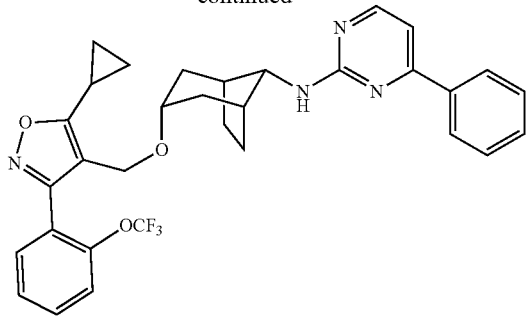

Example 8-8

Example 8-8 was prepared from compound (3f) following the same protocol as Example 8-7. LC/MS observed [M+H]+, 577.2.

Example 9

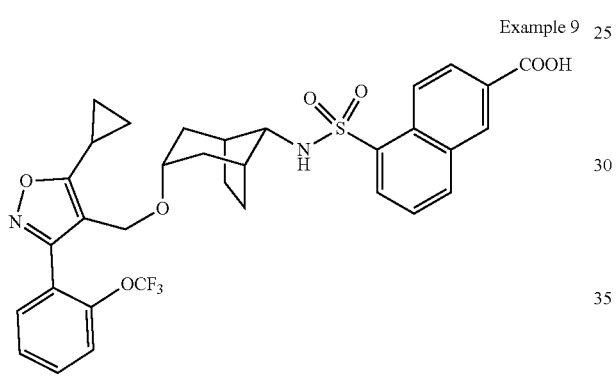

Example 9

Step 9a:

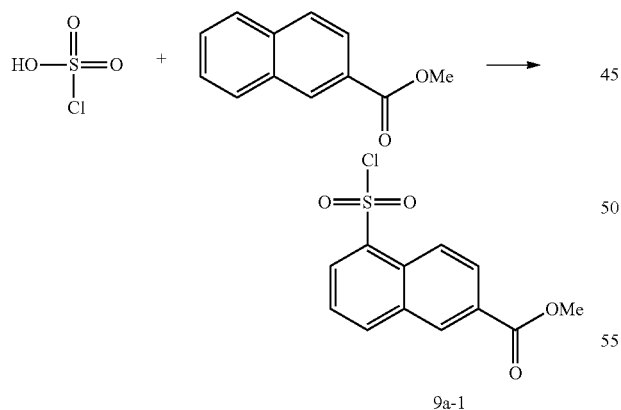

To an oven-dried vial charged with chlorosulfonic acid (4.50 ml, 67.1 mmol) was added methyl 2-naphthoate (2.5 g, 13.43 mmol) portionwise at 0° C. The resulting mixture was slowly warmed to RT and stirred overnight. The mixture was carefully poured on ice, and extracted with DCM. The organic layer was washed with brine, and dried over Na$_2$SO$_4$, and concentrated in vacuo to give methyl 5-(chlorosulfonyl)-2-naphthoate (9a-1) (1.9 g, 6.67 mmol, 49.7% yield) as an off-white solid. $^1$H NMR (400 MHz, Chloroform-d) δ 8.88 (d, J=9.0 Hz, 1H), 8.77 (d, J=1.8 Hz, 1H), 8.50 (dd, J=7.6, 1.2 Hz, 1H), 8.45-8.26 (m, 2H), 7.72 (t, J=7.9 Hz, 1H), 4.06 (s, 3H).

Step 9b:

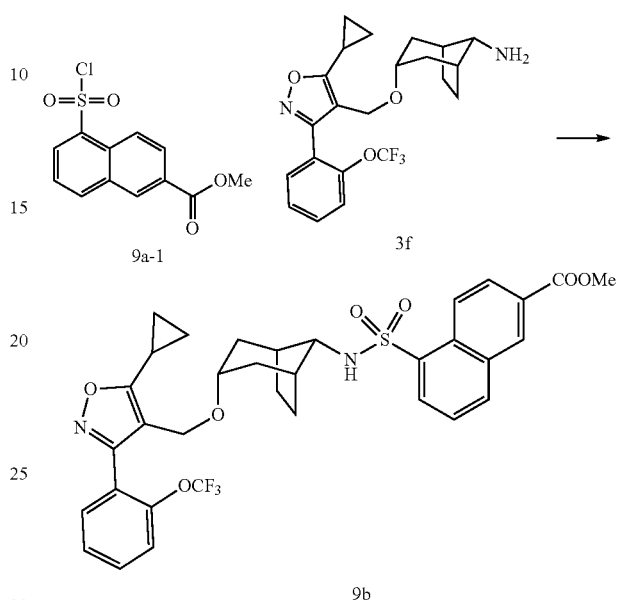

To (1R,3r,5S,8s)-3-((5-cyclopropyl-3-(2-(trifluoromethoxy)phenyl)isoxazol-4-yl)methoxy)bicyclo[3.2.1]octan-8-amine (3f) (60 mg, 0.142 mmol) in CH$_2$Cl$_2$ (0.710 ml) was added methyl 5-(chlorosulfonyl)-2-naphthoate (9a-1) (44.5 mg, 0.156 mmol) and DBU (21.41 μl, 0.142 mmol). The mixture was stirred at RT for 1 h, quenched with sat. NaHCO$_3$, and extracted with DCM. The organic layer was dried over Na$_2$SO$_4$ and concentrated in vacuo. The residue was purified on silica gel eluting with 0-50% EtOAc/hexane to provide methyl 5-(N-((1R,3r,5S,8s)-3-((5-cyclopropyl-3-(2-(trifluoromethoxy)phenyl)isoxazol-4-yl)methoxy)bicyclo[3.2.1]octan-8-yl)sulfamoyl)-2-naphthoate (9a) (86 mg, 0.128 mmol, 90% yield). $^1$H NMR (400 MHz, Chloroform-d) δ 8.74-8.64 (m, 2H), 8.38 (dd, J=7.3, 1.2 Hz, 1H), 8.27-8.16 (m, 2H), 7.63 (t, J=7.8 Hz, 1H), 7.48 (dd, J=8.4, 6.7 Hz, 2H), 7.37-7.29 (m, 2H), 4.57 (d, J=6.1 Hz, 1H), 4.15 (s, 2H), 4.03 (s, 3H), 3.27 (t, J=5.1 Hz, 1H), 3.19 (d, J=6.1 Hz, 1H), 2.10-1.99 (m, 2H), 1.79 (t, J=4.0 Hz, 2H), 1.70-1.62 (m, 2H), 1.52 (dd, J=27.0, 6.3 Hz, 3H), 1.45 (s, 1H), 1.33 (dd, J=9.2, 4.4 Hz, 2H), 1.23-1.14 (m, 2H), 1.06 (dt, J=8.5, 3.3 Hz, 2H).

Step 9c:

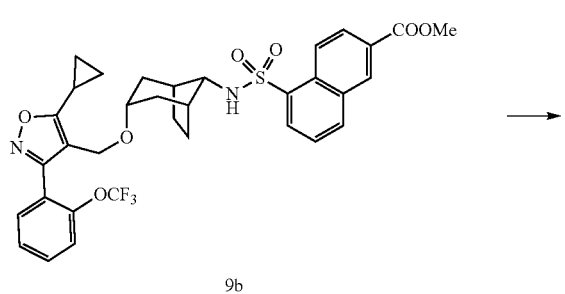

-continued

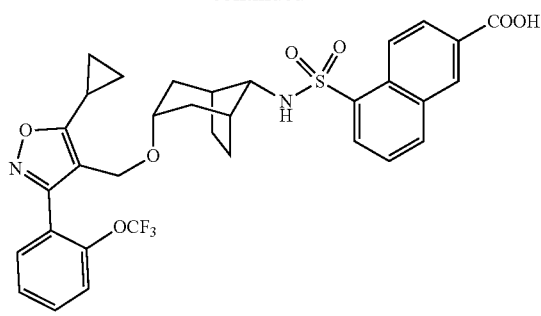

Example 9

To methyl 5-(N-((1R,3r,5S,8s)-3-((5-cyclopropyl-3-(2-(trifluoromethoxy)phenyl)isoxazol-4-yl)methoxy)bicyclo[3.2.1]octan-8-yl)sulfamoyl)-2-naphthoate (73 mg, 0.109 mmol) in THF (0.726 ml), MeOH (0.726 ml), and water (0.726 ml) was added sodium hydroxide solution (109 μl, 1.088 mmol, 10 N). The mixture was stirred at 50° C. for 1 h, cooled to RT, acidified with 1 M HCl, and extracted with EtOAc. The organic layer was dried over Na$_2$SO$_4$ and concentrated in vacuo to give 5-(N-((1R,3r,5S,8s)-3-((5-cyclopropyl-3-(2-(trifluoromethoxy)phenyl)isoxazol-4-yl)methoxy)bicyclo[3.2.1]octan-8-yl)sulfamoyl)-2-naphthoic acid (Example 9) (64 mg, 0.097 mmol, 90% yield) as a white solid. LC/MS observed [M–H]$^-$, 655.2.

Example 9-2

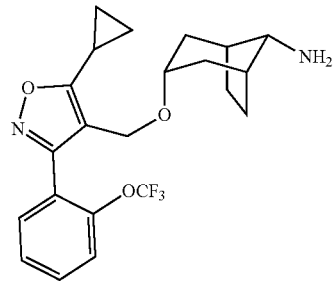

3f

+

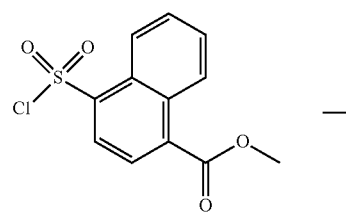

-continued

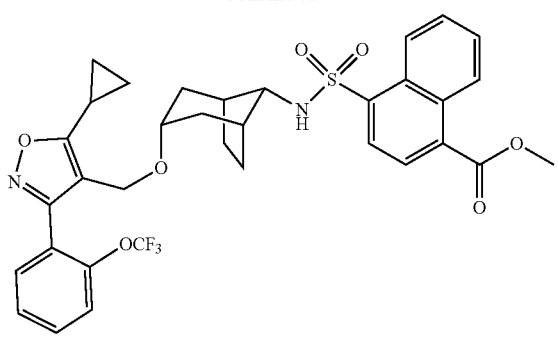

Example 9-2

Example 9-2 was prepared from compound (3f) following a similar procedure as in step 9b. $^1$H NMR (400 MHz, Chloroform-d) δ 8.93-8.83 (m, 1H), 8.72-8.63 (m, 1H), 8.30 (d, J=7.7 Hz, 1H), 8.13 (d, J=7.7 Hz, 1H), 7.78-7.67 (m, 2H), 7.48 (ddd, J=8.6, 7.3, 1.4 Hz, 2H), 7.38-7.29 (m, 2H), 4.58 (d, J=6.2 Hz, 1H), 4.07 (s, 3H), 3.27 (t, J=5.1 Hz, 1H), 3.18 (d, J=6.1 Hz, 1H), 2.11-1.99 (m, 1H), 1.79 (d, J=4.2 Hz, 2H), 1.66 (dd, J=14.8, 3.5 Hz, 2H), 1.55 (t, J=7.0 Hz, 2H), 1.51-1.40 (m, 2H), 1.24-1.10 (m, 2H), 1.12-1.01 (m, 2H).

Example 9-3

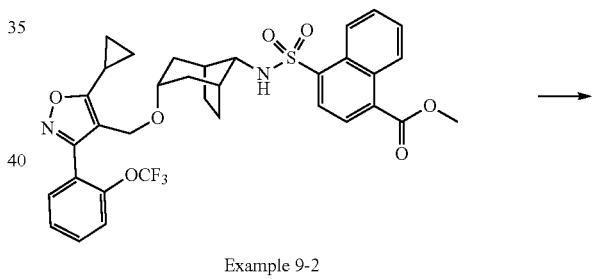

Example 9-2

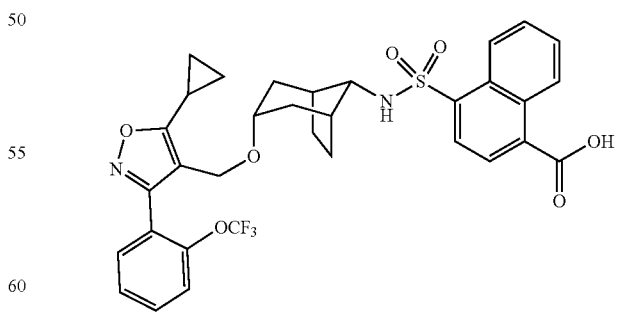

Example 9-3

Example 9-3 was prepared from compound (Example 9-2) following a similar procedure as in step 9c. LC/MS observed [M–H]$^-$, 655.2.

Example 9-4

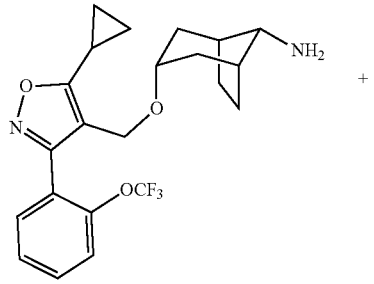

3f

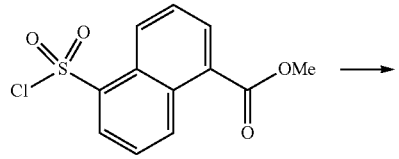

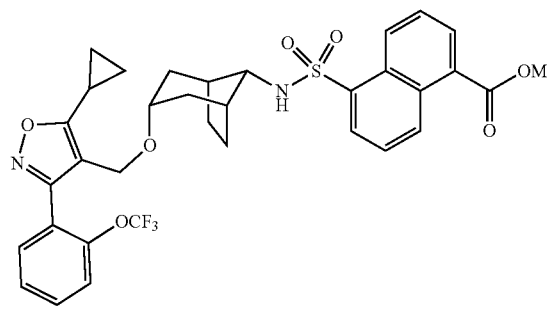

Example 9-4

Example 9-4 was prepared from compound (3f) following a similar procedure as in step 9b. $^1$H NMR (400 MHz, Chloroform-d) δ 9.19 (dd, J=8.7, 1.3 Hz, 1H), 8.91-8.83 (m, 1H), 8.35 (dd, J=7.4, 1.2 Hz, 1H), 8.27 (dd, J=7.3, 1.2 Hz, 1H), 7.69 (ddd, J=8.8, 7.3, 5.5 Hz, 2H), 7.52-7.44 (m, 2H), 7.42 (s, 1H), 7.38-7.29 (m, 2H), 4.47 (d, J=6.2 Hz, 1H), 4.06 (s, 3H), 3.27 (t, J=5.0 Hz, 1H), 3.18 (d, J=6.1 Hz, 1H), 2.11-2.00 (m, 1H), 1.78 (s, 2H), 1.66 (d, J=14.8 Hz, 2H), 1.51-1.40 (m, 2H), 1.18 (dt, J=6.3, 3.2 Hz, 2H), 1.12-1.01 (m, 2H).

Example 9-5

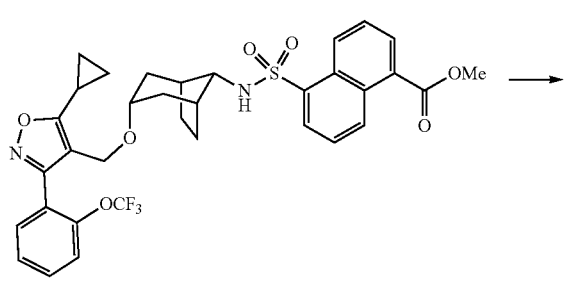

Example 9-4

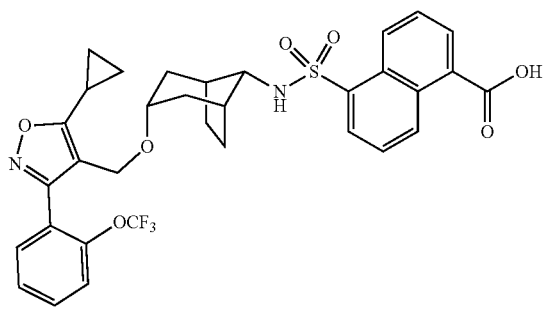

Example 9-5

Example 9-5 was prepared from compound (Example 9-4) following a similar procedure as in step 9c. LC/MS observed [M−H]⁻, 655.2.

Example 9-6

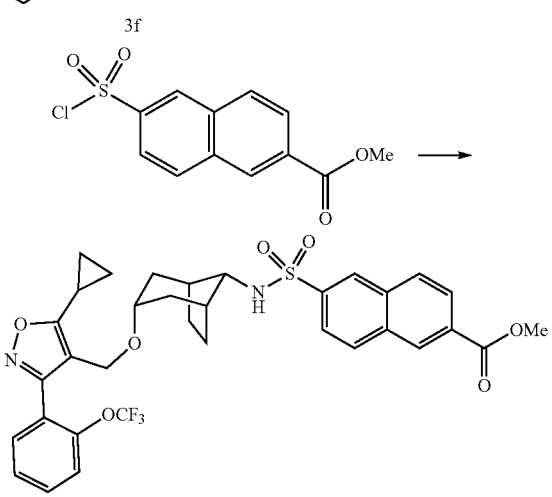

Example 9-6

Example 9-6 was prepared from compound (3f) following a similar procedure as in step 9b. $^1$H NMR (400 MHz, Chloroform-d) δ 8.71-8.66 (m, 1H), 8.47 (d, J=1.8 Hz, 1H), 8.21 (dd, J=8.6, 1.7 Hz, 1H), 8.09 (d, J=8.7 Hz, 1H), 8.03 (d, J=8.6 Hz, 1H), 7.89 (dd, J=8.7, 1.8 Hz, 1H), 7.54-7.44 (m, 2H), 7.39-7.30 (m, 2H), 4.49 (d, J=6.1 Hz, 1H), 4.19 (s, 2H), 4.04 (s, 3H), 3.32 (t, J=5.1 Hz, 1H), 3.24 (d, J=6.1 Hz, 1H), 2.13-2.02 (m, 1H), 1.95 (s, 2H), 1.70 (dd, J=28.0, 11.3 Hz, 3H), 1.54 (d, J=16.8 Hz, 4H), 1.25-1.15 (m, 2H), 1.13-1.02 (m, 2H).

Example 9-7

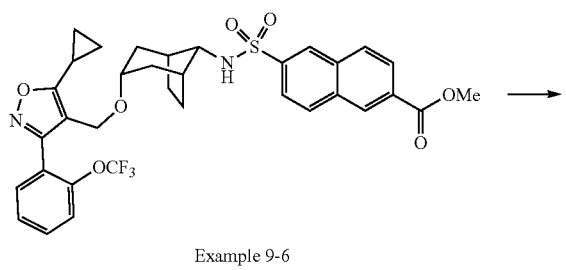

Example 9-6

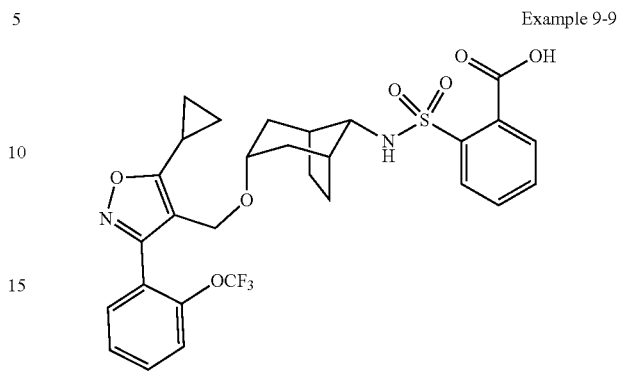

Step 9-9a:

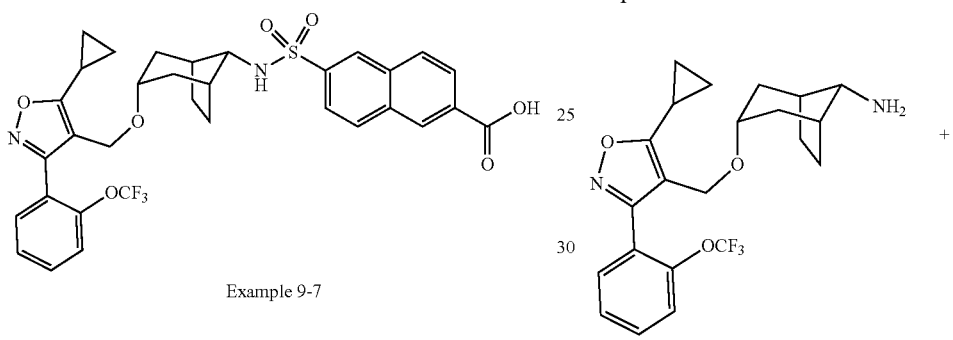

Example 9-7

Example 9-7 was prepared from compound (Example 9-6) following a similar procedure as in step 9c. LC/MS observed [M−H]⁻, 655.2.

Example 9-8

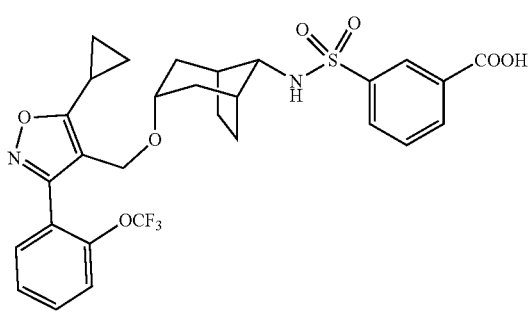

Example 9-8

Example 9-8 was prepared from compound (3f) following the same protocol as Example 9. LC/MS observed [M−H]⁻, 605.2.

Example 9-9

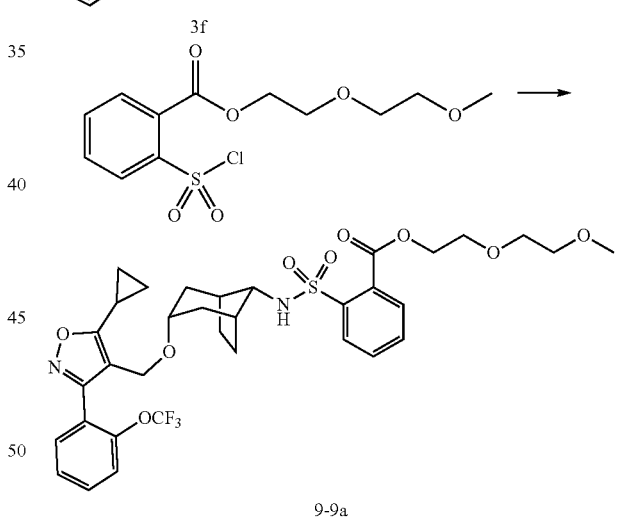

9-9a

To (1R,3r,5S,8s)-3-((5-cyclopropyl-3-(2-(trifluoromethoxy)phenyl)isoxazol-4-yl)methoxy)bicyclo[3.2.1]octan-8-amine (3f) (395 µl, 0.095 mmol, 0.24 M in THF) was added triethylamine (26.4 µl, 0.189 mmol) and 2-(2-methoxyethoxy)ethyl 2-(chlorosulfonyl)benzoate (20.04 µl, 0.095 mmol). The mixture was stirred at RT for 2 h, quenched with water, and extracted with DCM. The organic layer was loaded on silica gel and eluted with 0-100% EtOAc/hexane to give 2-(2-methoxyethoxy)ethyl 2-(N-((1R,3r,5S,8s)-3-((5-cyclopropyl-3-(2-(trifluoromethoxy)phenyl)isoxazol-4-yl)methoxy)bicyclo[3.2.1]octan-8-yl)sulfamoyl)benzoate (9-9a) (42 mg, 0.059 mmol, 62.6% yield). LC/MS observed [M+H]⁺, 709.2.

Step 9-9b:
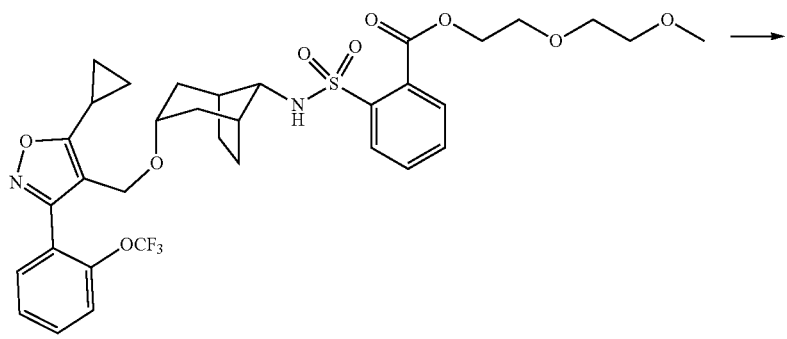
9-9a
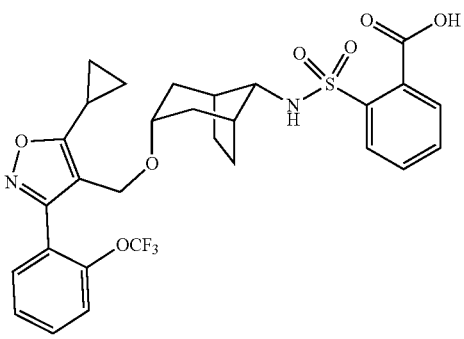
Example 9-9
Example 9-9 was prepared from compound (9-9a) following a similar procedure as in step 9c. LC/MS observed [M−H]⁻, 605.2.
Example 9-10
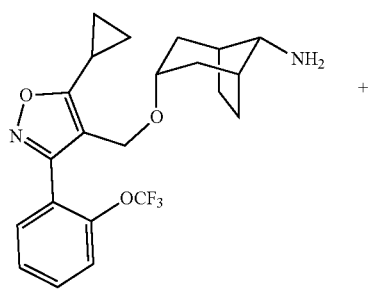
3f
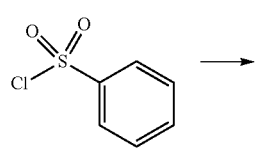
-continued
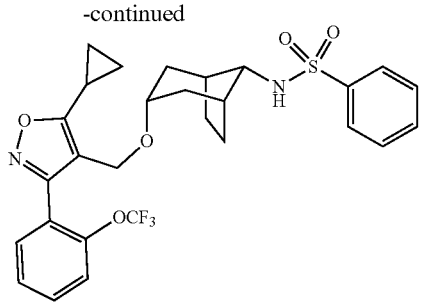
Example 9-10
Example 9-10 was prepared from compound (3f) following a similar procedure as in step 9-9a. LC/MS observed [M+H]⁺, 563.1.
Example 9-11
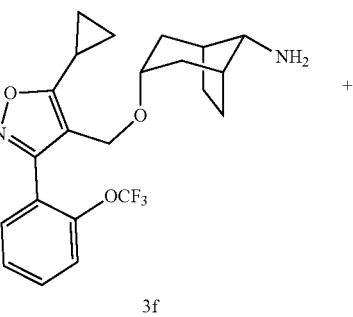
3f

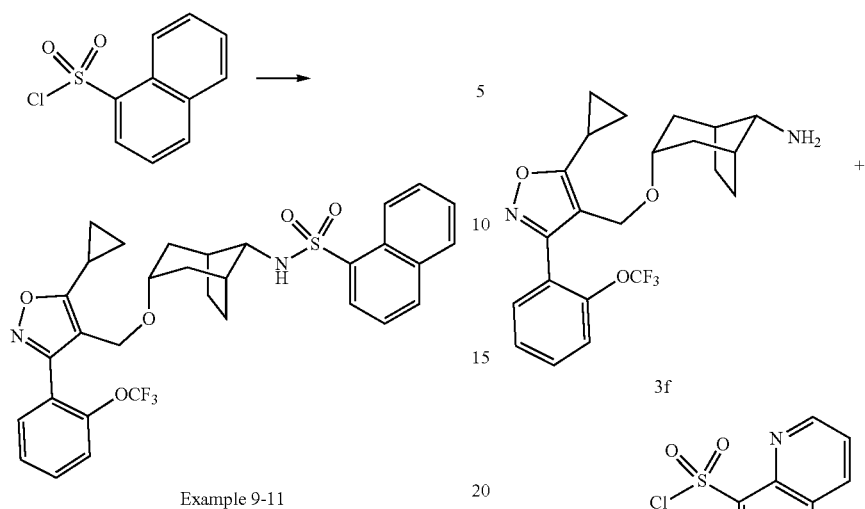
Example 9-11
Example 9-11 was prepared from compound (3f) following a similar procedure as in step 9-9a. LC/MS observed [M+H]⁺, 613.2.
Example 9-12
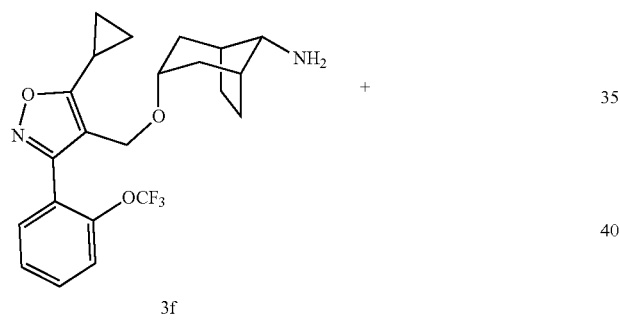
3f
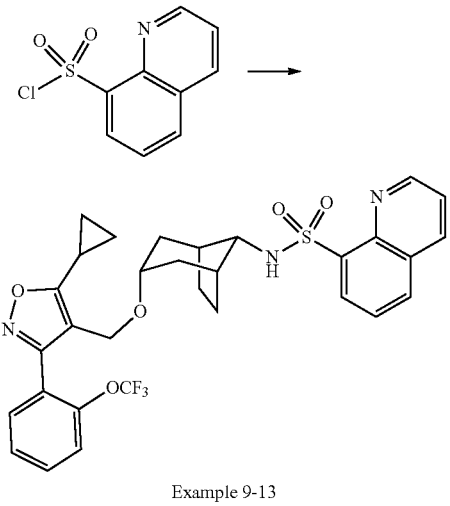
Example 9-12
Example 9-12 was prepared from compound (3f) following a similar procedure as in step 9-9a. LC/MS observed [M+H]⁺, 613.2.
Example 9-13
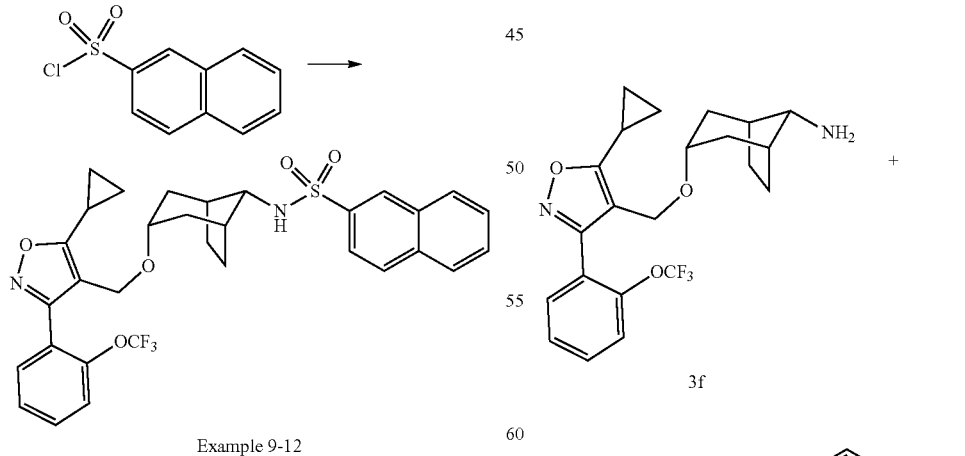
Example 9-13
Example 9-13 was prepared from compound (3f) following a similar procedure as in step 9-9a. LC/MS observed [M+H]⁺, 614.2.
Example 9-14

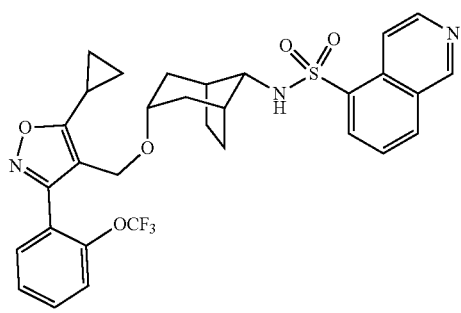
Example 9-14
Example 9-14 was prepared from compound (3f) following a similar procedure as in step 9-9a. LC/MS observed [M+H]⁺, 614.2.
Example 9-15
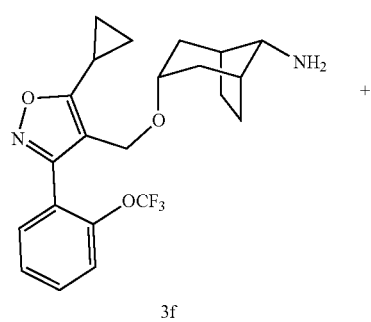
3f
+
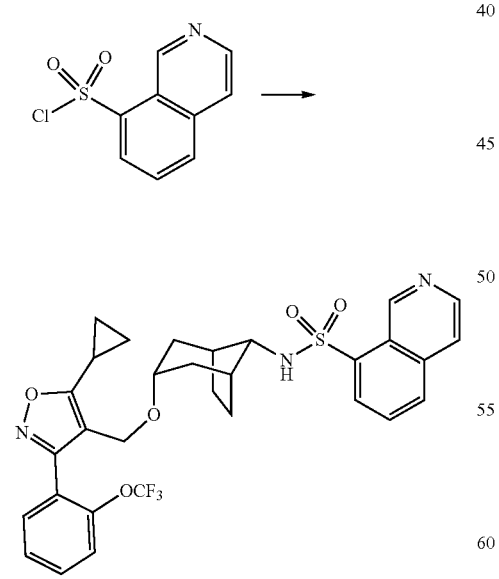
Example 9-15
Example 9-15 was prepared from compound (3f) following a similar procedure as in step 9-9a. LC/MS observed [M+H]⁺, 614.2.
Example 9-16
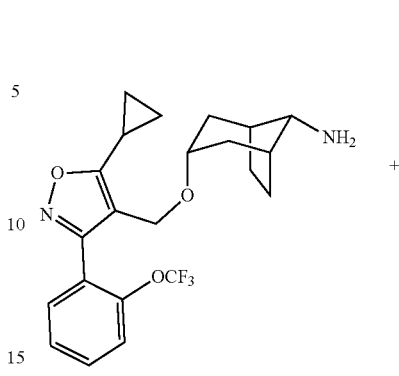
3f
+
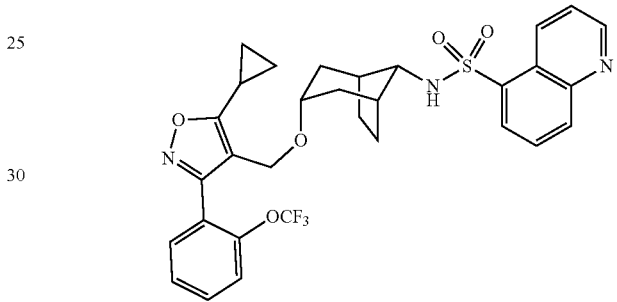
Example 9-16
Example 9-16 was prepared from compound (3f) following a similar procedure as in step 9-9a. LC/MS observed [M+H]⁺, 614.2.
Example 9-17
3f
+
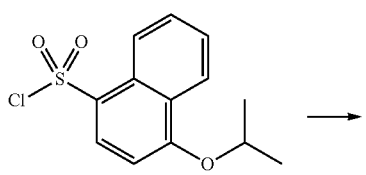

-continued

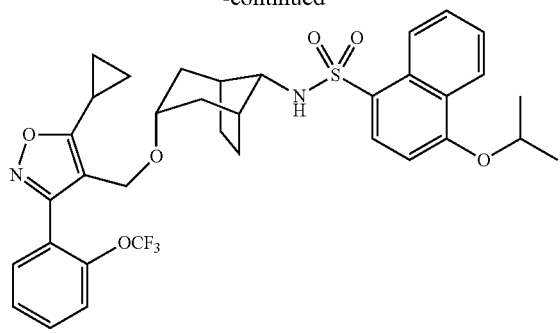

Example 9-17

Example 9-17 was prepared from compound (3f) following a similar procedure as in step 9-9a. $^1$H NMR (400 MHz, Chloroform-d) δ 8.54-8.47 (m, 1H), 8.45-8.38 (m, 1H), 8.21 (d, J=8.4 Hz, 1H), 7.66 (ddd, J=8.4, 6.8, 1.5 Hz, 1H), 7.58 (ddd, J=8.2, 6.8, 1.2 Hz, 1H), 7.53-7.43 (m, 2H), 7.34 (ddd, J=7.6, 5.7, 1.7 Hz, 2H), 6.82 (d, J=8.4 Hz, 1H), 4.88 (hept, J=6.0 Hz, 1H), 4.40-4.33 (m, 1H), 4.16 (s, 2H), 3.27 (t, J=5.1 Hz, 1H), 3.13 (d, J=6.0 Hz, 1H), 2.17-2.00 (m, 2H), 1.81 (s, 2H), 1.66 (d, J=14.4 Hz, 2H), 1.61-1.50 (m, 8H), 1.50-1.23 (m, 4H), 1.23-1.11 (m, 2H), 1.14-1.01 (m, 2H).

Example 10

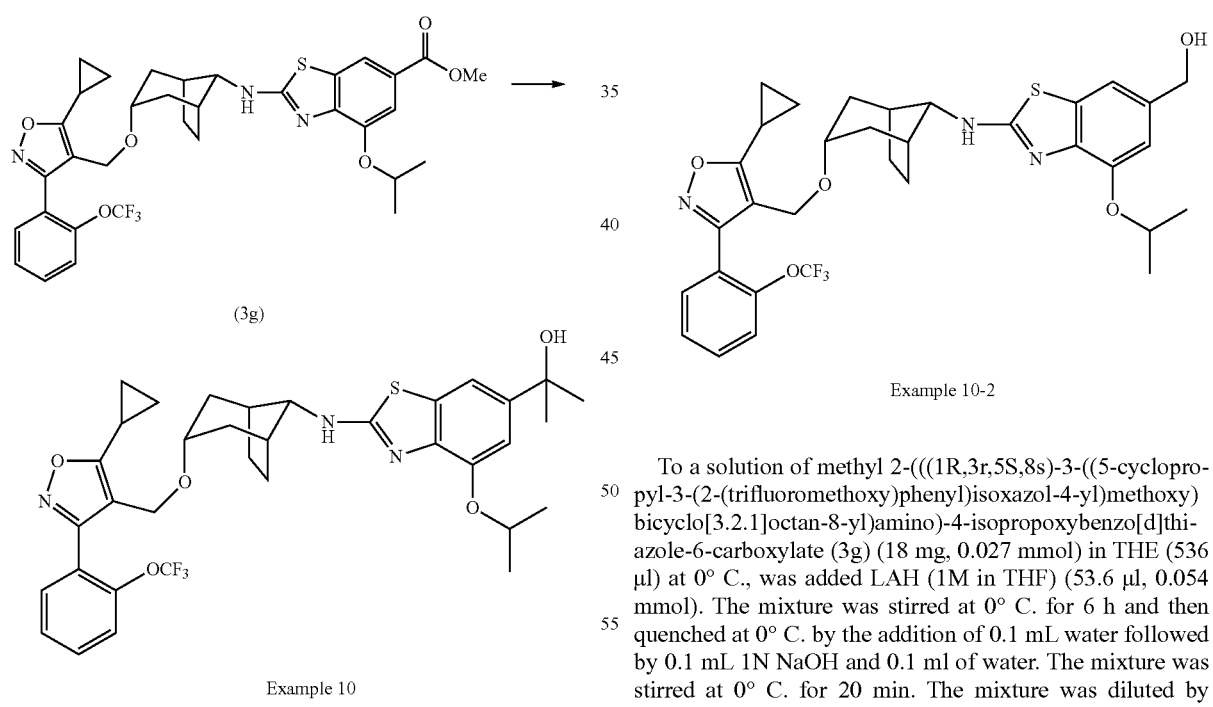

(3g)

Example 10

To a solution of methyl 2-(((1R,3r,5S,8s)-3-((5-cyceopropyl-3-(2-(trifluoromethoxy)phenyl)isoxazol-4-yl)methoxy)bicyclo[3.2.1]octan-8-yl)amino)-4-isopropoxybenzo[d]thiazole-6-carboxylate (3g) (7 mg, 10.42 μmol) in THF (0.261 ml) at RT was charged with a solution of methylmagnesium chloride (3M in THF) (104 μl, 0.313 mmol) dropwise over a few minutes. After stirring at RT for 3 h, the reaction was cooled to 0° C. and treated with MeOH (0.5 mL) dropwise. The reaction was allowed to warm to RT and diluted with ethyl acetate, washed with 1 N HCl and brine, dried over $Na_2SO_4$ and concentrated in vacuo to give Example 10 (6 mg) as a white solid. LC/MS observed [M+H]$^+$, 672.27; $^1$H NMR (400 MHz, Chloroform-d) δ 7.57-7.45 (m, 2H), 7.40-7.32 (m, 2H), 7.26 (s, 1H), 6.99 (s, 1H), 4.76-4.62 (m, 1H), 4.24 (s, 2H), 3.45-3.37 (m, 1H), 3.20 (s, 1H), 2.32-2.20 (m, 2H), 2.14-2.06 (m, 1H), 1.94-1.83 (m, 2H), 1.82-1.61 (m, 6H), 1.58 (s, 6H), 1.40 (d, J=6.1 Hz, 6H), 1.23-1.16 (m, 2H), 1.11-1.05 (m, 2H).

Example 10-2

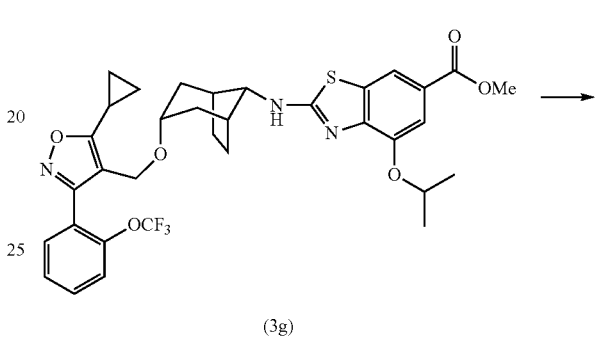

(3g)

Example 10-2

To a solution of methyl 2-(((1R,3r,5S,8s)-3-((5-cyclopropyl-3-(2-(trifluoromethoxy)phenyl)isoxazol-4-yl)methoxy)bicyclo[3.2.1]octan-8-yl)amino)-4-isopropoxybenzo[d]thiazole-6-carboxylate (3g) (18 mg, 0.027 mmol) in THF (536 μl) at 0° C., was added LAH (1M in THF) (53.6 μl, 0.054 mmol). The mixture was stirred at 0° C. for 6 h and then quenched at 0° C. by the addition of 0.1 mL water followed by 0.1 mL 1N NaOH and 0.1 ml of water. The mixture was stirred at 0° C. for 20 min. The mixture was diluted by EtOAc, The mixture was filtered through celite to give Example 1-2 (16 mg) as a white solid. LC/MS observed [M+H]$^+$, 644.0; $^1$H NMR (500 MHz, Chloroform-d) δ 7.58-7.43 (m, 2H), 7.36 (tt, J=7.5, 1.0 Hz, 2H), 7.17 (d, J=1.4 Hz, 1H), 6.80 (d, J=1.5 Hz, 2H), 5.47 (s, 1H), 4.82-4.69 (m, 1H), 4.66 (s, 2H), 4.24 (s, 2H), 3.42 (t, J=5.1 Hz, 1H), 3.26 (d, J=3.5 Hz, 1H), 2.23-2.16 (m, 2H), 2.16-2.06 (m, 1H), 1.93-1.79 (m, 2H), 1.80-1.53 (m, 6H), 1.40 (d, J=6.1 Hz, 6H), 1.22-1.17 (m, 2H), 1.10-1.05 (m, 2H).

Example 11

Step 11:

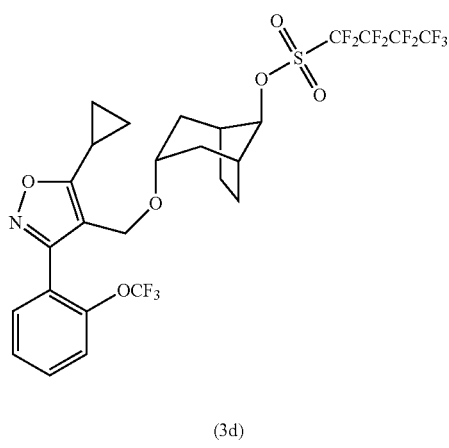

(3d)

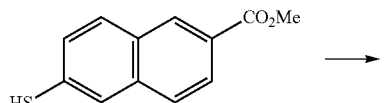

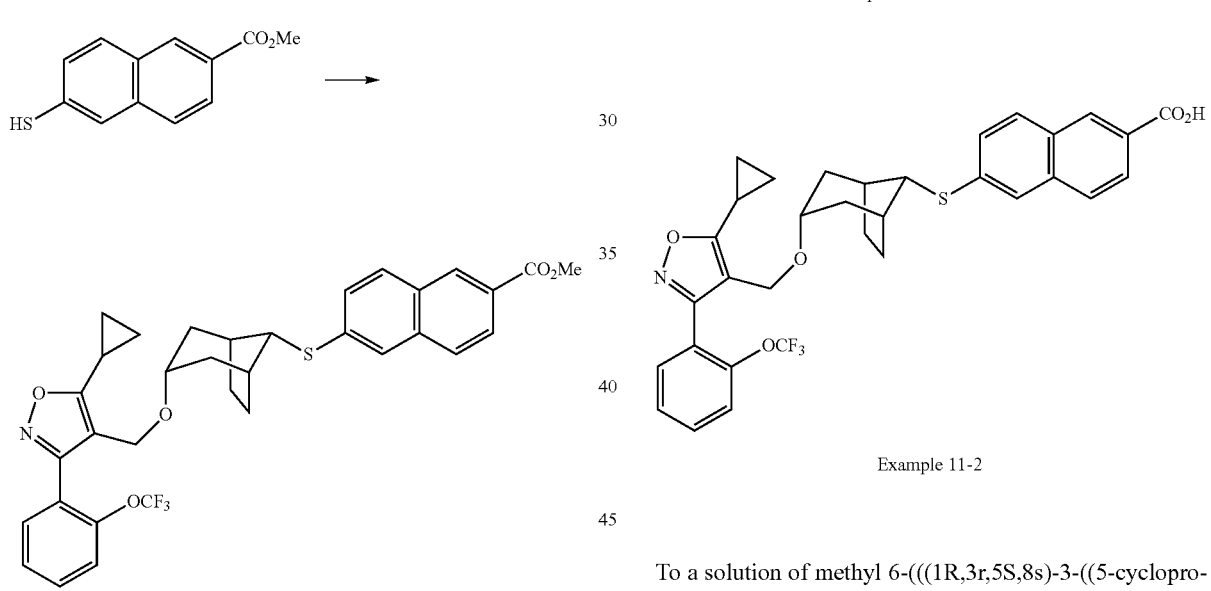

Example 11

To a solution of (1R,3r,5S,8r)-3-((5-cyclopropyl-3-(2-(trifluoromethoxy)phenyl)isoxazol-4-yl)methoxy)bicyclo[3.2.1]octan-8-yl, nonafluorobutane-1-sulfonate (3d) (114 mg, 0.162 mmol) and methyl 6-mercapto-2-naphthoate (42.3 mg, 0.194 mmol) in THF (1 ml) at room temperature under $N_2$ was added potassium tert-butoxide (0.194 ml, 0.194 mmol). The resulting mixture was heated to 45° C. and stirred overnight. It was then diluted with EtOAc, washed with sat $NaHCO_3$ and brine, dried over $Na_2SO_4$, filtered, and concentrated. The residue was purified by chromatography on silica gel eluting with 0-70% EtOAc/hexane to give methyl 6-(((1R,3r,5S,8s)-3-((5-cyclopropyl-3-(2-(trifluoromethoxy)phenyl)isoxazol-4-yl)methoxy)bicyclo[3.2.1]octan-8-yl)thio)-2-naphthoate (Example 11) (64 mg, 64%) as a colorless oil. LC/MS observed [M+H]⁺, 624.20; ¹H NMR (400 MHz, DMSO-d₆) δ 8.57 (s, 1H), 8.03 (t, J=8.9 Hz, 1H), 8.03-7.91 (m, 2H), 7.86 (d, J=1.8 Hz, 1H), 7.71-7.62 (m, 1H), 7.62 (dd, J=7.7, 1.8 Hz, 1H), 7.58-7.46 (m, 3H), 4.28 (s, 2H), 3.91 (s, 3H), 3.64 (s, 1H), 3.48 (s, 1H), 2.38-2.23 (m, 1H), 2.12-2.09 (m, 2H), 1.83 (s, 4H), 1.74-1.66 (m, 2H), 1.60 (t, J=6.5 Hz, 2H), 1.22-1.03 (m, 4H).

Example 11-2

Step 11-2:

To a solution of methyl 6-(((1R,3r,5S,8s)-3-((5-cyclopropyl-3-(2-(trifluoromethoxy)phenyl)isoxazol-4-yl)methoxy)bicyclo[3.2.1]octan-8-yl)thio)-2-naphthoate (Example 11) (23 mg, 0.037 mmol) in THF (0.5 ml) at room temperature was added lithium hydroxide (73.8 μl, 0.074 mmol, 1N). The mixture was stirred overnight at 40° C., cooled down, and concentrated to remove THF. The residue was diluted with water and acidified to pH 1 with 1 N HCl, and extracted with ethyl acetate. The combined organic layers were washed with brine, dried over $Na_2SO_4$, filtered, and concentrated. The residue was lyophilized to give 6-(((1R,3r,5S,8s)-3-((5-cyclopropyl-3-(2-(trifluoromethoxy)phenyl)isoxazol-4-yl)methoxy)bicyclo[3.2.1]octan-8-yl)thio)-2-naphthoic acid (Example 11-2) (22 mg, 98%) as a white solid. LC-MS: LC/MS observed [M+H]⁺, 610.11; ¹H NMR (400 MHz, DMSO-d₆) δ 13.05 (s, 1H), 8.53 (s, 1H), 8.02 (d, J=8.7 Hz, 1H), 7.94 (q, J=8.6 Hz, 2H), 7.86 (s, 1H), 7.71-7.59 (m, 2H), 7.58-7.45 (m, 3H), 4.28 (s, 2H), 3.63 (s, 1H), 3.48 (s, 1H), 2.31 (dd, J=8.0, 4.9 Hz, 1H), 2.10 (s, 2H), 1.83 (s, 4H), 1.70 (d, J=8.1 Hz, 2H), 1.59 (d, J=7.5 Hz, 2H), 1.21-1.03 (m, 4H).

145
Example 11-3

Step 11-3:

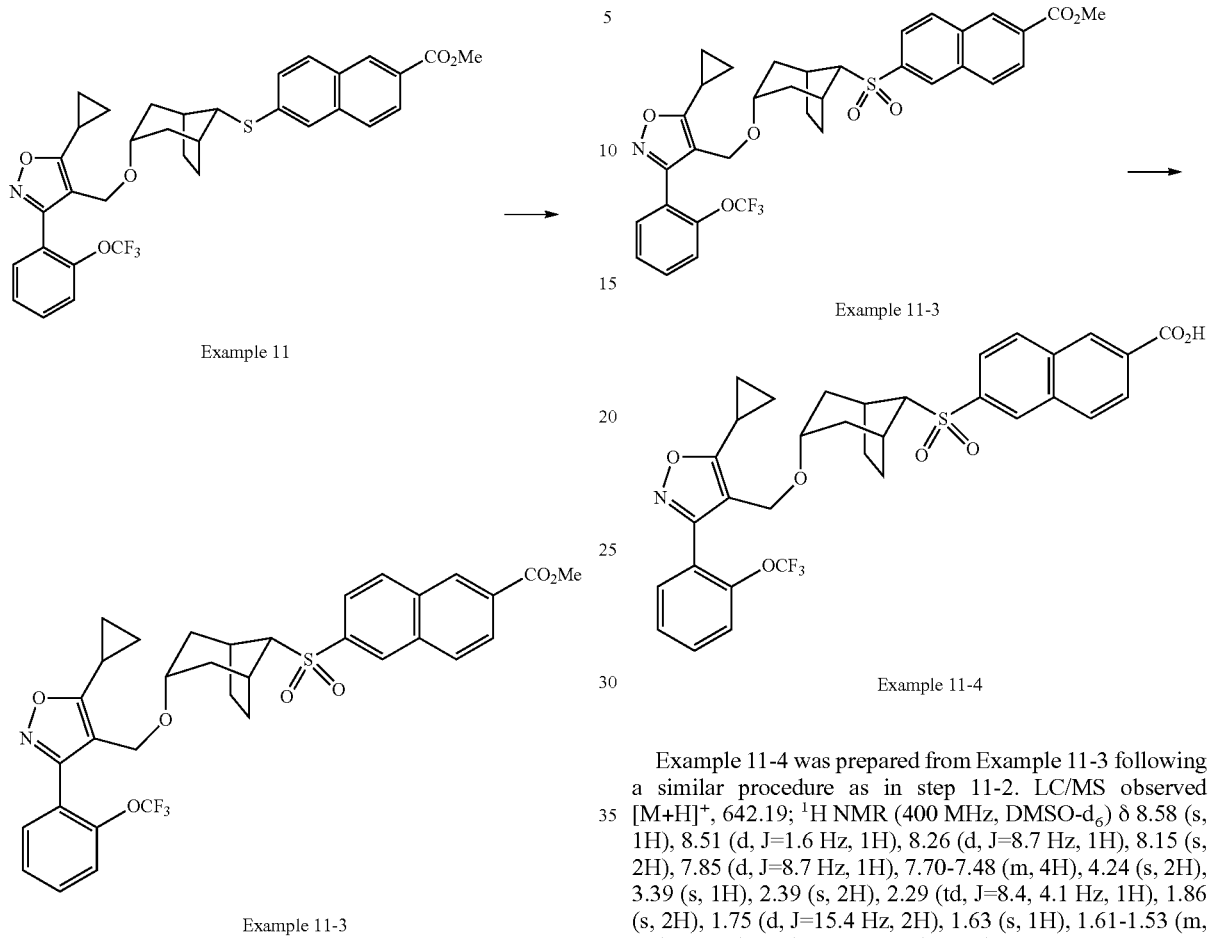

Example 11

Example 11-3

Example 11-3

Example 11-4

Example 11-4

Example 11-4 was prepared from Example 11-3 following a similar procedure as in step 11-2. LC/MS observed [M+H]+, 642.19; 1H NMR (400 MHz, DMSO-d6) δ 8.58 (s, 1H), 8.51 (d, J=1.6 Hz, 1H), 8.26 (d, J=8.7 Hz, 1H), 8.15 (s, 2H), 7.85 (d, J=8.7 Hz, 1H), 7.70-7.48 (m, 4H), 4.24 (s, 2H), 3.39 (s, 1H), 2.39 (s, 2H), 2.29 (td, J=8.4, 4.1 Hz, 1H), 1.86 (s, 2H), 1.75 (d, J=15.4 Hz, 2H), 1.63 (s, 1H), 1.61-1.53 (m, 3H), 1.24 (s, 1H), 1.20-1.01 (m, 4H).

Example 11-5

To a solution of methyl 6-(((1R,3r,5S,8s)-3-((5-cyclopropyl-3-(2-(trifluoromethoxy)phenyl)isoxazol-4-yl)methoxy)bicyclo[3.2.1]octan-8-yl)thio)-2-naphthoate (Example 11) (32 mg, 0.051 mmol) in THF (1.0 ml) was added m-CPBA (23.00 mg, 0.103 mmol) and the mixture was stirred overnight at room temperature, then quenched with sat. NaHCO3, and extracted with EtOAc. The combined organic layers were washed with brine, dried over Na2SO4, and concentrated. The residue was purified by chromatography on silica gel eluting with 0-35% EtOAc/hexane to give methyl 6-(((1R,3r,5S,8s)-3-((5-cyclopropyl-3-(2-(trifluoromethoxy)phenyl)isoxazol-4-yl)methoxy)bicyclo[3.2.1]octan-8-yl)sulfonyl)-2-naphthoate (Example 11-3) (27 mg, 80%) as a white solid. LC/MS observed [M+H]+, 656.20; 1H NMR (400 MHz, DMSO-d6) δ 8.79 (d, J=1.7 Hz, 1H), 8.62 (d, J=1.8 Hz, 1H), 8.41 (d, J=8.7 Hz, 1H), 8.35 (d, J=8.6 Hz, 1H), 8.14 (dd, J=8.6, 1.7 Hz, 1H), 7.97 (dd, J=8.7, 1.8 Hz, 1H), 7.66 (ddd, J=8.6, 7.1, 1.9 Hz, 1H), 7.59 (dd, J=7.6, 1.8 Hz, 1H), 7.57-7.48 (m, 2H), 4.24 (s, 2H), 3.96 (s, 3H), 3.44 (s, 1H), 3.37 (t, J=5.2 Hz, 1H), 2.40 (s, 2H), 2.35-2.24 (m, 1H), 1.90-1.83 (m, 2H), 1.76 (d, J=14.6 Hz, 2H), 1.59 (dd, J=19.1, 11.7 Hz, 4H), 1.17-1.01 (m, 4H).

Example 11-5

Example 11-5 was prepared from compound (3d) following the same protocol as Example 11. LC/MS observed [M+H]+, 588.20; 1H NMR (400 MHz, DMSO-d6) δ 7.79 (s, 1H), 7.84-7.72 (m, 2H), 7.71-7.61 (m, 1H), 7.65-7.57 (m, 1H), 7.61-7.42 (m, 3H), 4.36-4.28 (m, 2H), 4.27 (s, 2H), 3.47 (s, 1H), 3.45 (s, 1H), 2.32 (ddd, J=13.3, 8.2, 5.1 Hz, 1H), 2.03 (s, 2H), 1.79 (d, J=17.4 Hz, 4H), 1.77-1.64 (m, 2H), 1.64-1.52 (m, 2H), 1.32 (t, J=7.1 Hz, 3H), 1.20-1.03 (m, 4H).

Example 11-6

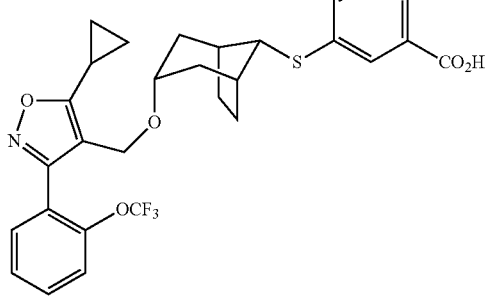

Example 11-6

Example 11-6 was prepared from Example 11-5 following a similar procedure as in step 11-2. LC/MS observed [M+H]$^+$, 560.17; H NMR (400 MHz, DMSO-d$_6$) δ 13.15 (bs, 1H), 7.81 (s, 1H), 7.74 (d, J=7.7 Hz, 1H), 7.71-7.58 (m, 2H), 7.54 (dt, J=10.3, 5.6 Hz, 3H), 7.43 (t, J=7.7 Hz, 1H), 4.26 (s, 2H), 3.44 (d, J=5.2 Hz, 2H), 2.37-2.26 (m, 1H), 2.02 (s, 2H), 1.83-1.64 (m, 6H), 1.58 (dd, J=15.5, 9.9 Hz, 2H), 1.17-1.03 (m, 4H).

Example 11-7

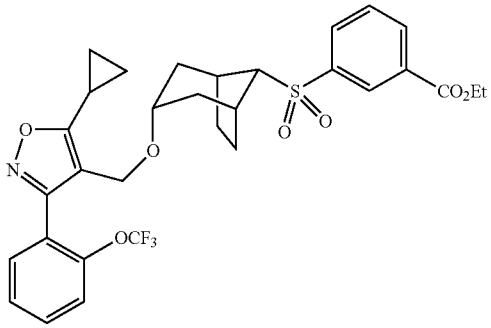

Example 11-7

Example 11-7 was prepared from Example 11-5 following a similar procedure as in step 11-3. LC/MS observed [M+H]$^+$, 620.19; H NMR (400 MHz, DMSO-d$_6$) δ 8.34-8.25 (m, 2H), 8.13 (ddd, J=7.9, 1.9, 1.1 Hz, 1H), 7.82 (t, J=7.8 Hz, 1H), 7.66 (ddd, J=8.3, 7.2, 1.9 Hz, 1H), 7.60 (dd, J=7.6, 1.9 Hz, 1H), 7.57-7.48 (m, 2H), 4.38 (q, J=7.1 Hz, 2H), 4.25 (s, 2H), 3.41 (s, 2H), 2.35 (s, 2H), 2.29 (td, J=8.4, 4.2 Hz, 1H), 1.85-1.71 (m, 4H), 1.59 (dd, J=27.0, 11.2 Hz, 4H), 1.35 (t, J=7.1 Hz, 3H), 1.26-0.99 (m, 4H).

Example 11-8

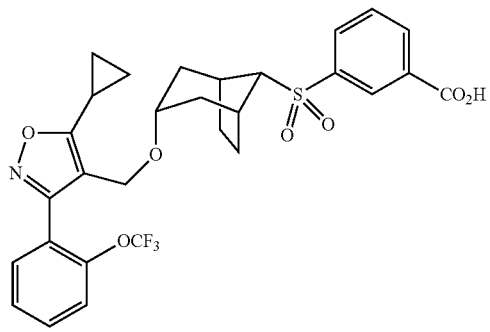

Example 11-8

Example 11-8 was prepared from Example 11-7 following a similar procedure as in step 11-2. LC/MS observed [M+H]$^+$, 592.16; H NMR (400 MHz, DMSO-d$_6$) δ 13.54 (s, 1H), 8.31 (d, J=1.8 Hz, 1H), 8.26 (d, J=7.7 Hz, 1H), 8.08 (d, J=8.0 Hz, 1H), 7.78 (t, J=7.8 Hz, 1H), 7.67 (ddd, J=8.6, 7.1, 1.9 Hz, 1H), 7.60 (dd, J=7.6, 1.9 Hz, 1H), 7.53 (ddd, J=12.0, 6.4, 2.7 Hz, 2H), 4.25 (s, 2H), 3.38 (d, J=9.4 Hz, 2H), 2.35 (s, 2H), 2.33-2.24 (m, 1H), 1.87-1.71 (m, 4H), 1.59 (dd, J=28.4, 11.1 Hz, 4H), 1.20-1.01 (m, 4H).

Example 11-9

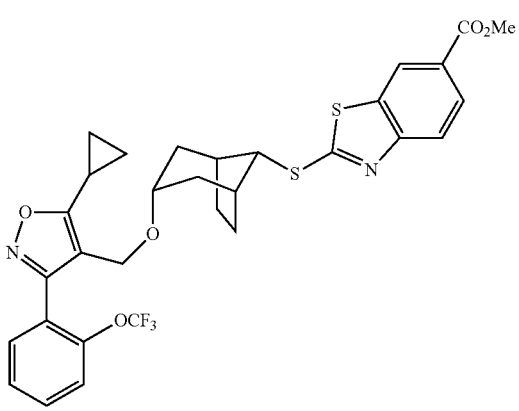

Example 11-9

Example 11-9 was prepared from compound (3d) following the same protocol as Example 11. LC/MS observed [M+H]$^+$, 631.16; H NMR (400 MHz, DMSO-d$_6$) δ 8.68 (dd, J=1.8, 0.6 Hz, 1H), 8.02 (dd, J=8.5, 1.8 Hz, 1H), 7.91 (dd, J=8.6, 0.6 Hz, 1H), 7.72-7.60 (m, 2H), 7.55 (ddd, J=11.7, 6.2, 2.5 Hz, 2H), 4.30 (s, 2H), 3.93 (s, 1H), 3.89 (s, 3H), 3.50 (s, 1H), 2.39-2.28 (m, 3H), 1.87 (s, 4H), 1.65 (s, 4H), 1.18-1.04 (m, 4H).

Example 11-10

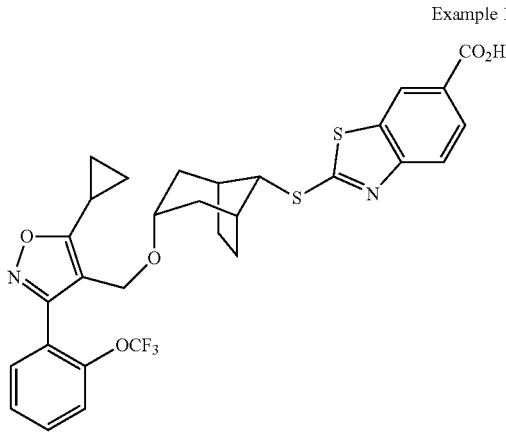

Example 11-10

Example 11-10 was prepared from Example 11-9 following a similar procedure as in step 11-2. LC/MS observed [M+H]$^+$, 617.14; H NMR (400 MHz, DMSO-d$_6$) δ 13.05 (bs, 1H), 8.63 (d, J=1.8 Hz, 1H), 8.00 (dd, J=8.8, 1.8 Hz, 1H), 7.88 (d, J=8.5 Hz, 1H), 7.72-7.60 (m, 2H), 7.60-7.50 (m, 2H), 4.30 (s, 2H), 3.93 (s, 1H), 3.50 (s, 1H), 2.31 (m, 3H), 1.87 (s, 4H), 1.65 (s, 4H), 1.20-1.04 (m, 4H).

Example 11-11

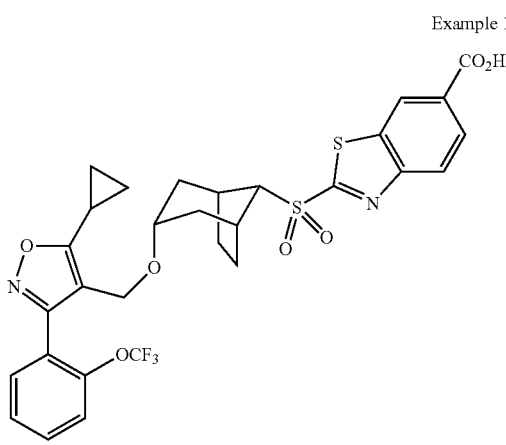

Example 11-11

Example 11-11 was prepared from Example 11-10 following a similar procedure as in step 11-3.

Example 11-12

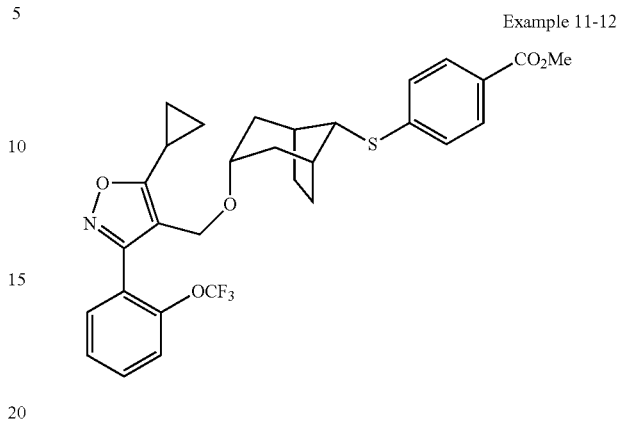

Example 11-12

Example 11-12 was prepared from compound (3d) following the same protocol as Example 11. LC/MS observed [M+H]$^+$, 574.11; H NMR (400 MHz, DMSO-d$_6$) δ 7.90-7.81 (m, 2H), 7.66 (tdd, J=7.2, 2.4, 1.1 Hz, 1H), 7.62 (dd, J=7.5, 1.8 Hz, 1H), 7.58-7.49 (m, 2H), 7.42-7.34 (m, 2H), 4.30-4.26 (m, 2H), 3.83 (d, J=1.0 Hz, 3H), 3.56 (s, 1H), 3.46 (d, J=3.8 Hz, 1H), 2.38-2.27 (m, 1H), 2.08 (s, 2H), 1.88-1.75 (m, 4H), 1.68-1.54 (m, 4H), 1.18-1.03 (m, 4H).

Example 11-13

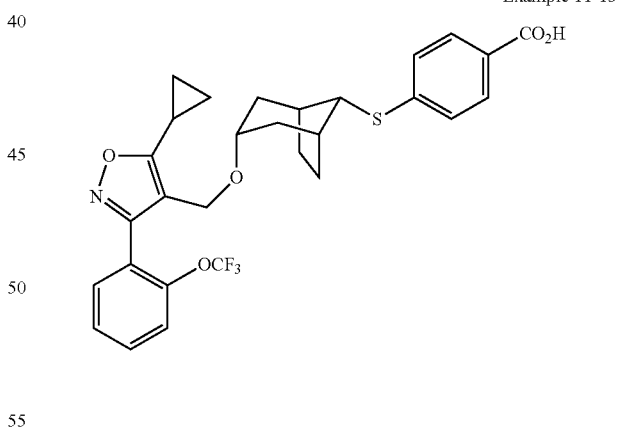

Example 11-13

Example 11-13 was prepared from Example 11-12 following a similar procedure as in step 11-2. LC/MS observed [M+H]$^+$, 560.17; H NMR (400 MHz, DMSO-d$_6$) δ 12.82 (s, 1H), 7.83 (d, J=8.2 Hz, 2H), 7.71-7.58 (m, 2H), 7.58-7.49 (m, 2H), 7.36 (d, J=8.4 Hz, 2H), 4.28 (s, 2H), 3.55 (s, 1H), 3.46 (q, J=4.1, 3.5 Hz, 1H), 2.32 (tt, J=8.3, 5.1 Hz, 1H), 2.15-2.04 (m, 2H), 1.88-1.75 (m, 4H), 1.69-1.52 (m, 4H), 1.20-1.04 (m, 4H).

Example 11-14

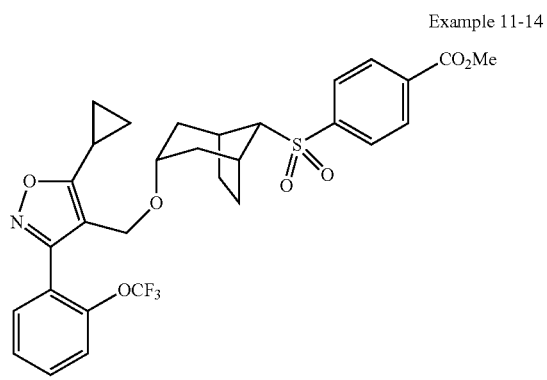 [SMILES: COC(=O)c1ccc(S(=O)(=O)C2C3CCC2CC(OCc2c(-c4ccccc4OC(F)(F)F)noc2C2CC2)C3)cc1]

Example 11-14 was prepared from Example 11-2 following a similar procedure as in step 11-3. LC/MS observed [M+H]⁺, 606.18; H NMR (400 MHz, DMSO-d$_6$) δ 8.18 (d, J=8.2 Hz, 2H), 8.00 (d, J=8.2 Hz, 2H), 7.71-7.57 (m, 2H), 7.57-7.48 (m, 2H), 4.25 (s, 2H), 3.91 (s, 3H), 3.38 (s, 1H), 3.36 (s, 1H), 2.35 (s, 2H), 2.31 (m, 1H), 1.84-1.71 (m, 4H), 1.58 (dd, J=25.9, 11.2 Hz, 4H), 1.22-1.01 (m, 4H).

Example 11-15

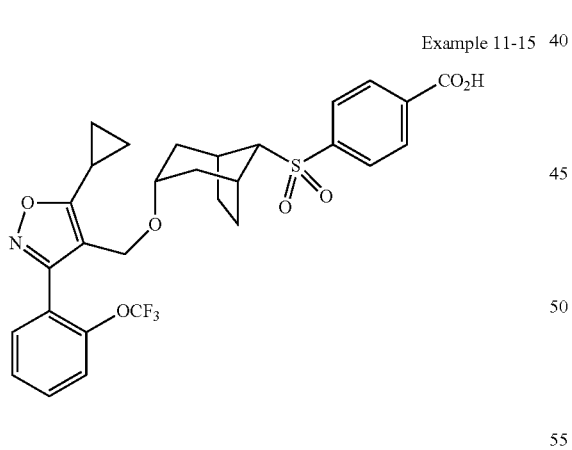

Example 11-15 was prepared from Example 11-14 following a similar procedure as in step 11-2. LC/MS observed [M+H]⁺, 592.17; H NMR (400 MHz, DMSO-d$_6$) δ 13.55 (s, 1H), 8.16 (d, J=8.2 Hz, 2H), 7.97 (d, J=8.1 Hz, 2H), 7.73-7.55 (m, 2H), 7.58-7.48 (m, 2H), 4.25 (s, 2H), 3.36 (s, 1H), 3.33 (s, 1H), 2.35 (s, 2H), 2.30 (m, 1H), 1.82-1.70 (m, 4H), 1.67-1.50 (m, 4H), 1.20-1.08 (m, 4H).

Example 11-16

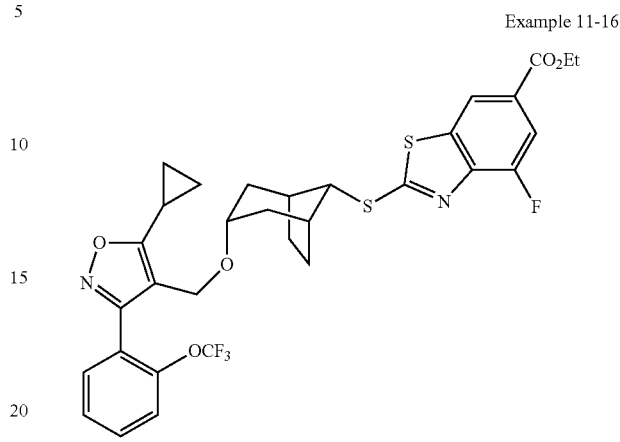

Example 11-16 was prepared from compound (3d) following the same protocol as Example 11. LC/MS observed [M+H]⁺, 663.06; H NMR (400 MHz, DMSO-d$_6$) δ 8.54 (t, J=1.2 Hz, 1H), 7.81-7.73 (m, 1H), 7.72-7.60 (m, 2H), 7.59-7.50 (m, 2H), 4.40-4.28 (m, 4H), 3.95 (s, 1H), 3.53 (s, 1H), 2.37-2.28 (m, 3H), 1.87 (s, 4H), 1.66 (s, 4H), 1.35 (td, J=7.1, 0.8 Hz, 3H), 1.20-1.04 (m, 4H).

Example 11-17

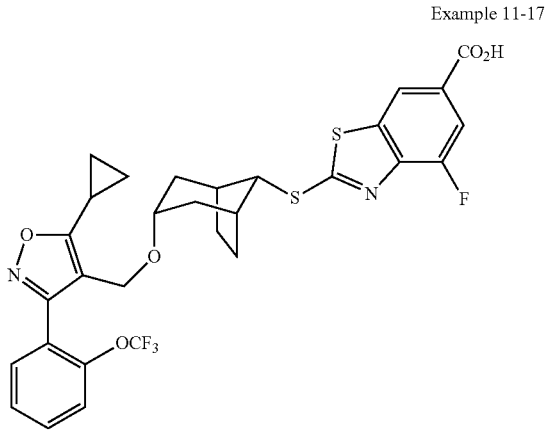 [SMILES: O=C(O)c1cc(F)c2nc(SC3C4CCC3CC(OCc3c(-c5ccccc5OC(F)(F)F)noc3C3CC3)C4)sc2c1]

Example 11-17 was prepared from Example 11-16 following a similar procedure as in step 11-2. LC/MS observed [M+H]⁺, 635.14; H NMR (400 MHz, DMSO-d$_6$) δ 13.36 (s, 1H), 8.50 (d, J=1.4 Hz, 1H), 7.74 (dd, J=11.1, 1.6 Hz, 1H), 7.71-7.60 (m, 2H), 7.55 (ddd, J=11.5, 6.1, 2.5 Hz, 2H), 4.30 (s, 2H), 3.94 (s, 1H), 3.50 (s, 1H), 2.39-2.29 (m, 3H), 1.87 (s, 4H), 1.66 (s, 4H), 1.20-1.04 (m, 4H).

Example 11-18

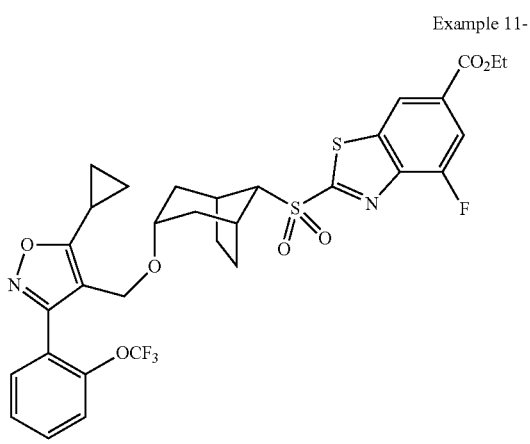

Example 11-18

Example 11-18 was prepared from Example 11-16 following a similar procedure as in step 11-3. LC/MS observed [M+H]+, 695.14; H NMR (400 MHz, DMSO-d6) δ 8.88 (t, J=1.3 Hz, 1H), 8.00 (dd, J=10.8, 1.4 Hz, 1H), 7.89 (dt, J=4.8, 1.6 Hz, 1H), 7.72-7.64 (m, 1H), 7.69-7.49 (m, 2H), 4.46-4.36 (m, 2H), 4.27 (s, 1H), 3.80 (s, 1H), 2.42 (s, 1H), 2.63 (s, 2H), 2.36-2.27 (m, 1H), 1.86-1.70 (m, 6H), 1.64 (t, J=6.7 Hz, 2H), 1.38 (td, J=7.1, 1.1 Hz, 3H), 1.17-1.08 (m, 2H), 1.07 (dt, J=5.5, 2.8 Hz, 2H).

Example 11-19

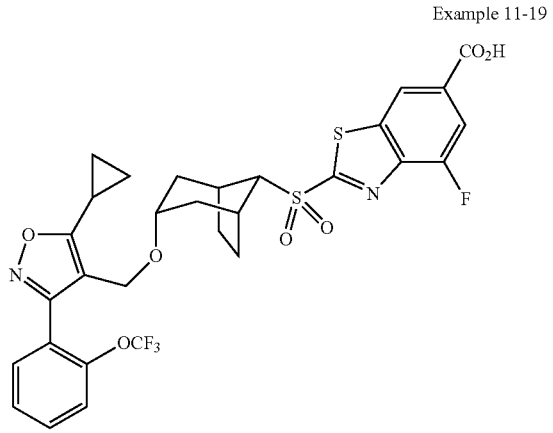 [SMILES: O=C(O)c1cc(F)c2nc(S(=O)(=O)C3C4CCC3CC(OCc3c(-c5ccccc5OC(F)(F)F)noc3C3CC3)C4)sc2c1]

Example 11-19

Example 11-19 was prepared from Example 11-17 following a similar procedure as in step 11-3. LC/MS observed [M+H]+, 667.12; ¹H NMR (400 MHz, DMSO-d6) δ 8.74 (s, 1H), 7.93 (d, J=11.2 Hz, 1H), 7.67 (ddd, J=8.7, 7.2, 1.9 Hz, 1H), 7.66-7.53 (m, 3H), 7.57-7.49 (m, 1H), 4.27 (s, 2H), 3.78 (s, 1H), 3.41 (s, 1H), 2.62 (s, 2H), 2.35-2.26 (m, 1H), 1.86-1.70 (m, 6H), 1.63 (d, J=7.7 Hz, 2H), 1.20-1.02 (m, 4H).

Example 12

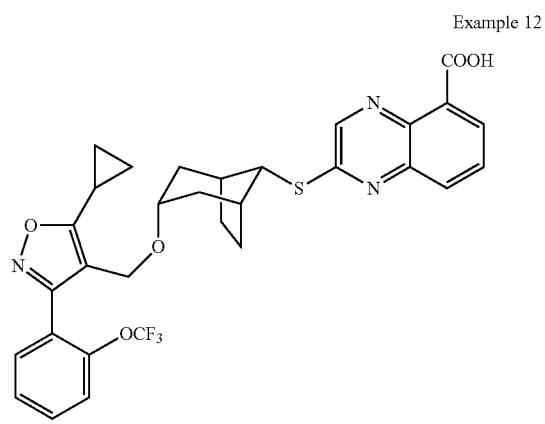 [SMILES: O=C(O)c1cccc2nc(SC3C4CCC3CC(OCc3c(-c5ccccc5OC(F)(F)F)noc3C3CC3)C4)cnc12]

Example 12

Step 12a:

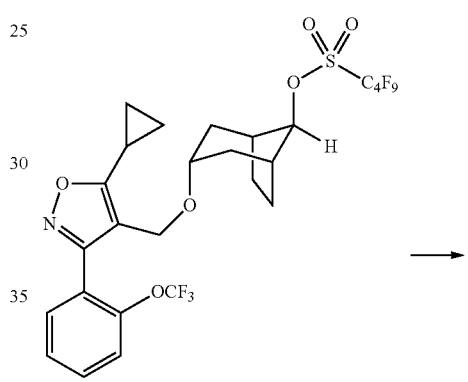

3d

→

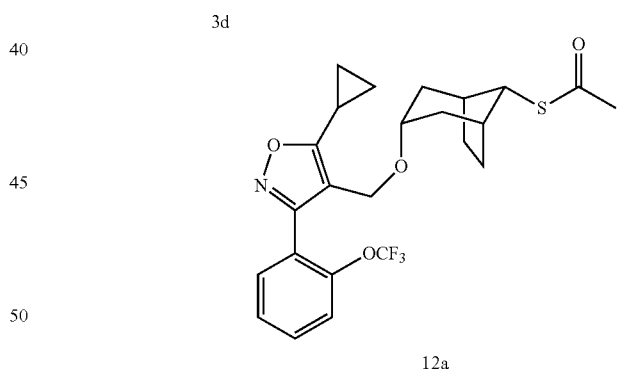

12a (1R,3r,5S,8r)-3-((5-cyclopropyl-3-(2-(trifluoromethoxy)phenyl)isoxazol-4-yl)methoxy)bicyclo[3.2.1]octan-8-yl-nonafluorobutane-1-sulfonate (3d) (150 mg, 0.213 mmol) was dissolved in DMA (0.709 ml) and potassium ethanethioate (121 mg, 1.063 mmol) was added. The mixture was stirred at rt for 16 h, quenched with water, and extracted with MTBE. The organic layer was dried over Na₂SO₄ and concentrated in vacuo. Purification of the residue on silica gel with 0-30% EtOAc/hexane provided S-((1R,3r,5S,8s)-3-((5-cyclopropyl-3-(2-(trifluoromethoxy)phenyl)isoxazol-4-yl)methoxy)bicyclo[3.2.1]octan-8-yl) ethanethioate (12a) (70 mg, 0.145 mmol, 68.4% yield). LC/MS observed [M+H]+, 482.16.

Step 12b:

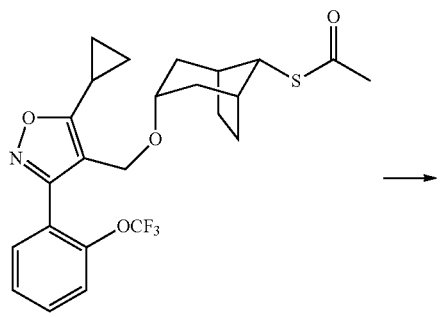

12a

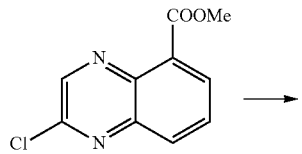

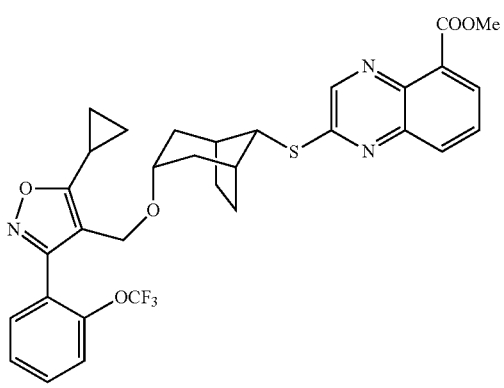

12c

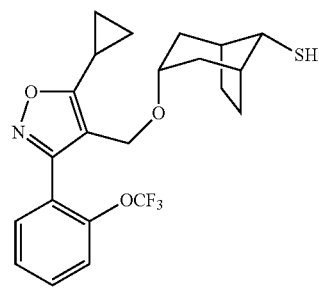

12b

S-((1R,3r,5S,8s)-3-((5-cyclopropyl-3-(2-(trifluoromethoxy)phenyl)isoxazol-4-yl)methoxy)bicyclo[3.2.1]octan-8-yl) ethanethioate (12a) (70 mg, 0.145 mmol) was dissolved in MeOH (1.454 ml) and potassium carbonate (100 mg, 0.727 mmol) was added. The mixture was stirred at rt for 1 h, quenched with water, and extracted with MTBE. The organic layer was dried over MgSO₄ and concentrated in vacuo. Purification of the residue on silica gel with 0-30% EtOAc/hexane provided (1R,3r,5S,8s)-3-((5-cyclopropyl-3-(2-(trifluoromethoxy)phenyl)isoxazol-4-yl)methoxy)bicyclo[3.2.1]octane-8-thiol (12b) (43.5 mg, 0.099 mmol, 68.1% yield). LC/MS observed [M+H]⁺, 440.15.

Step 12c:

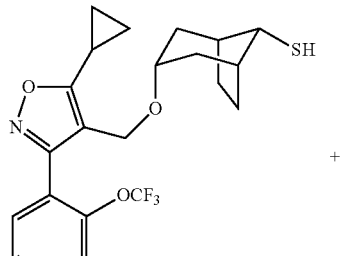

12b

+

(1R,3r,5S,8s)-3-((5-cyclopropyl-3-(2-(trifluoromethoxy)phenyl)isoxazol-4-yl)methoxy)bicyclo[3.2.1]octane-8-thiol (12b) (43.5 mg, 0.099 mmol) and methyl 2-chloroquinoxaline-5-carboxylate (26.4 mg, 0.119 mmol) was dissolved in DMA (0.330 ml). Hunig's base (35.3 μl, 0.198 mmol) was added. The mixture was stirred in microwave reactor at 170° C. for 20 min. The reaction was quenched with water and extracted with MTBE. The organic layer was dried over MgSO₄ and concentrated in vacuo. Purification of the residue on silica gel with 0-40% EtOAc/hexane provided methyl 2-(((1R,3r,5S,8s)-3-((5-cyclopropyl-3-(2-(trifluoromethoxy)phenyl)isoxazol-4-yl)methoxy)bicyclo[3.2.1]octan-8-yl)thio)quinoxaline-5-carboxylate (12c) (36 mg, 0.058 mmol, 58.1% yield). LC/MS observed [M+H]⁺, 626.19.

Step 12d:

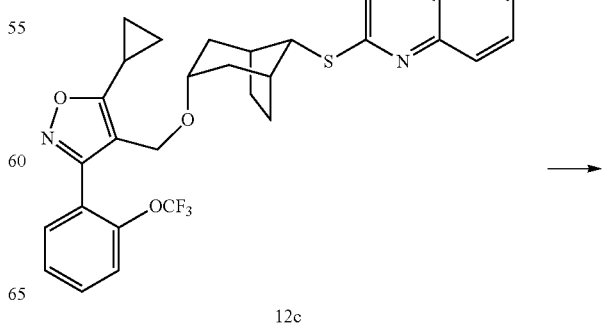

12c

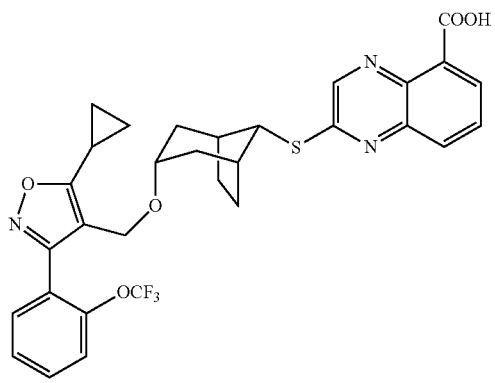

Example 12

Methyl 2-(((1R,3r,5S,8s)-3-((5-cyclopropyl-3-(2-(trifluoromethoxy)phenyl)isoxazol-4-yl)methoxy)bicyclo[3.2.1]octan-8-yl)thio)quinoxaline-5-carboxylate (12c) (36 mg, 0.058 mmol) was dissolved in THF (0.288 ml) and MeOH (0.288 ml). 2 M NaOH solution (288 μl, 0.575 mmol) was added. The mixture was stirred at 40° C. for 1 h, quenched with 1 M HCl, and extracted with EtOAc. The organic layer was concentrated in vacuo. Purification of the residue on prep-HPLC with 50-95% MeCN/H$_2$O afforded 2-(((1R,3r,5S,8s)-3-((5-cyclopropyl-3-(2-(trifluoromethoxy)phenyl)isoxazol-4-yl)methoxy)bicyclo[3.2.1]octan-8-yl)thio)quinoxaline-5-carboxylic acid (Example 12) (15 mg, 0.025 mmol, 42.6% yield). LC/MS observed [M+H]$^+$, 612.18; $^1$H NMR (400 MHz, Chloroform-d) δ 14.60 (s, 1H), 8.66 (dd, J=7.5, 1.5 Hz, 1H), 8.53 (s, 1H), 8.16 (dd, J=8.4, 1.5 Hz, 1H), 7.89 (dd, J=8.4, 7.4 Hz, 1H), 7.59 (dd, J=7.8, 1.8 Hz, 1H), 7.57-7.49 (m, 1H), 7.45-7.37 (m, 2H), 4.32 (s, 2H), 4.08 (s, 1H), 3.57 (td, J=4.2, 2.3 Hz, 1H), 2.38-2.32 (m, 2H), 2.17 (tt, J=8.4, 5.1 Hz, 1H), 2.05-1.89 (m, 4H), 1.87-1.77 (m, 4H), 1.30-1.17 (m, 2H), 1.20-1.09 (m, 2H).

Example 13

Step 13a:

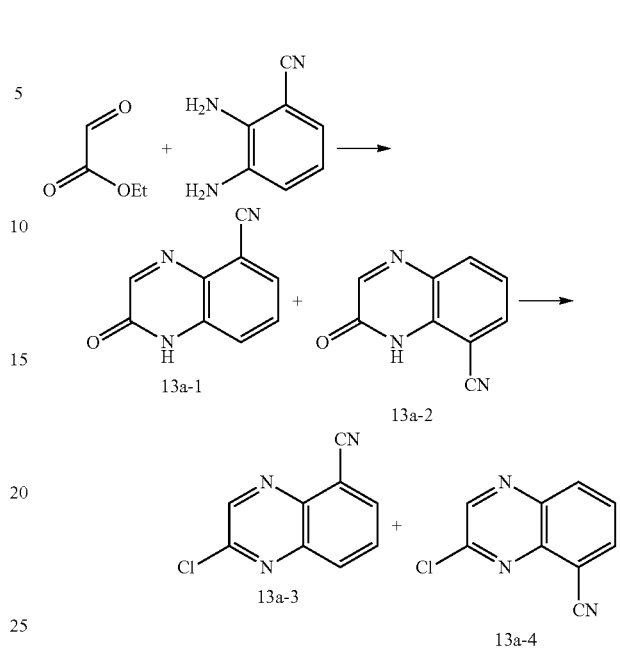

2,3-diaminobenzonitrile (500 mg, 3.76 mmol) was dissolved in ethanol (1.502 ml). A solution of ethyl 2-oxoacetate (917 μl, 4.51 mmol) in toluene was added. The mixture was stirred at 50° C. for 16 h. The reaction was cooled to rt, diluted with MTBE, and filtered. The solid was dried to afford a mixture of 2-oxo-1,2-dihydroquinoxaline-5-carbonitrile (13a-1) and 3-oxo-3,4-dihydroquinoxaline-5-carbonitrile (13a-2) (6:1, 396 mg, 1.157 mmol, 30.8% yield). To the solid was added phosphorus oxychloride (4.6 mL, 49.4 mmol) and DMF (8.96 μl, 0.116 mmol). The resulting mixture was stirred at 100° C. for 45 min, cooled to rt, poured on ice, and extracted with DCM. The organic layer was dried over MgSO$_4$ and concentrated in vacuo. Purification of the residue on silica gel with 0-30% EtOAc/hexane provided 2-chloroquinoxaline-5-carbonitrile (13a-3) (241 mg) and 3-chloroquinoxaline-5-carbonitrile (13a-4) (79 mg).

Step 13b:

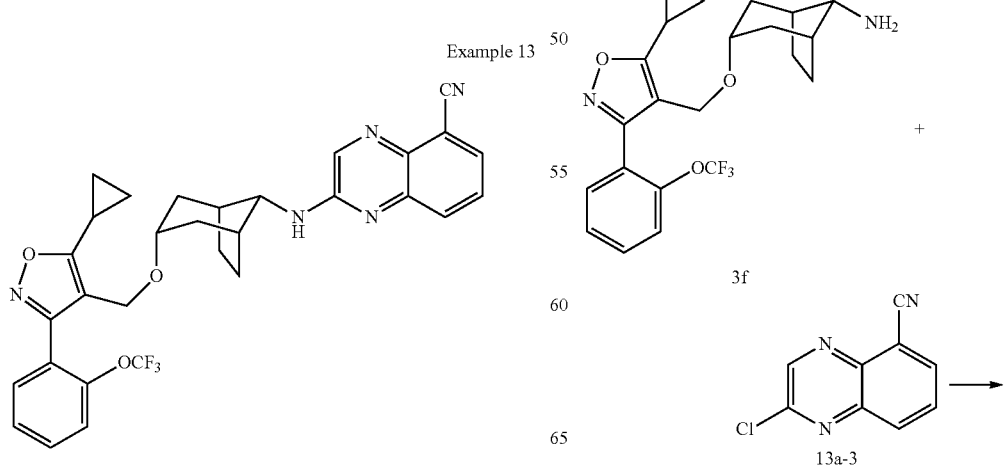

Example 13

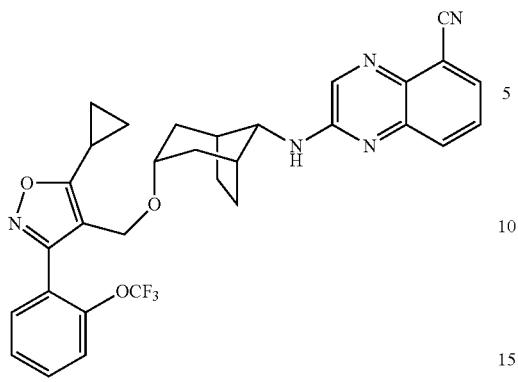

Example 13

(1R,3r,5S,8s)-3-((5-cyclopropyl-3-(2-(trifluoromethoxy)phenyl)isoxazol-4-yl)methoxy)bicyclo[3.2.1]octan-8-amine (3f) (140 mg, 0.331 mmol) and 2-chloroquinoxaline-5-carbonitrile (13a-3) (50 mg, 0.264 mmol) were dissolved in DMA (0.879 ml) and hunig's base (57.9 µl, 0.331 mmol) was added. The mixture was stirred in microwave ractor at 170° C. for 20 min. The reaction was quenched with water, and extracted with MTBE. The organic layer was dried over $Na_2SO_4$ and concentrated in vacuo. Purification of the residue on silica gel with 0-50% EtOAc/hexane provided 2-(((1R,3r,5S,8s)-3-((5-cyclopropyl-3-(2-(trifluoromethoxy)phenyl)isoxazol-4-yl)methoxy)bicyclo[3.2.1]octan-8-yl)amino)quinoxaline-5-carbonitrile (Example 13) (47 mg, 0.082 mmol, 49.3% yield). LC/MS observed $[M+H]^+$, 576.22; $^1H$ NMR (400 MHz, Chloroform-d) δ 8.31 (s, 1H), 7.87 (dd, J=8.5, 1.4 Hz, 1H), 7.74 (dd, J=7.3, 1.3 Hz, 1H), 7.64-7.57 (m, 2H), 7.53 (td, J=7.7, 1.8 Hz, 1H), 7.45-7.37 (m, 2H), 4.93 (d, J=6.5 Hz, 1H), 4.31 (s, 2H), 3.93 (d, J=6.4 Hz, 1H), 3.52 (t, J=5.0 Hz, 1H), 2.26 (s, 2H), 2.17 (tt, J=8.4, 5.1 Hz, 1H), 1.94 (d, J=14.6 Hz, 2H), 1.90-1.75 (m, 4H), 1.72-1.65 (m, 2H), 1.32-1.19 (m, 2H), 1.14 (dt, J=8.5, 3.3 Hz, 2H).

Example 13-2

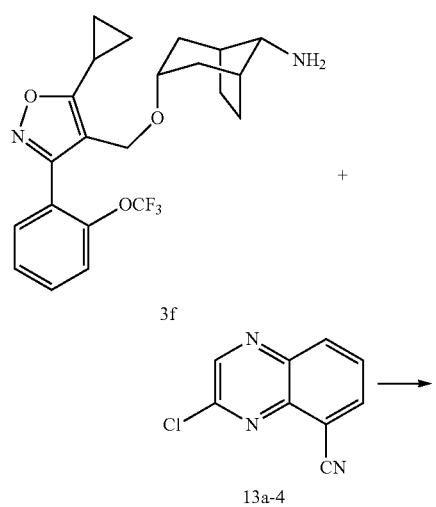

3f

+

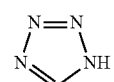

13a-4

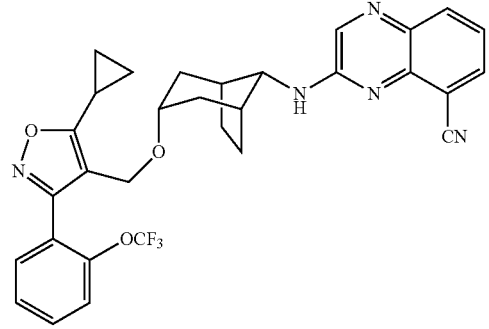

Example 13-2

Example 13-2 was prepared employing the same protocol as in Example 13. LC/MS observed $[M+H]^+$, 576.22; $^1H$ NMR (400 MHz, Chloroform-d) δ 8.25 (s, 1H), 8.05 (dd, J=8.3, 1.5 Hz, 1H), 7.91 (dd, J=7.5, 1.5 Hz, 1H), 7.59 (dd, J=7.8, 1.8 Hz, 1H), 7.52 (td, J=7.8, 1.9 Hz, 1H), 7.44-7.33 (m, 3H), 5.15 (d, J=6.1 Hz, 1H), 4.29 (s, 2H), 4.01 (d, J=6.1 Hz, 1H), 3.51 (tt, J=4.0, 1.9 Hz, 1H), 2.31 (q, J=3.4 Hz, 2H), 2.17 (ddt, J=10.2, 8.4, 4.0 Hz, 1H), 1.99-1.85 (m, 4H), 1.82 (t, J=6.9 Hz, 2H), 1.67 (dt, J=7.8, 4.7 Hz, 2H), 1.25 (tt, J=6.3, 3.6 Hz, 2H), 1.24-1.07 (m, 2H).

Example 13-3

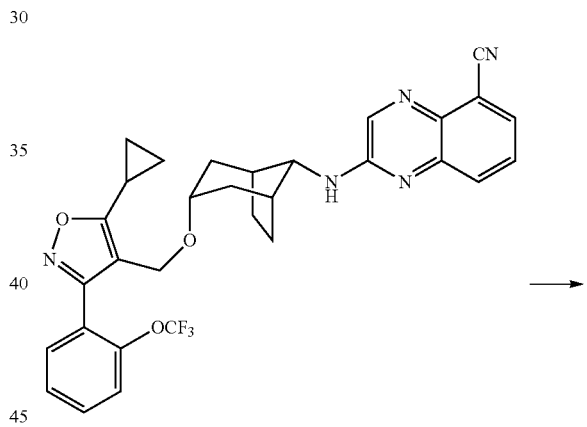

Example 13

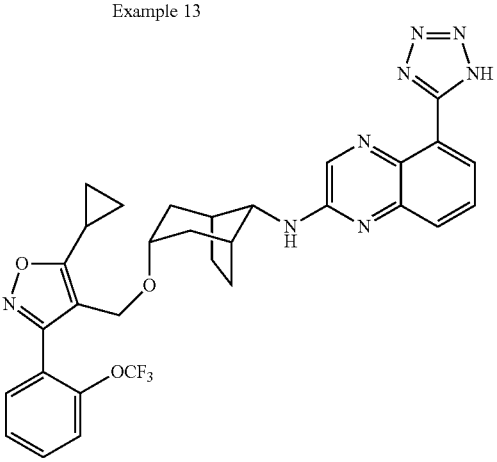

Example 13-3

To 2-(((1R,3r,5S,8s)-3-((5-cyclopropyl-3-(2-trifluoromethoxy)phenyl)isoxazol-4-yl)methoxy)bicyclo[3.2.1]

octan-8-yl)amino)quinoxaline-5-carbonitrile (Example 13) (35 mg, 0.061 mmol) in toluene (1.216 ml) was added TMSN₃ (16.14 μl, 0.122 mmol) and Bu₂SnO (16.66 mg, 0.067 mmol). The mixture was heated at 170° C. under microwave condition for 55 min. The mixture was diluted with EtOAc and washed with EtOAc. The organic layer was dried over MgSO₄, and concentrated in vacuo. Purification of the residue on C18 column with 0-100% MeCN/H₂O provided N-((1R,3r,5S,8s)-3-((5-cyclopropyl-3-(2-(trifluoromethoxy)phenyl)isoxazol-4-yl)methoxy)bicyclo[3.2.1]octan-8-yl)-5-(1H-tetrazol-5-yl)quinoxalin-2-amine (Example 13-3) (5.5 mg, 8.89 μmol, 14.62% yield). LC/MS observed [M+H]⁺, 619.24; ¹H NMR (400 MHz, Chloroform-d) δ 8.59 (dd, J=7.3, 1.4 Hz, 1H), 8.27 (s, 1H), 7.86 (dd, J=8.4, 1.5 Hz, 1H), 7.81-7.72 (m, 1H), 7.60 (dd, J=7.9, 1.8 Hz, 1H), 7.57-7.49 (m, 1H), 7.45-7.37 (m, 1H), 4.94 (d, J=6.4 Hz, 1H), 4.33 (s, 2H), 3.97 (d, J=6.5 Hz, 1H), 3.54 (t, J=4.8 Hz, 1H), 2.29 (s, 2H), 2.23-2.12 (m, 1H), 2.00-1.83 (m, 6H), 1.74-1.67 (m, 2H), 1.32-1.23 (m, 3H), 1.18-1.09 (m, 2H).

Example 13-4

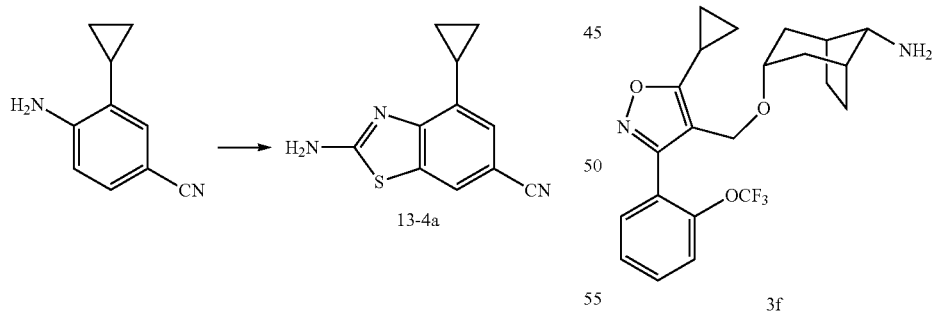

Step 13-4a:

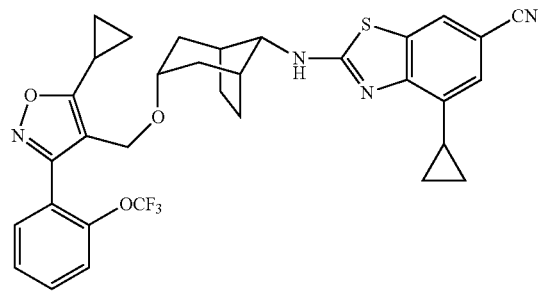

To a flask containing sodium thiocyanate (2.050 g, 25.3 mmol) and 4-amino-3-cyclopropylbenzonitrile (1 g, 6.32 mmol) at rt, was added AcOH (7.44 ml). To the resulted solution was added Br₂ (0.358 ml, 6.95 mmol) in AcOH (5.21 ml) dropwise at 0° C. The mixture was stirred at rt for 48 h. The mixture was concentrated and the pH was adjusted to 9 by slowly adding Na₂CO₃ with stirring. The resulted yellow slurry was filtered, and the solid was washed with water (2×20 ml) and dried to give 2-amino-4-cyclopropylbenzo[d]thiazole-6-carbonitrile (13-4a) as yellow solid (1.4 g). ¹H NMR (400 MHz, DMSO-d₆) δ 8.07 (bs, 2H), 7.98-7.94 (m, 1H), 7.15-7.10 (m, 1H), 2.46-2.35 (m, 1H), 1.00-0.93 (m, 2H), 0.87-0.80 (m, 2H).

Step 13-4b:

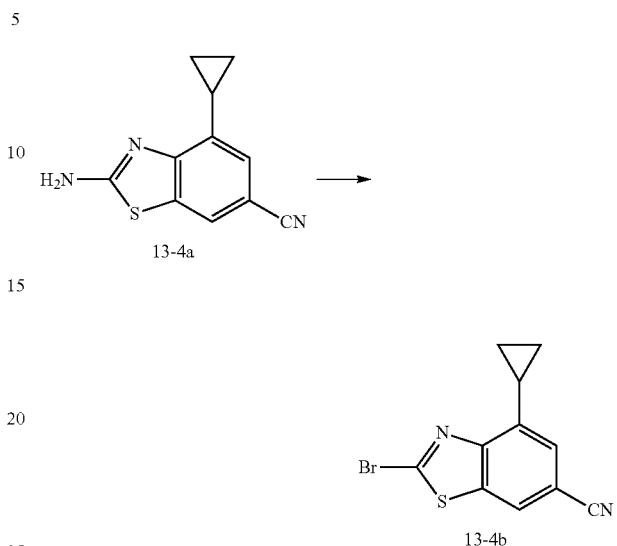

To a suspension of 2-amino-4-cyclopropylbenzo[d]thiazole-6-carbonitrile (13-4a; 1.4 g, 6.50 mmol) in acetonitrile (32.5 ml) was added copper(II) bromide (2.179 g, 9.76 mmol) at rt, To the mixture was added tert-butyl nitrite (1.802 ml, 15.15 mmol) over 10 min at 0° C. The reaction mixture was warmed up to rt and stirred for 40 h. The mixture was filtered through celite and the filtrate was concentrated and purified by silica gel column eluting with 0-60% EtOAc in hexanes to give 2-bromo-4-cyclopropylbenzo[d]thiazole-6-carbonitrile (13-4b) (210 mg) as a white solid. ¹H NMR (400 MHz, Chloroform-d) δ 7.89 (d, J=1.5 Hz, 1H), 7.11 (d, J=1.5 Hz, 1H), 2.88-2.62 (m, 1H), 1.33-1.09 (m, 2H), 1.00-0.81 (m, 2H).

Step 13-4c:

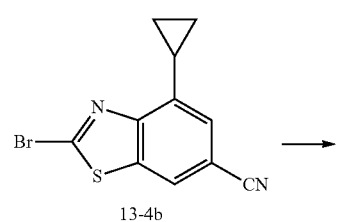

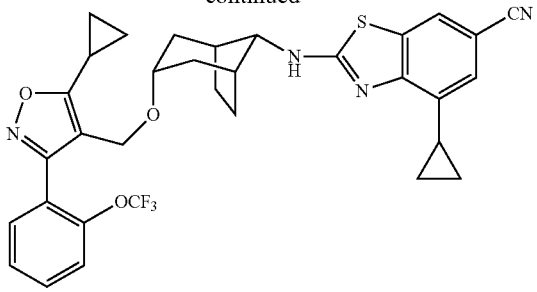

Example 13-4

Example 13-4 was prepared from compound 3f and compound 13-4b following a similar procedure in step 1j as in Example 1. LC/MS observed [M+H]⁺, 621.21; ¹H NMR (400 MHz, Chloroform-d) δ 7.64 (d, J=1.6 Hz, 1H), 7.56-7.45 (m, 2H), 7.39-7.33 (m, 2H), 7.00 (d, J=1.6 Hz, 1H), 5.57-5.40 (m, 1H), 4.26 (s, 2H), 3.44 (t, J=5.1 Hz, 1H), 3.42-3.37 (m, 1H), 2.48-2.37 (m, 1H), 2.28-2.22 (m, 2H), 2.17-2.05 (m, 1H), 1.93-1.83 (m, 2H), 1.81-1.69 (m, 4H), 1.65-1.58 (m, 2H), 1.23-1.18 (m, 2H), 1.11-1.02 (m, 4H), 0.84-0.78 (m, 2H).

Example 13-5

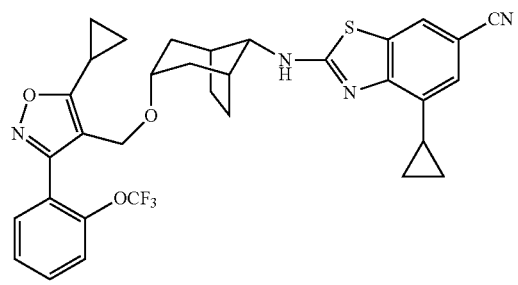

Example 13-5

Example 13-5 was prepared from example 13-4 employing the same protocol as in Example 13-3. LC/MS observed [M+H]⁺, 664.23; ¹H NMR (400 MHz, Methanol-d₄) δ 8.02 (d, J=1.7 Hz, 1H), 7.66-7.57 (m, 2H), 7.54-7.44 (m, 3H), 4.34 (s, 2H), 3.72 (s, 1H), 3.54-3.45 (m, 1H), 2.59-2.46 (m, 1H), 2.33-2.23 (m, 3H), 1.94-1.78 (m, 4H), 1.77-1.66 (m, 4H), 1.19-1.13 (m, 4H), 1.06-0.99 (m, 2H), 0.99-0.94 (m, 2H).

Example 13-6

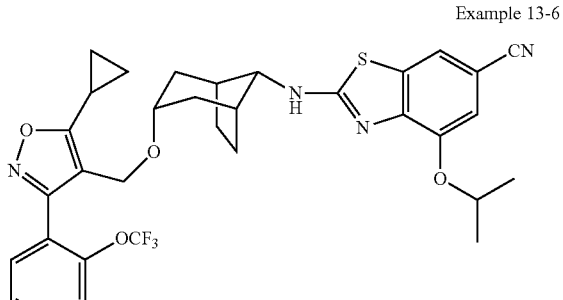

Example 13-6

Example 13-6 was prepared employing the same protocol as in Example 13-4. LC/MS observed [M+H]⁺, 639.21; ¹H NMR (400 MHz, Chloroform-d) δ 7.56-7.44 (m, 3H), 7.39-7.33 (m, 2H), 6.99 (d, J=1.4 Hz, 1H), 5.68 (d, J=6.7 Hz, 1H), 4.69 (hept, J=6.1 Hz, 1H), 4.25 (s, 2H), 3.43 (t, J=5.0 Hz, 1H), 3.27 (d, J=6.6 Hz, 1H), 2.24-2.17 (m, 2H), 2.14-2.06 (m, 1H), 1.92-1.82 (m, 2H), 1.79-1.65 (m, 4H), 1.61-1.52 (m, 2H), 1.42 (d, J=6.1 Hz, 6H), 1.23-1.18 (m, 2H), 1.11-1.05 (m, 2H).

Example 13-7

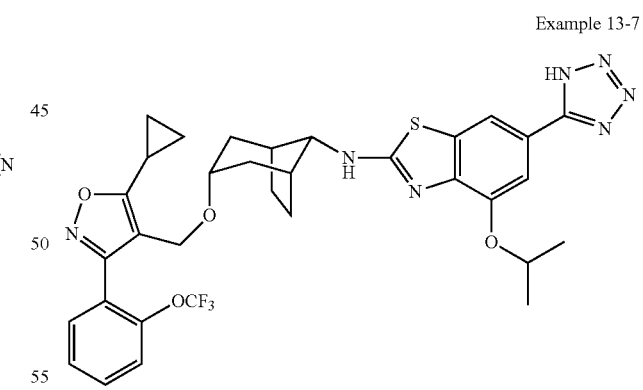

Example 13-7

Example 13-7 was prepared from example 13-6 employing the same protocol as in Example 13-3. LC/MS observed [M+H]⁺, 682.24 (M+1); ¹H NMR (400 MHz, Methanol-d4) δ 7.87 (d, J=1.5 Hz, 1H), 7.66-7.57 (m, 2H), 7.57-7.45 (m, 3H), 4.95-4.87 (m, 1H), 4.36-4.30 (m, 2H), 3.74 (s, 1H), 3.52-3.45 (m, 1H), 2.31-2.19 (m, 3H), 1.93-1.79 (m, 4H), 1.71 (s, 4H), 1.42 (d, J=6.1 Hz, 6H), 1.19-1.12 (m, 4H).

Example 14

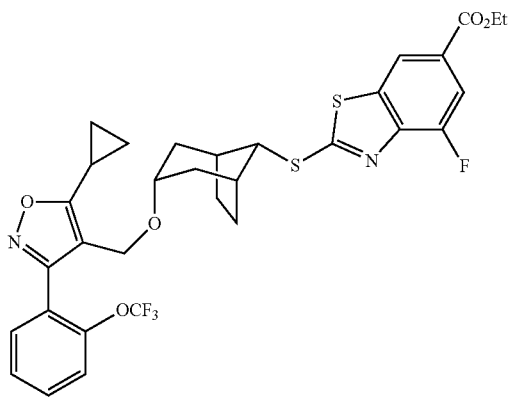

Example 14

Step 14a:

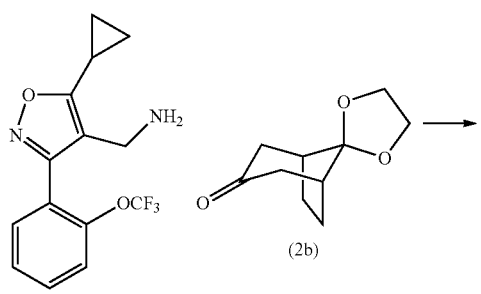

A mixture of (5-cyclopropyl-3-(2-(trifluoromethoxy)phenyl)isoxazol-4-yl)methanamine (400 mg, 1.341 mmol), (1R,5S)-spiro[bicyclo[3.2.1]octane-8,2'-[1,3]dioxolan]-3-one (2b) (244 mg, 1.341 mmol) and sodium triacetoxyborohydride (568 mg, 2.68 mmol) in 1,2-Dichloroethane (8 ml) was heated to 55° C. and stirred overnight. The mixture was cooled down to rt, diluted with EtOAc, and then washed with sat.NaHCO$_3$ and brine. The organic layer was dried over Na$_2$SO$_4$ and concentrated. The residue was purified by chromatography on silica gel eluting with 0-40% EtOAc/hexane to give (1R,3r,5S)—N-((5-cyclopropyl-3-(2-(trifluoromethoxy)phenyl)isoxazol-4-yl)methyl)spiro[bicyclo[3.2.1]octane-8,2'-[1,3]dioxolan]-3-amine (14a) as a colorless oil (470 mg, 75%). $^1$H NMR (400 MHz, DMSO-d$_6$) δ 7.70-7.61 (m, 2H), 7.57-7.47 (m, 2H), 4.01-3.93 (m, 1H), 3.79 (s, 4H), 3.46 (d, J=5.2 Hz, 2H), 2.61 (t, J=6.2 Hz, 1H), 2.31 (tt, J=8.3, 5.2 Hz, 1H), 2.14-2.07 (m, 1H), 1.94-1.81 (m, 2H), 1.60 (s, 2H), 1.52-1.40 (m, 5H), 1.14-1.00 (m, 4H).

Step 14b:

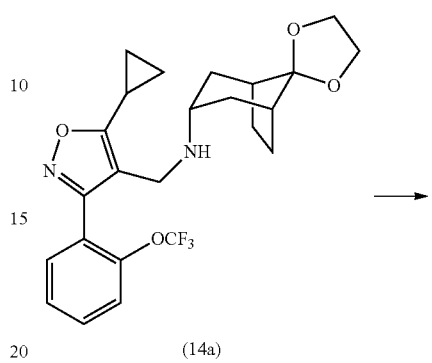

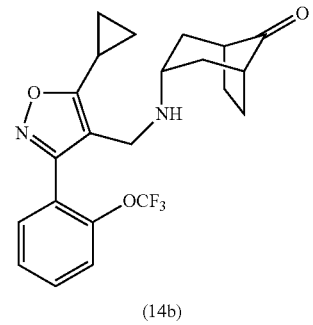

To (1R,3r,5S)—N-((5-cyclopropyl-3-(2-(trifluoromethoxy)phenyl)isoxazol-4-yl)methyl)spiro[bicyclo[3.2.1]octane-8,2'-[1,3]dioxolan]-3-amine (14a) (190 mg, 0.409 mmol) was added THF (2 ml) and concentrated HCl (336 μl, 4.09 mmol). The mixture was stirred at rt for 1 d. The reaction mixture was quenched with sat NaHCO$_3$ and extracted with EtOAc. The organic layers were washed with brine, dried over Na$_2$SO$_4$, filtered and concentrated. The residue was purified by chromatography on silica gel eluting with 0-30% EtOAc/hexane to give (1R,3r,5S)-3-(((5-cyclopropyl-3-(2-(trifluoromethoxy)phenyl)isoxazol-4-yl)methyl)amino)bicycle[3.2.1]-octan-8-one (14b) (120 mg, 70%) as a pale yellow oil. This material was used directly for the next reaction.

Step 14c:

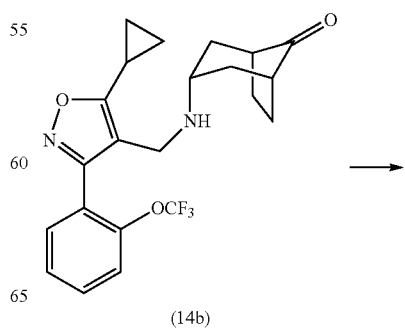

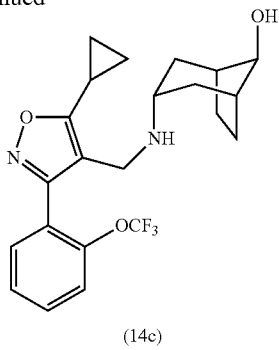

(14c)

To a solution of (1R,3r,5S)-3-(((5-cyclopropyl-3-(2-(trifluoromethoxy)phenyl)isoxazol-4-yl)methyl)amino)bicycle[3.2.1]-octan-8-one (14b) (120 mg, 0.285 mmol) in THF (2 ml) was added LAH (1 M in THF) (285 μl, 0.285 mmol) at −78° C. over 10 min. The mixture was stirred at this temperature for 1h, then quench with 0.5 ml water, followed by 0.5 ml 1N NaOH and 2 ml of brine. The mixture was stirred at 0° C. for 20 min, and then extracted with EtOAc. The combined organic layers were washed with brine, dried over Na$_2$SO$_4$, and concentrated. The residue was purified by chromatography on silica gel eluting with 0-60% EtOAc/hexane to give (1R,3r,5S,8r)-3-(((5-cyclopropyl-3-(2-(trifluoromethoxy)phenyl)isoxazol-4-yl)methyl)amino)bicyclo[3.2.1]octan-8-ol (14c) (115 mg, 95%) as a colorless oil. $^1$H NMR (400 MHz, DMSO-d$_6$) δ 7.65 (td, J=7.5, 1.7 Hz, 2H), 7.58-7.47 (m, 2H), 4.60 (d, J=3.2 Hz, 1H), 3.68-3.60 (m, 1H), 3.47 (s, 2H), 2.63 (t, J=6.2 Hz, 1H), 2.32 (tt, J=8.3, 5.3 Hz, 1H), 2.02-1.90 (m, 2H), 1.66 (s, 2H), 1.52 (q, J=5.4, 4.9 Hz, 2H), 1.41-1.32 (m, 2H), 1.26-1.00 (m, 6H).

Step 14d:

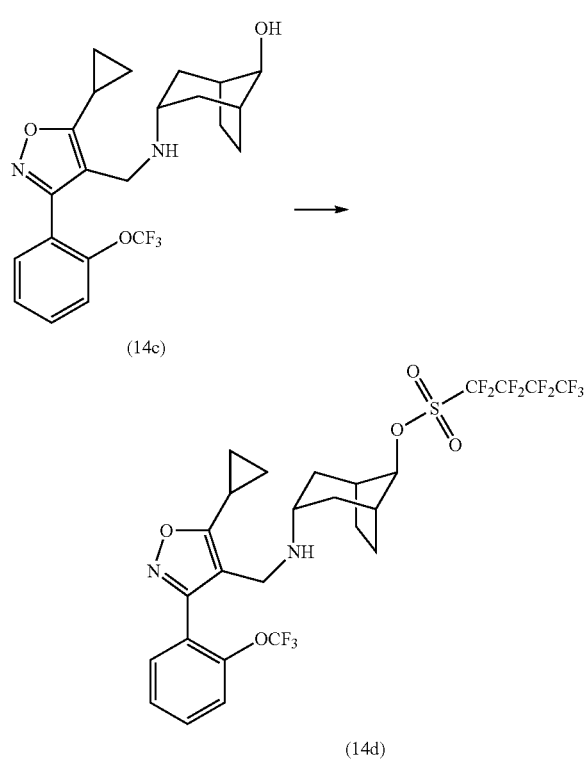

To a solution of (1R,3r,5S,8r)-3-(((5-cyclopropyl-3-(2-(trifluoromethoxy)phenyl)isoxazol-4-yl)methyl)amino)bicyclo[3.2.1]octan-8-ol (14c) (110 mg, 0.260 mmol) and DBU (58.9 μl, 0.391 mmol) in DCM (1 ml) at 0° C. was added nonafluorobutane-1-sulfonyl fluoride (51.5 μl, 0.286 mmol). The resulting mixture was stirred at 0° C. for 1 h, and then diluted with EtOAc, washed with sat NaHCO$_3$, brine, dried over Na$_2$SO$_4$, filtered, and concentrated. The residue was purified by chromatography on silica gel eluting with 0-30% EtOAc/hexane to give the product (1R,3r,5S,8r)-3-(((5-cyclopropyl-3-(2-(trifluoromethoxy)phenyl)isoxazol-4-yl)methyl)amino)bicyclo[3.2.1]octan-8-yl nonafluorobutane-1-sulfonate (14d) (160 mg, 87%) as a colorless oil. LC/MS observed [M+H], 705.13; $^1$H NMR (400 MHz, DMSO-d$_6$) δ 7.69-7.60 (m, 2H), 7.57-7.47 (m, 2H), 5.16 (t, J=5.2 Hz, 1H), 3.50 (d, J=5.0 Hz, 2H), 2.75 (t, J=6.0 Hz, 1H), 2.31 (ddd, J=11.8, 6.6, 4.1 Hz, 1H), 2.11 (s, 2H), 1.81-1.72 (m, 2H), 1.61 (q, J=5.2, 4.7 Hz, 2H), 1.57 (s, 1H), 1.47 (d, J=14.7 Hz, 4H), 1.12-1.01 (m, 4H).

Step 14e:

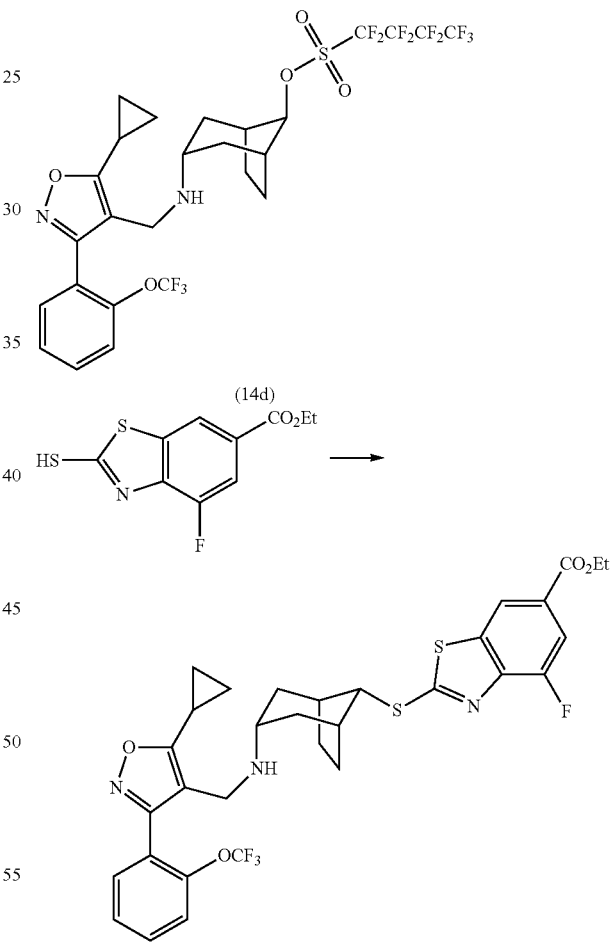

Example 14

To a solution of (1R,3r,5S,8r)-3-(((5-cyclopropyl-3-(2-(trifluoromethoxy)phenyl)isoxazol-4-yl)methyl)amino)bicyclo[3.2.1]octan-8-yl nonafluorobutane-1-sulfonate (14d) (155 mg, 0.220 mmol) and ethyl 4-fluoro-2-mercaptobenzo[d]thiazole-6-carboxylate (85 mg, 0.330 mmol) in THF (1.5 ml) at room temperature under N$_2$ was added potassium tert-butoxide (330 μl, 0.330 mmol). The reaction mixture was heated to 40° C. and stirred overnight, and then diluted with EtOAc, washed with sat NaHCO$_3$ and brine, dried over Na$_2$SO$_4$, filtered, and concentrated. The residue was first dissolved in DCM/TEA (triethyl amine) (1.5/0.5 ml) and purified by chromatography on silica gel eluting with 0-30% EtOAc/hexane to give ethyl 2-(((1R,3r,5S,8s)-3-(((5-cyclopropyl-3-(2-(trifluoromethoxy)phenyl)isoxazol-4-yl)methyl)amino)bicyclo[3.2.1]octan-8-yl)thio)-4-fluorobenzo[d]thiazole-6-carboxylate Example 14 (75 mg, 52%) as a pale yellow oil. LC/MS observed [M+H]$^+$, 662.19; $^1$H NMR (400 MHz, DMSO-d$_6$) δ 8.54 (d, J=1.5 Hz, 1H), 7.77 (dd, J=11.1, 1.5 Hz, 1H), 7.66 (td, J=7.9, 1.5 Hz, 2H), 7.58-7.48 (m, 2H), 4.35 (q, J=7.1 Hz, 2H), 3.89 (s, 1H), 3.50 (d, J=5.3 Hz, 2H), 2.76 (t, J=6.0 Hz, 1H), 2.39-2.27 (m, 1H), 2.28 (s, 2H), 1.85 (d, J=15.2 Hz, 2H), 1.76-1.55 (m, 6H), 1.49 (s, 1H), 1.35 (t, J=7.1 Hz, 3H), 1.15-1.01 (m, 4H).

Example 14-2

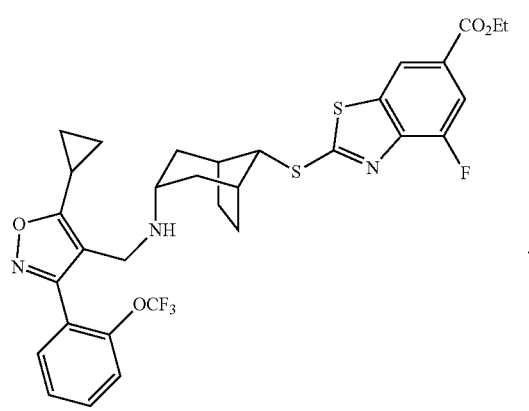

Example 14

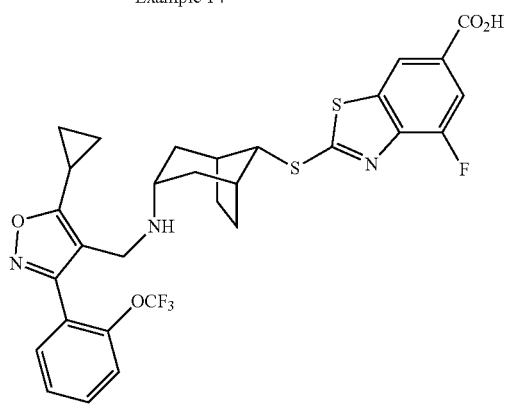

Example 14-2

To a solution of Example 14 (65 mg, 0.098 mmol) in THF (2 ml) was added 1N lithium hydroxide (196 μl, 0.196 mmol). The mixture was stirred overnight at 40° C., cooled to rt, and concentrated to remove THF. The residue was diluted with water and acidified with 1 N HCl to pH 5, and then extracted with ethyl acetate. The combined organic layers were washed with brine, dried over Na$_2$SO$_4$, filtered, and concentrated. The residue was lyophilized to give 2-(((1R,3r,5S,8s)-3-(((5-cyclopropyl-3-(2-(trifluoromethoxy)phenyl)isoxazol-4-yl)methyl)amino)bicyclo[3.2.1]octan-8-yl)thio)-4-fluorobenzo[d]thiazole-6-carboxylic acid Example 14-2 (62 mg) as a white solid. LC/MS observed [M+H]$^+$, 634.15; $^1$H NMR (400 MHz, DMSO-d$_6$) δ 8.50 (d, J=1.4 Hz, 1H), 7.74 (dd, J=11.1, 1.5 Hz, 1H), 7.66 (t, J=7.5 Hz, 2H), 7.58-7.49 (m, 2H), 3.88 (s, 1H), 3.51 (s, 2H), 2.77 (t, J=5.9 Hz, 1H), 2.33 (ddd, J=13.2, 8.3, 5.2 Hz, 1H), 2.28 (s, 2H), 1.85 (s, 2H), 1.71 (dd, J=14.4, 3.8 Hz, 3H), 1.69-1.61 (m, 3H), 1.60 (s, 1H), 1.14-1.02 (m, 4H).

Example 14-3

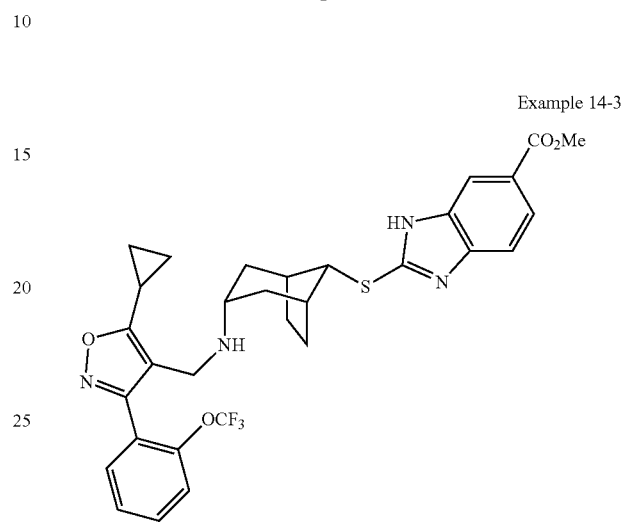

Example 14-3

Example 14-3 was prepared from compound (14d) following the same protocol as Example 14. LC/MS observed [M+H]$^+$, 613.21; H NMR (400 MHz, DMSO-d$_6$) δ 12.82 (s, 1H), 8.11-8.02 (m, 1H), 7.77 (d, J=8.4 Hz, 1H), 7.70-7.59 (m, 2H), 7.58-7.41 (m, 3H), 3.88 (d, J=17.4 Hz, 1H), 3.86 (s, 3H), 3.48 (s, 2H), 2.74 (t, J=5.8 Hz, 1H), 2.37-2.27 (m, 1H), 2.17 (s, 2H), 1.82 (d, J=14.4 Hz, 2H), 1.69 (s, 1H), 1.64 (s, 4H), 1.44 (s, 1H), 1.26-1.01 (m, 4H).

Example 14-4

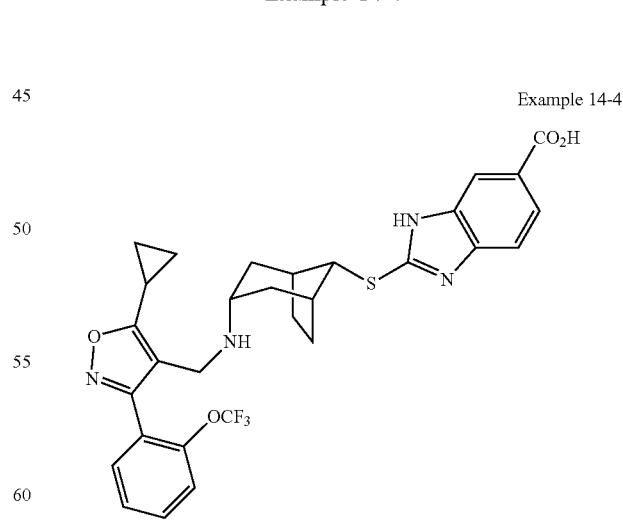

Example 14-4

Example 14-4 was prepared from Example 14-3 following the same protocol as Example 14-1. LC/MS observed [M+H]$^+$, 599.19.

Example 15

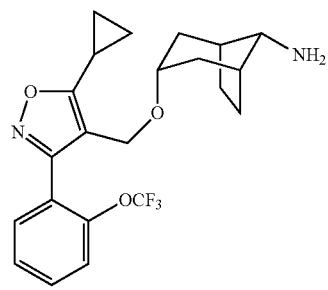

3f

+

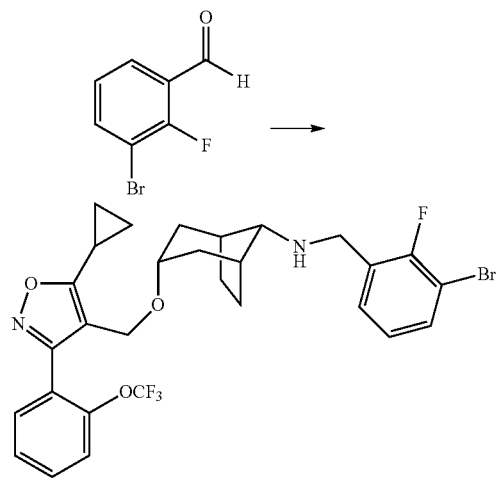

Example 15

To 3-bromo-2-fluorobenzaldehyde (13.23 mg, 0.065 mmol) in CH₂Cl₂ (0.2 ml) was added (1R,3r,5S,8s)-3-((5-cyclopropyl-3-(2-(trifluoromethoxy)phenyl)isoxazol-4-yl)methoxy)bicyclo[3.2.1]octan-8-amine (0.261 ml, 0.065 mmol, 0.25 M in THF), and sodium triacetoxyborohydride (13.81 mg, 0.065 mmol). The mixture was stirred at RT for 16 h, quenched with water, and extracted with DCM. The organic layer was loaded on silica gel column and eluted with 0-100% EtOAc/hexane to provided (1R,3r,5S,8s)-N-(3-bromo-2-fluorobenzyl)-3-((5-cyclopropyl-3-(2-(trifluoromethoxy)phenyl)isoxazol-4-yl)methoxy)bicyclo[3.2.1]octan-8-amine (Example 15) (3.5 mg, 5.74 μmol, 8.81% yield). LC/MS observed [M+H]⁺, 611.1.

Example 15-2

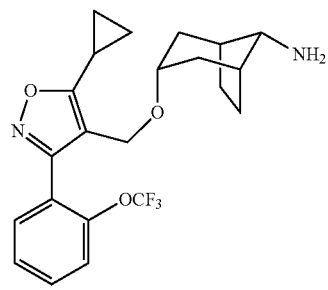

3f

+

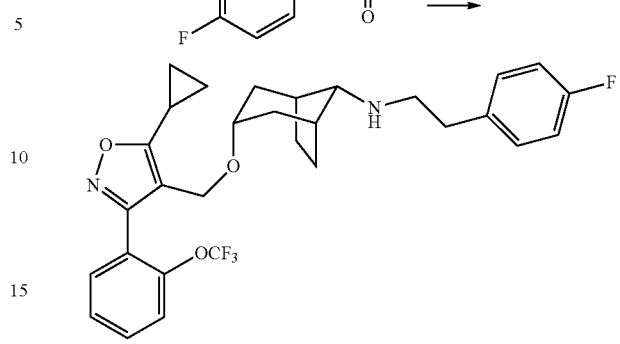

Example 15-2

Example 15-2 was prepared from compound (3f) following the same protocol as Example 15. LC/MS observed [M+H]⁺, 545.2.

Example 16

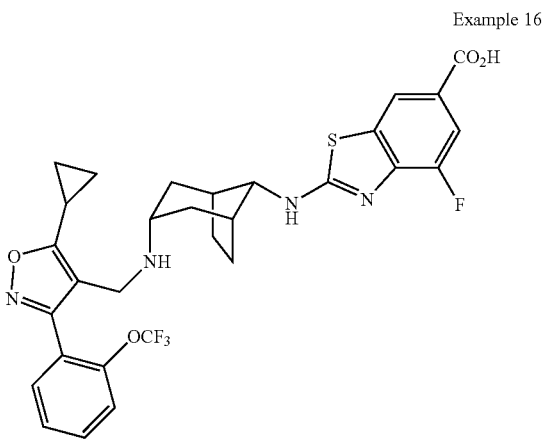 [SMILES: O=C(O)c1cc(F)c2nc(NC3C4CCC3CC(NCc3c(-c5ccccc5OC(F)(F)F)noc3C3CC3)C4)sc2c1]

Example 16

Step 16a:

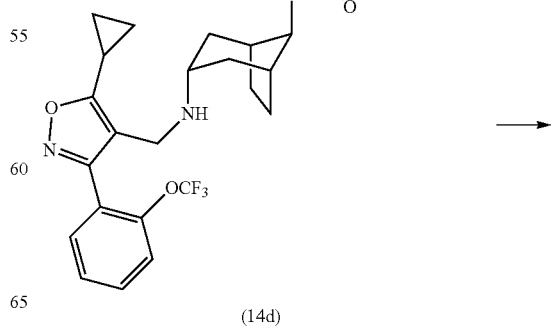

(14d)

-continued

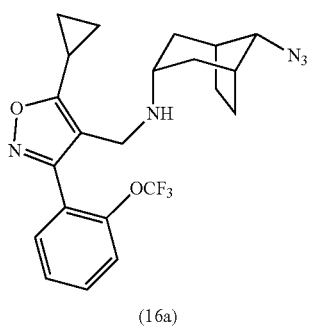

(16a)

A mixture of (1R,3r,5S,8r)-3-(((5-cyclopropyl-3-(2-(trifluoromethoxy)phenyl)isoxazol-4-yl)methyl)amino)bicyclo[3.2.1]octan-8-yl nonafluorobutane-1-sulfonate (14d) (490 mg, 0.696 mmol) and sodium azide (136 mg, 2.087 mmol) in DMA (3 ml) was stirred at rt for 18 h, then quenched with water, and extracted with ethyl acetate. The combined organic layers were washed brine, dried over $Na_2SO_4$, and concentrated. The residue (dissolved in DCM/MeOH 90/10) was purified by chromatography on silica gel eluting with 0-30% EtOAc/hexane to give (1R,3r,5S,8s)-8-azido-N-((5-cyclopropyl-3-(2-(trifluoromethoxy)phenyl)isoxazol-4-yl)methyl)bicyclo[3.2.1]octan-3-amine (16a) as a colorless oil. LC/MS observed [M+H]$^+$, 448.20; $^1$H NMR (400 MHz, DMSO-d$_6$) δ 7.70-7.61 (m, 2H), 7.60-7.48 (m, 2H), 3.64 (s, 1H), 3.45 (d, J=3.9 Hz, 2H), 2.65-2.57 (m, 1H), 2.31 (tt, J=8.3, 5.2 Hz, 1H), 1.99 (d, J=3.9 Hz, 2H), 1.67-1.47 (m, 6H), 1.42 (dd, J=8.7, 4.4 Hz, 2H), 1.26-1.00 (m, 4H).

Step 16b:

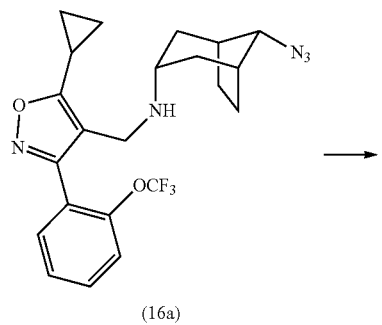

(16a)

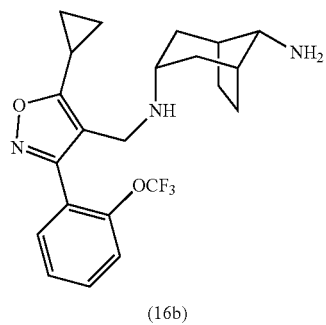

(16b)

To a solution of (1R,3r,5S,8s)-8-azido-N-((5-cyclopropyl-3-(2-(trifluoromethoxy)phenyl)isoxazol-4-yl)methyl)bicyclo[3.2.1]octan-3-amine (16a) (240 mg, 0.536 mmol) in THF (3 ml) was added triphenylphosphine (211 mg, 0.805 mmol). The resulting mixture was heated to 60° C. and stirred for 30 min, water (58.0 µl, 3.22 mmol) was added, and the reaction mixture was stirred overnight at 60° C., cooled down rt, and then concentrated. The residue was purified by chromatography on silica gel eluting with 0-15% (1% TEA in MeOH)/DCM to give (1R,3r,5S,8s)-N3-((5-cyclopropyl-3-(2-(trifluoromethoxy)phenyl)isoxazol-4-yl)methyl)bicyclo[3.2.1]octane-3,8-diamine (16b) as a colorless oil. LC/MS observed [M+H]$^+$, 422.21.

Step 16c:

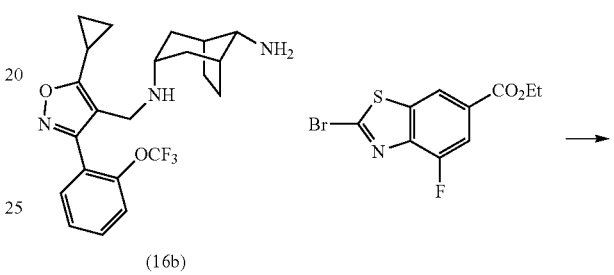

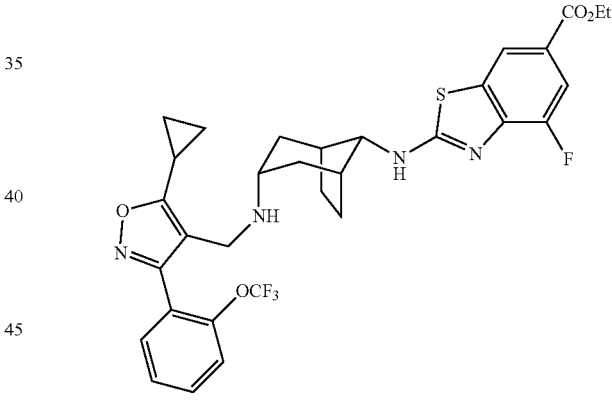

(16c)

To a mixture of (1R,3r,5S,8s)-N3-((5-cyclopropyl-3-(2-(trifluoromethoxy)phenyl)isoxazol-4-yl)methyl)bicyclo[3.2.1]octane-3,8-diamine (16b) (53 mg, 0.126 mmol), methyl 2-bromo-4-fluorobenzo[d]thiazole-6-carboxylate (73.0 mg, 0.252 mmol), and copper(I) iodide (11.97 mg, 0.063 mmol) in DMSO (3 ml) was added 2-((2,6-dimethylphenyl)amino)-2-oxoacetic acid (36.4 mg, 0.189 mmol) and potassium phosphate (53.4 mg, 0.252 mmol). The resulting mixture was stirred at 75° C. for 16h, then diluted with EtOAc, washed with water, brine, dried, filtered and concentrated. The residue was purified by CombiFlash (silica gel) eluting with 0 to 50% EtOAc/hexane to give ethyl 2-(((1R,3r,5S,8s)-3-(((5-cyclopropyl-3-(2-(trifluoromethoxy)phenyl)isoxazol-4-yl)methyl)amino)bicyclo[3.2.1]octan-8-yl)amino)-4-fluorobenzo[d]thiazole-6-carboxylate (16c) as a pale yellow foam. LC/MS observed

[M+H]+, 631.20; 1H NMR (400 MHz, DMSO-d6) δ 8.36 (s, 1H), 8.17 (d, J=1.5 Hz, 1H), 7.71-7.61 (m, 2H), 7.61-7.49 (m, 3H), 3.84 (s, 3H), 3.65 (s, 1H), 3.48 (s, 2H), 2.69 (t, J=5.9 Hz, 1H), 2.33 (tt, J=8.3, 5.1 Hz, 1H), 2.11 (d, J=6.2 Hz, 2H), 1.74 (d, J=15.1 Hz, 2H), 1.66-1.61 (m, 2H), 1.58 (s, 4H), 1.38 (s, 1H), 1.15-1.01 (m, 4H).

Step 16d:

residue was lyophilized to give a product as a white solid. LC/MS observed [M+H]+, 617.19.

Example 17

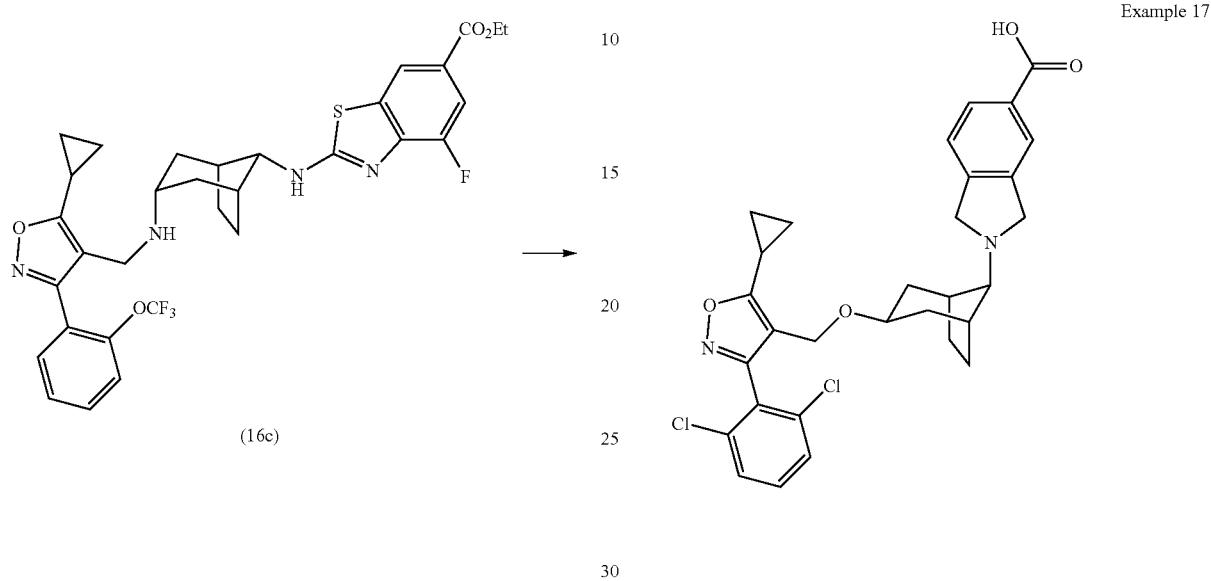

Step 17a:

To a solution of ethyl 2-(((1R,3r,5S,8s)-3-(((5-cyclopropyl-3-(2-(trifluoromethoxy)phenyl)isoxazol-4-yl)methyl)amino)bicyclo[3.2.1]octan-8-yl)amino)-4-fluorobenzo[d]thiazole-6-carboxylate (16c) (58 mg, 0.092 mmol) in THF (2 ml) was added lithium hydroxide 1N (184 μl, 0.184 mmol). The mixture was stirred for 2d at 45° C., cooled to rt, and concentrated. The residue was diluted with water and acidified with 1 N HCl to pH 5, and extracted with ethyl acetate. The combined organic layers were washed with brine, dried over Na2SO4, filtered, and concentrated. The To (1R,5S)-spiro[bicyclo[3.2.1]octane-8,2'-[1,3]dioxolan]-3-one (2b) (100 mg, 0.549 mmol) in DCM (1.5 ml) and MeOH (0.500 ml) was added sodium borohydride (20.76 mg, 0.549 mmol) and the mixture was stirred at RT for 2h. The mixture was quenched with water, stirred for 10 min, diluted with EtOAc. The organic layer was separated, washed with water, brine, dried, filtered and concentrated to give (1R,5S)-spiro[bicyclo[3.2.1]octane-8,2'-[1,3]dioxolan]-3-ol (17a) (101 mg) as a colorless oil. The material was directly used to the next step.

Step 17b:

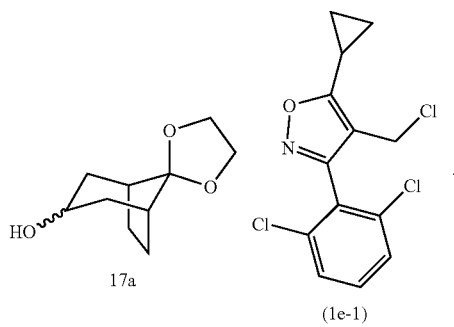

(1e-1)

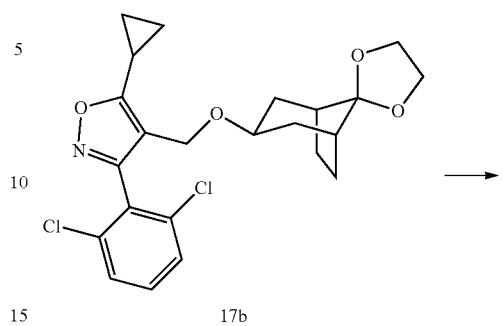

17b

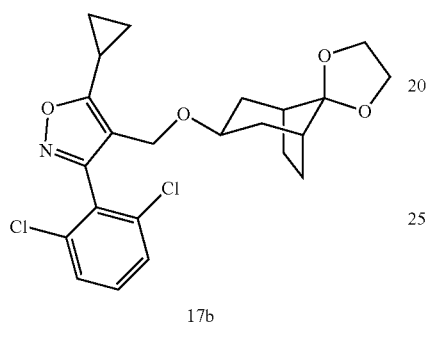

17b

To (1R,5S)-spiro[bicyclo[3.2.1]octane-8,2'-[1,3]dioxolan]-3-ol (17a) (101 mg, 0.549 mmol) in THF (3 ml) was added 18-crown-6 (145 mg, 0.549 mmol) and potassium tert-butoxide (92 mg, 0.824 mmol). The resulting mixture was stirred at RT for 20 min, and to the mixture was added TBAI (20.28 mg, 0.055 mmol) and 4-(chloromethyl)-5-cyclopropyl-3-(2,6-dichlorophenyl)isoxazole (1e-1) (216 mg, 0.714 mmol). The mixture was stirred at 70° C. for 16h. The mixture was quenched with NaHCO$_3$ solution, extracted with EtOAc, and the organic layer was separated, washed with water, brine, dried, filtered and concentrated. The residue was purified by CombiFlash eluting with 0-40% EtOAc/hexane to give 5-cyclopropyl-3-(2,6-dichlorophenyl)-4-((((1R,3s,5S)-spiro[bicyclo[3.2.1]octane-8,2'-[1,3]dioxolan]-3-yl)oxy)methyl)isoxazole (17b) (80 mg, 0.178 mmol, 32.4% yield). LC/MS observed [M+H], 450.13; $^1$H NMR (500 MHz, Chloroform-d) δ 7.33-7.27 (m, 2H), 7.20 (dd, J=8.9, 7.2 Hz, 1H), 4.14 (s, 2H), 3.77 (d, J=1.4 Hz, 4H), 3.34 (tt, J=10.4, 6.3 Hz, 1H), 2.12-2.00 (m, 1H), 1.73-1.65 (m, 4H), 1.64-1.43 (m, 4H), 1.25-1.06 (m, 4H), 1.03-0.85 (m, 2H).

Step 17c:

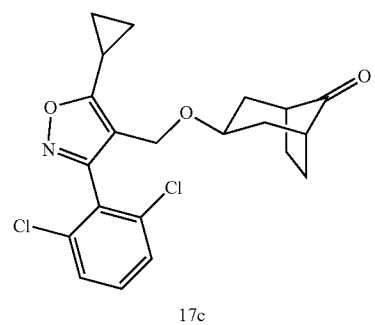

17c

To 5-cyclopropyl-3-(2,6-dichlorophenyl)-4-((((1R,3s,5S)-spiro[bicyclo[3.2.1]octane-8,2'-[1,3]dioxolan]-3-yl)oxy)methyl)isoxazole (17b) (80 mg, 0.178 mmol) in acetonitrile (4 ml) was added copper(II) chloride hydrate (108 mg, 0.711 mmol) and the mixture was stirred at RT for 3 days, then heated up to 70° C. for 6h. The mixture was concentrated and the residue was purified by CombiFlash eluting with 0-30% EtOAc/hexane to give (1R,3s,5S)-3-((5-cyclopropyl-3-(2,6-dichlorophenyl)isoxazol-4-yl)methoxy)bicyclo[3.2.1]octan-8-one (17c) (13 mg). $^1$H NMR (400 MHz, Chloroform-d) δ 7.52-7.31 (m, 3H), 4.31 (s, 2H), 3.85 (tt, J=10.6, 5.7 Hz, 1H), 2.21-2.05 (m, 5H), 2.02-1.89 (m, 2H), 1.78-1.65 (m, 3H), 1.37-1.23 (m, 3H), 1.23-1.00 (m, 2H).

Step 17d:

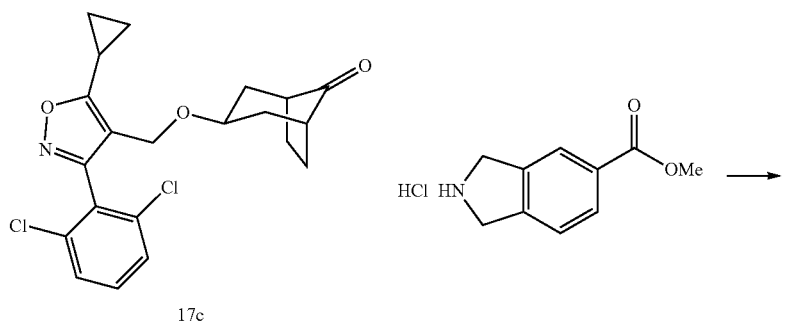

17c

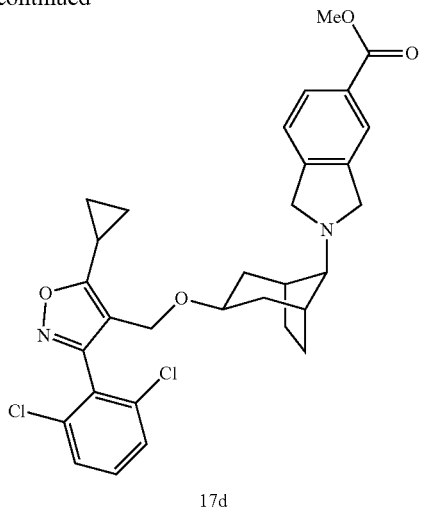

17d

A solution of (1R,3s,5S)-3-((5-cyclopropyl-3-(2,6-dichlorophenyl)isoxazol-4-yl)methoxy)bicyclo[3.2.1]octan-8-one (17c) (21 mg, 0.052 mmol) and methyl isoindoline-5-carboxylate hydrochloride (16.56 mg, 0.078 mmol) in CF$_3$CH$_2$OH (2 ml) was heated up to 45° C. for 1h, sodium borohydride (5.87 mg, 0.155 mmol) was then added and the mixture was stirred at 45° C. for 16h. The mixture was quenched with water, concentrated and the residue was purified by CombiFlash eluting with 0-40% EtOAc/hexane to give methyl 2-((1R,3s,5S,8r)-3-((5-cyclopropyl-3-(2,6-dichlorophenyl)isoxazol-4-yl)methoxy)bicyclo[3.2.1]octan-8-yl)isoindoline-5-carboxylate (17d) (26 mg, 0.046 mmol, 89% yield). LC/MS observed [M+H], 567.18; $^1$H NMR (500 MHz, Chloroform-d) δ 7.84 (dd, J=7.8, 1.6 Hz, 1H), 7.79 (d, J=1.4 Hz, 1H), 7.25-7.15 (m, 3H), 7.07 (dd, J=8.6, 7.6 Hz, 1H), 4.20 (s, 2H), 3.84 (s, 3H), 3.83-3.74 (m, 4H), 3.40 (tt, J=10.4, 6.1 Hz, 1H), 2.29 (t, J=4.3 Hz, 1H), 2.10-2.02 (m, 3H), 1.72-1.58 (m, 2H), 1.58-1.40 (m, 4H), 1.39-1.28 (m, 2H), 1.28-1.10 (m, 2H), 1.08-0.81 (m, 2H).

Step 17e:

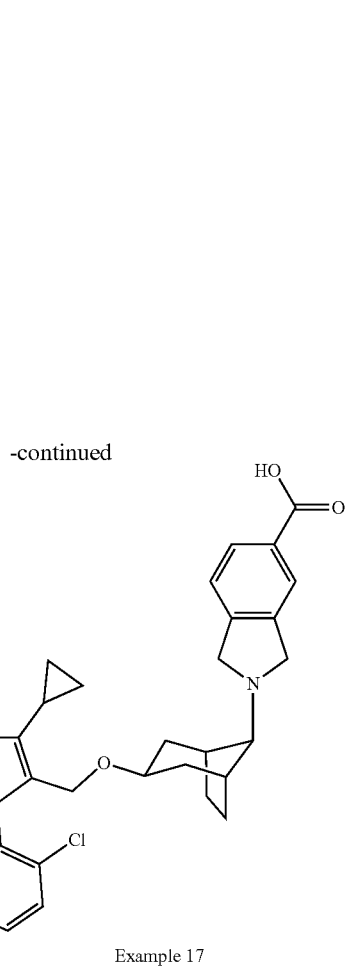

Example 17

Example 17 was prepared from compound (17d) following a similar procedure as in step 2i. LC/MS observed [M+H]$^+$, 553.38.

Example 18

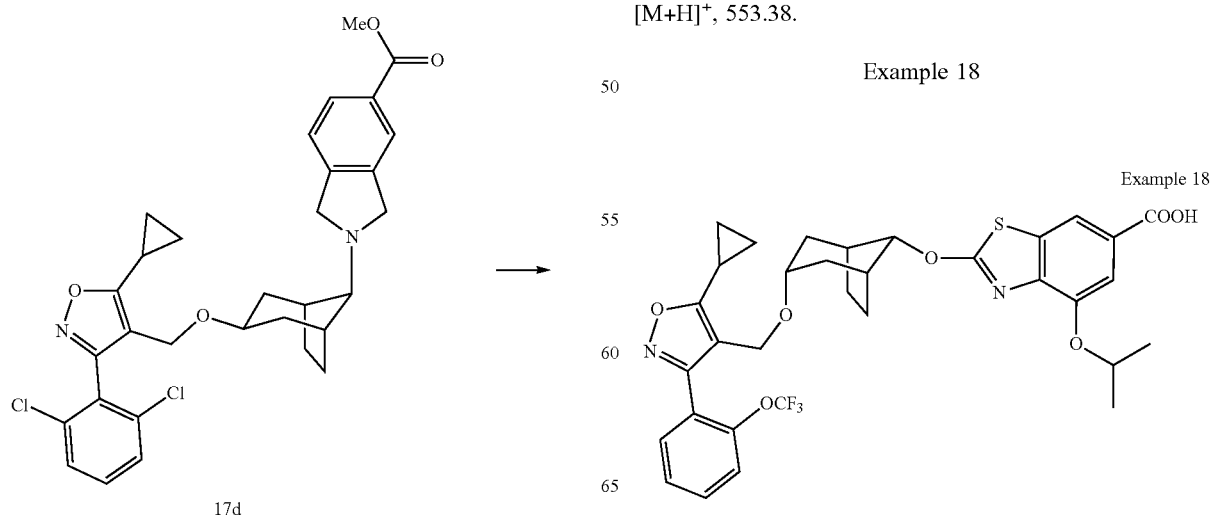

Example 18

Step 18a:

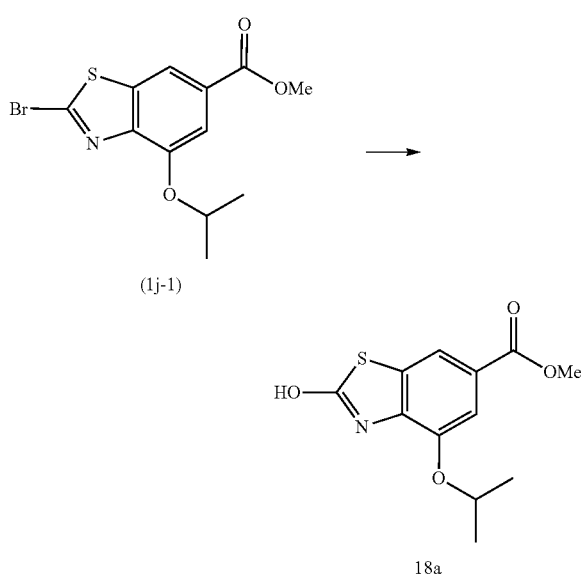

To methyl 2-bromo-4-isopropoxybenzo[d]thiazole-6-carboxylate (1j-10 (377 mg, 1.142 mmol) in DMA (2283 μl) was added cesium carbonate (744 mg, 2.283 mmol) and water (25.7 μl, 1.427 mmol). The mixture was stirred at 80° C. for 48 h, quenched with 1 M HCl, and extracted with EtOAc. The combined organic layer was dried over Na$_2$SO$_4$, and concentrated in vacuo. The residue was purified on silica gel eluting with 0-70% EtOAc/hexane to provided methyl 2-hydroxy-4-isopropoxybenzo[d]thiazole-6-carboxylate (18a) (105 mg) as a white solid. LC/MS observed [M−H]$^−$, 266.06; H NMR (400 MHz, Chloroform-d) δ 8.36 (s, 1H), 7.70 (d, J=1.4 Hz, 1H), 7.46 (d, J=1.3 Hz, 1H), 4.73 (p, J=6.1 Hz, 1H), 3.90 (s, 3H), 1.38 (d, J=6.1 Hz, 7H).

Step 18b:

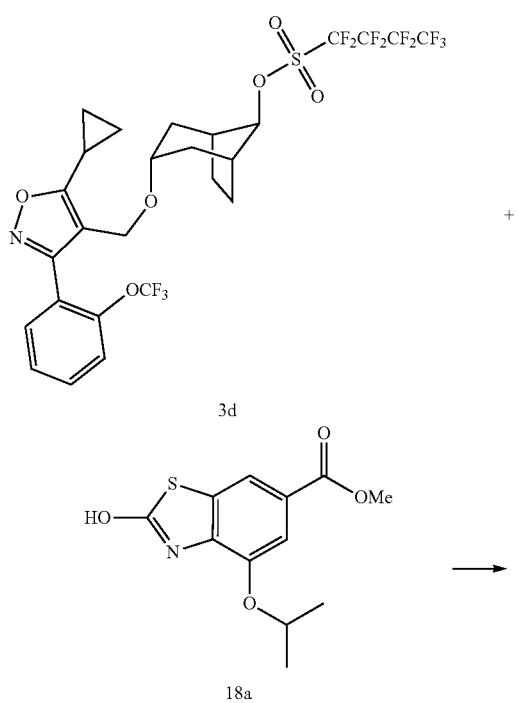

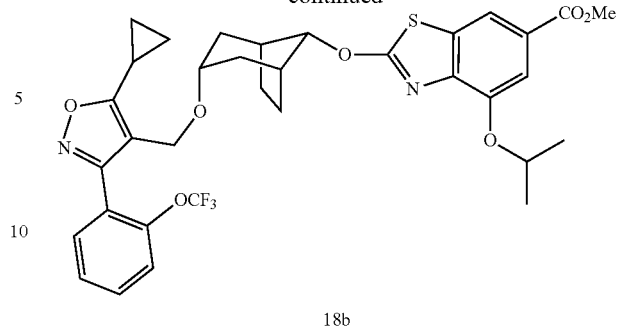

To a solution of methyl 2-hydroxy-4-isopropoxybenzo[d]thiazole-6-carboxylate (18a) (25.5 mg, 0.095 mmol) and (1R,3r,5S,8r)-3-((5-cyclopropyl-3-(2-(trifluoromethoxy)phenyl)isoxazol-4-yl)methoxy)bicyclo[3.2.1]octan-8-yl nonafluorobutane-1-sulfonate (3d) (48 mg, 0.068 mmol) in THF (0.680 ml) at rt under N$_2$ was added potassium tert-butoxide (1 M in THF) (95 μl, 0.095 mmol) and the mixture was heated to 40° C. for 16h. The mixture was diluted with EtOAc, washed with sat NaHCO3 and brine, dried over Na$_2$SO$_4$, filtered, and concentrated. The residue was purified by chromatography on silica gel eluting with 0-40% acetone/hexane to give methyl 2-(((1R,3r,5S,8s)-3-((5-cyclopropyl-3-(2-(trifluoromethoxy)phenyl)isoxazol-4-yl)methoxy)bicyclo[3.2.1]octan-8-yl)oxy)-4-isopropoxybenzo[d]thiazole-6-carboxylate (18b) (7.6 mg, 0.011 mmol, 16.61% yield) as an oil. LC/MS observed [M+H]$^+$, 673.22; $^1$H NMR (400 MHz, Chloroform-d) δ 7.61 (d, J=1.6 Hz, 1H), 7.55-7.31 (m, 5H), 4.76-4.67 (m, 1H), 4.60 (s, 1H), 4.25 (s, 2H), 3.88 (s, 3H), 3.50-3.45 (m, 1H), 2.77 (s, 2H), 2.17-2.07 (m, 1H), 1.92-1.80 (m, 4H), 1.74-1.66 (m, 2H), 1.62-1.54 (m, 2H), 1.37 (d, J=6.1 Hz, 6H), 1.22-1.16 (m, 2H), 1.11-1.03 (m, 2H).

Step 18c:

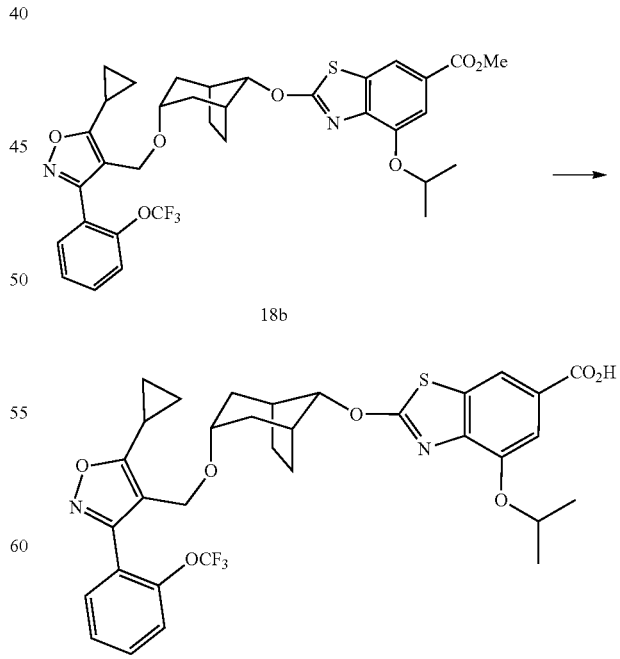

Example 18 was prepared from compound (18b) following a similar procedure as in step 3h. LC/MS observed [M+H]$^+$, 659.20; $^1$H NMR (500 MHz, Chloroform-d) δ 7.67 (d, J=1.5 Hz, 1H), 7.53 (dd, J=7.8, 1.8 Hz, 1H), 7.51-7.43 (m, 2H), 7.38-7.31 (m, 2H), 4.72 (hept, J=6.1 Hz, 1H), 4.62 (s, 1H), 4.25 (s, 2H), 3.52-3.44 (m, 1H), 2.78 (s, 2H), 2.14-2.07 (m, 1H), 1.94-1.81 (m, 4H), 1.74-1.67 (m, 2H), 1.62-1.53 (m, 2H), 1.38 (d, J=6.1 Hz, 6H), 1.22-1.17 (m, 2H), 1.11-1.03 (m, 2H).

The Following compounds in Table 2 were prepared by using the methods described above:

TABLE 2

| Example # | Example | observed [M + H]$^+$ | $^1$HNMR |
|---|---|---|---|
| 19 | | 682.24 | $^1$H NMR (400 MHz, Methanol-d$_4$) δ 7.87 (d, J = 1.5 Hz, 1H), 7.66-7.57 (m, 2H), 7.57-7.45 (m, 3H), 4.95-4.87 (m, 1H), 4.36-4.30 (m, 2H), 3.74 (s, 1H), 3.52-3.45 (m, 1H), 2.31-2.19 (m, 3H), 1.93-1.79 (m, 4H), 1.71 (s, 4H), 1.42 (d, J = 6.1 Hz, 6H), 1.19-1.12 (m, 4H). |
| 20 | | 664.23 | $^1$H NMR (400 MHz, Methanol-d$_4$) δ 8.02 (d, J = 1.7 Hz, 1H), 7.66-7.57 (m, 2H), 7.54-7.44 (m, 3H), 4.34 (s, 2H), 3.72 (s, 1H), 3.54-3.45 (m, 1H), 2.59-2.46 (m, 1H), 2.33-2.23 (m, 3H), 1.94-1.78 (m, 4H), 1.77-1.66 (m, 4H), 1.19-1.13 (m, 4H), 1.06-0.99 (m, 2H), 0.99-0.94 (m, 2H). |
| 21 | | 639.21 | $^1$H NMR (400 MHz, Chloroform-d) δ 7.56-7.44 (m, 3H), 7.39-7.33 (m, 2H), 6.99 (d, J = 1.4 Hz, 1H), 5.68 (d, J = 6.7 Hz, 1H), 4.69 (hept, J = 6.1 Hz, 1H), 4.25 (s, 2H), 3.43 (t, J = 5.0 Hz, 1H), 3.27 (d, J = 6.6 Hz, 1H), 2.24-2.17 (m, 2H), 2.14-2.06 (m, 1H), 1.92-1.82 (m, 4H), 1.79-1.65 (m, 4H), 1.61-1.52 (m, 2H), 1.42 (d, J = 6.1 Hz, 6H), 1.23-1.18 (m, 2H), 1.11-1.05 (m, 2H). |
| 22 | | 595.21 | $^1$H NMR (500 MHz, DMSO-d$_6$) δ 9.88 (s, 1H), 7.78-7.74 (m, 1H), 7.71 (t, J = 7.8 Hz, 1H), 7.69-7.60 (m, 3H), 7.57-7.51 (m, 2H), 4.27 (s, 2H), 3.73-3.66 (m, 1H), 3.48-3.44 (m, 1H), 2.36-2.29 (m, 1H), 2.20-2.11 (m, 2H), 1.81-1.66 (m, 6H), 1.56-1.48 (m, 2H), 1.17-1.10 (m, 2H), 1.10-1.04 (m, 2H). |

TABLE 2-continued

| Example # | Example | observed [M + H]+ | 1HNMR |
|---|---|---|---|
| 23 | | 659.20 | 1H NMR (500 MHz, Chloroform-d) δ 7.67 (d, J = 1.5 Hz, 1H), 7.53 (dd, J = 7.8, 1.8 Hz, 1H), 7.51-7.43 (m, 2H), 7.38-7.31 (m, 2H), 4.72 (hept, J = 6.1 Hz, 1H), 4.62 (s, 1H), 4.25 (s, 2H), 3.52-3.44 (m, 1H), 2.78 (s, 2H), 2.14-2.07 (m, 1H), 1.94-1.81 (m, 4H), 1.74-1.67 (m, 2H), 1.62-1.53 (m, 2H), 1.38 (d, J = 6.1 Hz, 6H), 1.22-1.17 (m, 2H), 1.11-1.03 (m, 2H). |
| 24 | | 636.16 | 1H NMR (400 MHz, Methanol-d4) δ 7.92 (d, J = 5.9 Hz, 1H), 7.67-7.55 (m, 2H), 7.50 (t, J = 7.6 Hz, 2H), 4.34 (s, 2H), 3.82-3.74 (m, 1H), 3.52-3.44 (m, 1H), 2.32-2.12 (m, 3H), 1.97-1.79 (m, 4H), 1.77-1.62 (m, 4H), 1.22-1.10 (m, 4H). |
| 25 | | 619.21 | |
| 26 | | 613.35 | 1H NMR (400 MHz, Methanol-d4) δ 8.46 (s, 1H), 8.14 (dd, J = 9.1, 3.1 Hz, 1H), 7.78 (dd, J = 8.5, 3.1 Hz, 1H), 7.66-7.57 (m, 2H), 7.53-7.46 (m, 2H), 4.36 (s, 2H), 3 64 (s, 1H), 3.57-3.50 (m, 1H), 2.33-2.23 (m, 3H), 1.98-1.82 (m, 4H), 1.81-1.71 (m, 4H), 1.21-1.12 (m, 4H). |

TABLE 2-continued

| Example # | Example | observed [M + H]+ | 1HNMR |
|---|---|---|---|
| 27 | (structure) | 616.09 | 1H NMR (400 MHz, Chloroform-d) δ 8.21 (s, 1H), 7.57-7.52 (m, 1H), 7.51-7.41 (m, 3H), 7.39-7.33 (m, 2H), 5.19-4.81 (m, 1H), 4.26 (s, 2H), 3.86 (d, J = 6.4 Hz, 1H), 3.53-3.42 (m, 1H), 2.24-2.17 (m, 2H), 2.12 (tt, J = 8.4, 5.1 Hz, 1H), 2.04-1.96 (m, 1H), 1.92-1.74 (m, 6H), 1.67-1.63 (m, 2H), 1.24-1.18 (m, 2H), 1.12-1.06 (m, 4H), 0.84-0.79 (m, 2H). |
| 28 | (structure) | 659.10 | 1H NMR (400 MHz, Chloroform-d) δ 14.65 (s, 1H), 8.27 (d, J = 2.0 Hz, 1H), 8.15 (s, 1H), 7.55 (dd, J = 7.8, 1.8 Hz, 1H), 7.52-7.44 (m, 2H), 7.39-7.34 (m, 2H), 4.28 (s, 2H), 3.89 (d, J = 6.3 Hz, 1H), 3.49 (t, J = 4.9 Hz, 1H), 2.28-2.20 (m, 2H), 2.17-2.06 (m, 2H), 1.95-1.75 (m, 6H), 1.71-1.64 (m, 2H), 1.24-1.20 (m, 2H), 1.16-1.05 (m, 4H), 0.95-0.87 (m, 2H). |
| 29 | (structure) | 595.19 | 1H NMR (400 MHz, Methanol-d4) δ 8.41 (d, J = 2.0 Hz, 1H), 8.28 (s, 1H), 8.10 (dd, J = 8.7, 2.0 Hz, 1H), 7.66-7.57 (m, 3H), 7.52-7.46 (m, 2H), 4.34 (s, 2H), 3.89 (s, 1H), 3.55-3.46 (m, 1H), 2.32-2.23 (m, 1H), 2.23-2.16 (m, 2H), 1.95-1.80 (m, 4H), 1.80-1.68 (m, 4H), 1.19-1.11 (m, 4H). |
| 30 | (structure) | 635.24 | 1H NMR (400 MHz, DMSO-d6) δ 8.30 (s, 1H), 7.71-7.61 (m, 2H), 7.59-7.44 (m, 4H), 7.35 (s, 1H), 4.29 (s, 2H), 3.82-3.75 (m, 1H), 3.51-3.43 (m, 1H), 2.37-2.29 (m, 1H), 2.15-2.09 (m, 3H), 1.83-1.72 (m, 4H), 1.70-1.50 (m, 4H), 1.18-1.10 (m, 2H), 1.10-1.01 (m, 4H), 0.83-0.78 (m, 2H). |

TABLE 2-continued
| Example # | Example | observed [M + H]+ | 1HNMR |
|---|---|---|---|
| 31 | 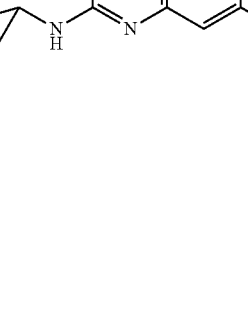 | 594.40 | 1H NMR (400 MHz, DMSO-d6) δ 8.21-7.45 (m, 8H), 7.04-6.73 (m, 2H), 4.30 (s, 2H), 3.92-3.78 (m, 1H), 3.49 (s, 1H), 2.39-2.31 (m, 1H), 2.19-2.11 (m, 2H), 1.90-1.73 (m, 4H), 1.70-1.52 (m, 4H), 1.19-1.12 (m, 2H), 1.12-1.05 (m, 2H). |
| 32 | 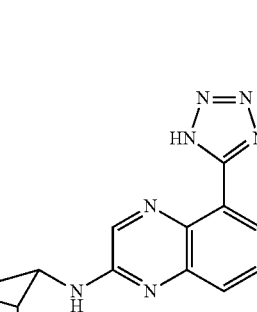 | 637.21 | 1H NMR (400 MHz, Methanol-d4) δ 8.37-8.30 (m, 1H), 7.87 (dd, J = 9.1, 2.8 Hz, 1H), 7.65-7.58 (m, 2H), 7.53-7.46 (m, 2H), 7.45-7.38 (m, 1H), 4.35 (s, 2H), 3.88 (s, 1H), 3.56-3.48 (m, 1H), 2.32-2.24 (m, 1H), 2.24-2.18 (m, 2H), 1.96-1.81 (m, 4H), 1.81-1.67 (m, 4H), 1.21-1.13 (m, 4H). |
| 33 |  | 712.45 | 1H NMR (400 MHz, Methanol-d4) δ 8.55 (s, 1H), 8.34 (s, 1H), 8.03 (s, 1H), 7.87-7.78 (m, 1H), 7.70-7.56 (m, 3H), 7.55-7.42 (m, 2H), 4.35 (s, 2H), 3.89 (s, 1H), 3.57-3.49 (m, 1H), 2.33-2.25 (m, 1H), 2.25-2.16 (m, 2H), 1.96-1.81 (m, 4H), 1.79-1.68 (m, 4H), 1.68-1.62 (m, 2H), 1.58 (s, 3H), 1.20-1.12 (m, 4H), 0.97-0.89 (m, 2H). |

TABLE 2-continued

| Example # | Example | observed [M + H]+ | 1HNMR |
|---|---|---|---|
| 34 | | 698.39 | 1H NMR (400 MHz, Methanol-d4) δ 8.53 (s, 1H), 8.31 (s, 1H), 8.01-7.88 (m, 1H), 7.82-7.72 (m, 1H), 7.66-7.54 (m, 3H), 7.54-7.44 (m, 2H), 4.34 (s, 2H), 3.87 (s, 1H), 3.54-3.49 (m, 1H), 3.17-3.07 (m, 1H), 2.32-2.23 (m, 1H), 2.23-2.15 (m, 2H), 1.95-1.80 (m, 4H), 1.79-1.64 (m, 4H), 1.31-1.23 (m, 2H), 1.19-1.12 (m, 4H), 1.12-1.03 (m, 2H). |
| 35 | | 576.20 | 1H NMR (400 MHz, Chloroform-d) δ 8.19 (s, 1H), 8.15 (d, J = 1.7 Hz, 1H), 7.71-7.62 (m, 2H), 7.57-7.52 (m, 1H), 7.52-7.45 (m, 1H), 7.39-7.33 (m, 2H), 5.01 (s, 1H), 4.27 (s, 2H), 3.91 (d, J = 6.5 Hz, 1H), 3.48 (t, J = 5.0 Hz, 1H), 2.27-2.17 (m, 2H), 2.17-2.07 (m, 1H), 1.95-1.75 (m, 6H), 1.68-1.60 (m, 2H), 1.23-1.19 (m, 2H), 1.12-1.06 (m, 2H). |
| 36 | | 640.33 | 1H NMR (400 MHz, Methanol-d4) δ 8.10-7.94 (m, 1H), 7.69-7.55 (m, 2H), 7.54-7.38 (m, 3H), 4.33 (s, 2H), 3.71 (s, 1H), 3.48 (t, J = 4.9 Hz, 1H), 2.52-2.42 (m, 1H), 2.32-2.21 (m, 3H), 1.93-1.77 (m, 4H), 1.75-1.56 (m, 4H), 1.19-1.11 (m, 4H), 1.04-0.96 (m, 2H), 0.91-0.84 (m, 2H). |
| 37 | | 684.40 | 1H NMR (400 MHz, Methanol-d4) δ 8.23 (d, J = 1.5 Hz, 1H), 7.81-7.76 (m, 1H), 7.66-7.55 (m, 2H), 7.53-7.45 (m, 2H), 4.33 (s, 2H), 3.79-3.73 (m, 1H), 3.52-3.44 (m, 1H), 2.30-2.21 (m, 3H), 1.98-1.78 (m, 4H), 1.78-1.58 (m, 4H), 1.18-1 12 (m, 4H). |

TABLE 2-continued
| Example # | Example | observed [M + H]+ | 1HNMR |
|---|---|---|---|
| 38 | 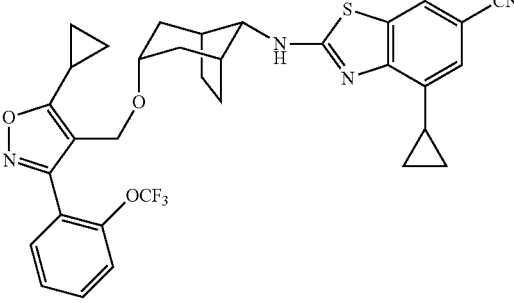 | 621.21 | 1H NMR (400 MHz, Chloroform-d) δ 7.64 (d, J = 1.6 Hz, 1H), 7.56-7.45 (m, 2H), 7.39-7.33 (m, 2H), 7.00 (d, J = 1.6 Hz, 1H), 5.57-5.40 (m, 1H), 4.26 (s, 2H), 3.44 (t, J = 5.1 Hz, 1H), 3.42-3.37 (m, 1H), 2.48-2.37 (m, 1H), 2.28-2.22 (m, 2H), 2.17-2.05 (m, 1H), 1.93-1.83 (m, 2H), 1.81-1.69 (m, 4H), 1.65-1.58 (m, 2H), 1.23-1.18 (m, 2H), 1.11-1.02 (m, 4H), 0.84-0.78 (m, 2H). |
| 39 | 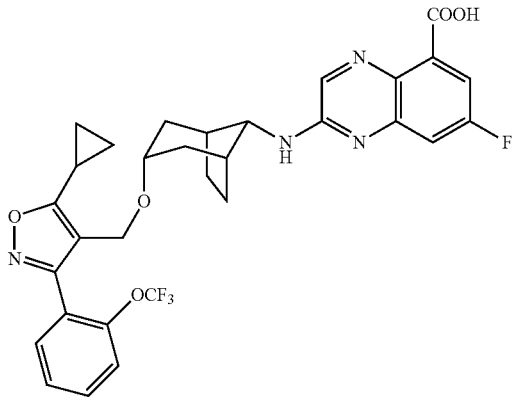 [SMILES: O=C(O)c1cc(F)cc2nc(NC3C4CCC3CC(OCc3c(-c5ccccc5OC(F)(F)F)noc3C3CC3)C4)cnc12] | 613.18 | 1H NMR (400 MHz, Methanol-d4) δ 8.24 (s, 1H), 7 84-7.76 (m, 1H), 7.65-7.56 (m, 2H), 7.52-7.40 (m, 3H), 4.34 (s, 2H), 3.86 (s, 1H), 3.54-3.47 (m, 1H), 2.32-2.23 (m, 1H), 2.23-2.17 (m, 2H), 1.94-1.81 (m, 4H), 1.78-1.67 (m, 4H), 1.19-1.13 (m, 4H). |
| 40 | 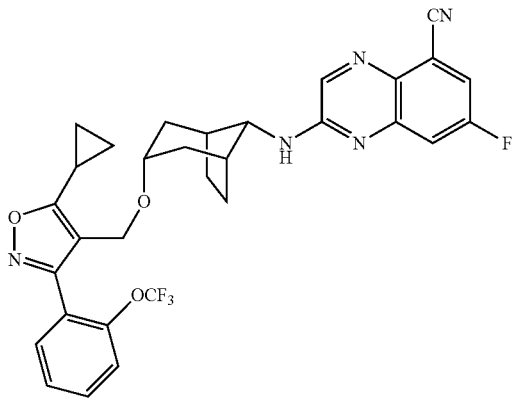 [SMILES: N#Cc1cc(F)cc2nc(NC3C4CCC3CC(OCc3c(-c5ccccc5OC(F)(F)F)noc3C3CC3)C4)cnc12] | 594.20 | 1H NMR (400 MHz, Chloroform-d) δ 8.32-8.22 (m, 1H), 7.58-7.52 (m, 1H), 7.52-7.44 (m, 2H), 7.44-7.39 (m, 1H), 7.39-7.33 (m, 2H), 5.10 (s, 1H), 4.27 (s, 2H), 3.88 (d, J = 6.4 Hz, 1H), 3.47 (t, J = 4.9 Hz, 1H), 2.23-2.17 (m, 2H), 2.17-2.08 (m, 1H), 1.92-1.75 (m, 6H), 1.68-1.60 (m, 2H), 1.24-1.18 (m, 2H), 1.12-1.05 (m, 2H). |
| 41 | 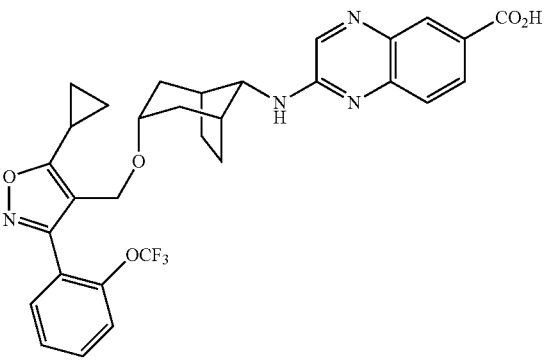 [SMILES: O=C(O)c1ccc2nc(NC3C4CCC3CC(OCc3c(-c5ccccc5OC(F)(F)F)noc3C3CC3)C4)cnc2c1] | 595.20 | 1H NMR (500 MHz, Methanol-d4) δ 9.09 (s, 1H), 8.55-8.35 (m, 1H), 8.23 (dd, J = 8.9, 2.0 Hz, 1H), 7.67-7.56 (m, 2H), 7.56-7.43 (m, 3H), 4.34 (s, 2H), 3.87 (s, 1H), 3.54-3.48 (m, 1H), 2.32-2.24 (m, 1H), 2.24-2.18 (m, 2H), 1.94-1.83 (m, 4H), 1.73 (t, J = 2.7 Hz, 4H), 1.20-1.10 (m, 4H). |

TABLE 2-continued

| Example # | Example | observed [M + H]+ | 1HNMR |
|---|---|---|---|
| 42 | | 617.19 | |
| 43 | | 634.15 | 1H NMR (400 MHz, DMSO-d6) δ 8.50 (d, J = 1.4 Hz, 1H), 7.74 (dd, J = 11.1, 1.5 Hz, 1H), 7.69 (s, 1H), 7.66 (t, J = 7.5 Hz, 2H), 7.58-7.49 (m, 2H), 3.88 (s, 1H), 3.51 (s, 2H), 2.77 (t, J = 5.9 Hz, 1H), 2.33 (ddd, J = 13.2, 8.3, 5.2 Hz, 1H), 2.28 (s, 2H), 1.85 (s, 2H), 1.71 (dd, J = 14.4, 3.8 Hz, 3H), 1.69-1.61 (m, 3H), 1.60 (s, 1H), 1.22-1.02 (m, 4H). |
| 44 | | 599.19 | |
| 45 | | 667.12 | 1H NMR (400 MHz, DMSO-d6) δ 8.74 (s, 1H), 7.93 (d, J = 11.2 Hz, 1H), 7.67 (ddd, J = 8.7, 7.2, 1.9 Hz, 1H), 7.66-7.53 (m, 3H), 7.57-7.49 (m, 1H), 4.27 (s, 2H), 3.78 (s, 1H), 3.42 (s, 1H), 2.62 (s, 2H), 2.35-2.26 (m, 1H), 1.86-1.70 (m, 6H), 1.63 (d, J = 7.7 Hz, 2H), 1.20-1.02 (m, 4H). |

TABLE 2-continued

| Example # | Example | observed [M + H]+ | 1HNMR |
|---|---|---|---|
| 46 | 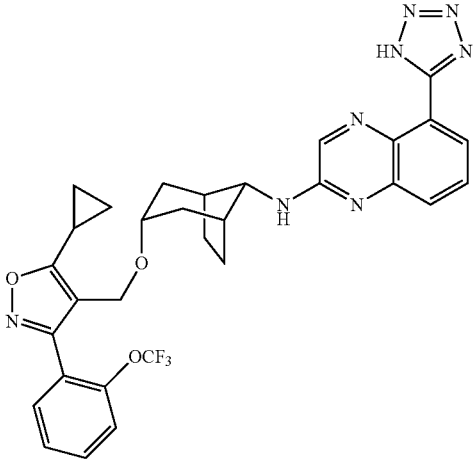 [SMILES: FC(F)(F)Oc1ccccc1-c1noc(C2CC2)c1COC1CC2CCC(C1)C2Nc1cnc2c(-c3nnn[nH]3)cccc2n1] | 619.24 | 1H NMR (400 MHz, Chloroform-d) δ 8.59 (dd, J = 7.3, 1.4 Hz, 1H), 8.27 (s, 1H), 7.86 (dd, J = 8.4, 1.5 Hz, 1H), 7.82-7.70 (m, 1H), 7.60 (dd, J = 7.8, 1.8 Hz, 1H), 7.57-7.47 (m, 1H), 7.42 (dd, J = 7.5, 3.7 Hz, 2H), 4.94 (d, J = 6.4 Hz, 1H), 4.33 (s, 2H), 3.97 (d, J = 6.4 Hz, 1H), 3.54 (t, J = 4.9 Hz, 1H), 2.29 (s, 2H), 2.18 (ddd, J = 13.6, 8.5, 5.1 Hz, 1H), 2.00-1.78 (m, 6H), 1.75-1.59 (m, 2H), 1.33-1.22 (m, 2H), 1.18-1.05 (m, 2H). |
| 47 | 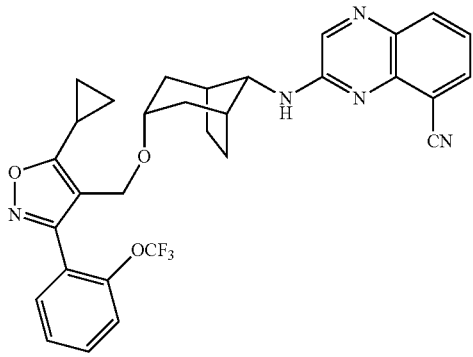 [SMILES: N#Cc1cccc2ncc(NC3C4CCC3CC(OCc3c(-c5ccccc5OC(F)(F)F)noc3C3CC3)C4)nc12] | 576.22 | 1H NMR (400 MHz, Chloroform-d) δ 8.25 (s, 1H), 8.05 (dd, J = 8.3, 1.5 Hz, 1H), 7.91 (dd, J = 7.5, 1.5 Hz, 1H), 7.59 (dd, J = 7.8, 1 8 Hz, 1H), 7.52 (td, J = 7.8, 1.9 Hz, 1H), 7.45-7.32 (m, 3H), 5.15 (d, J = 6.1 Hz, 1H), 4.29 (s, 2H), 4.01 (d, J = 6.1 Hz, 1H), 3.51 (tt, J = 4.0, 1.9 Hz, 1H), 2.31 (q, J = 3.4 Hz, 2H), 2.17 (ddt, J = 10.2, 8.4, 4.0 Hz, 1H), 1.98-1.76 (m, 6H), 1.67 (dt, J = 7.8, 4.7 Hz, 2H), 1.33-1.17 (m, 2H), 1.13 (dt, J = 8.5, 3.3 Hz, 2H). |
| 48 | 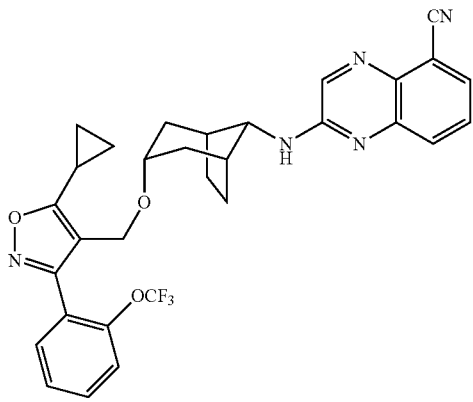 [SMILES: N#Cc1cccc2nc(NC3C4CCC3CC(OCc3c(-c5ccccc5OC(F)(F)F)noc3C3CC3)C4)cnc12] | 576.22 | 1H NMR (400 MHz, Chloroform-d) δ 8.31 (s, 1H), 7.87 (dd, J = 8.4, 1.4 Hz, 1H), 7.74 (dd, J = 7.3, 1.4 Hz, 1H), 7.65-7.56 (m, 2H), 7.53 (td, J = 7.8, 1.8 Hz, 1H), 7.45-7.36 (m, 2H), 4.93 (d, J = 6.5 Hz, 1H), 4.31 (s, 2H), 3.93 (d, J = 6.4 Hz, 1H), 3.52 (t, J = 5.0 Hz, 1H), 2.26 (s, 2H), 2.17 (tt, J = 8.4, 5.1 Hz, 1H), 1.98-1.75 (m, 6H), 1.75-1.62 (m, 2H), 1.33-1.18 (m, 2H), 1.14 (dt, J = 8.4, 3.3 Hz, 2H). |

TABLE 2-continued

| Example # | Example | observed [M + H]+ | 1HNMR |
|---|---|---|---|
| 49 | (structure: cyclopropyl-isoxazole with OCF3-phenyl, linked via CH2-O to bicyclic amine connected to quinoxaline-COOH) | 612.18 | 1H NMR (400 MHz, Chloroform-d) δ 8.66 (dd, J = 7.5, 1.5 Hz, 1H), 8.53 (s, 1H), 8.16 (dd, J = 8.4, 1.5 Hz, 1H), 7.89 (dd, J = 8.4, 7.4 Hz, 1H), 7.59 (dd, J = 7.8, 1.8 Hz, 1H), 7.56-7.48 (m, 1H), 7.45-7.35 (m, 2H), 4.32 (s, 2H), 4.08 (s, 1H), 3.58 (tt, J = 3.8, 1.6 Hz, 1H), 2.44-2.26 (m, 2H), 2.17 (tt, J = 8.4, 5.1 Hz, 1H), 2.06-1.88 (m, 4H), 1.88-1.72 (m, 4H), 1.31-1.19 (m, 2H), 1.19-1.05 (m, 2H). |

Assays

Human FXR (NRIH4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 μl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 μl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

To assess the FXR agonistic potency of the example compounds as well as for the reference compound (1), potency ranges were determined in the Human FXR (NRIH4) Assay as listed below in Table 2. The efficacy was normalized to CDCA set as 100%. (A:=EC50<0.025 μM; B=0.025 μM<EC50<0.500 μM; C=EC50>0.5 μM).

TABLE 2

| Example # | EC50 |
|---|---|
| 1 | A |
| 2 | A |
| 2-2 | A |
| 3 | A |
| 3-2 | A |
| 3-3 | B |
| 3-4 | A |
| 3-5 | B |
| 3-6 | A |
| 3-7 | A |
| 3-9 | A |
| 3-10 | A |
| 3-11 | A |
| 3-12 | A |
| 3-13 | A |
| 4 | A |
| 5 | B |
| 6 | B |
| 7 | A |
| 8 | B |
| 8-2 | B |
| 8-3 | B |
| 8-4 | B |
| 8-5 | B |
| 8-6 | B |
| 8-7 | C |
| 8-8 | C |
| 9 | A |

TABLE 2-continued

| Example # | EC50 |
|---|---|
| 9-2 | A |
| 9-3 | B |
| 9-4 | B |
| 9-5 | A |
| 9-6 | A |
| 9-7 | B |
| 9-8 | C |
| 9-9 | C |
| 9-10 | B |
| 9-11 | A |
| 9-12 | A |
| 9-13 | B |
| 9-14 | A |
| 9-15 | A |
| 9-16 | A |
| 9-17 | B |
| 10 | A |
| 10-2 | A |
| 11 | B |
| 11-2 | B |
| 11-3 | B |
| 11-4 | B |
| 11-5 | C |
| 11-6 | B |
| 11-7 | B |
| 11-8 | C |
| 11-9 | B |
| 11-10 | A |
| 11-11 | B |
| 11-12 | B |
| 11-13 | B |
| 11-14 | B |
| 11-15 | B |
| 11-16 | B |
| 11-17 | A |
| 11-18 | C |
| 11-19 | B |
| 12 | A |
| 13 | A |
| 13-2 | C |
| 13-3 | A |
| 13-4 | B |
| 13-5 | A |
| 13-6 | A |
| 13-7 | A |
| 14 | C |
| 14-2 | B |
| 14-3 | B |
| 15 | B |
| 15-2 | C |
| 16 | B |
| 17 | B |
| 18 | B |
| 19 | A |
| 20 | A |
| 21 | A |
| 22 | A |
| 23 | B |
| 24 | A |
| 25 | B |
| 26 | C |
| 27 | B |
| 28 | A |
| 29 | A |
| 30 | A |
| 31 | B |
| 32 | A |
| 33 | A |
| 34 | A |
| 35 | A |
| 36 | A |
| 37 | A |
| 38 | B |
| 39 | A |
| 40 | A |
| 41 | A |
| 42 | B |
| 43 | B |

TABLE 2-continued

| Example # | EC50 |
|---|---|
| 45 | B |
| 46 | A |
| 47 | B |
| 48 | A |
| 49 | A |

While this invention has been particularly shown and described with references to preferred embodiments thereof, it will be understood by those skilled in the art that various changes in form and details may be made therein without departing from the scope of the invention encompassed by the appended claims.

We claim:

1. A compound represented by Formula I or a pharmaceutically acceptable salt thereof:

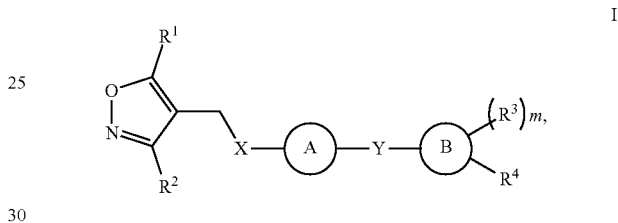

wherein

R$^1$ is hydrogen, halogen, cyano, optionally substituted —C$_1$-C$_6$ alkyl, optionally substituted —C$_2$-C$_6$ alkenyl, optionally substituted —C$_2$-C$_6$ alkynyl, or optionally substituted —C$_3$-C$_6$ cycloalkyl;

R$^2$ is optionally substituted aryl optionally substituted cycloalkenyl;

cyclopentyl or cyclohexyl, wherein said cyclopentyl or cyclohexyl is optionally substituted with up to 3 groups which are independently selected from halogen, optionally substituted —C$_1$-C$_6$ alkyl, optionally substituted —C$_1$-C$_6$ alkoxy, optionally substituted —C$_3$-C$_6$ cycloalkyl, optionally substituted, —C$_3$-C$_6$ cycloalkenyl, optionally substituted aryl, and optionally substituted heteroaryl;

X is O or NR$^x$; wherein R$^x$ is selected from hydrogen, —C$_1$-C$_6$-alkyl, —C$_1$-C$_6$ haloalkyl, —C$_3$-C$_6$ cycloalkyl, and formyl;

A is

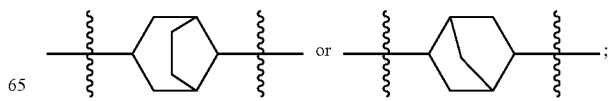

Y is O, NR$^{x1}$, S, SO, or SO$_2$, wherein R$^{x}$i is selected from the group consisting of hydrogen, —C$_1$-C$_6$-alkyl, —C$_1$-C$_6$ haloalkyl, —C$_3$-C$_6$ cycloalkyl, and formyl;

B is benzothiazol-2-yl;

each R$^3$ is independently selected from the group consisting of halo, hydroxy, —OMe, —OCH$_2$F, —OCHF$_2$, —OCF$_3$, —C$_2$-C$_6$-alkoxy, —C$_1$-C$_6$-alkyl, —C$_1$-C$_6$ haloalkyl, —C$_2$-C$_6$ alkenyl, —C$_2$-C$_6$ alkynyl, —C$_3$-C$_6$ cycloalkyl, —O—C$_1$-C$_2$alkylphenyl, —C$_1$-C$_6$-hydroxyalkyl, —C$_1$-C$_6$ hydroxylhaloalkyl, —C$_3$-C$_6$ hydroxylcycloalkyl, aryl, cyano, —SCF$_3$, —NH$_2$, —NHMe, —NMe$_2$, —C$_1$-C$_6$-alkylamine, and alkylaryl; alternatively, two adjacent or geminal R$^3$ groups are taken together with the atom or atoms to which they are connected to form an optionally substituted carbocyclic;

m is 0, 1, 2, or 3;

R$^4$ is hydrogen, hydroxy, tetrazolyl, cyano,

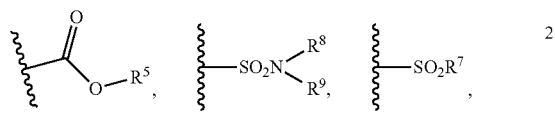

—(C(R$^{10}$)$_2$)$_n$C(O)OR$^5$, CONH(CH$_2$)$_n$CO$_2$R$^6$, or CONH(CH$_2$)$_n$SO$_2$R$^7$; wherein n is 1, 2, 3 or 4;

R$^5$ and R$^6$ are independently selected from the group consisting of hydrogen, —C$_1$-C$_8$ alkyl, and —C$_3$-C$_8$ cycloalkyl;

R$^7$ is selected from the group consisting of hydroxyl, —C$_1$-C$_8$ alkyl, —C$_3$-C$_8$ cycloalkyl, and aryl;

R$^8$ and R$^9$ are each independently selected from hydrogen, optionally substituted —C$_1$-C$_8$ alkyl, optionally substituted —C$_2$-C$_8$ alkenyl, optionally substituted C$_2$-C$_8$ alkynyl, optionally substituted —C$_3$-C$_8$ cycloalkyl, optionally substituted aryl, and optionally substituted alkylaryl; and each R$^{10}$ is independently hydrogen or halogen, or two geminal R$^{10}$ groups, together with the carbon atom to which they are attached, form a C$_3$-C$_6$-cycloalkyl;

wherein unless otherwise stated each optionally substituted group is optionally substituted with 1 to 3 substituents independently selected from halo, C$_1$-C$_4$-alkyl, halo-C$_1$-C$_4$-alkyl, C$_2$-C$_4$-alkenyl, halo-C$_2$-C$_4$-alkenyl, C$_3$-C$_6$-cycloalkyl, C$_1$-C$_4$-alkoxy, halo-C$_1$-C$_4$-alkoxy, —CN; —OH; NH$_2$; C$_1$-C$_4$-alkylamino; di(C$_1$-C$_4$-alkyl)amino; and NO$_2$.

2. The compound of claim 1, wherein R$^2$ is selected from the group consisting of

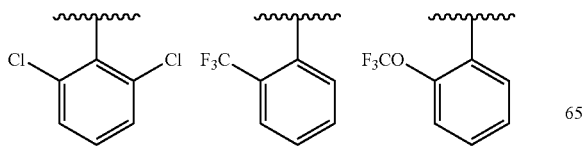

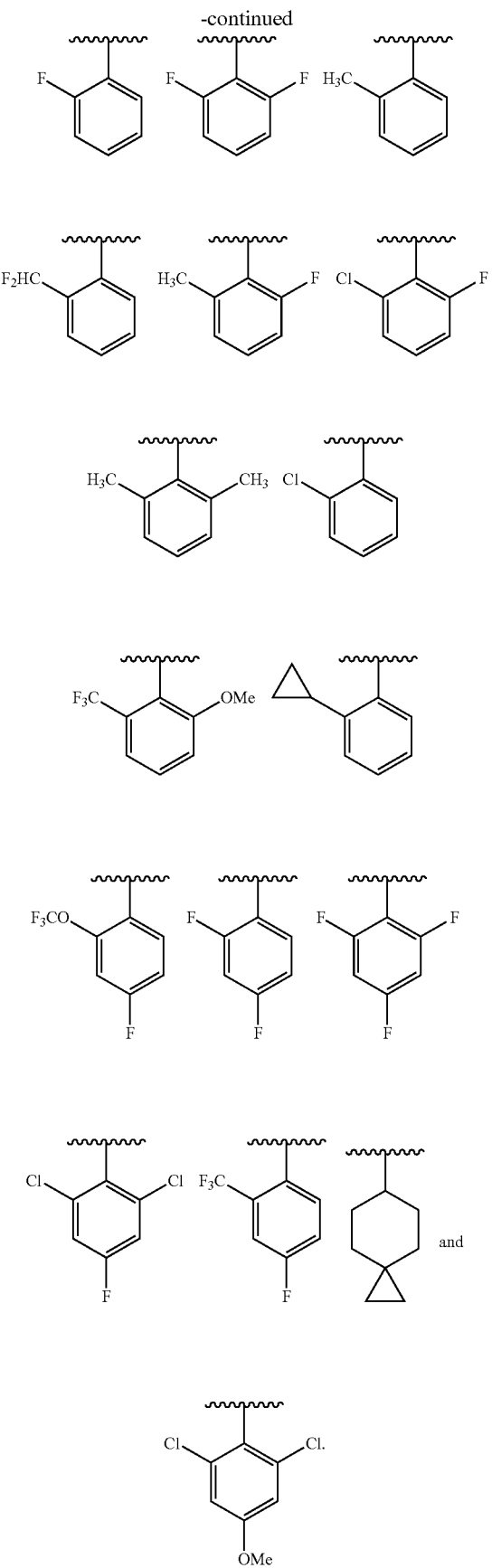

3. The compound of claim 1, wherein A is

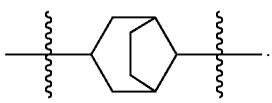

.

4. The compound of claim 1, selected from compounds of Formula (I), wherein $R^2$ and

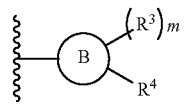

are delineated for each compound in the Table below:

| Entry | $R^2$ | ![B with (R³)m and R⁴] |
|---|---|---|
| 1 | 2,6-dichlorophenyl | 2-benzothiazole-6-COOH |
| 2 | 2-(trifluoromethoxy)phenyl | 2-benzothiazole-6-COOH |
| 3 | 2,6-dichlorophenyl | 2-benzothiazole-5-COOH |
| 4 | 2-(trifluoromethoxy)phenyl | 2-benzothiazole-5-COOH |
| 5 | 2,6-dichlorophenyl | 2-benzothiazole-6-COOH, 4-O-iPr |
| 6 | 2-(trifluoromethoxy)phenyl | 2-benzothiazole-6-COOH, 4-O-iPr |
| 7 | 2,6-dichlorophenyl | 2-benzothiazole-6-COOH, 4-OMe |

-continued

| Entry | R² | |
|---|---|---|
| 8 | 2-(trifluoromethoxy)phenyl | 2-yl-7-methoxy-benzothiazole-6-carboxylic acid |
| 9 | 2,6-dichlorophenyl | 2-yl-7-(trifluoromethoxy)-benzothiazole-6-carboxylic acid |
| 10 | 2-(trifluoromethoxy)phenyl | 2-yl-7-(trifluoromethoxy)-benzothiazole-6-carboxylic acid |
| 11 | 2,6-dichlorophenyl | 2-yl-7-cyclopropyl-benzothiazole-6-carboxylic acid |
| 12 | 2-(trifluoromethoxy)phenyl | 2-yl-7-cyclopropyl-benzothiazole-6-carboxylic acid |
| 13 | 2,6-dichlorophenyl | 2-yl-7-fluoro-benzothiazole-6-carboxylic acid |
| 14 | 2-(trifluoromethoxy)phenyl | 2-yl-7-fluoro-benzothiazole-6-carboxylic acid |
| 15 | 2,6-dichlorophenyl | 2-yl-7-(difluoromethoxy)-benzothiazole-6-carboxylic acid |

-continued

| Entry | R² | ![B ring with (R³)m and R⁴] |
|---|---|---|
| 16 | 2-(F₃CO)phenyl | 2-linked benzothiazole, 6-COOH, 7-OCHF₂ |
| 17 | 2,6-dichlorophenyl | 2-linked benzothiazole, 6-COOH, 7-OCH₂F |
| 18 | 2-(F₃CO)phenyl | 2-linked benzothiazole, 6-COOH, 7-OCH₂F |
| 19 | 2,6-dichlorophenyl | 2-linked benzothiazole, 6-COOH, 7-isopropyl |
| 20 | 2-(F₃CO)phenyl | 2-linked benzothiazole, 6-COOH, 7-isopropyl |
| 21 | 2,6-dichlorophenyl | 2-linked benzothiazole, 6-COOH, 7-tert-butyl |
| 22 | 2-(F₃CO)phenyl | 2-linked benzothiazole, 6-COOH, 7-tert-butyl |
| 23 | 2,6-dichlorophenyl | 2-linked benzothiazole, 6-COOH, 7-cyclobutyl |

-continued

| Entry | R² | ![B ring with (R³)m and R⁴] |
|---|---|---|
| 24 | 2-(trifluoromethoxy)phenyl | 2-linked benzothiazole-6-COOH with cyclobutyl at 7-position |
| 25 | 2,6-dichlorophenyl | 2-linked benzothiazole-6-COOH with cyclopentyl at 7-position |
| 26 | 2-(trifluoromethoxy)phenyl | 2-linked benzothiazole-6-COOH with cyclopentyl at 7-position |
| 31 | 2,6-dichlorophenyl | 2-linked benzothiazole-6-COOH with CF₃ at 7-position |
| 32 | 2-(trifluoromethoxy)phenyl | 2-linked benzothiazole-6-COOH with CF₃ at 7-position |
| 33 | 2,6-dichlorophenyl | 2-linked benzothiazole-6-COOH with Me at 7-position |
| 34 | 2-(trifluoromethoxy)phenyl | 2-linked benzothiazole-6-COOH with Me at 7-position |
| 35 | 2,6-dichlorophenyl | 2-linked benzothiazole-6-COOH with F at 5-position and OCF₃ at 7-position |

-continued
| Entry | R² | 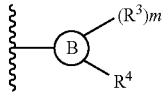 |
|---|---|---|
| 36 | 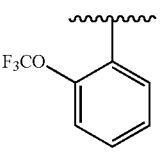 [SMILES: *c1ccccc1OC(F)(F)F] | 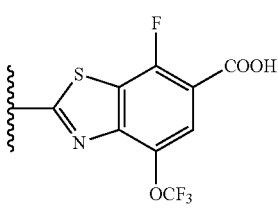 |
| 37 | 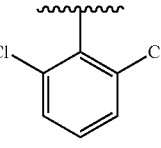 | 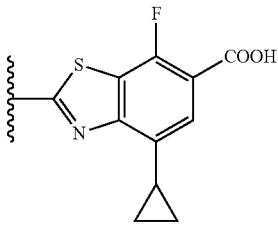 [SMILES: *c1nc2c(C3CC3)cc(C(=O)O)c(F)c2s1] |
| 38 | 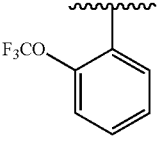 [SMILES: *c1ccccc1OC(F)(F)F] | 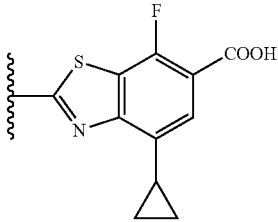 [SMILES: *c1nc2c(C3CC3)cc(C(=O)O)c(F)c2s1] |
| 39 | 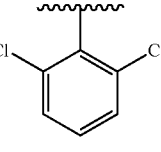 | 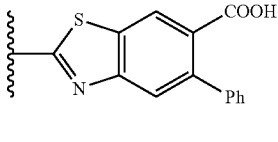 [SMILES: *c1nc2cc(-c3ccccc3)c(C(=O)O)cc2s1] |
| 40 | 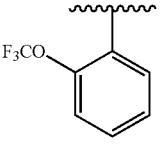 | 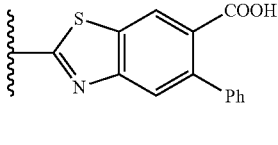 [SMILES: *c1nc2cc(-c3ccccc3)c(C(=O)O)cc2s1] |
| 41 | 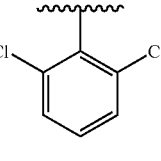 | 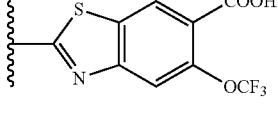 |
| 42 | 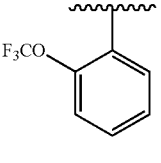 [SMILES: *c1ccccc1OC(F)(F)F] | 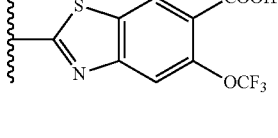 |
| 43 | 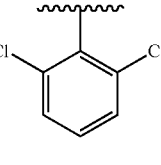 | 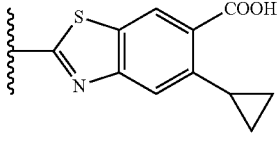 [SMILES: *c1nc2cc(C3CC3)c(C(=O)O)cc2s1] |

-continued

| Entry | R² | ![B ring with (R³)m and R⁴] |
|---|---|---|
| 44 | 2-(F₃CO)phenyl | 2-yl-6-cyclopropyl-benzothiazole-5-COOH |
| 45 | 2,6-dichlorophenyl | naphtho[2,1-d]thiazol-2-yl with COOH |
| 46 | 2-(F₃CO)phenyl | naphtho[2,1-d]thiazol-2-yl with COOH |
| 147 | 2,6-dichlorophenyl | benzothiazol-2-yl-6-CN |
| 148 | 2-(F₃CO)phenyl | benzothiazol-2-yl-6-COOH |
| 149 | 2,6-dichlorophenyl | benzothiazol-2-yl-6-(1H-tetrazol-5-yl) |
| 150 | 2-(F₃CO)phenyl | benzothiazol-2-yl-6-(1H-tetrazol-5-yl) |
| 151 | 2,6-dichlorophenyl | benzothiazol-2-yl-6-CN-4-OiPr |
| 152 | 2-(F₃CO)phenyl | benzothiazol-2-yl-6-CN-4-OiPr |

-continued

| Entry | R² | m / R⁴ |
|---|---|---|
| 153 | 2,6-dichlorophenyl | 6-(hydroxymethyl)-7-OiPr-benzothiazol-2-yl |
| 154 | 2-(trifluoromethoxy)phenyl | 6-(hydroxymethyl)-7-OiPr-benzothiazol-2-yl |
| 155 | 2,6-dichlorophenyl | 6-SO₂NH₂-7-OiPr-benzothiazol-2-yl |
| 156 | 2-(trifluoromethoxy)phenyl | 6-SO₂NH₂-7-OiPr-benzothiazol-2-yl |
| 161 | 2,6-dichlorophenyl | 6-(cyclopentylsulfonyl)-7-OiPr-benzothiazol-2-yl |
| 162 | 2-(trifluoromethoxy)phenyl | 6-(cyclopentylsulfonyl)-7-OiPr-benzothiazol-2-yl |
| 165 | 2,6-dichlorophenyl | 6-(CH₂COOH)-7-OiPr-benzothiazol-2-yl |
| 166 | 2-(trifluoromethoxy)phenyl | 6-(CH₂COOH)-7-OiPr-benzothiazol-2-yl |

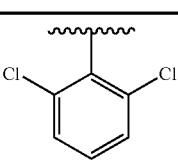
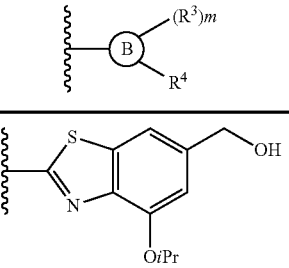
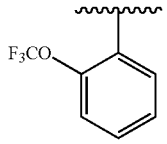 [SMILES: *c1ccccc1OC(F)(F)F]
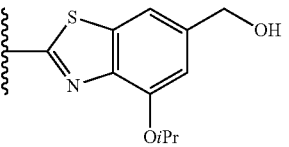 [SMILES: *c1nc2c(OC(C)C)cc(CO)cc2s1]
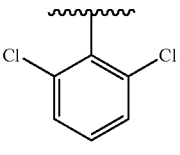 [SMILES: *c1c(Cl)cccc1Cl]
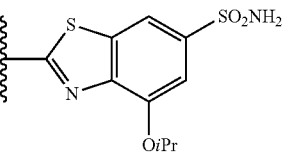 [SMILES: *c1nc2c(OC(C)C)cc(S(N)(=O)=O)cc2s1]
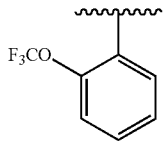 [SMILES: *c1ccccc1OC(F)(F)F]
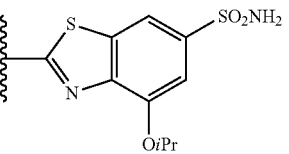 [SMILES: *c1nc2c(OC(C)C)cc(S(N)(=O)=O)cc2s1]
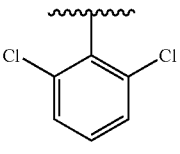 [SMILES: *c1c(Cl)cccc1Cl]
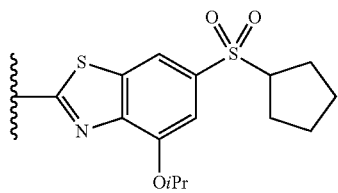 [SMILES: *c1nc2c(OC(C)C)cc(S(=O)(=O)C3CCCC3)cc2s1]
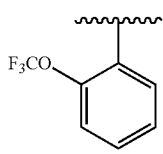 [SMILES: *c1ccccc1OC(F)(F)F]
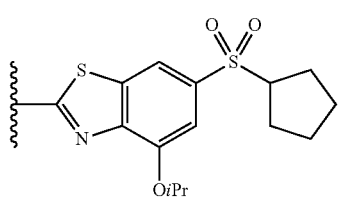 [SMILES: *c1nc2c(OC(C)C)cc(S(=O)(=O)C3CCCC3)cc2s1]
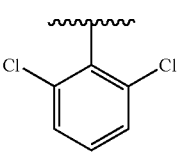 [SMILES: *c1c(Cl)cccc1Cl]
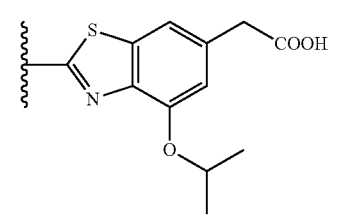 [SMILES: *c1nc2c(OC(C)C)cc(CC(=O)O)cc2s1]
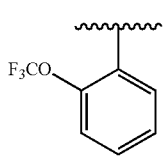 [SMILES: *c1ccccc1OC(F)(F)F]
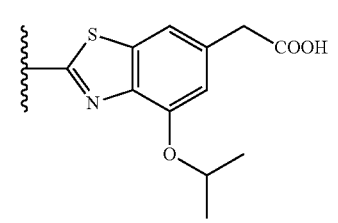 [SMILES: *c1nc2c(OC(C)C)cc(CC(=O)O)cc2s1]

-continued

| Entry | R² | ⸝⸝⸝—B—(R³)m / R⁴ |
|---|---|---|
| 167 | 2,6-dichlorophenyl | 2-yl-7-isopropoxy-benzothiazol-6-yl-1-(cyclopropane)-COOH |
| 168 | 2-(trifluoromethoxy)phenyl | 2-yl-7-isopropoxy-benzothiazol-6-yl-1-(cyclopropane)-COOH |
| 169 | 2,6-dichlorophenyl | 2-yl-7-isopropoxy-benzothiazol-6-yl-CF₂-COOH |
| 170 | 2-(trifluoromethoxy)phenyl | 2-yl-7-isopropoxy-benzothiazol-6-yl-CF₂-COOH |
| 175 | 2,6-dichlorophenyl | 2-yl-7-(OiPr)-benzothiazol-6-yl-C(O)NH-CH₂-COOH |
| 176 | 2-(trifluoromethoxy)phenyl | 2-yl-7-(OiPr)-benzothiazol-6-yl-C(O)NH-CH₂-COOH |

-continued

| Entry | R² | ![B ring with (R³)m and R⁴] |
|-------|-----|------|
| 177 | 2,6-dichlorophenyl | benzothiazole-6-C(O)NH-CH₂CH₂-SO₃H, 7-OiPr |
| 178 | 2-(trifluoromethoxy)phenyl | benzothiazole-6-C(O)NH-CH₂CH₂-SO₃H, 7-OiPr |
| 179 | 2,6-dichlorophenyl | benzothiazole-6-C(CH₃)₂OH, 7-OiPr |
| 180 | 2-(trifluoromethoxy)phenyl | benzothiazole-6-C(CH₃)₂OH, 7-OiPr |
| 181 | 2,6-dichlorophenyl | benzothiazole-6-CH₂OH, 7-OiPr |
| 182 | 2-(trifluoromethoxy)phenyl | benzothiazole-6-CH₂OH, 7-OiPr |
| 193 | 2,6-dichlorophenyl | benzothiazole-6-CF₃, 7-OiPr |
| 194 | 2-(trifluoromethoxy)phenyl | benzothiazole-6-CF₃, 7-OiPr |

-continued
| Entry | R² | 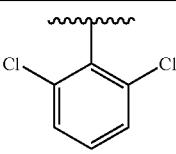 |
|---|---|---|
| 195 | 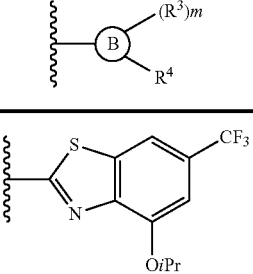 | 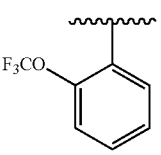 [SMILES: *c1ccccc1OC(F)(F)F] |
| 196 | 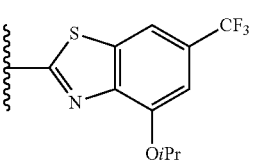 [SMILES: *c1nc2c(OC(C)C)cc(C(F)(F)F)cc2s1] | 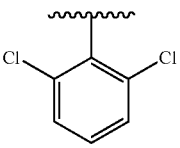 [SMILES: *c1c(Cl)cccc1Cl] |
| 201 | 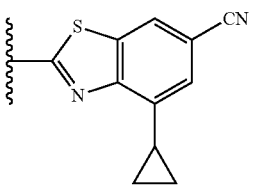 [SMILES: *c1nc2c(C3CC3)cc(C#N)cc2s1] | 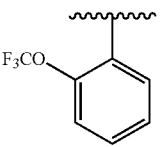 [SMILES: *c1ccccc1OC(F)(F)F] |
| 202 | 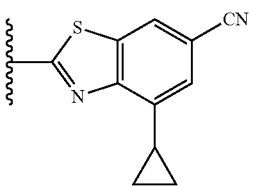 [SMILES: *c1nc2c(C3CC3)cc(C#N)cc2s1] | 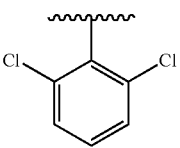 [SMILES: *c1c(Cl)cccc1Cl] |
| 203 | 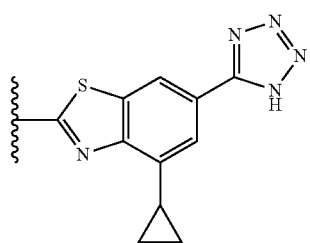 [SMILES: *c1nc2c(C3CC3)cc(-c3nnn[nH]3)cc2s1] | 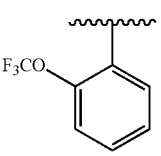 [SMILES: *c1ccccc1OC(F)(F)F] |
| 204 | 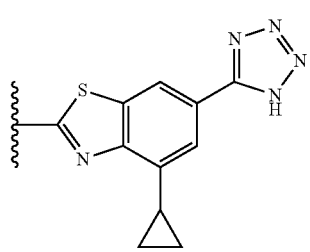 [SMILES: *c1nc2c(C3CC3)cc(-c3nnn[nH]3)cc2s1] | 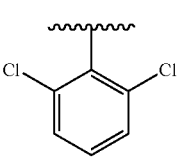 [SMILES: *c1c(Cl)cccc1Cl] |
| 209 | 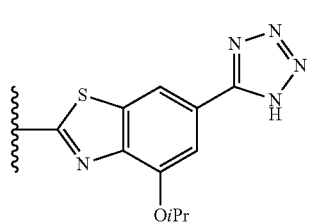 [SMILES: *c1nc2c(OC(C)C)cc(-c3nnn[nH]3)cc2s1] | |

-continued

| Entry | R² | 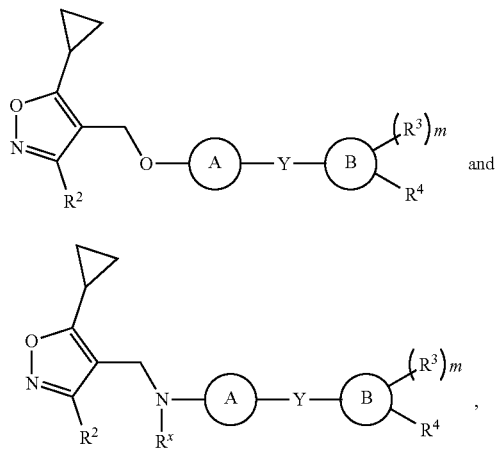 |
|---|---|---|
| 210 | F₃CO-phenyl | benzothiazole-OiPr with tetrazole |

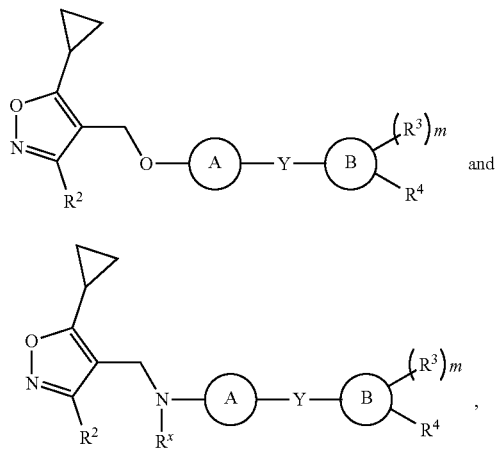

5. The compound of claim 1, represented by one of Formula (IIIa) and Formula (IIIb), IIIa

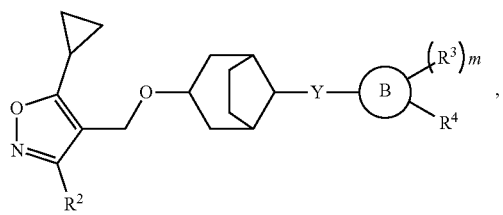

and

IIIb

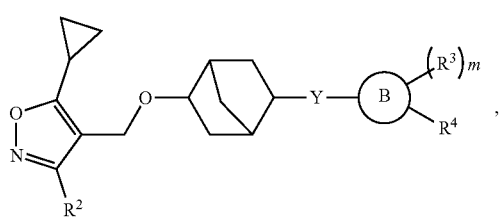

or a pharmaceutically acceptable salt thereof, wherein R², Rˣ, A, Y, R³, m, B and R⁴ are as defined in claim 1.

6. The compound of claim 1, represented by one of Formulas (IVa), (IVb), (IVc) or (IVd),

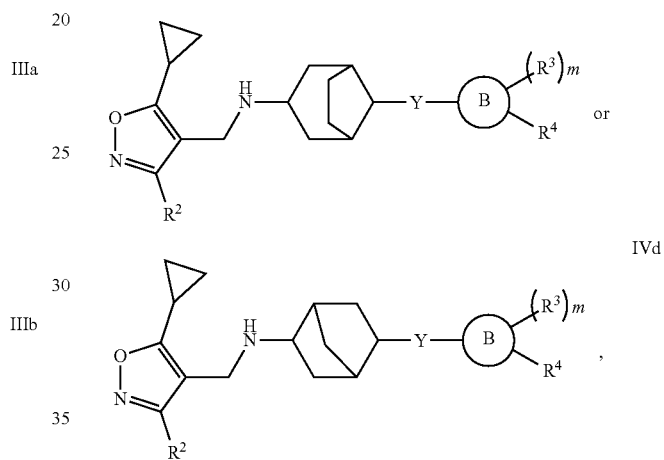

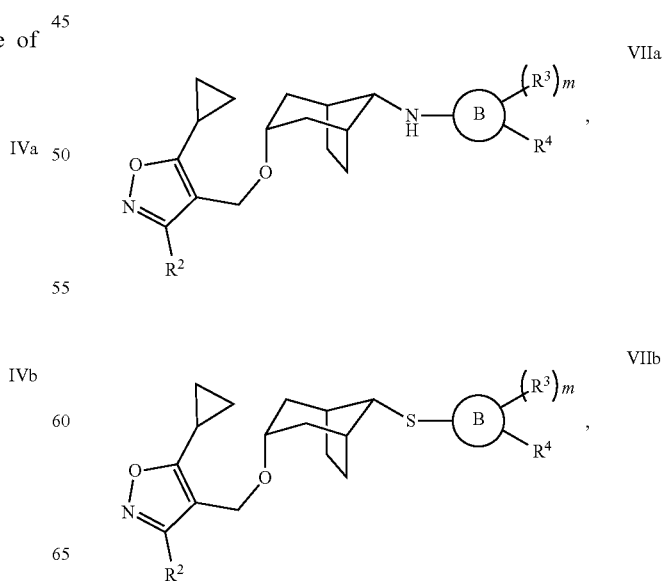

or a pharmaceutically acceptable salt thereof, wherein R², Y, R³, m, B and R⁴ are as defined in claim 1.

7. The compound of claim 1, represented by one of Formulas (VIIa), (VIIb), (VIIc) and (VIIe), VIIc

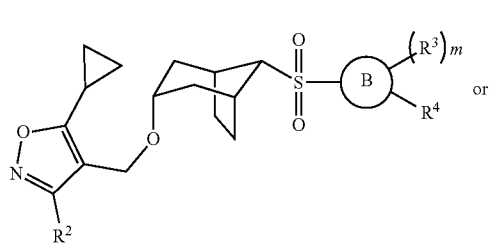

or

VIIe

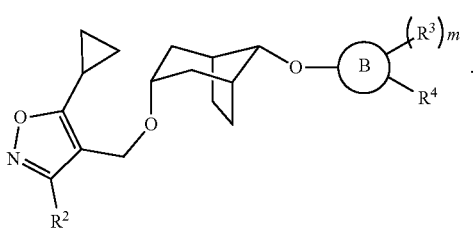

or a pharmaceutically acceptable salt thereof, wherein $R^2$, B, $R^3$, m and $R^4$ are as defined in claim 1.

8. The compound of claim 1, represented by one of Formulas (VIIIa), (VIIIb), (VIIIc) and (VIIIe), VIIIa

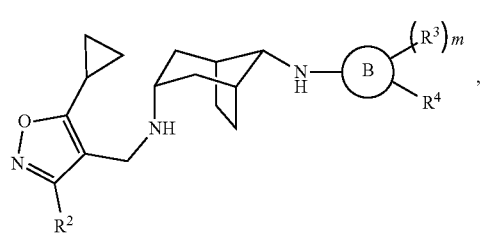

,

VIIIb

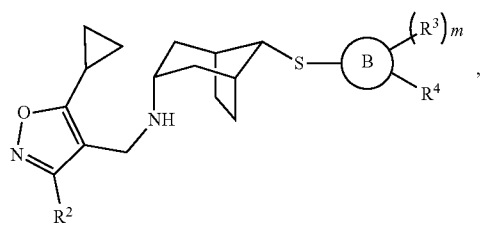

,

VIIIc

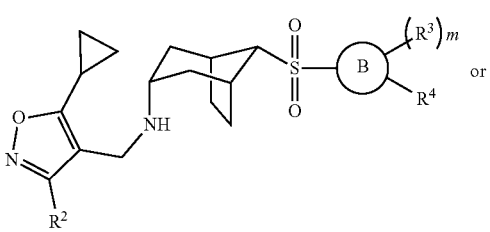

or

VIIIe

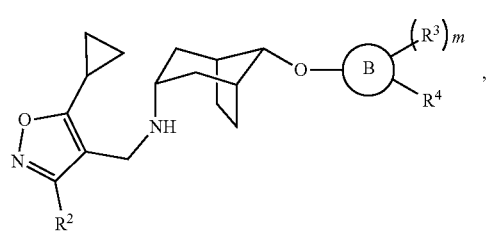

, or a pharmaceutically acceptable salt thereof, wherein $R^2$, B, $R^3$, m and $R^4$ are as defined in claim 1.

9. A method for preventing or treating an FXR-mediated disease or condition in a subject in need thereof, comprising administering to the subject a therapeutically effective amount of a compound according to claim 1.

10. The method according to claim 9, wherein the FXR-mediated disease or condition is selected from the group consisting of chronic liver disease, gastrointestinal disease, renal disease, cardiovascular disease, fibrotic diseases, and metabolic disease.

11. The method according to claim 10, wherein the FXR-mediated disease or condition is a fibrotic disease selected from primary biliary cirrhosis, primary sclerosing cholangitis, pulmonary fibrosis, renal fibrosis, and liver fibrosis.

12. The method according to claim 10, wherein the FXR-mediated disease or condition is a chronic liver disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

13. The method according to claim 10, wherein the FXR-mediated disease or condition is a renal disease selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

14. The method according to claim 10, wherein the FXR-mediated disease or condition is a cardiovascular disease selected from the group consisting of atherosclerosis, arteriosclerosis, dyslipidemia, hypercholesterolemia, and hypertriglyceridemia.

15. A method according to claim 10, wherein the FXR-mediated disease or condition is a metabolic disease selected from the group consisting of insulin resistance, Type I and Type II diabetes, and obesity.

16. A pharmaceutical composition comprising a compound according to claim 1 and a pharmaceutically acceptable carrier.
17. The compound of claim 1, selected from the compounds set forth below or a pharmaceutically acceptable salt thereof:
| Compound | Structure |
|---|---|
| 1 | 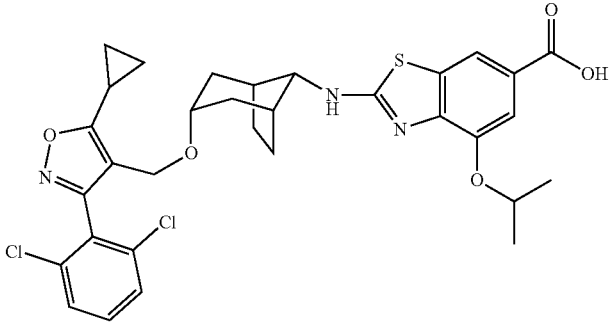 [SMILES: CC(C)Oc1cc(C(=O)O)cc2sc(NC3C4CCC3CC(OCc3c(-c5c(Cl)cccc5Cl)noc3C3CC3)C4)nc12] |
| 2 | 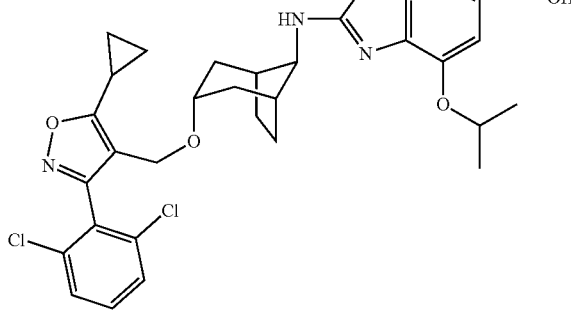 |
| 3 | 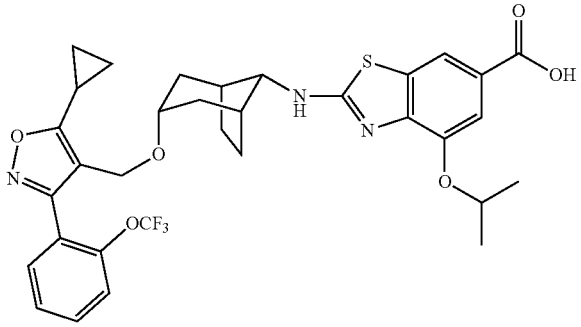 [SMILES: CC(C)Oc1cc(C(=O)O)cc2sc(NC3C4CCC3CC(OCc3c(-c5ccccc5OC(F)(F)F)noc3C3CC3)C4)nc12] |
| 3-2 | 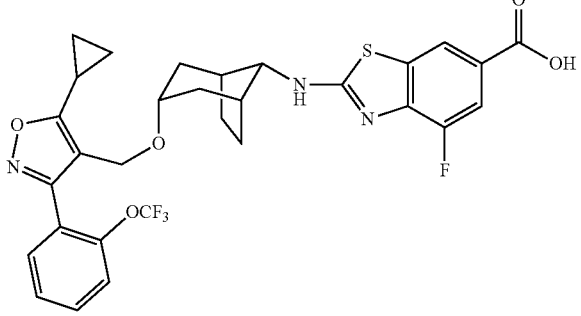 |

-continued

| Compound | Structure |
|---|---|
| 3-9 | 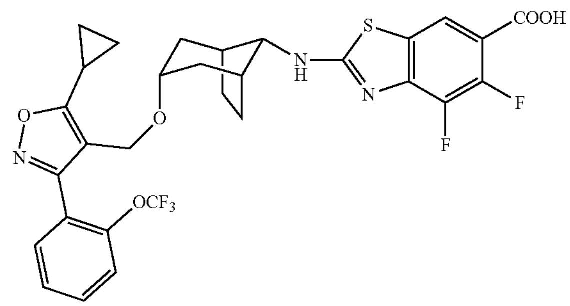 [SMILES: O=C(O)c1cc2sc(NC3C4CCC3CC(OCc3c(-c5ccccc5OC(F)(F)F)noc3C3CC3)C4)nc2c(F)c1F] |
| 3-10 | 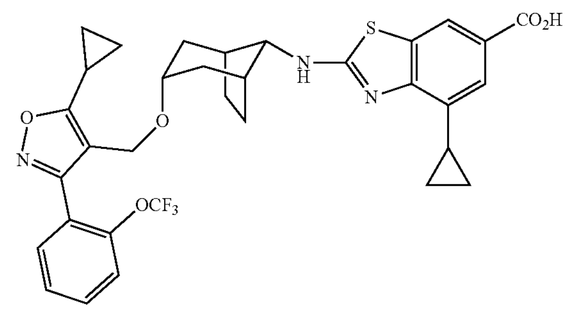 [SMILES: O=C(O)c1cc(C2CC2)c2nc(NC3C4CCC3CC(OCc3c(-c5ccccc5OC(F)(F)F)noc3C3CC3)C4)sc2c1] |
| 3-11 | 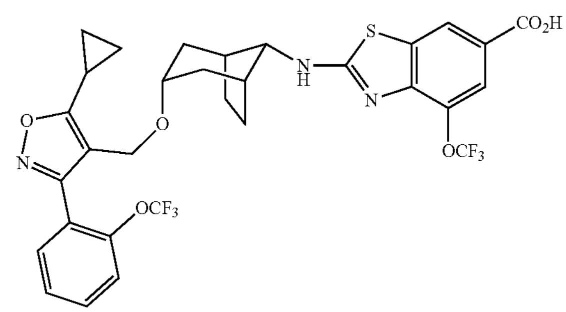 [SMILES: O=C(O)c1cc(OC(F)(F)F)c2nc(NC3C4CCC3CC(OCc3c(-c5ccccc5OC(F)(F)F)noc3C3CC3)C4)sc2c1] |
| 4 | 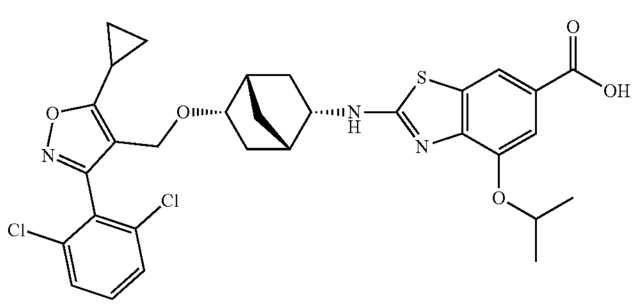 [SMILES: CC(C)Oc1cc(C(=O)O)cc2sc(N[C@H]3C[C@@H]4C[C@H]3C[C@@H]4OCc3c(-c4c(Cl)cccc4Cl)noc3C3CC3)nc12] |
| 5 | 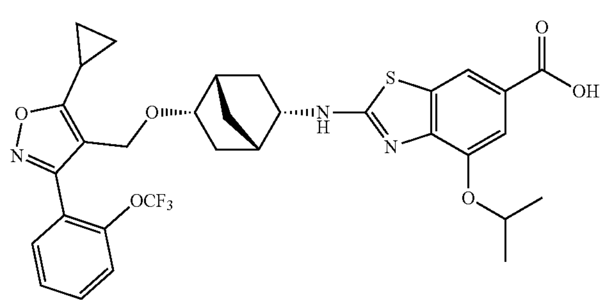 [SMILES: CC(C)Oc1cc(C(=O)O)cc2sc(N[C@H]3C[C@@H]4C[C@H]3C[C@@H]4OCc3c(-c4ccccc4OC(F)(F)F)noc3C3CC3)nc12] |

| Compound | Structure |
|---|---|
| 6 | 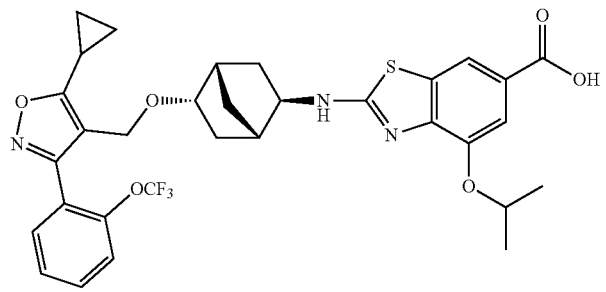 [SMILES: CC(C)Oc1cc(C(=O)O)cc2sc(N[C@@H]3C[C@@H]4C[C@H]3C[C@@H]4OCc3c(-c4ccccc4OC(F)(F)F)noc3C3CC3)nc12] |
| 8 | 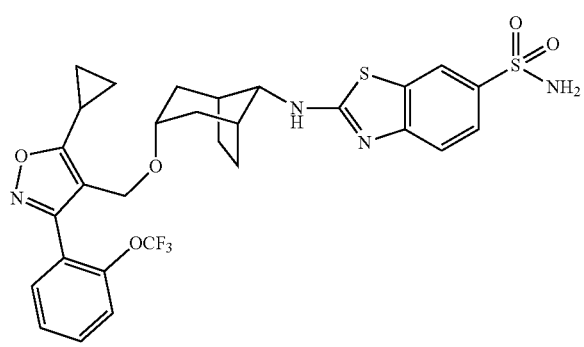 [SMILES: NS(=O)(=O)c1ccc2nc(NC3C4CCC3CC(OCc3c(-c5ccccc5OC(F)(F)F)noc3C3CC3)C4)sc2c1] |
| 8-6 | 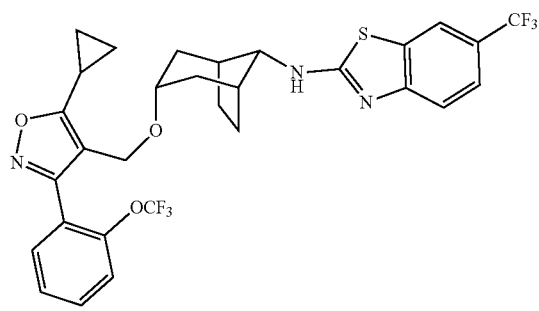 [SMILES: FC(F)(F)Oc1ccccc1-c1noc(C2CC2)c1COC1CC2CCC(C1)C2Nc1nc2ccc(C(F)(F)F)cc2s1] |
| 10 | 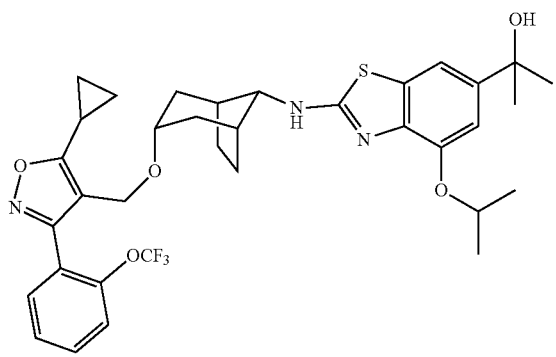 [SMILES: CC(C)Oc1cc(C(C)(C)O)cc2sc(NC3C4CCC3CC(OCc3c(-c5ccccc5OC(F)(F)F)noc3C3CC3)C4)nc12] |

-continued
| Compound | Structure |
|---|---|
| 10-2 | 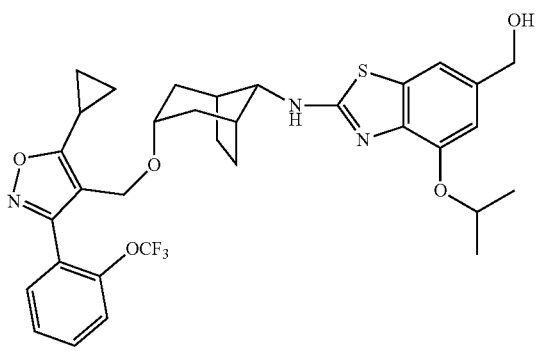 [SMILES: CC(C)Oc1cc(CO)cc2sc(NC3C4CCC3CC(OCc3c(-c5ccccc5OC(F)(F)F)noc3C3CC3)C4)nc12] |
| 11-9 | 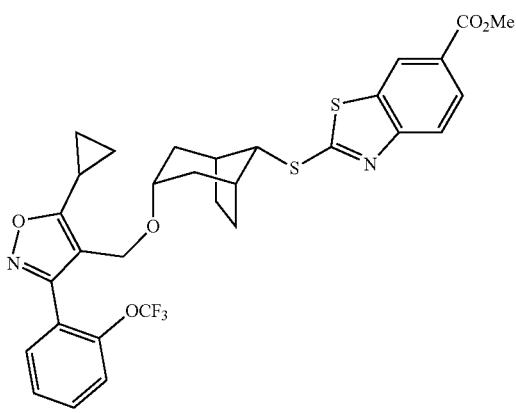 [SMILES: COC(=O)c1ccc2nc(SC3C4CCC3CC(OCc3c(-c5ccccc5OC(F)(F)F)noc3C3CC3)C4)sc2c1] |
| 11-10 | 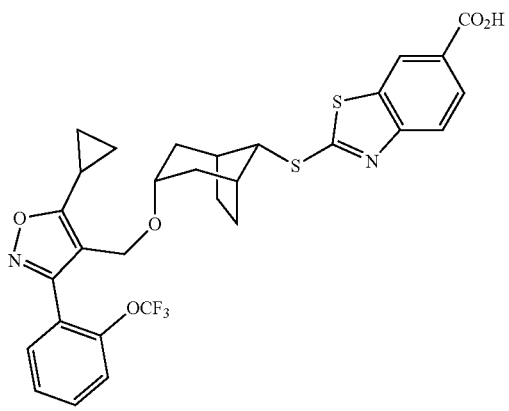 [SMILES: O=C(O)c1ccc2nc(SC3C4CCC3CC(OCc3c(-c5ccccc5OC(F)(F)F)noc3C3CC3)C4)sc2c1] |
| 11-11 | 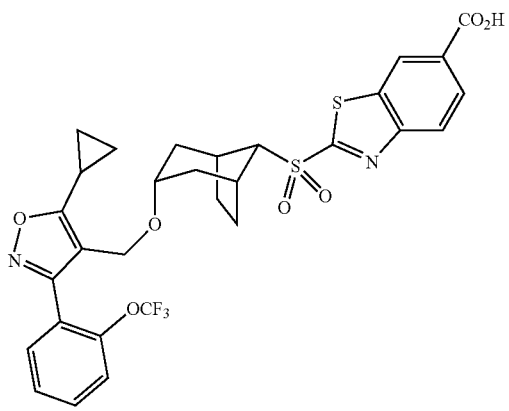 [SMILES: O=C(O)c1ccc2nc(S(=O)(=O)C3C4CCC3CC(OCc3c(-c5ccccc5OC(F)(F)F)noc3C3CC3)C4)sc2c1] |

-continued
| Compound | Structure |
|---|---|
| 11-16 | 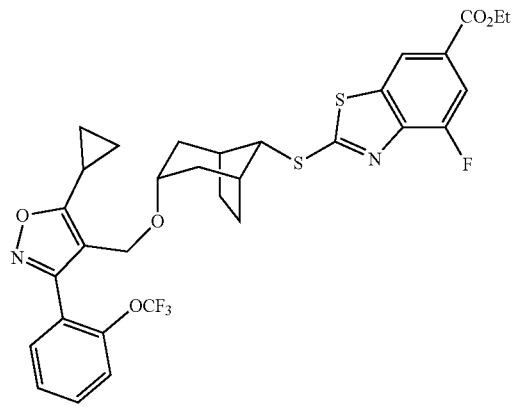 [SMILES: CCOC(=O)c1cc(F)c2nc(SC3C4CCC3CC(OCc3c(-c5ccccc5OC(F)(F)F)noc3C3CC3)C4)sc2c1] |
| 11-17 | 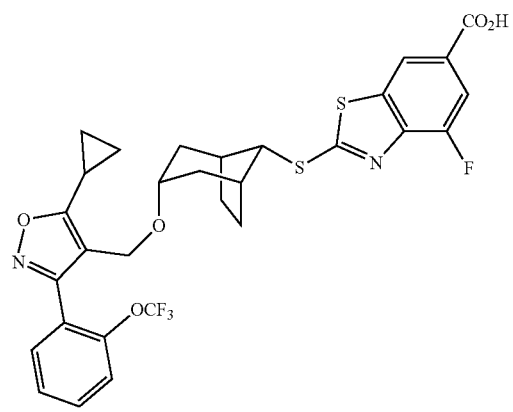 [SMILES: O=C(O)c1cc(F)c2nc(SC3C4CCC3CC(OCc3c(-c5ccccc5OC(F)(F)F)noc3C3CC3)C4)sc2c1] |
| 11-18 | 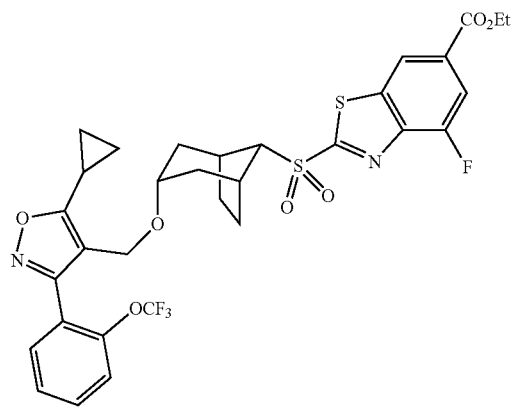 [SMILES: CCOC(=O)c1cc(F)c2nc(S(=O)(=O)C3C4CCC3CC(OCc3c(-c5ccccc5OC(F)(F)F)noc3C3CC3)C4)sc2c1] |

-continued
| Compound | Structure |
|---|---|
| 11-19 | 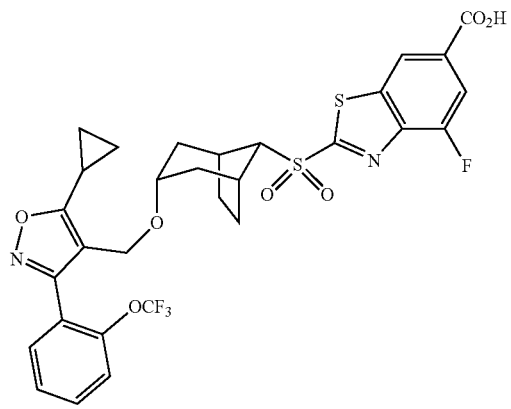 [SMILES: O=C(O)c1cc(F)c2nc(S(=O)(=O)C3C4CCC3CC(OCc3c(-c5ccccc5OC(F)(F)F)noc3C3CC3)C4)sc2c1] |
| 13-4 | 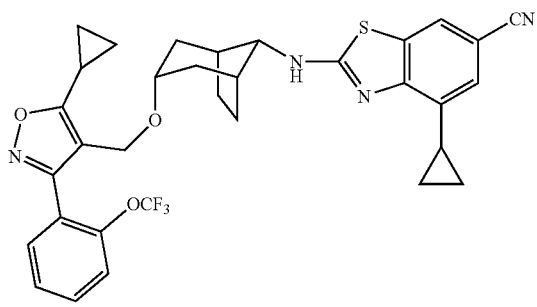 [SMILES: N#Cc1cc(C2CC2)c2nc(NC3C4CCC3CC(OCc3c(-c5ccccc5OC(F)(F)F)noc3C3CC3)C4)sc2c1] |
| 13-5 | 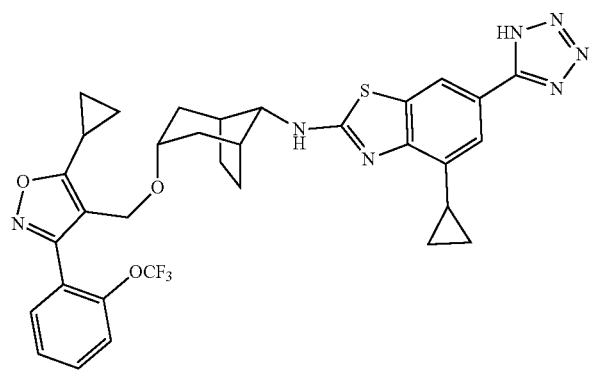 [SMILES: FC(F)(F)Oc1ccccc1-c1noc(C2CC2)c1COC1CC2CCC(C1)C2Nc1nc2c(C3CC3)cc(-c3nnn[nH]3)cc2s1] |
| 13-6 | 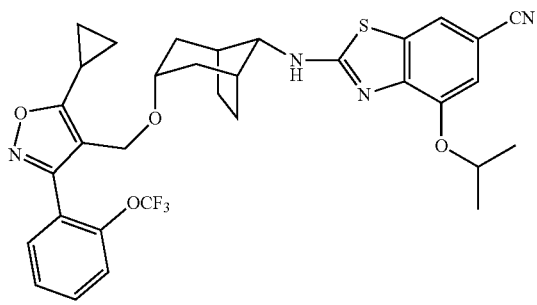 [SMILES: CC(C)Oc1cc(C#N)cc2sc(NC3C4CCC3CC(OCc3c(-c5ccccc5OC(F)(F)F)noc3C3CC3)C4)nc12] |

-continued

| Compound | Structure |
|---|---|
| 13-7 | 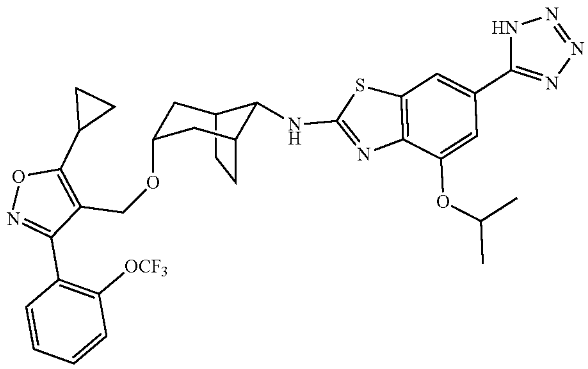 [SMILES: CC(C)Oc1cc(-c2nnn[nH]2)cc2sc(NC3C4CCC3CC(OCc3c(-c5ccccc5OC(F)(F)F)noc3C3CC3)C4)nc12] |
| 14 | 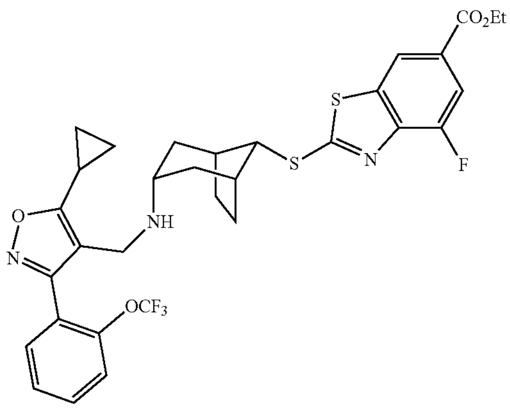 [SMILES: CCOC(=O)c1cc(F)c2nc(SC3C4CCC3CC(NCc3c(-c5ccccc5OC(F)(F)F)noc3C3CC3)C4)sc2c1] |
| 14-2 | 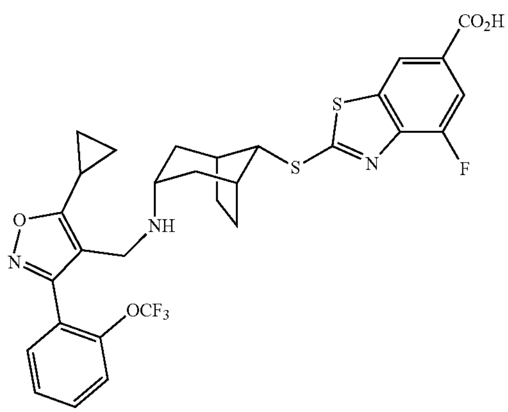 [SMILES: O=C(O)c1cc(F)c2nc(SC3C4CCC3CC(NCc3c(-c5ccccc5OC(F)(F)F)noc3C3CC3)C4)sc2c1] |
| 16 | 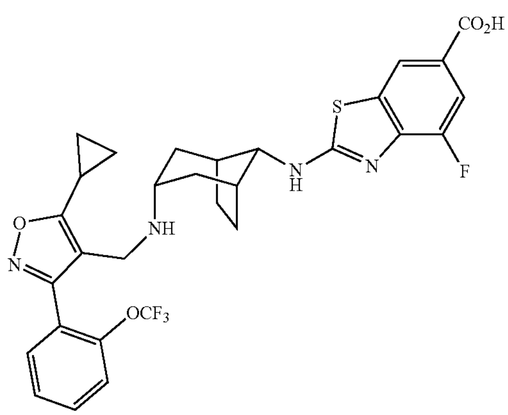 [SMILES: O=C(O)c1cc(F)c2nc(NC3C4CCC3CC(NCc3c(-c5ccccc5OC(F)(F)F)noc3C3CC3)C4)sc2c1] |

-continued
| Compound | Structure |
|---|---|
| 18 | 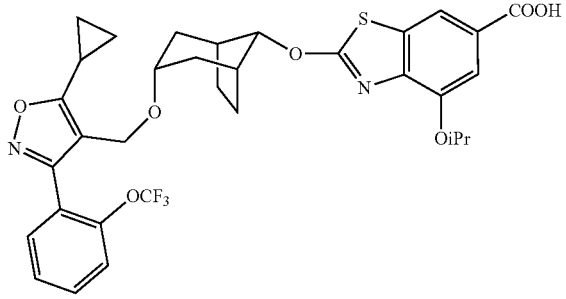 [SMILES: CC(C)Oc1cc(C(=O)O)cc2sc(OC3C4CCC3CC(OCc3c(-c5ccccc5OC(F)(F)F)noc3C3CC3)C4)nc12] |
| 19 | 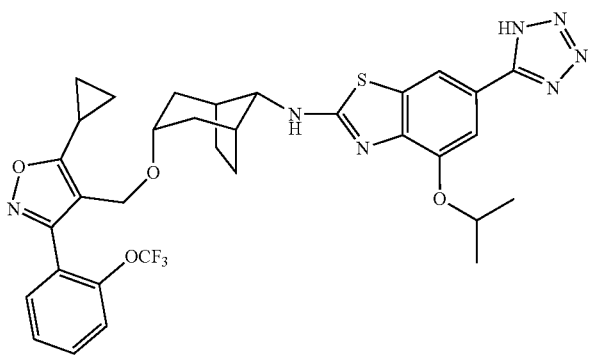 [SMILES: CC(C)Oc1cc(-c2nnn[nH]2)cc2sc(NC3C4CCC3CC(OCc3c(-c5ccccc5OC(F)(F)F)noc3C3CC3)C4)nc12] |
| 20 | 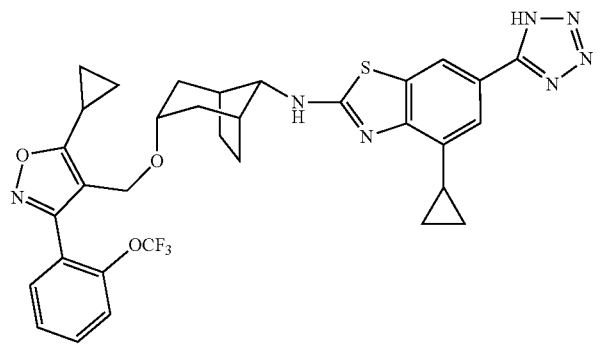 [SMILES: FC(F)(F)Oc1ccccc1-c1noc(C2CC2)c1COC1CC2CCC(C1)C2Nc1nc2c(C3CC3)cc(-c3nnn[nH]3)cc2s1] |
| 21 | 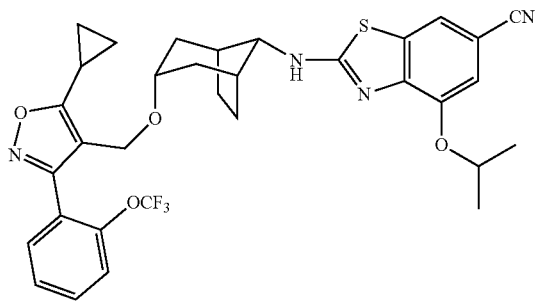 [SMILES: CC(C)Oc1cc(C#N)cc2sc(NC3C4CCC3CC(OCc3c(-c5ccccc5OC(F)(F)F)noc3C3CC3)C4)nc12] |

| Compound | Structure |
|---|---|
| 23 | 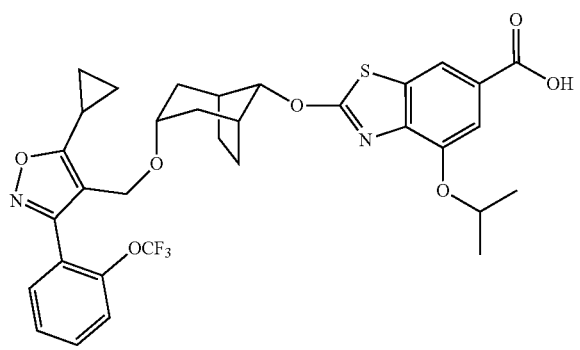 [SMILES: CC(C)Oc1cc(C(=O)O)cc2sc(OC3C4CCC3CC(OCc3c(-c5ccccc5OC(F)(F)F)noc3C3CC3)C4)nc12] |
| 24 | 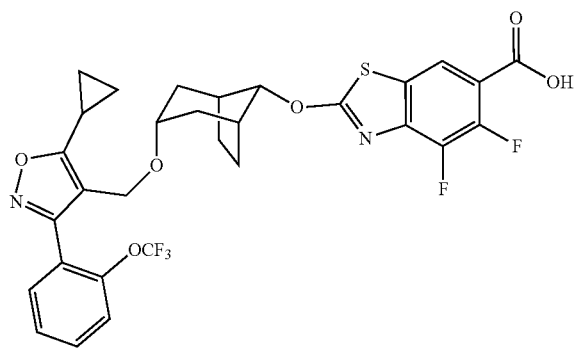 [SMILES: O=C(O)c1cc2sc(OC3C4CCC3CC(OCc3c(-c5ccccc5OC(F)(F)F)noc3C3CC3)C4)nc2c(F)c1F] |
| 36 | 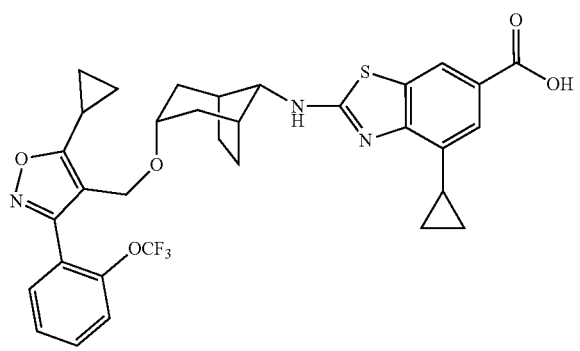 [SMILES: O=C(O)c1cc(C2CC2)c2nc(NC3C4CCC3CC(OCc3c(-c5ccccc5OC(F)(F)F)noc3C3CC3)C4)sc2c1] |
| 37 | 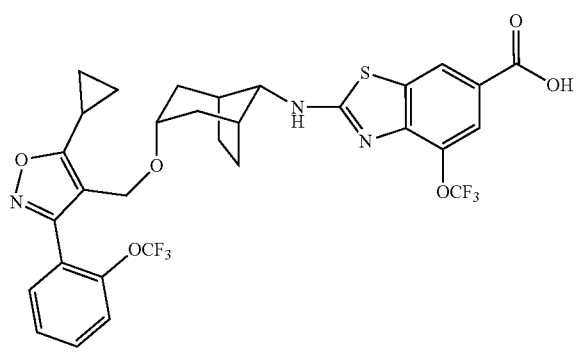 [SMILES: O=C(O)c1cc(OC(F)(F)F)c2nc(NC3C4CCC3CC(OCc3c(-c5ccccc5OC(F)(F)F)noc3C3CC3)C4)sc2c1] |

-continued

| Compound | Structure |
|---|---|
| 38 | 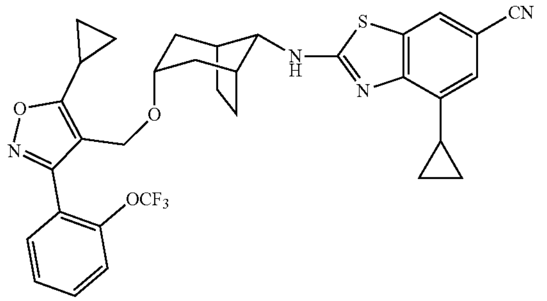 [SMILES: N#Cc1cc(C2CC2)c2nc(NC3C4CCC3CC(OCc3c(-c5ccccc5OC(F)(F)F)noc3C3CC3)C4)sc2c1] |
| 42 | 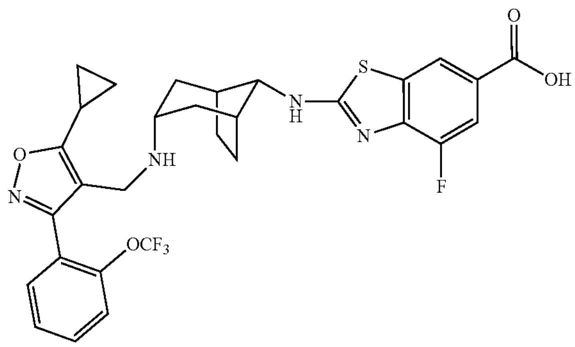 [SMILES: O=C(O)c1cc(F)c2nc(NC3C4CCC3CC(NCc3c(-c5ccccc5OC(F)(F)F)noc3C3CC3)C4)sc2c1] |
| 43 | 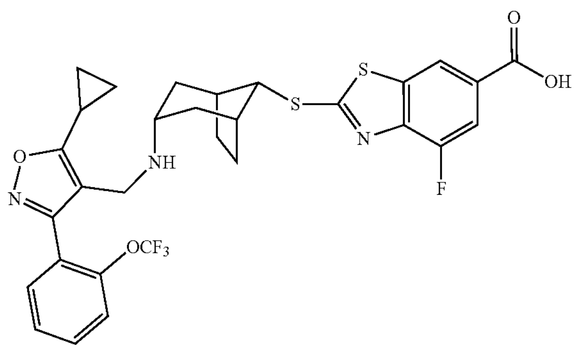 [SMILES: O=C(O)c1cc(F)c2nc(SC3C4CCC3CC(NCc3c(-c5ccccc5OC(F)(F)F)noc3C3CC3)C4)sc2c1] |
| 45 | 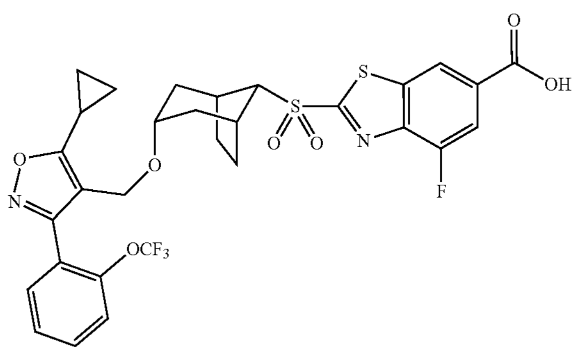 [SMILES: O=C(O)c1cc(F)c2nc(S(=O)(=O)C3C4CCC3CC(OCc3c(-c5ccccc5OC(F)(F)F)noc3C3CC3)C4)sc2c1] |

* * * * *

UNITED STATES PATENT AND TRADEMARK OFFICE
CERTIFICATE OF CORRECTION

PATENT NO. : 11,555,032 B2  
APPLICATION NO. : 16/871551  
DATED : January 17, 2023  
INVENTOR(S) : Guoqiang Wang et al.

Page 1 of 1

It is certified that error appears in the above-identified patent and that said Letters Patent is hereby corrected as shown below:

In the Claims

Column 215

In Claim 4 at Entry 148, delete " 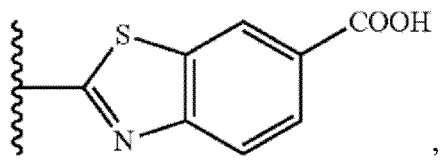 " and insert

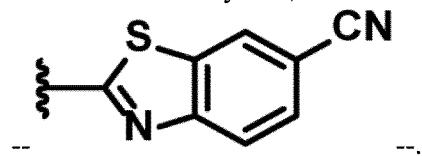

--.

Signed and Sealed this  
Twenty-fifth Day of April, 2023

Katherine Kelly Vidal  
*Director of the United States Patent and Trademark Office*